US006293159B1

(12) United States Patent
Kriesel et al.

(10) Patent No.: US 6,293,159 B1
(45) Date of Patent: Sep. 25, 2001

(54) FLUID DELIVERY APPARATUS WITH RESERVOIR FILL ASSEMBLY

(75) Inventors: Marshall S. Kriesel, Saint Paul; Steven M. Arnold, Minnetanka; James Garrison, South Minneapolis; Farhad Kazemzadeh, Bloomington, all of MN (US)

(73) Assignee: Science Incorporated, Bloomington ( * ) Notice: Subject to any disclaimer, the term of this patent is extended or adjusted under 35 U.S.C. 154(b) by 0 days.

This patent is subject to a terminal disclaimer.

(21) Appl. No.: 09/488,961

(22) Filed: Jan. 21, 2000

Related U.S. Application Data

(60) Continuation-in-part of application No. 09/363,288, filed on Jul. 28, 1999, which is a division of application No. 09/017,047, filed on Feb. 2, 1998, now Pat. No. 5,962,794, which is a continuation-in-part of application No. 08/718,686, filed on Sep. 24, 1996, now Pat. No. 5,721,382, which is a continuation-in-part of application No. 08/432,220, filed on May 1, 1995, now abandoned.

(51) Int. Cl.[7] ......................................................... G01F 1/38
(52) U.S. Cl. .................... 73/861.47; 604/133; 73/864.91
(58) Field of Search ........................ 73/700, 706, 861.47, 73/861.52, 861.54, 864.91; 604/131, 133, 141

(56) References Cited

U.S. PATENT DOCUMENTS

| | | | | |
|---|---|---|---|---|
| 5,348,539 | * | 9/1994 | Glennn | 604/141 |
| 5,554,123 | * | 9/1996 | Herskowitz | 604/141 |
| 5,823,096 | * | 10/1998 | Shih | 99/302 P |
| 5,840,071 | * | 11/1998 | Kriesel et al. | 604/132 |
| 5,962,794 | * | 10/1999 | Kriesel et al. | 73/861.47 |
| 5,993,425 | * | 11/1999 | Kriesel | 604/191 |
| 6,086,561 | * | 7/2000 | Kriesel et al. | 604/133 |
| 6,090,071 | * | 7/2000 | Kriesel | 604/131 |

* cited by examiner

Primary Examiner—Max Noori
(74) Attorney, Agent, or Firm—James E. Brunton

(57) ABSTRACT

An apparatus for delivering fluids at a precisely controlled rate which includes a fluid dispensing component having a fluid reservoir for containing the fluids to be delivered and a reservoir fill component which can be removably interconnected with the fluid dispensing component. The reservoir fill assembly is uniquely designed to accept a vial component of conventional construction which is factory filled with the medicinal fluid to be delivered to the patient. The dispenser component embodies a highly novel fluid flow indicator that provides a readily discernible visual indication of fluid flow status through the device.

52 Claims, 69 Drawing Sheets

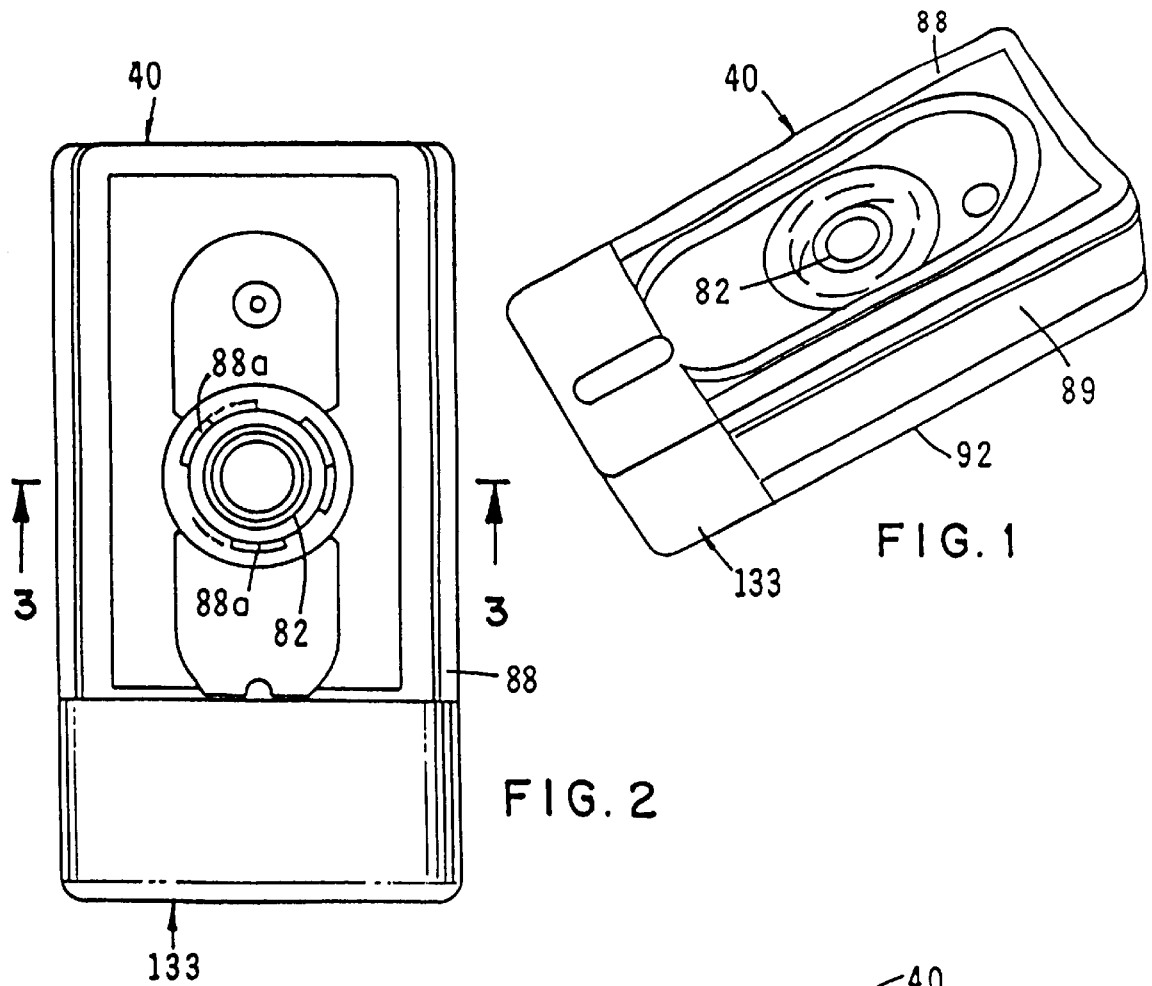
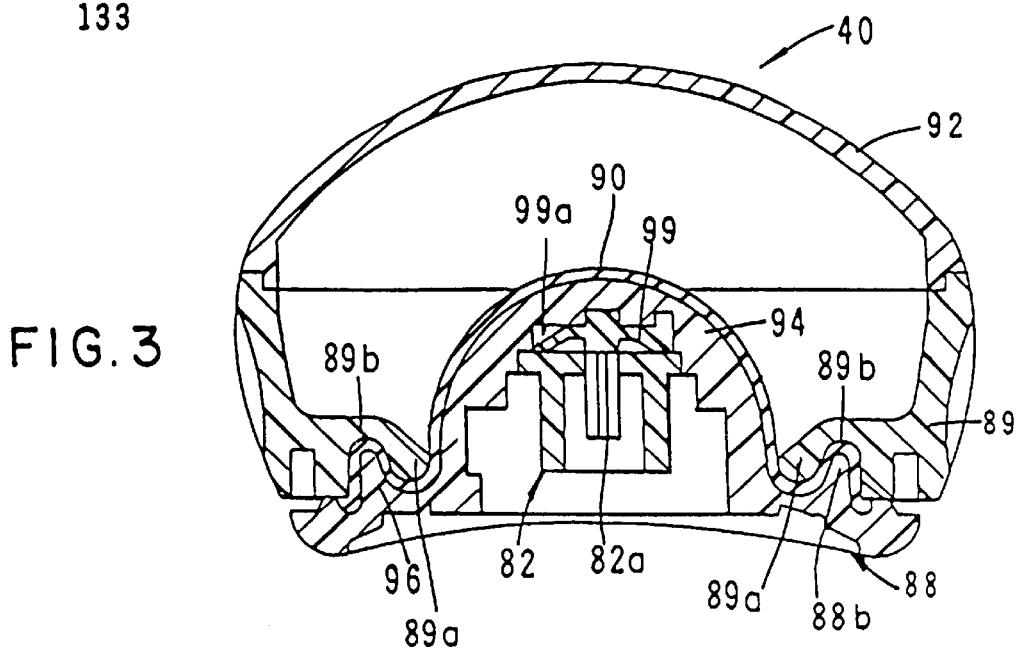

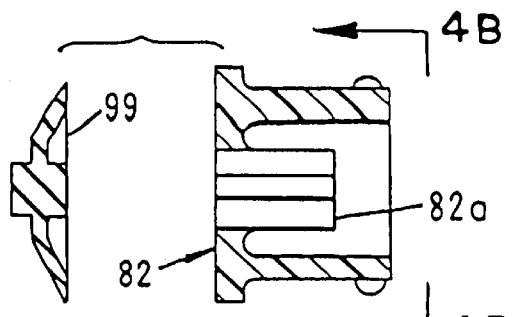
FIG.4A
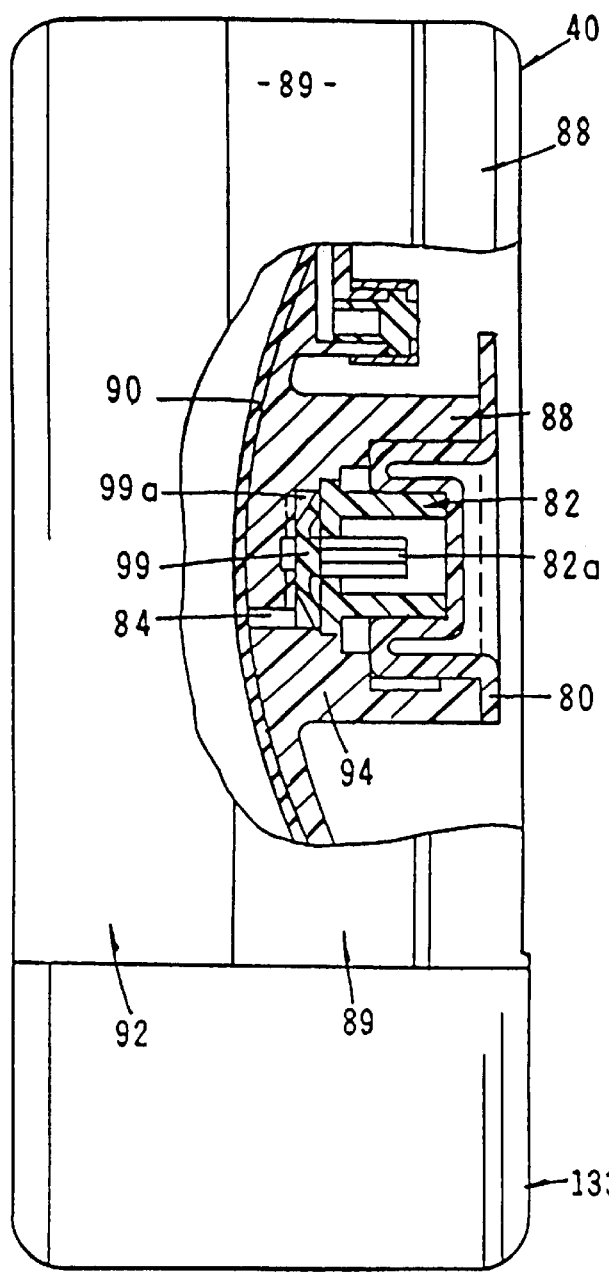
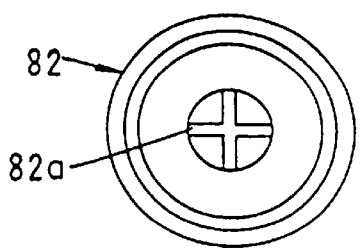
FIG.4B
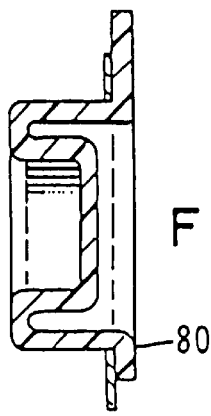
FIG.5
FIG.4
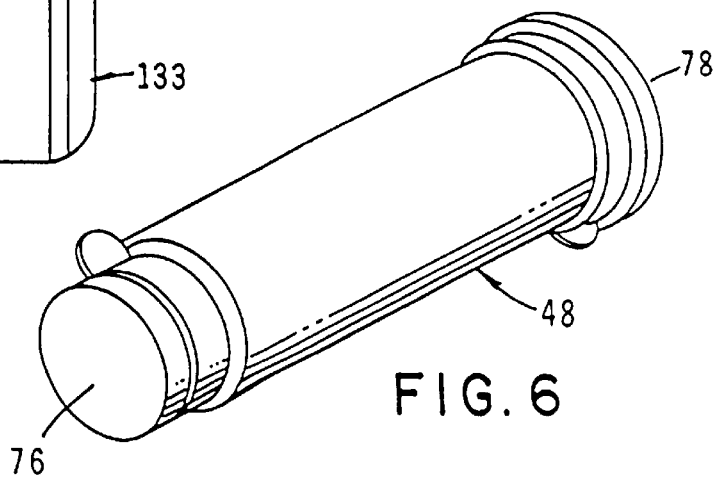
FIG.6

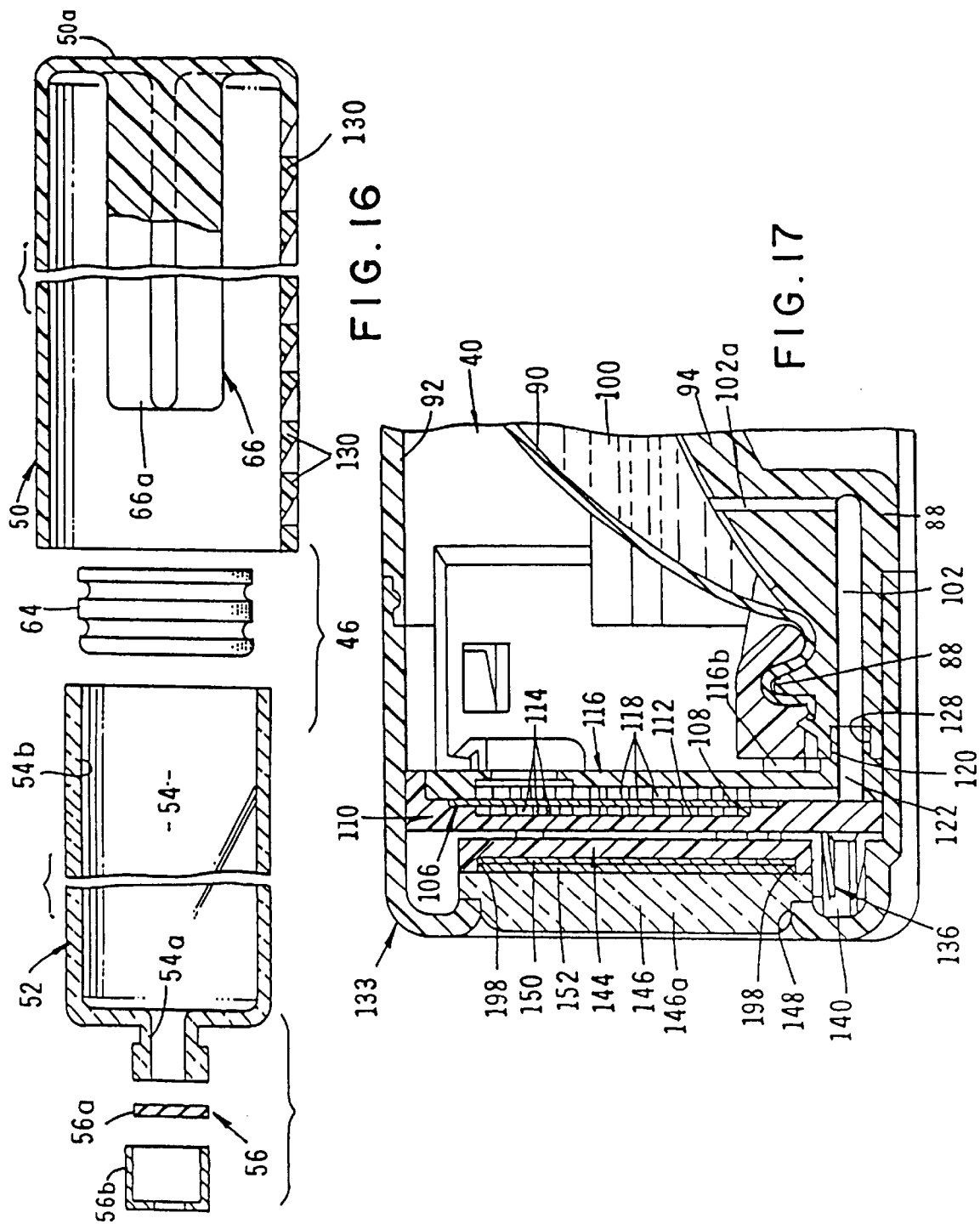

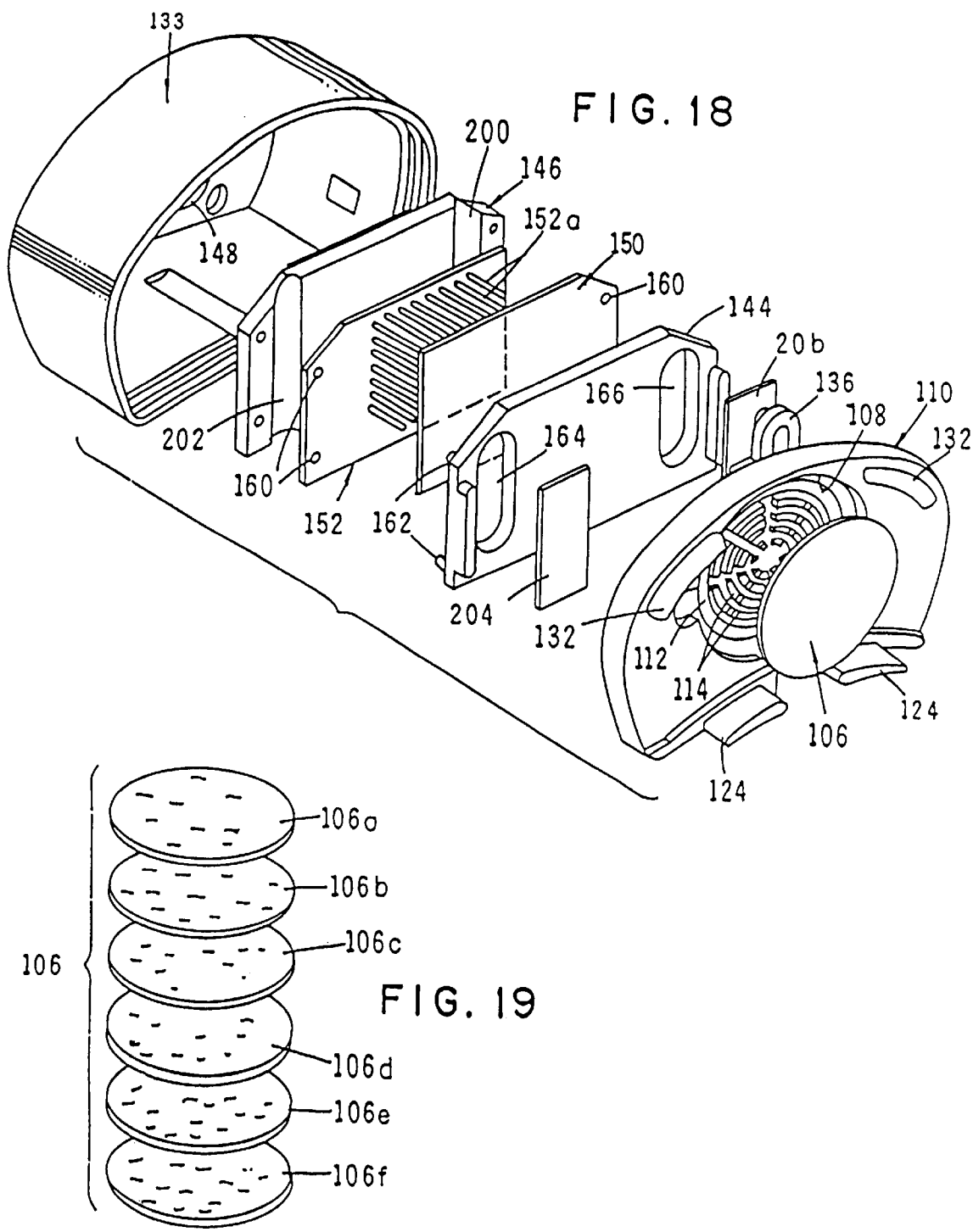

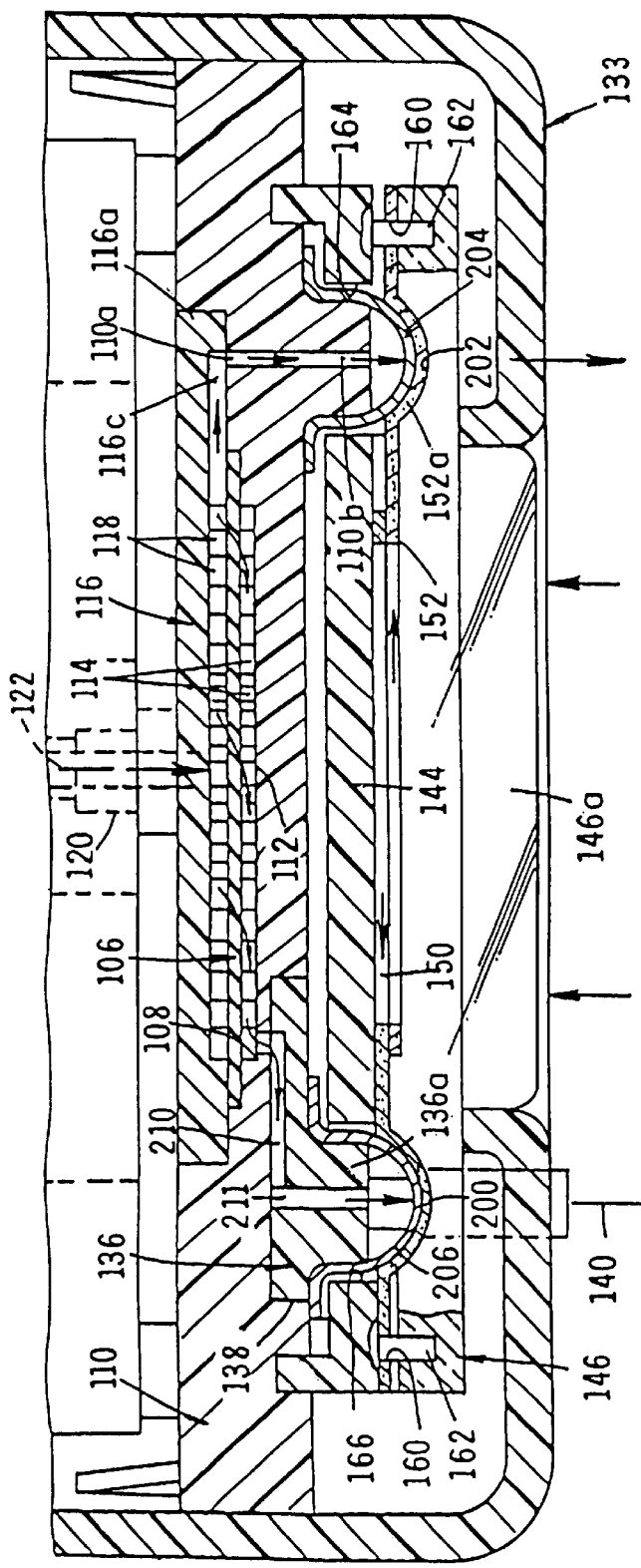
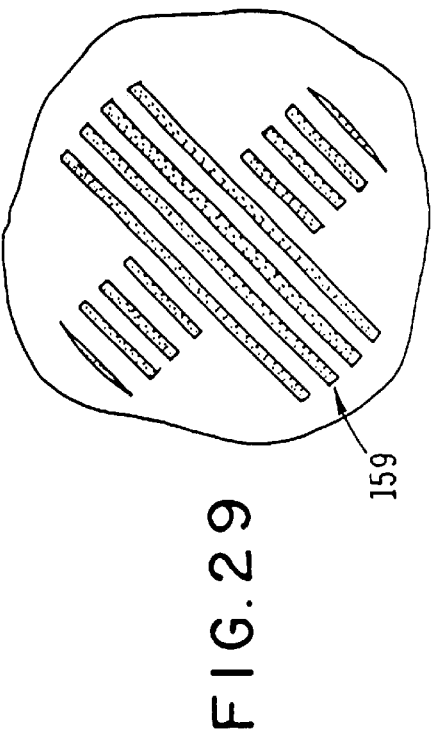
FIG. 28
FIG. 29

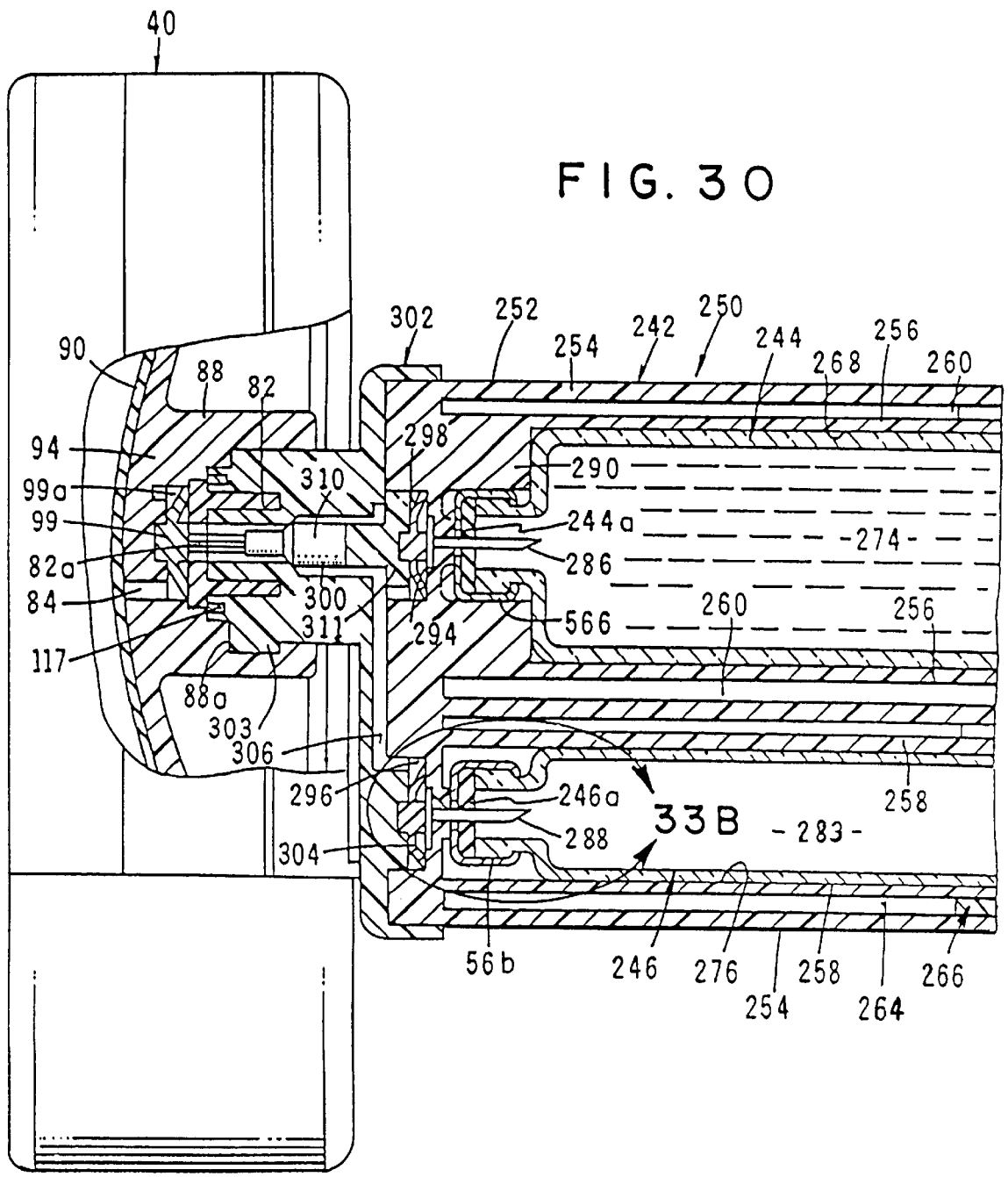

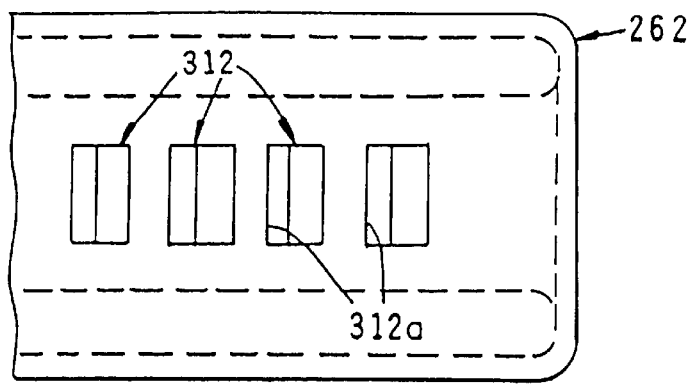
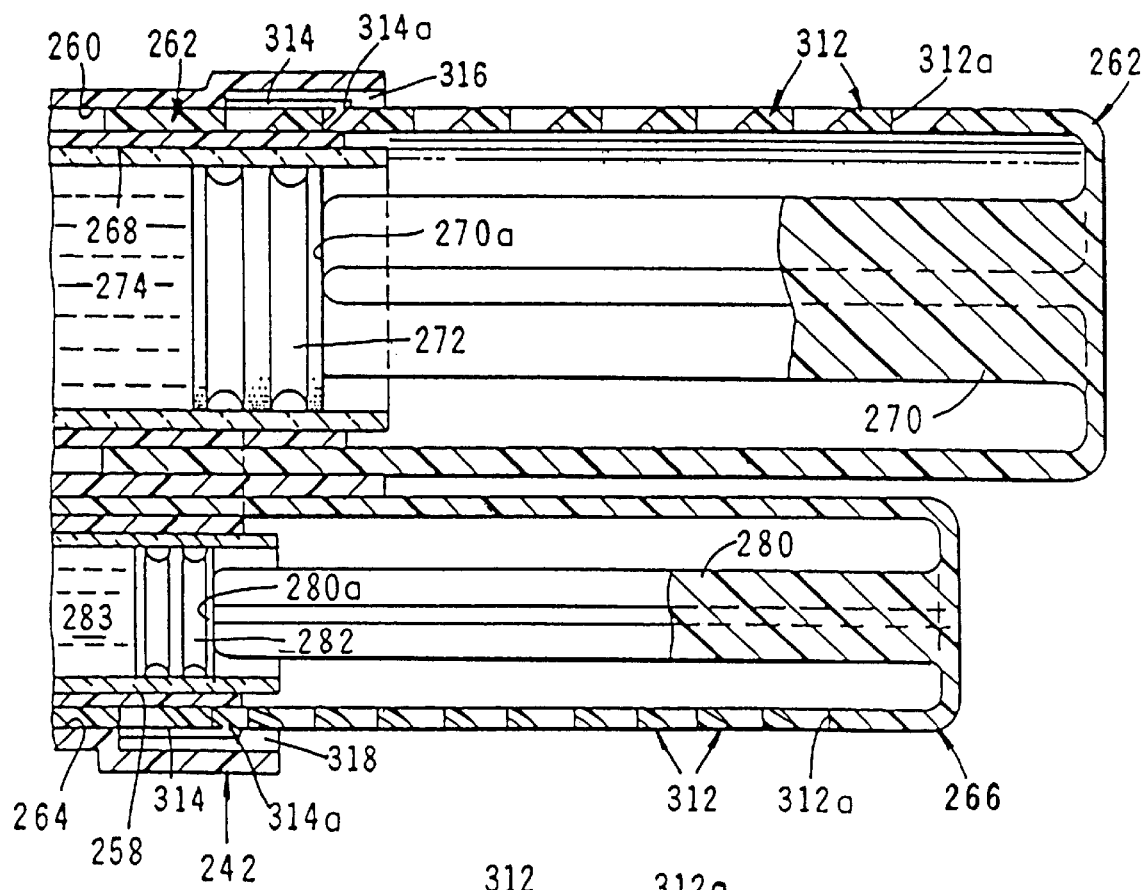
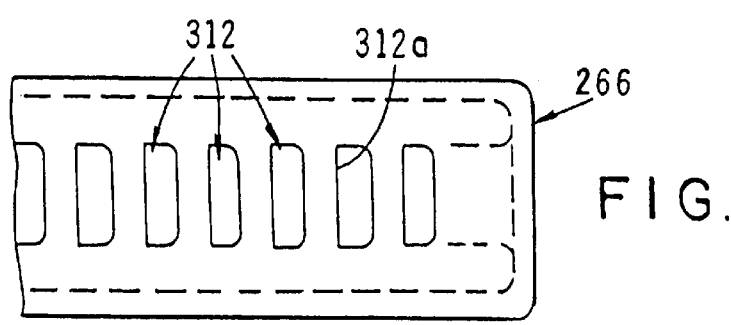

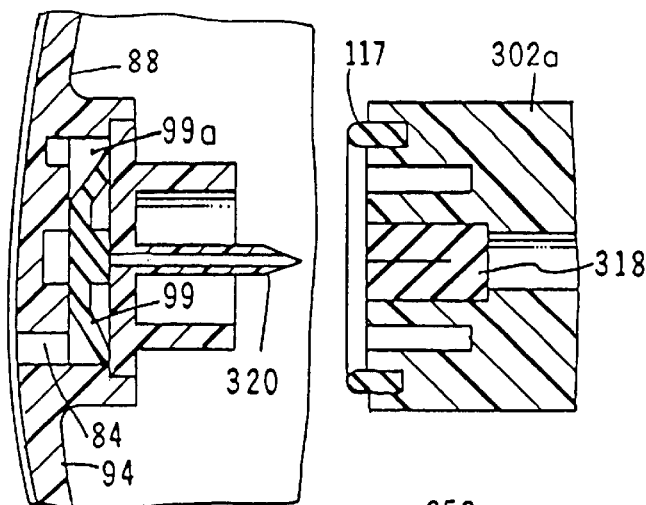
FIG. 32
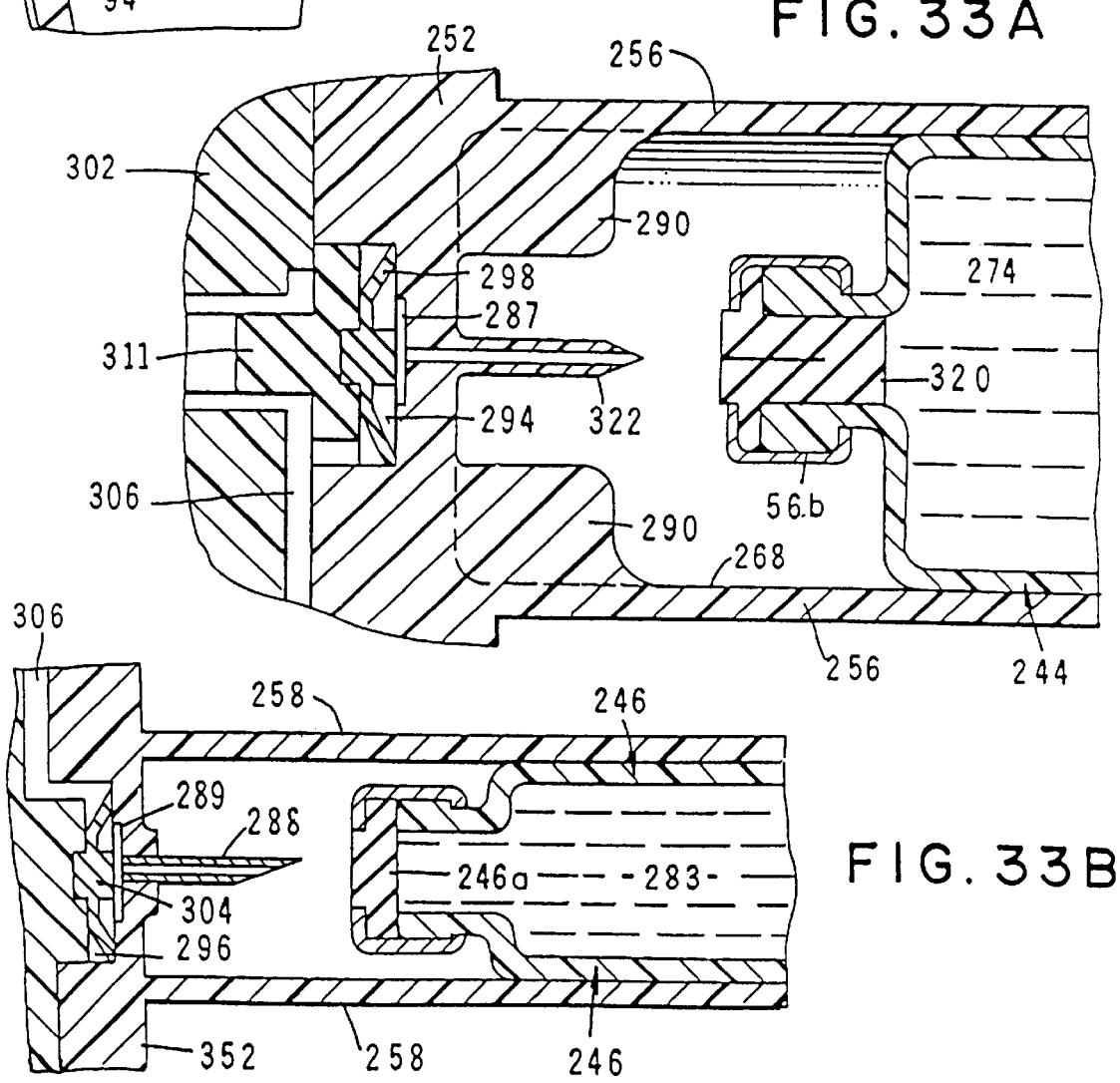
FIG. 33A
FIG. 33B

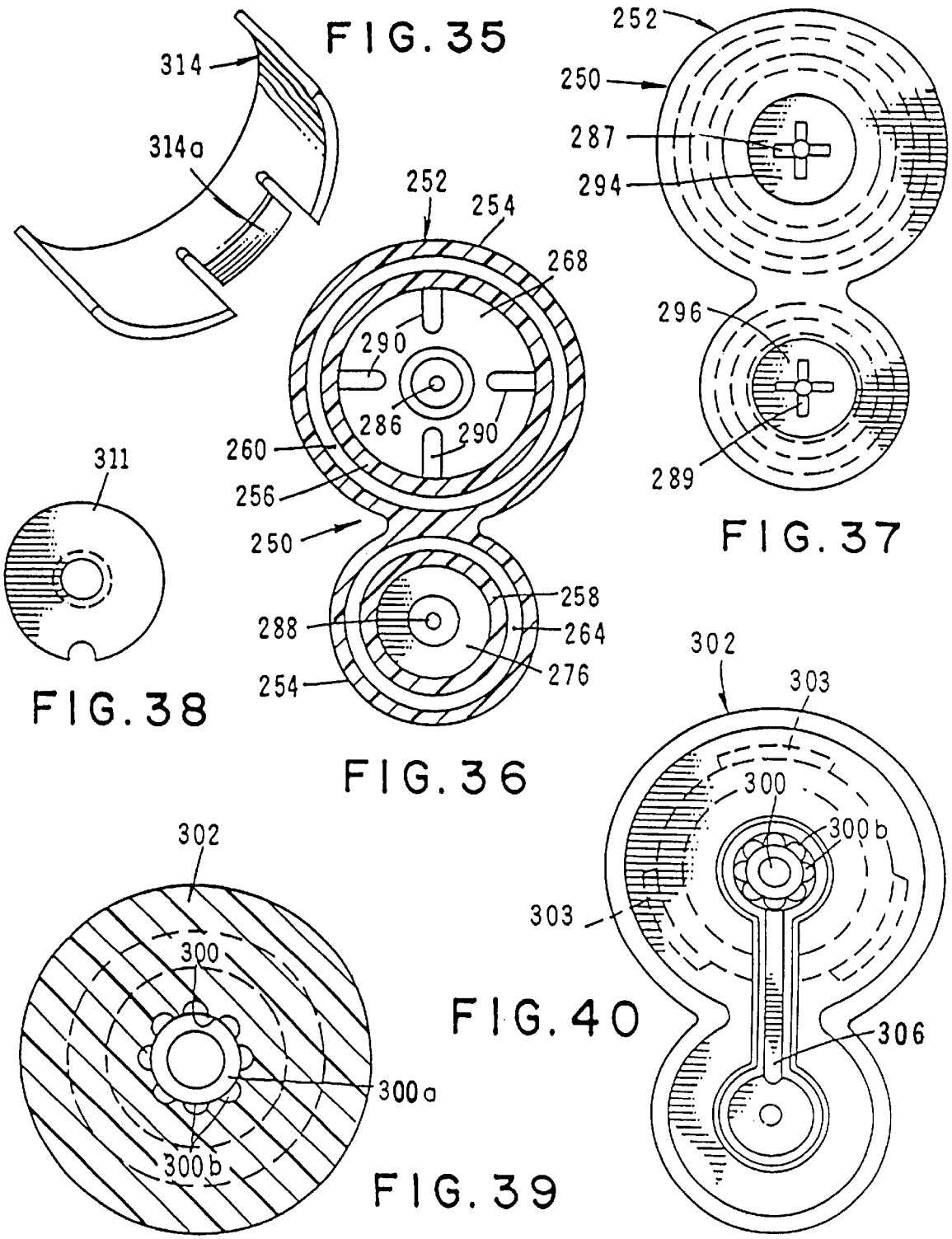

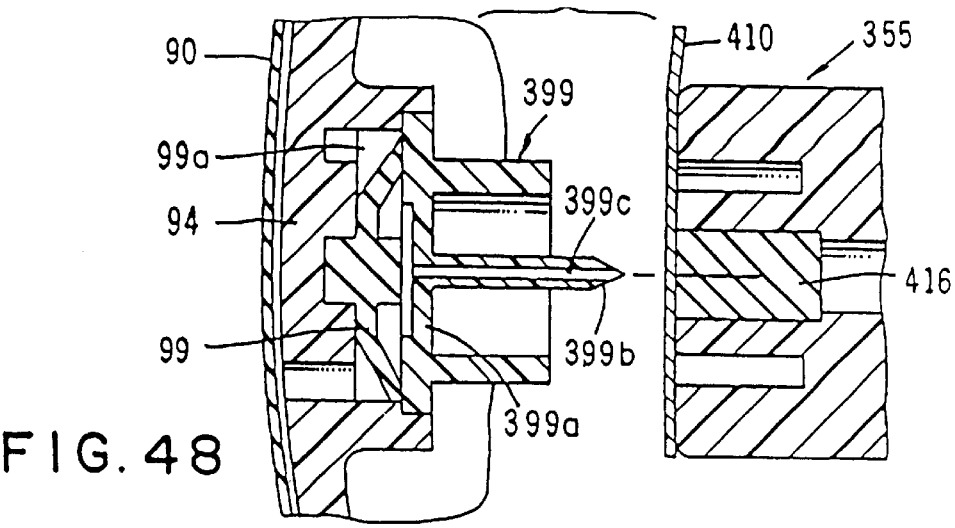
FIG. 48
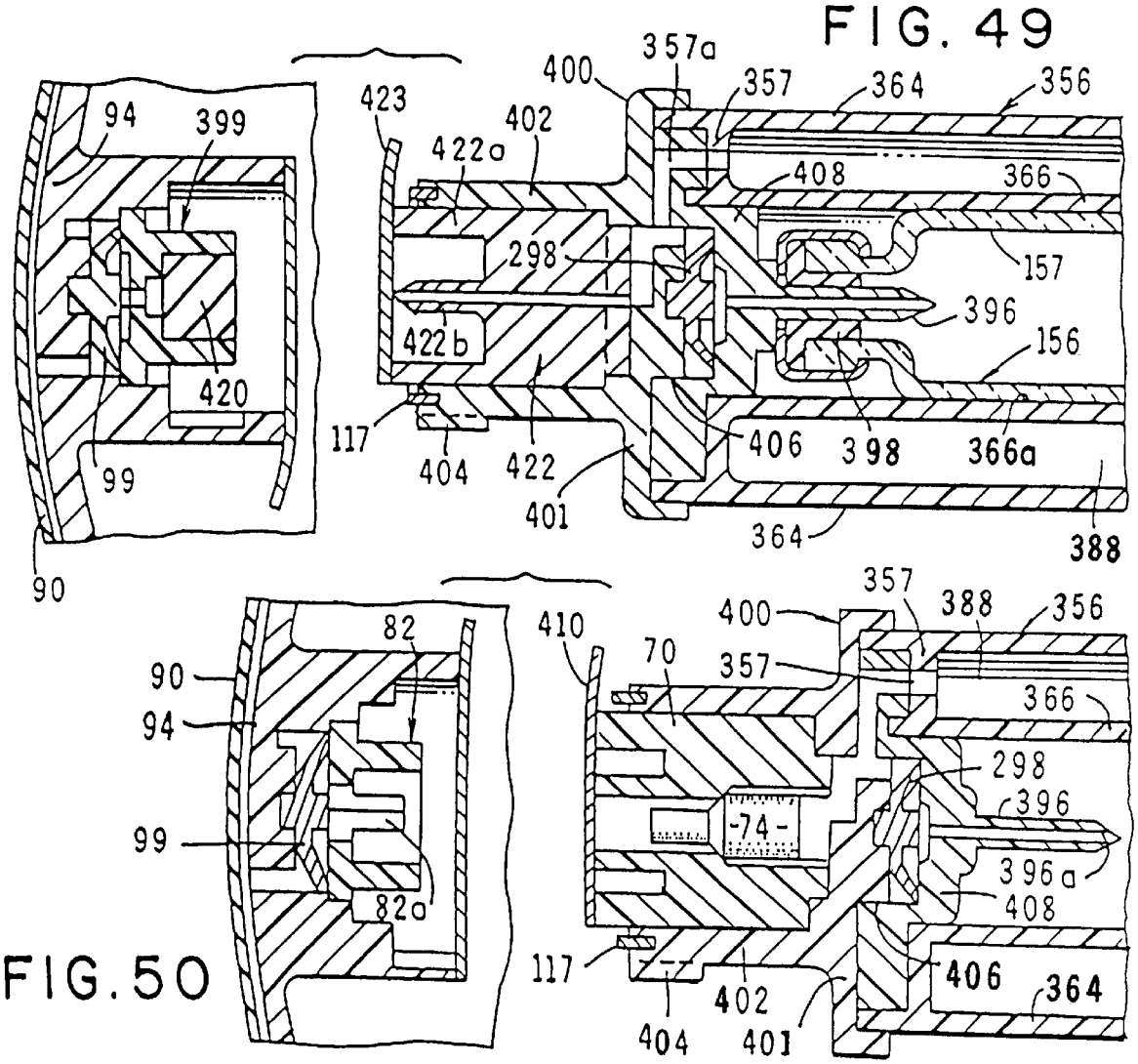
FIG. 49
FIG. 50

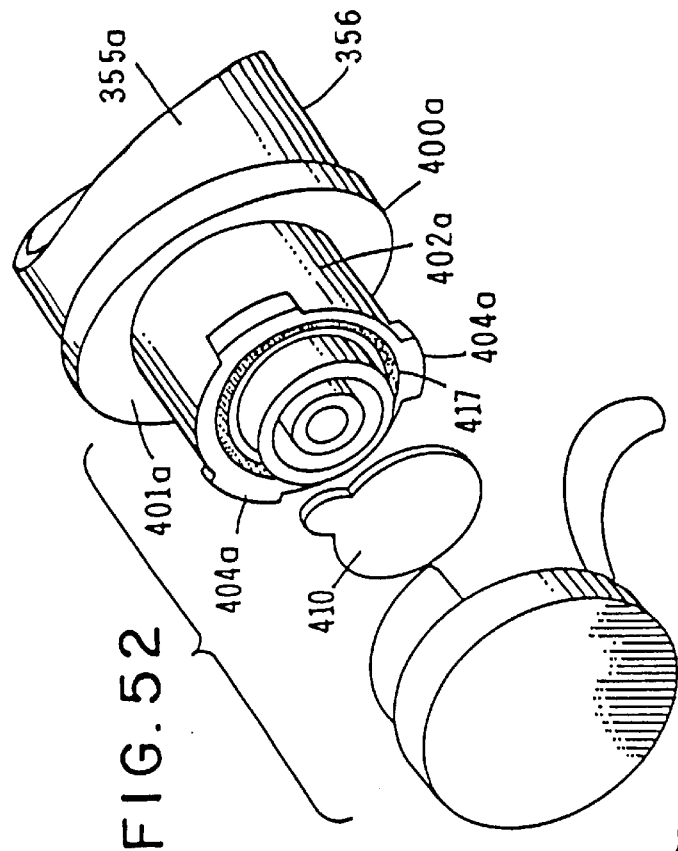
FIG. 52
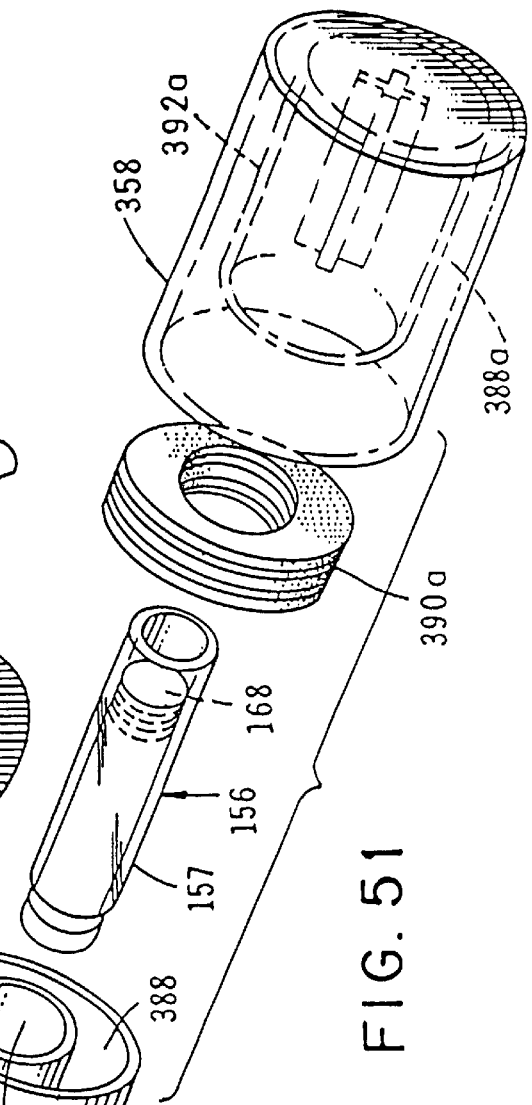
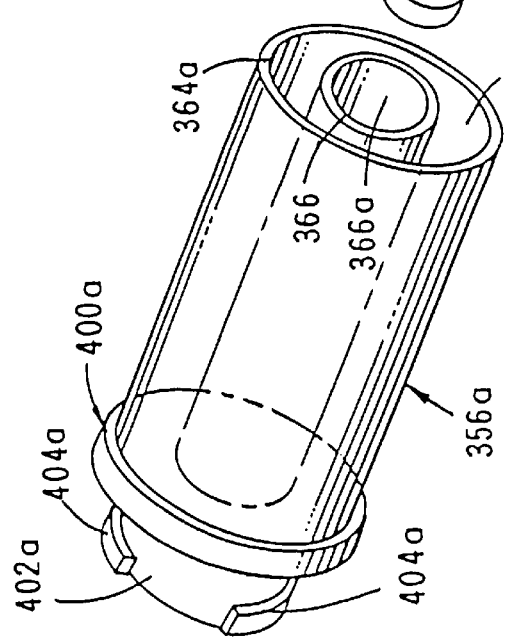
FIG. 51

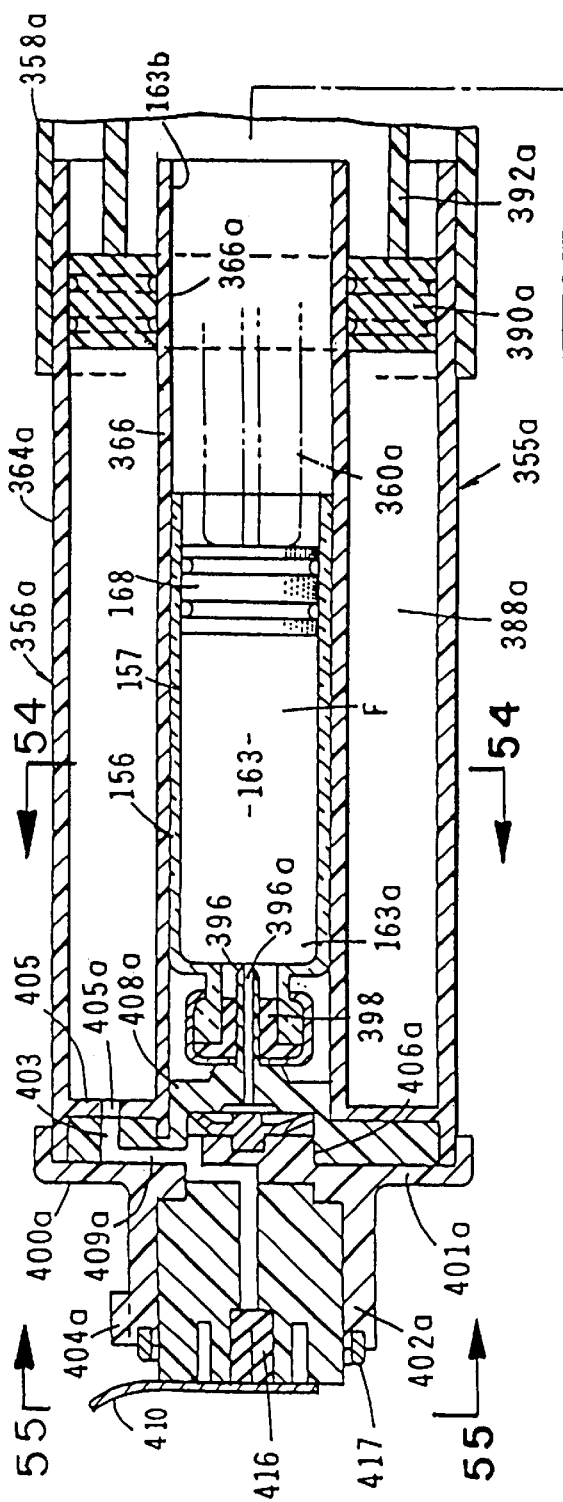
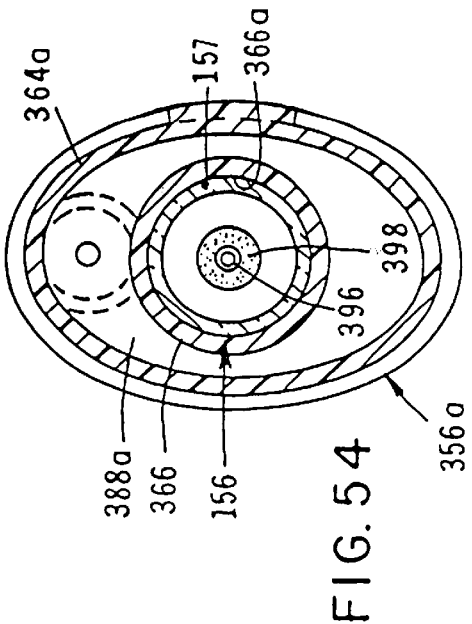
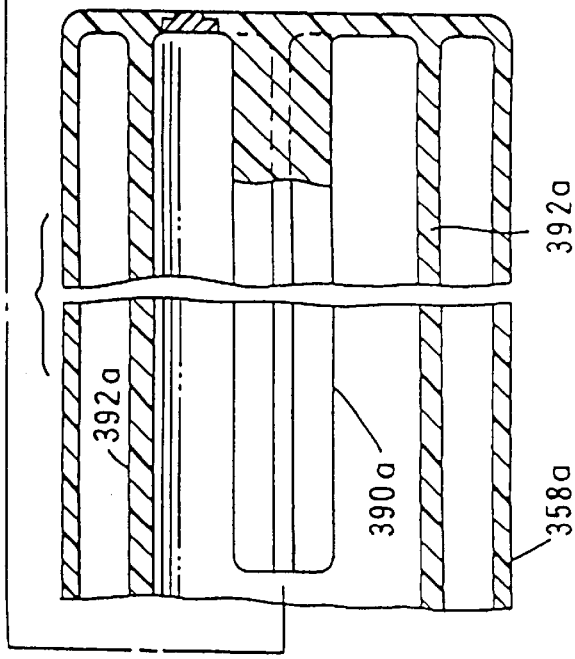
FIG. 53
FIG. 54

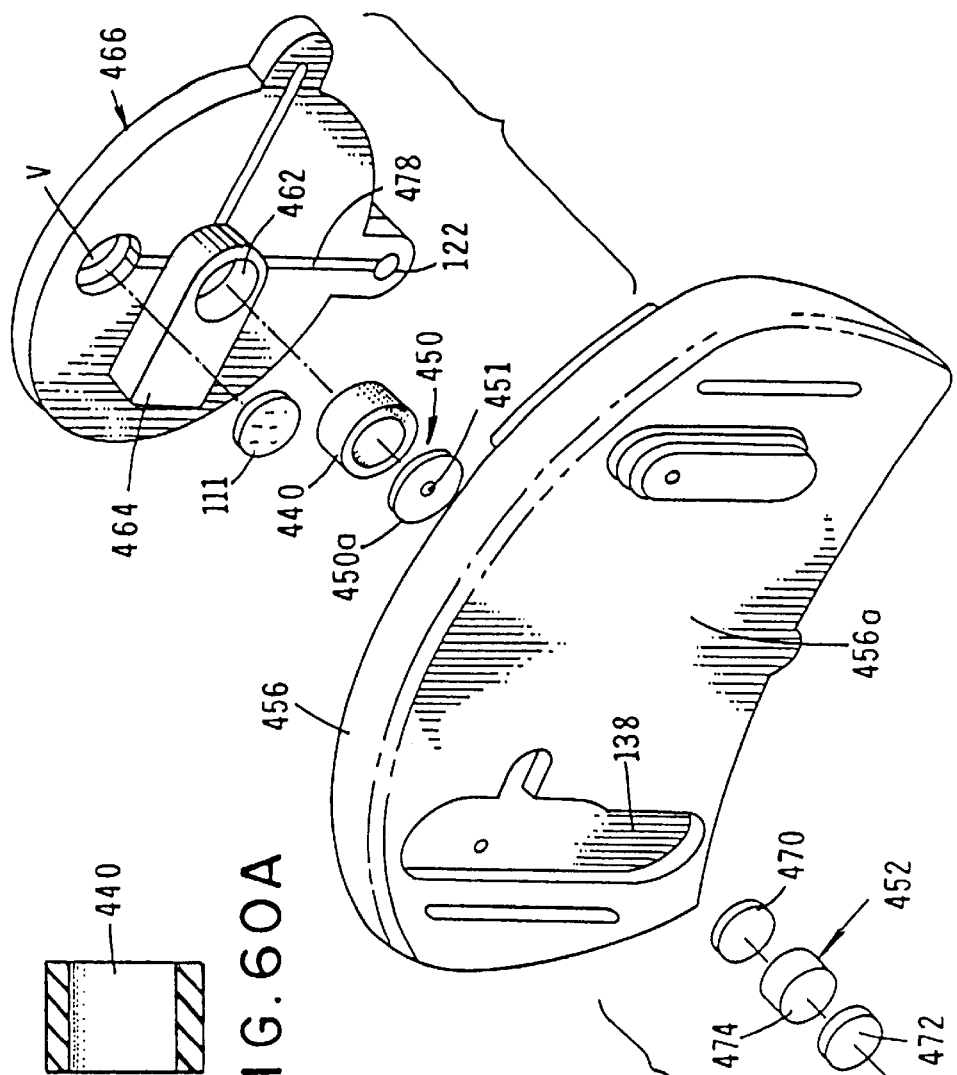
FIG. 60
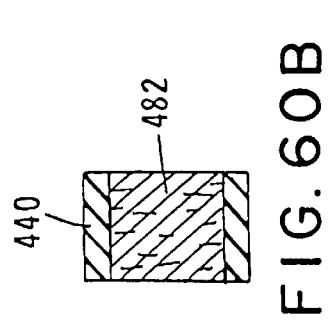
FIG. 60A
FIG. 60B

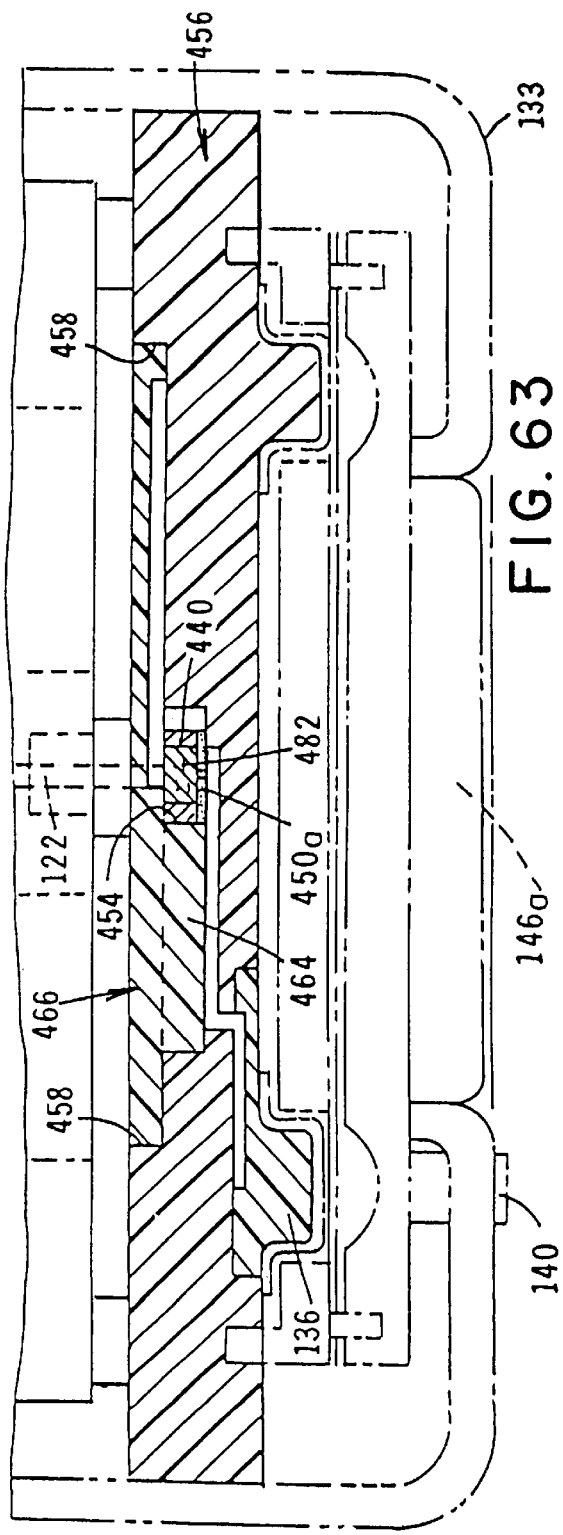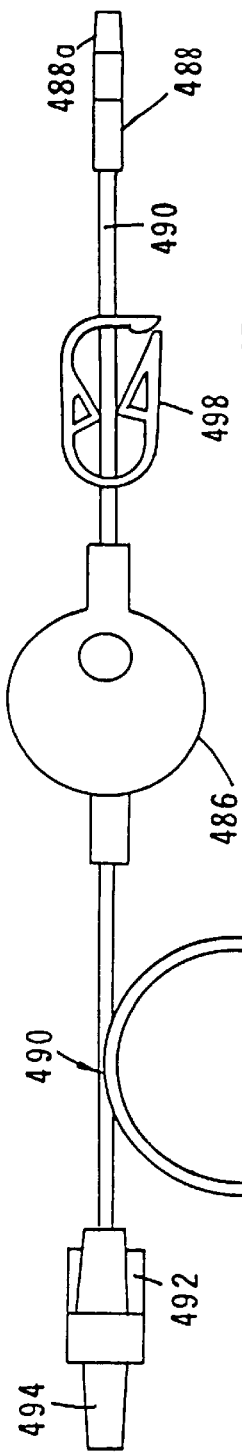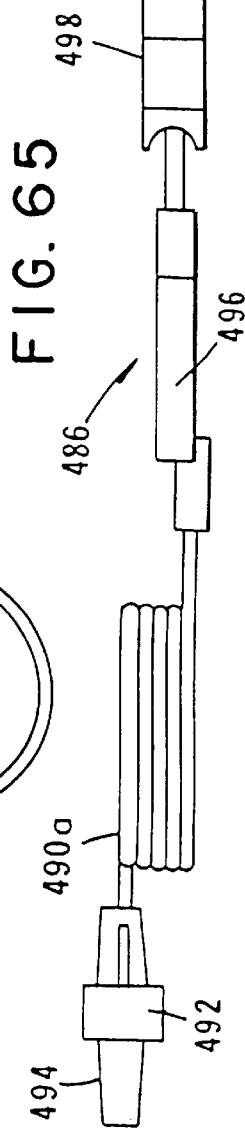

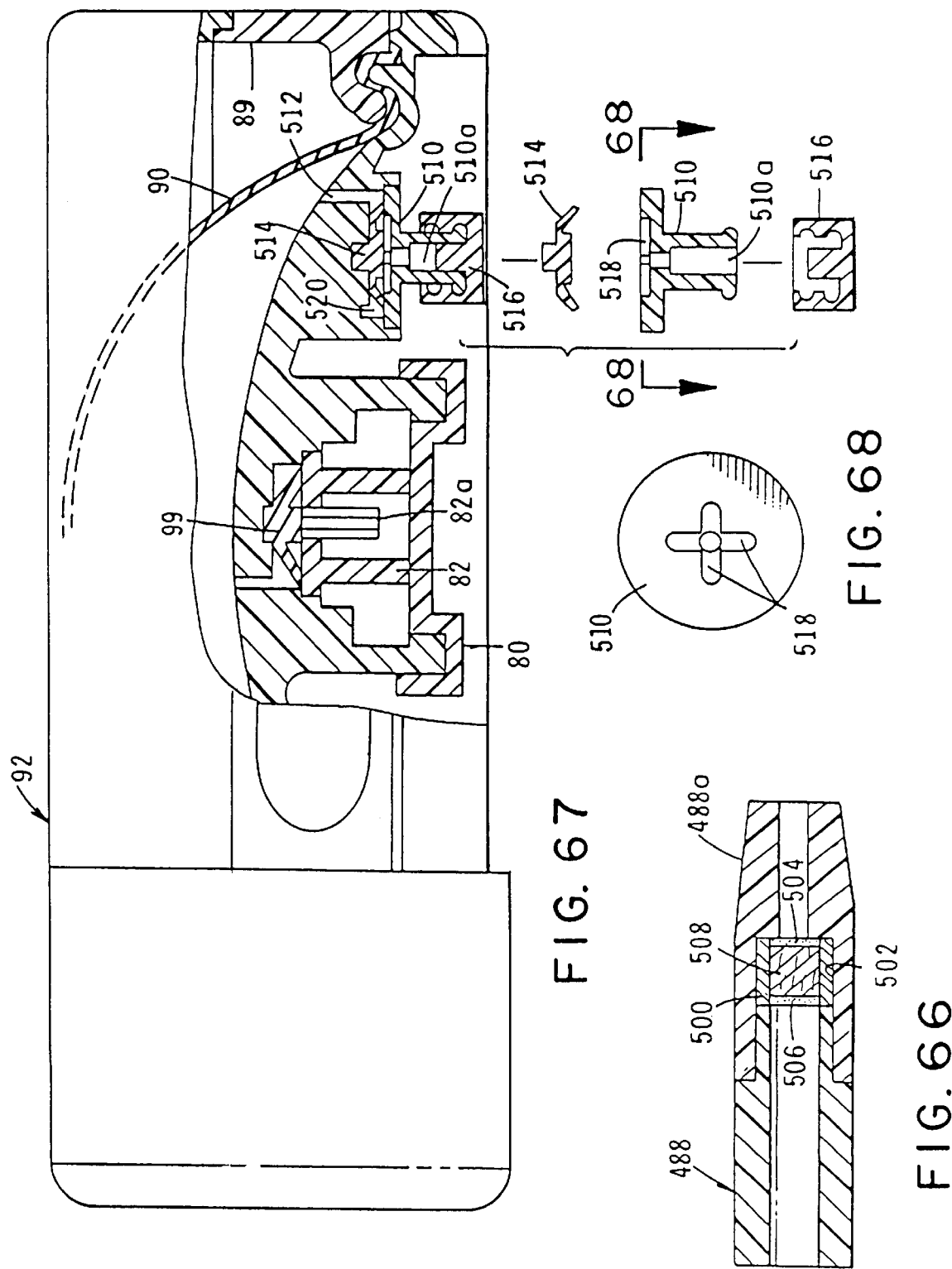

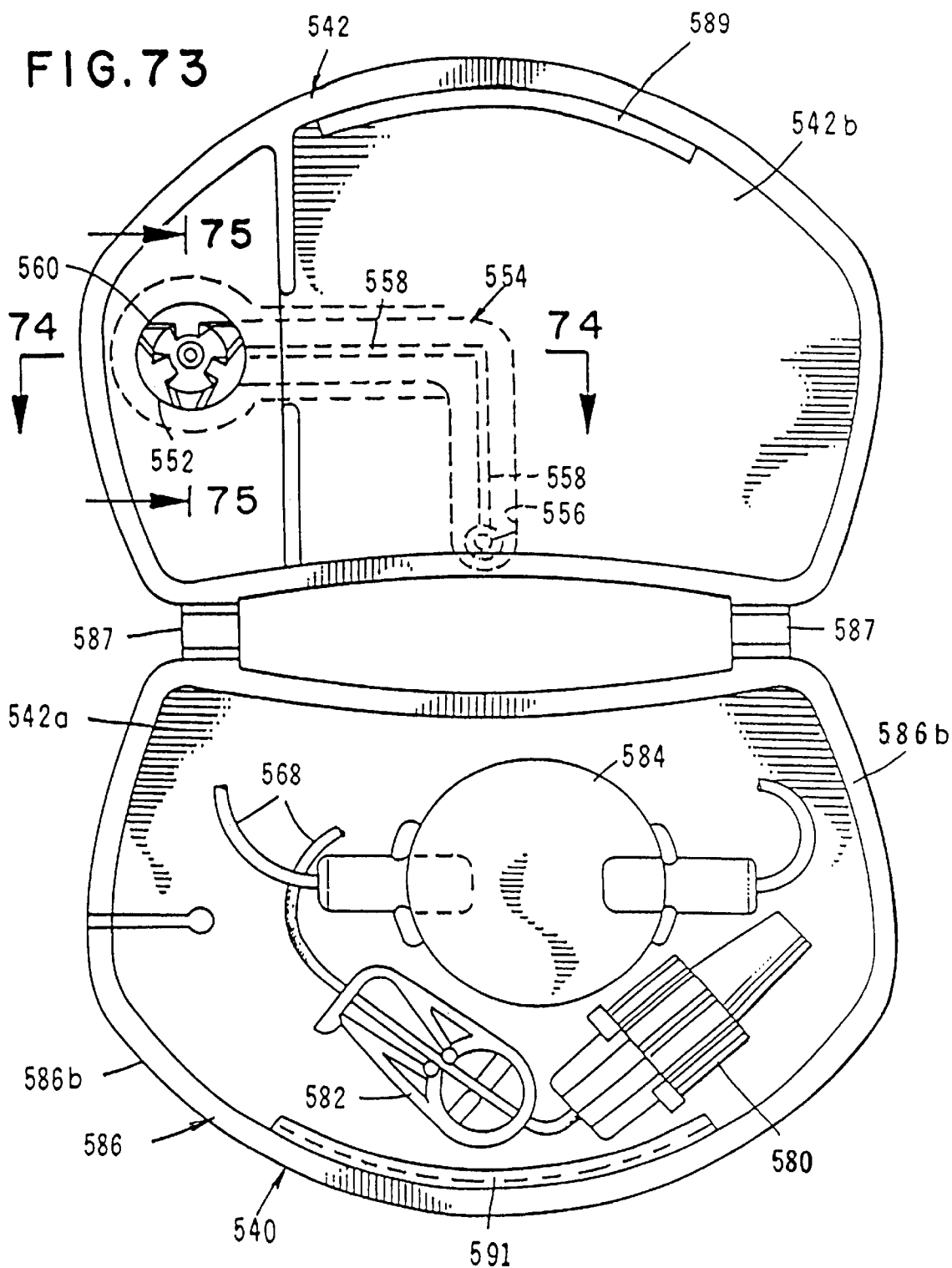

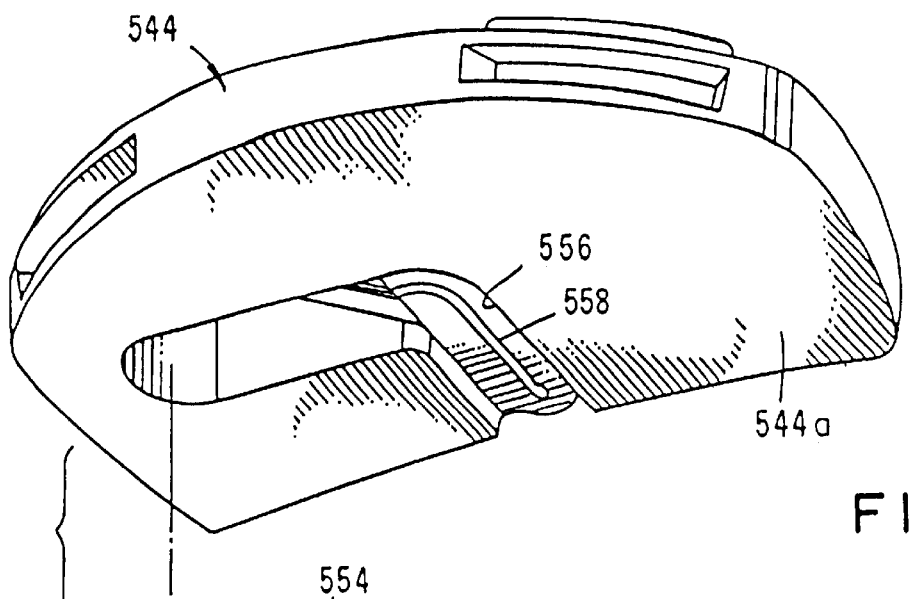
FIG. 78
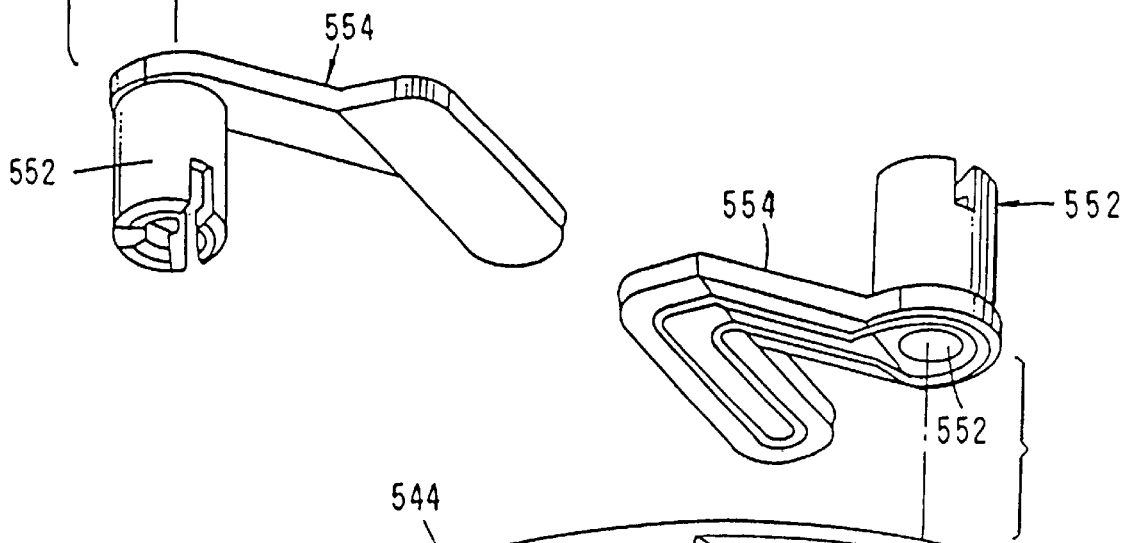
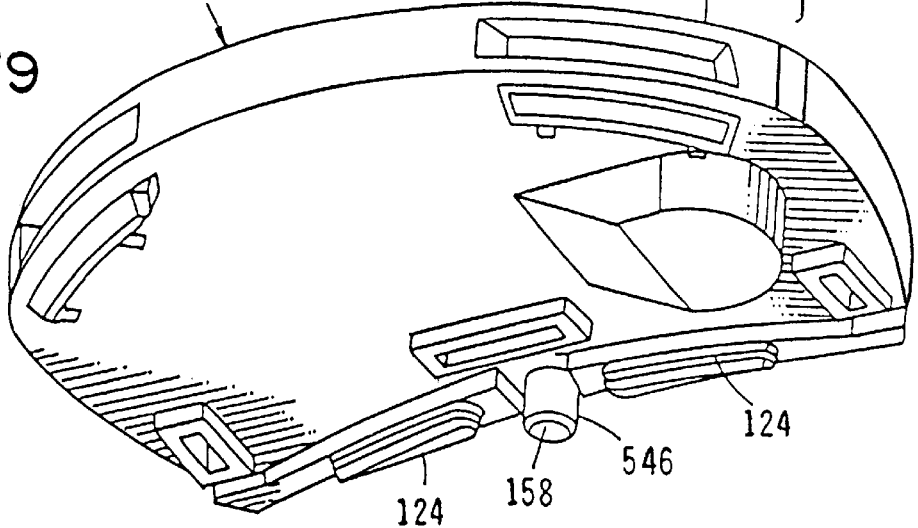
FIG. 79

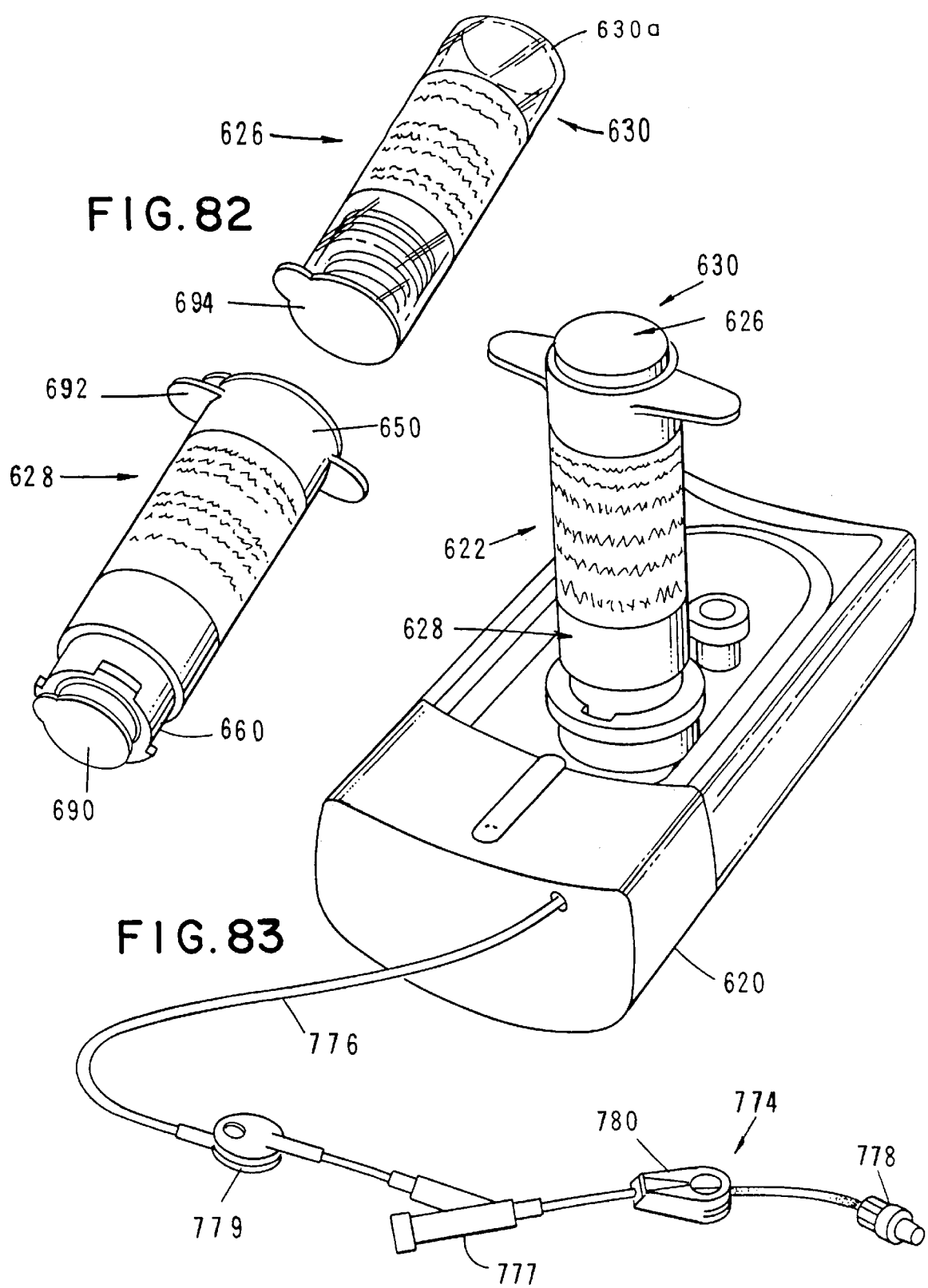

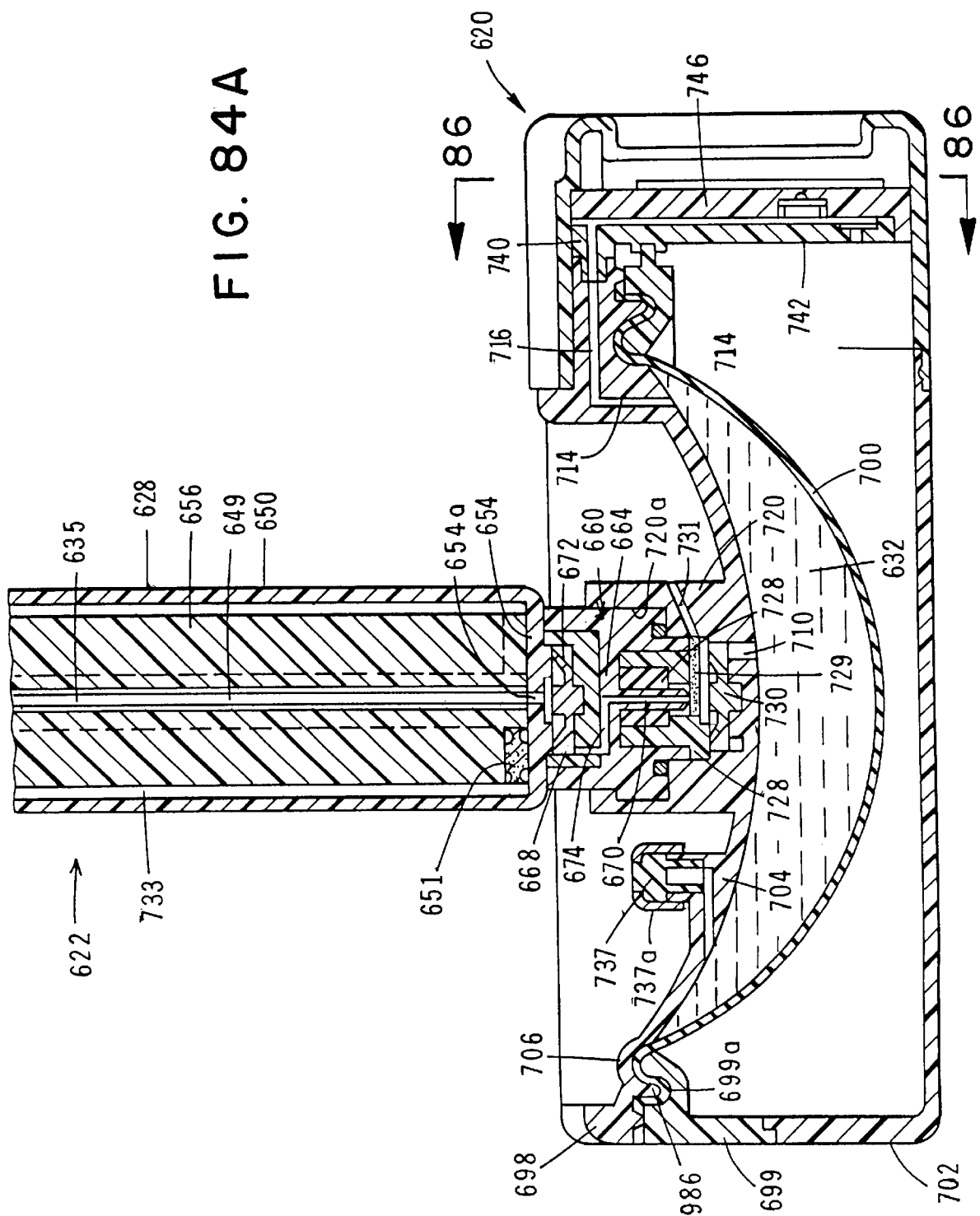

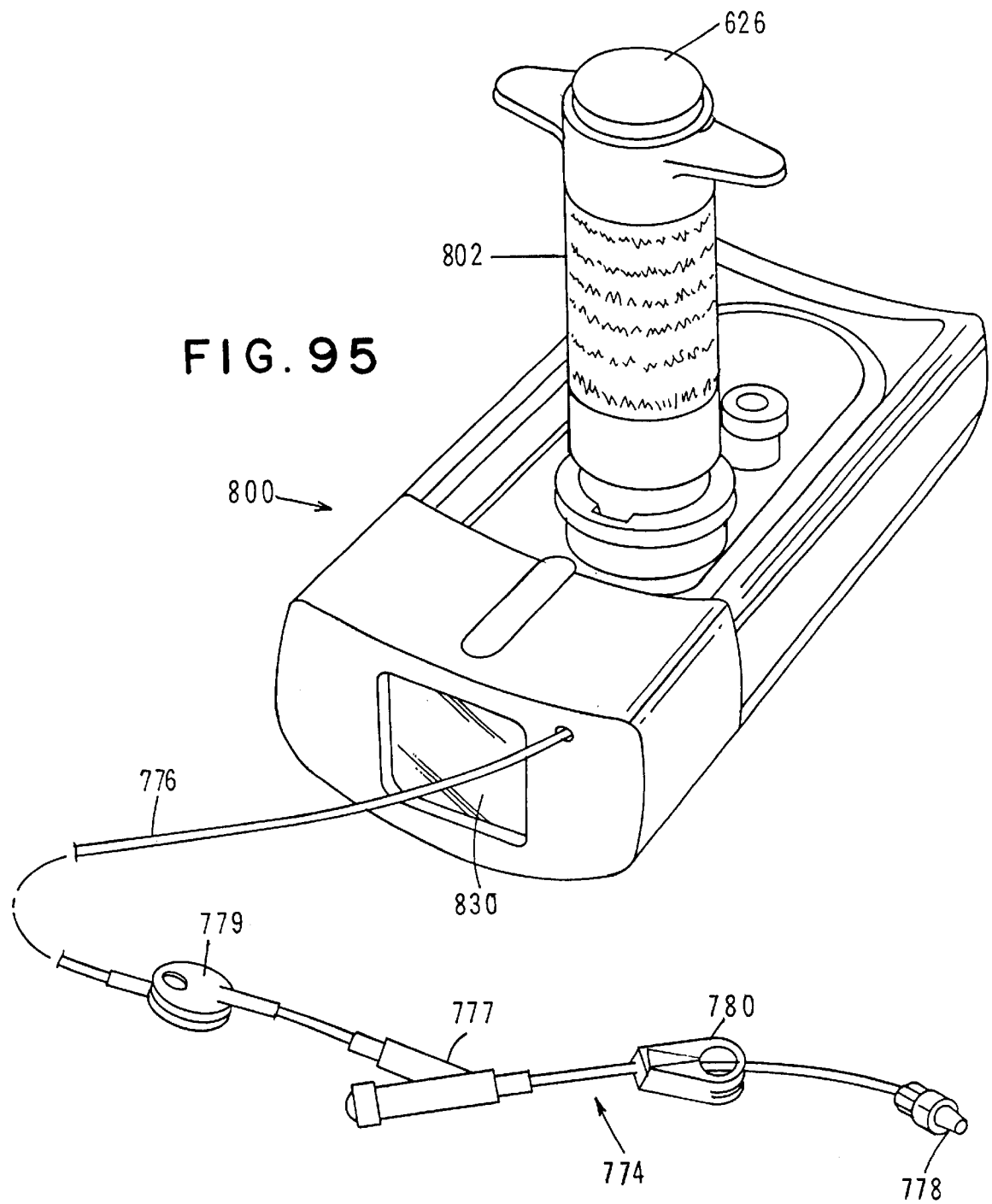

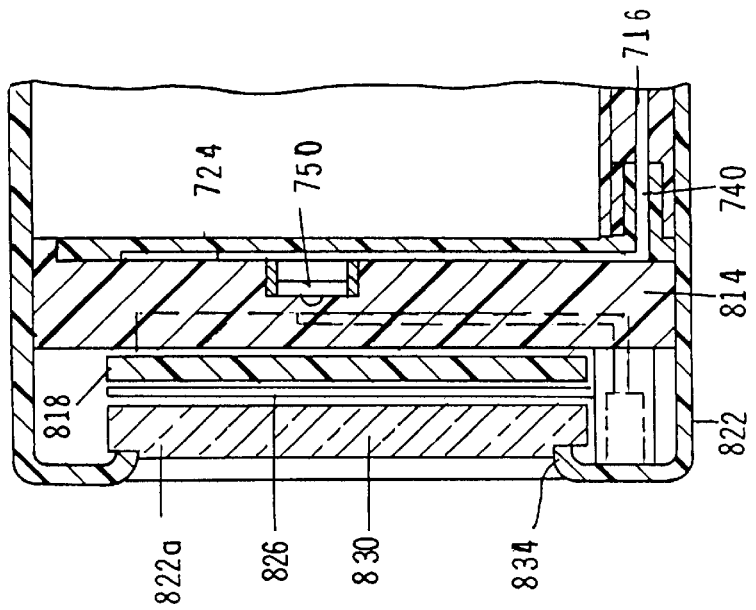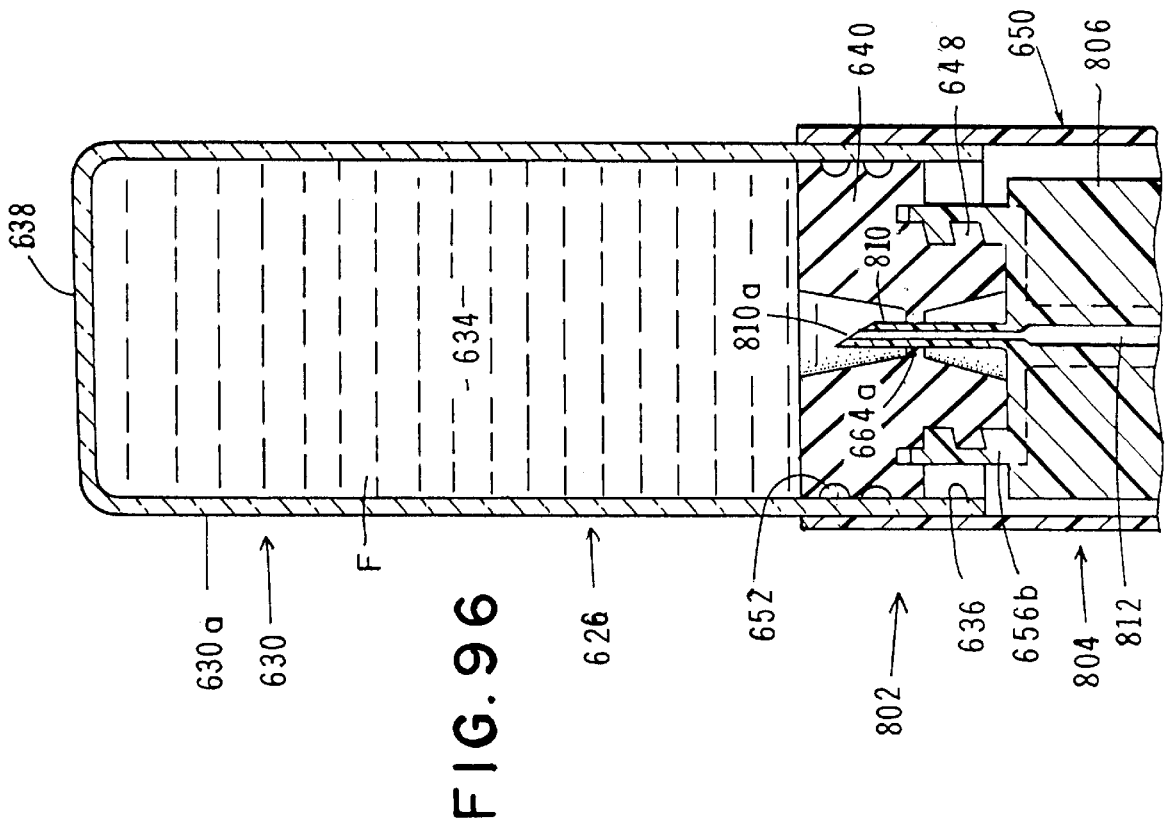

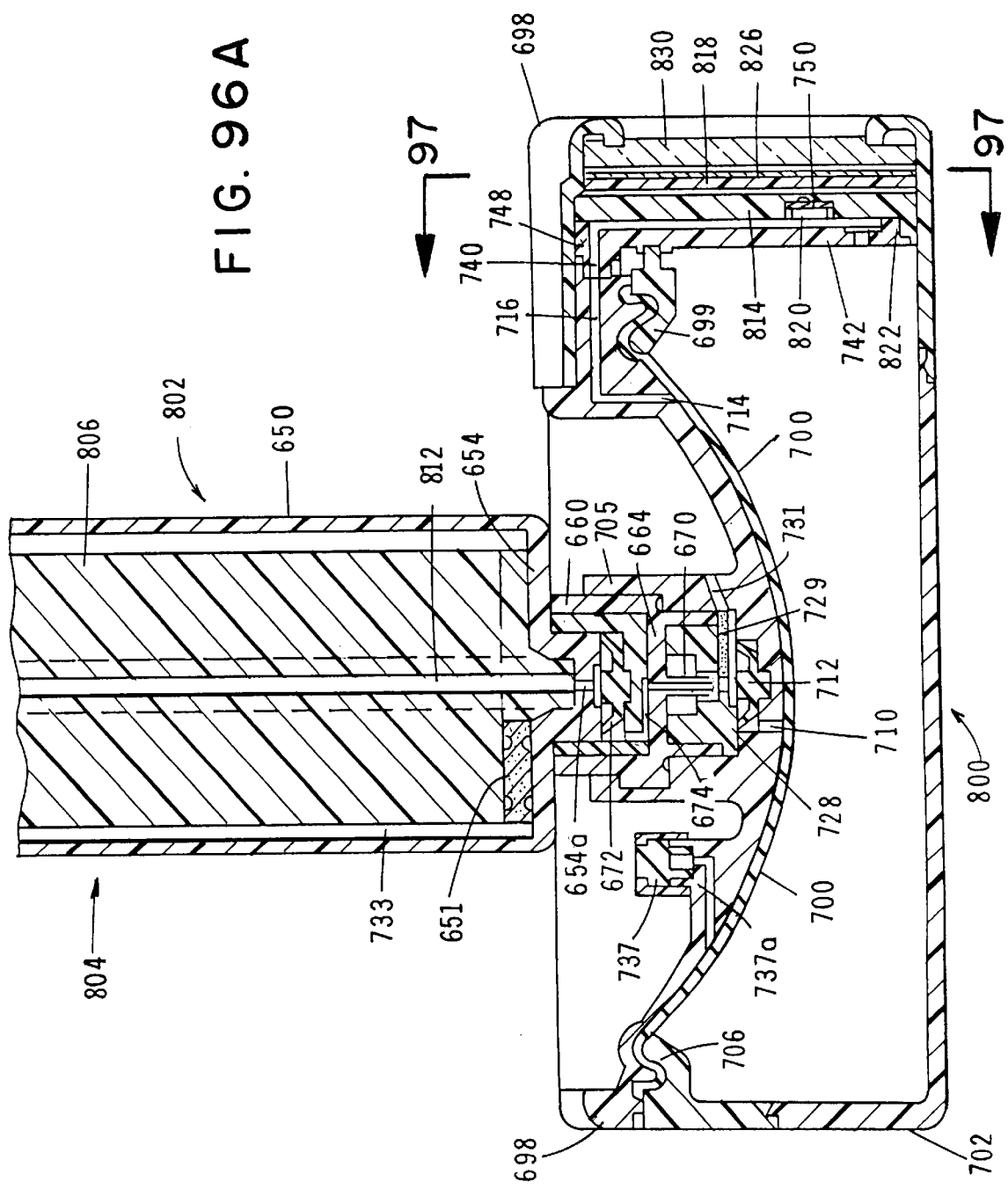

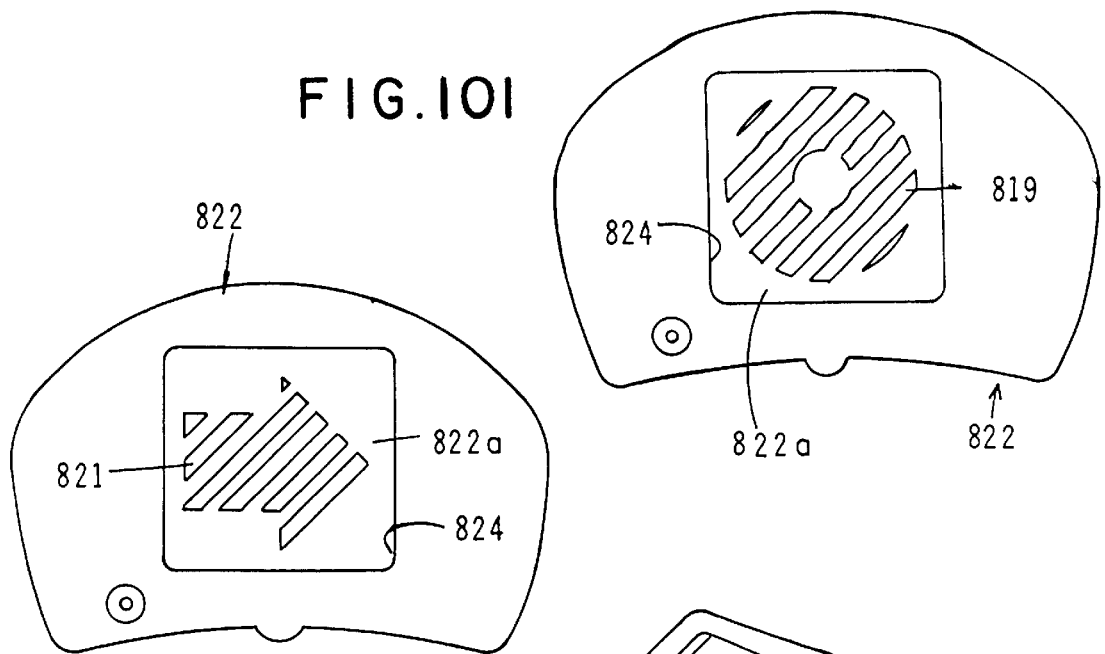
FIG.101
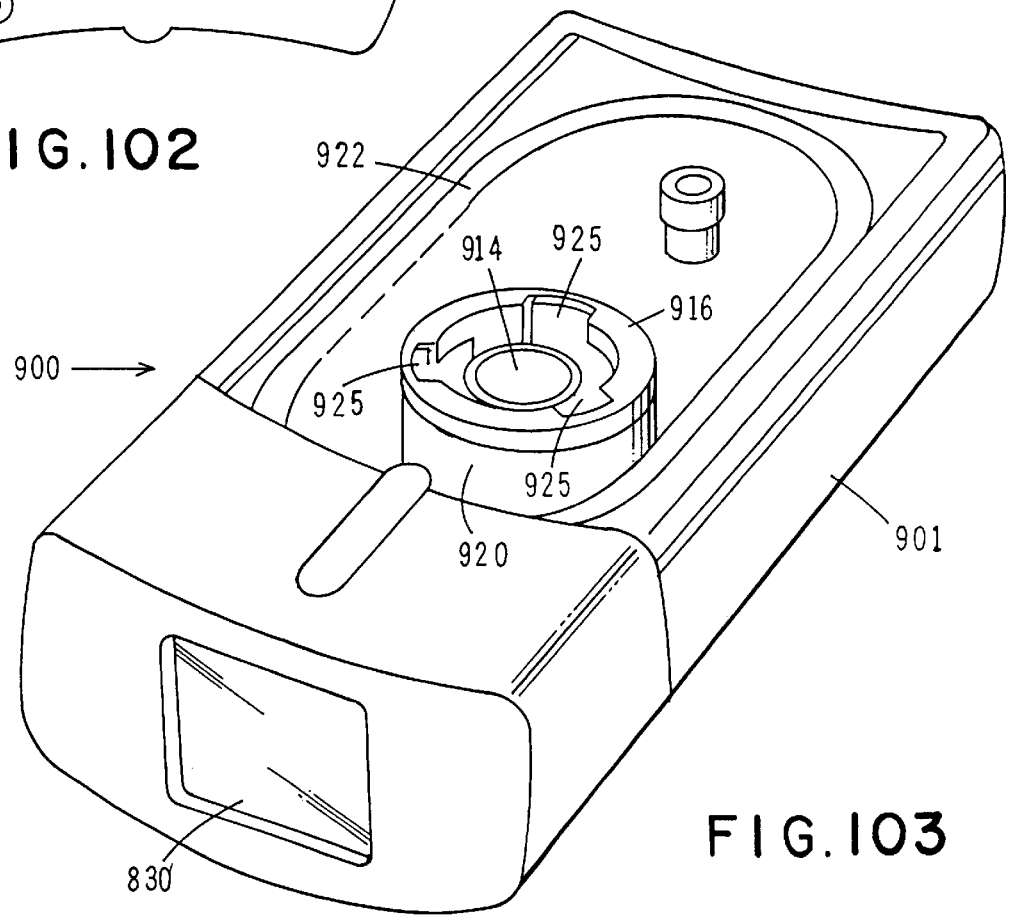
FIG.102
FIG.103

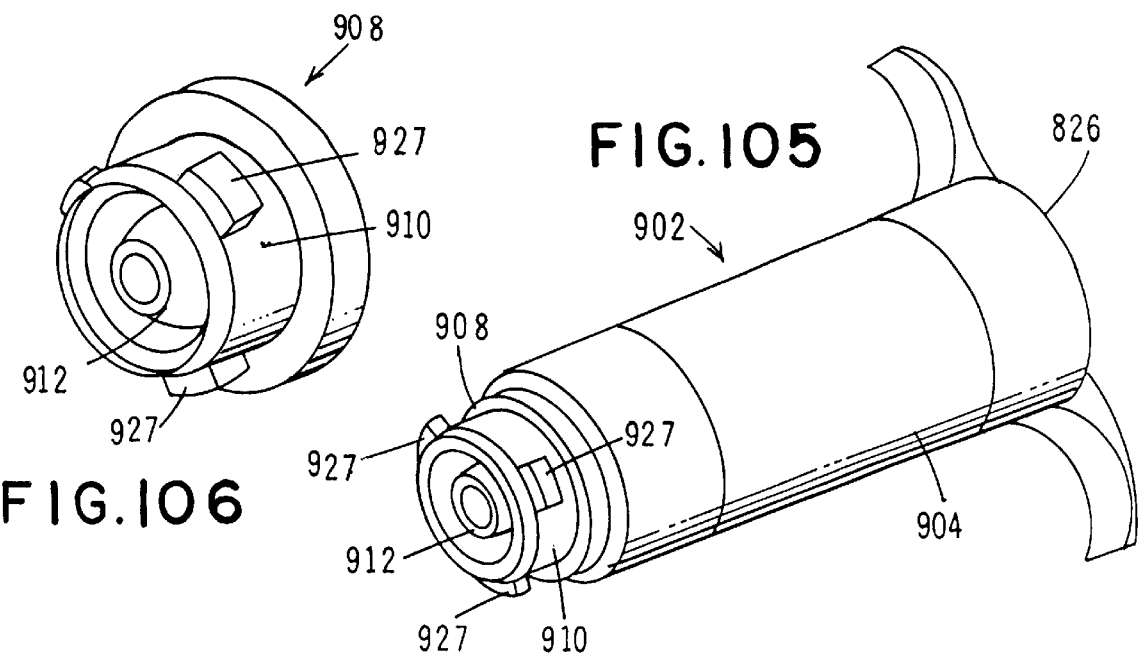
FIG. 105
FIG. 106
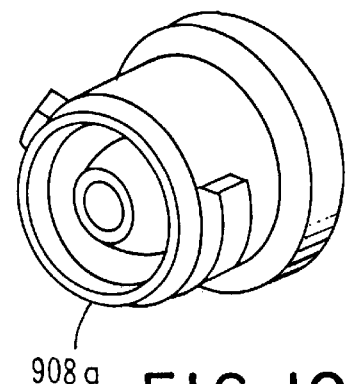
FIG. 106A
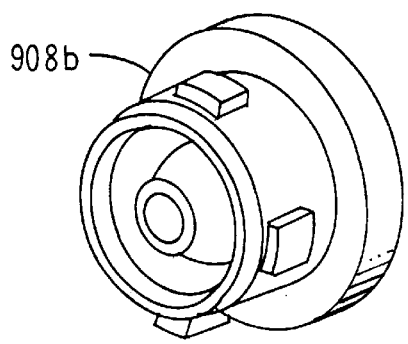
FIG. 106B
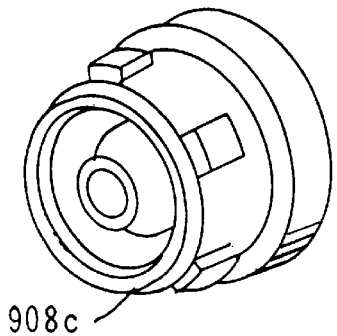
FIG. 106C
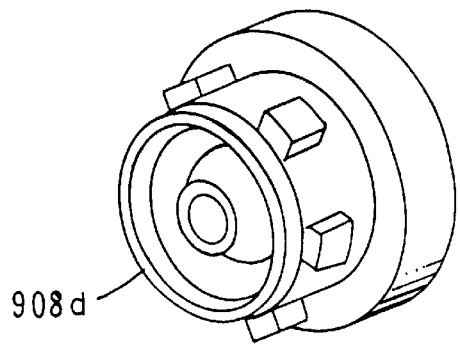
FIG. 106D

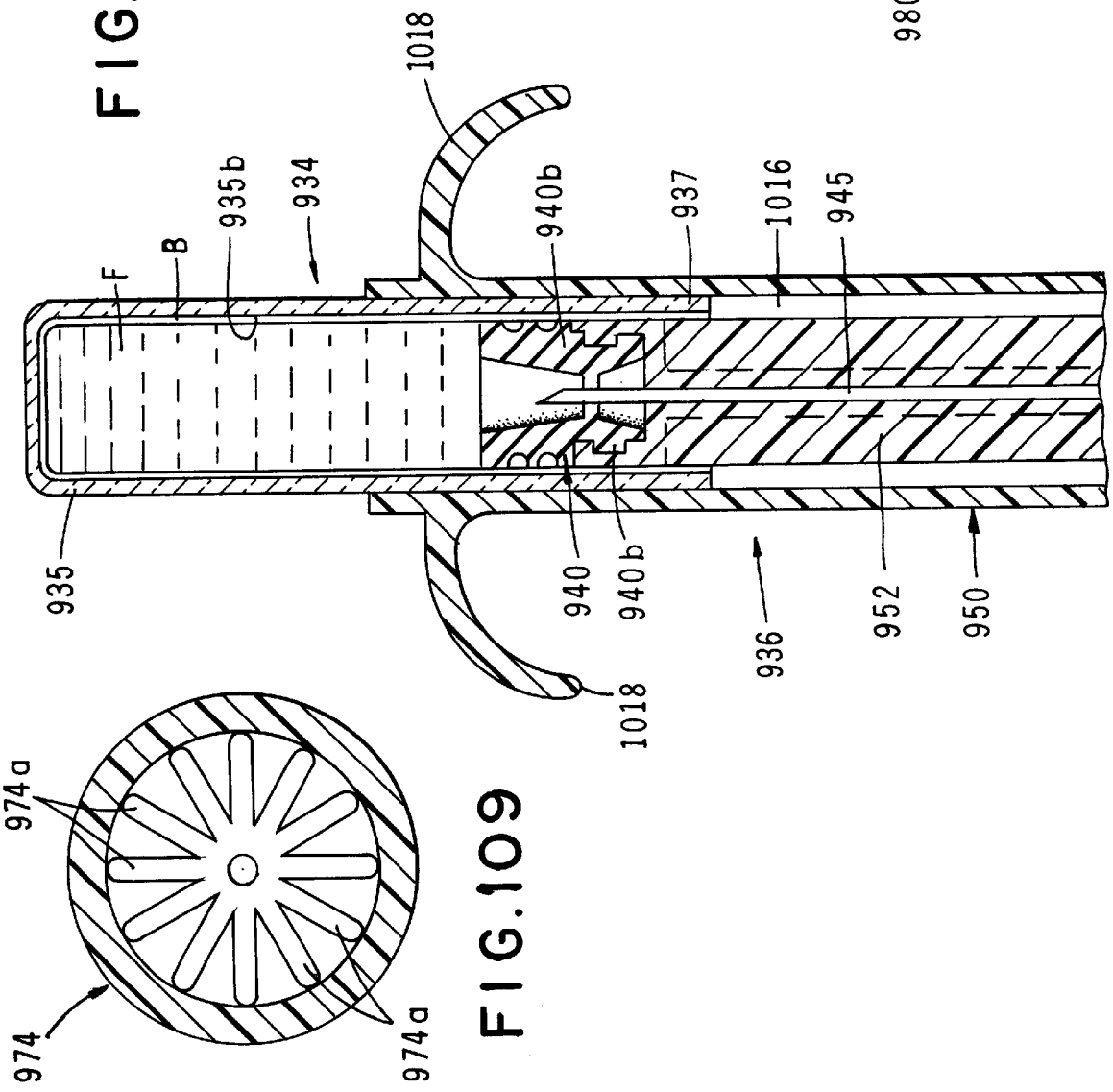

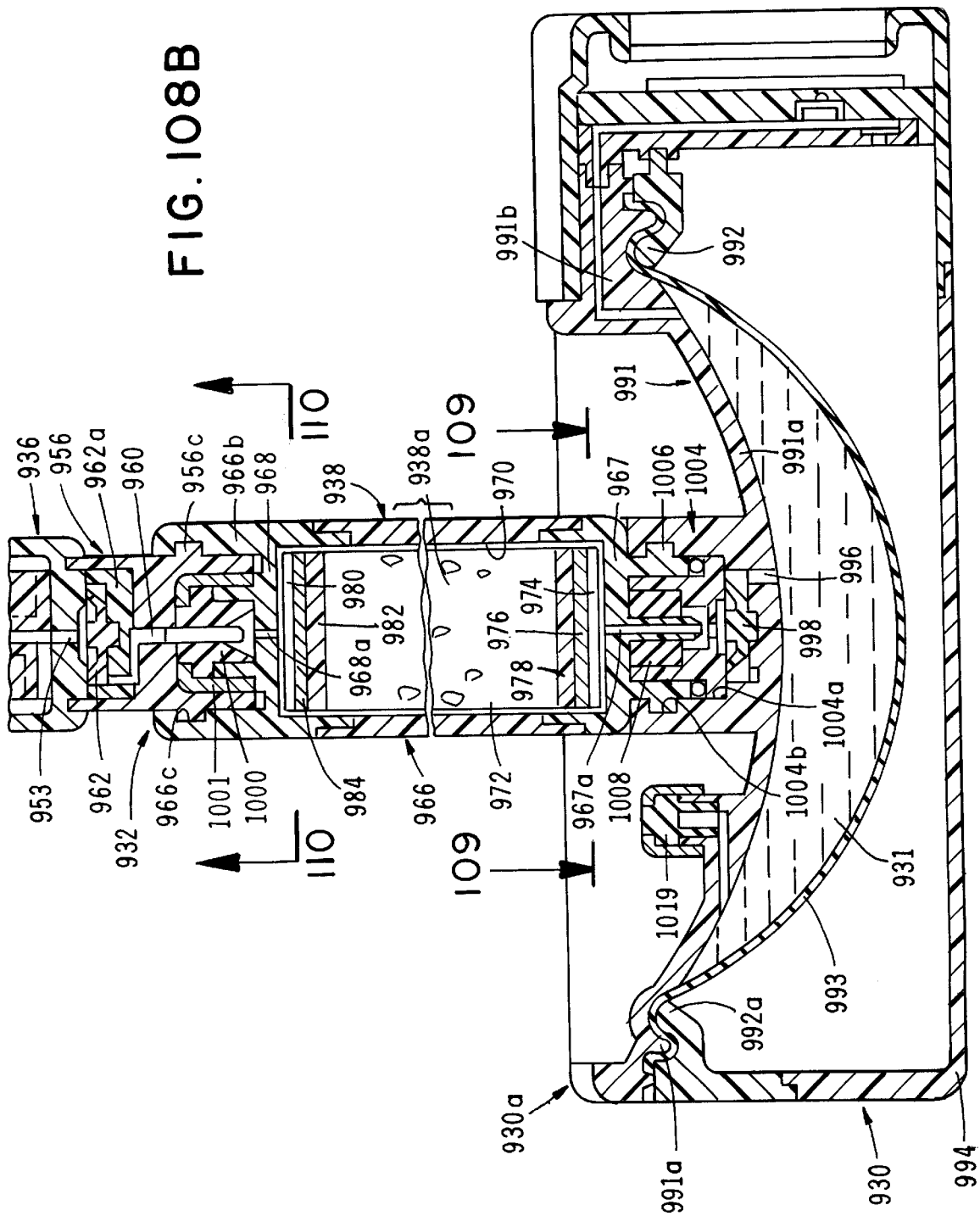

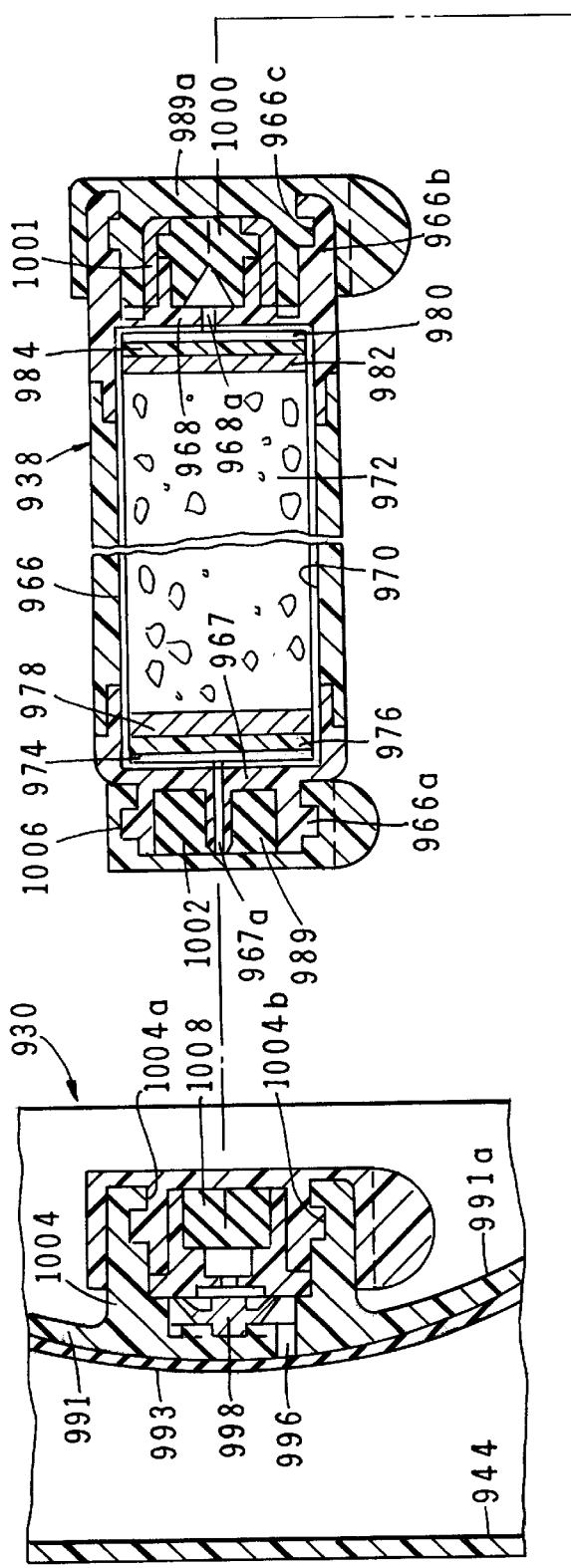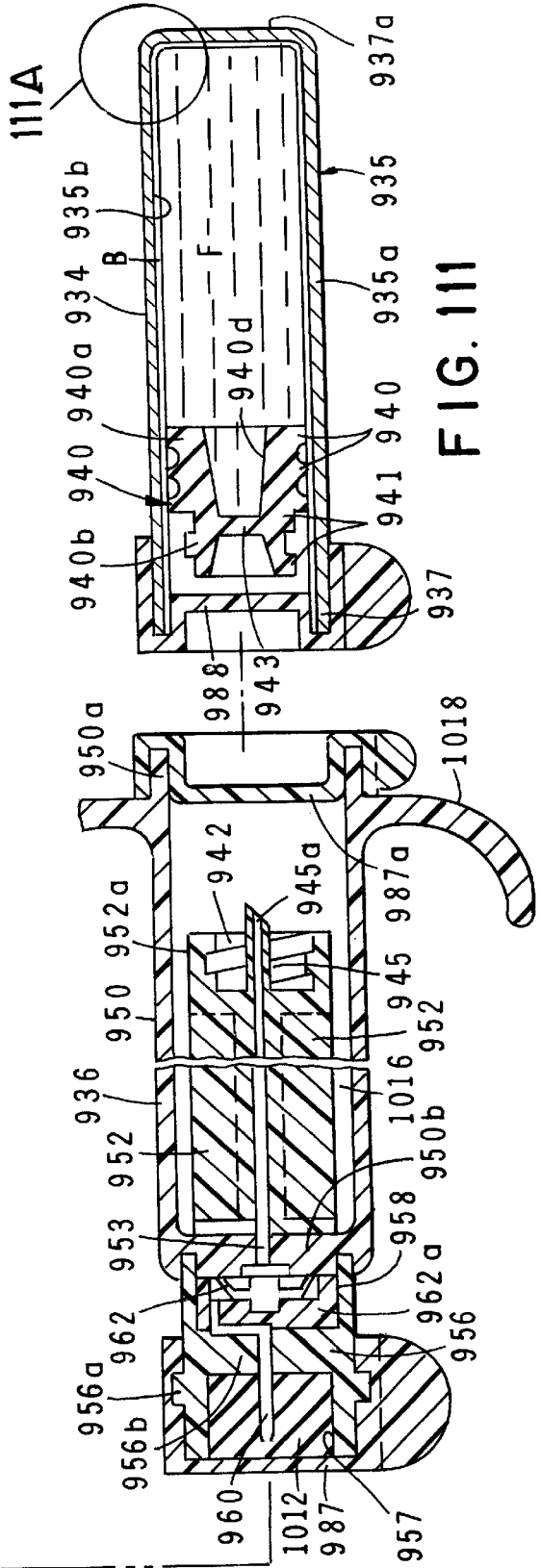
FIG. 111

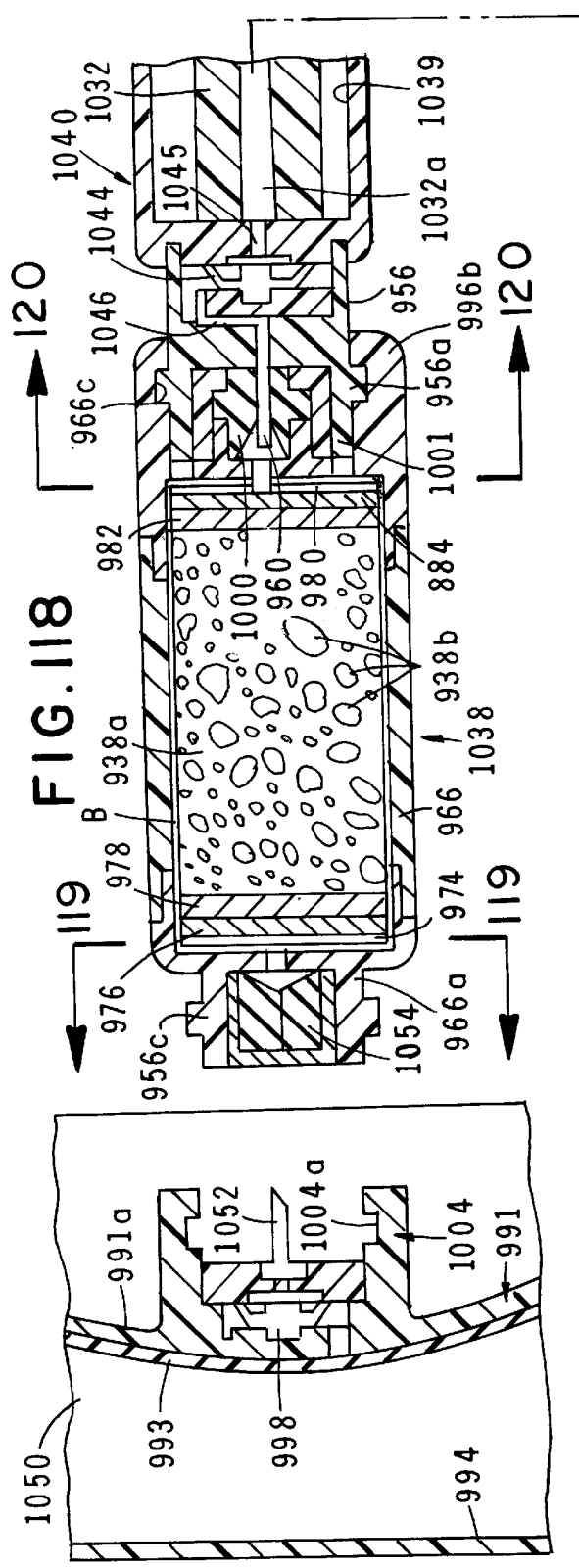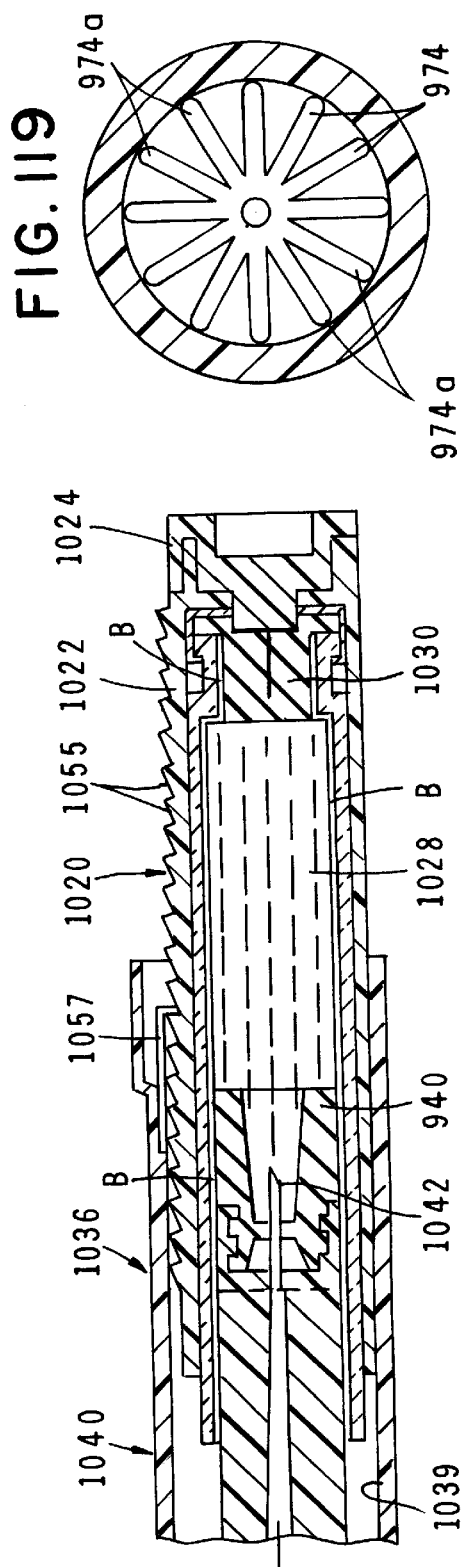

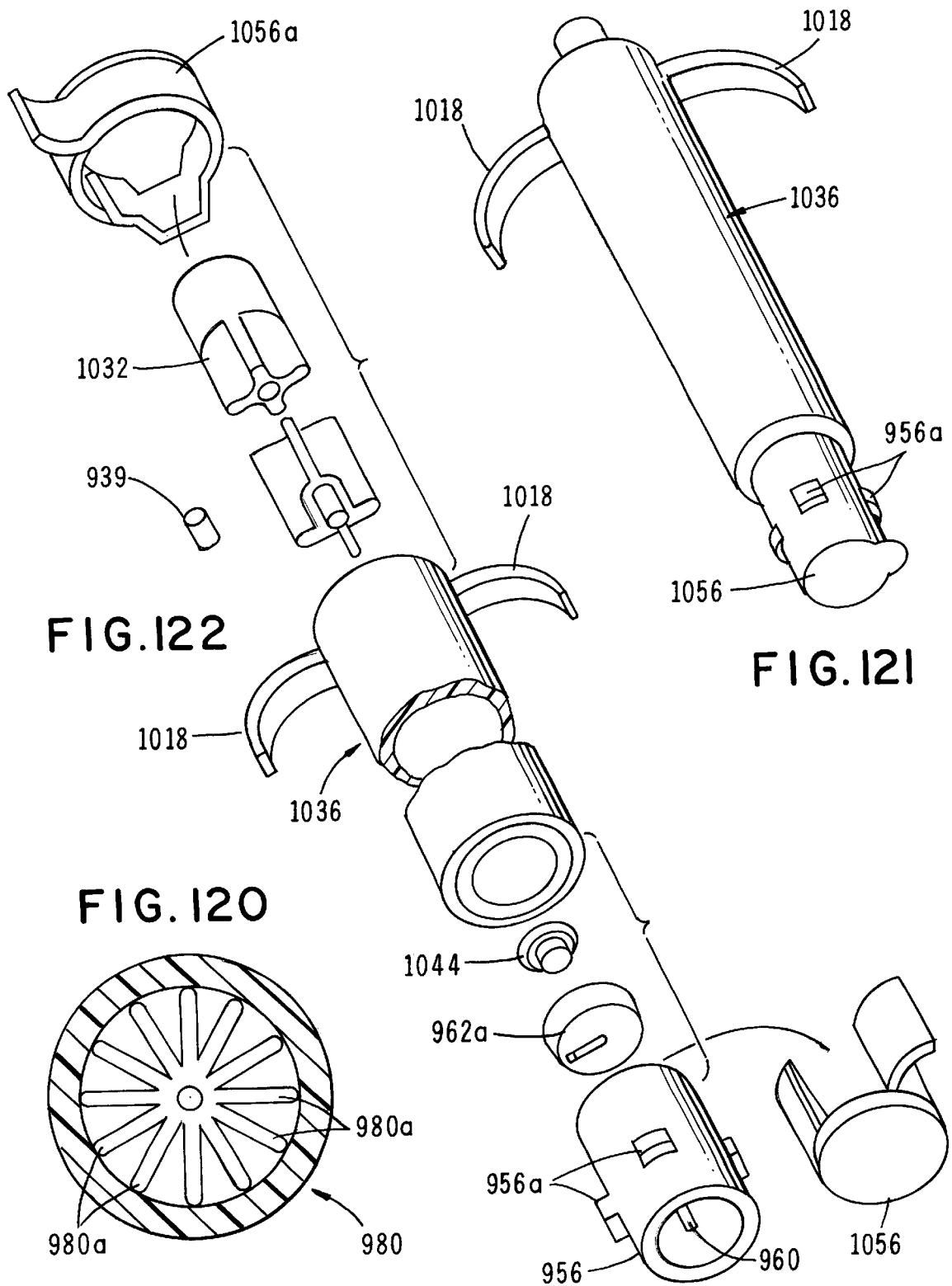

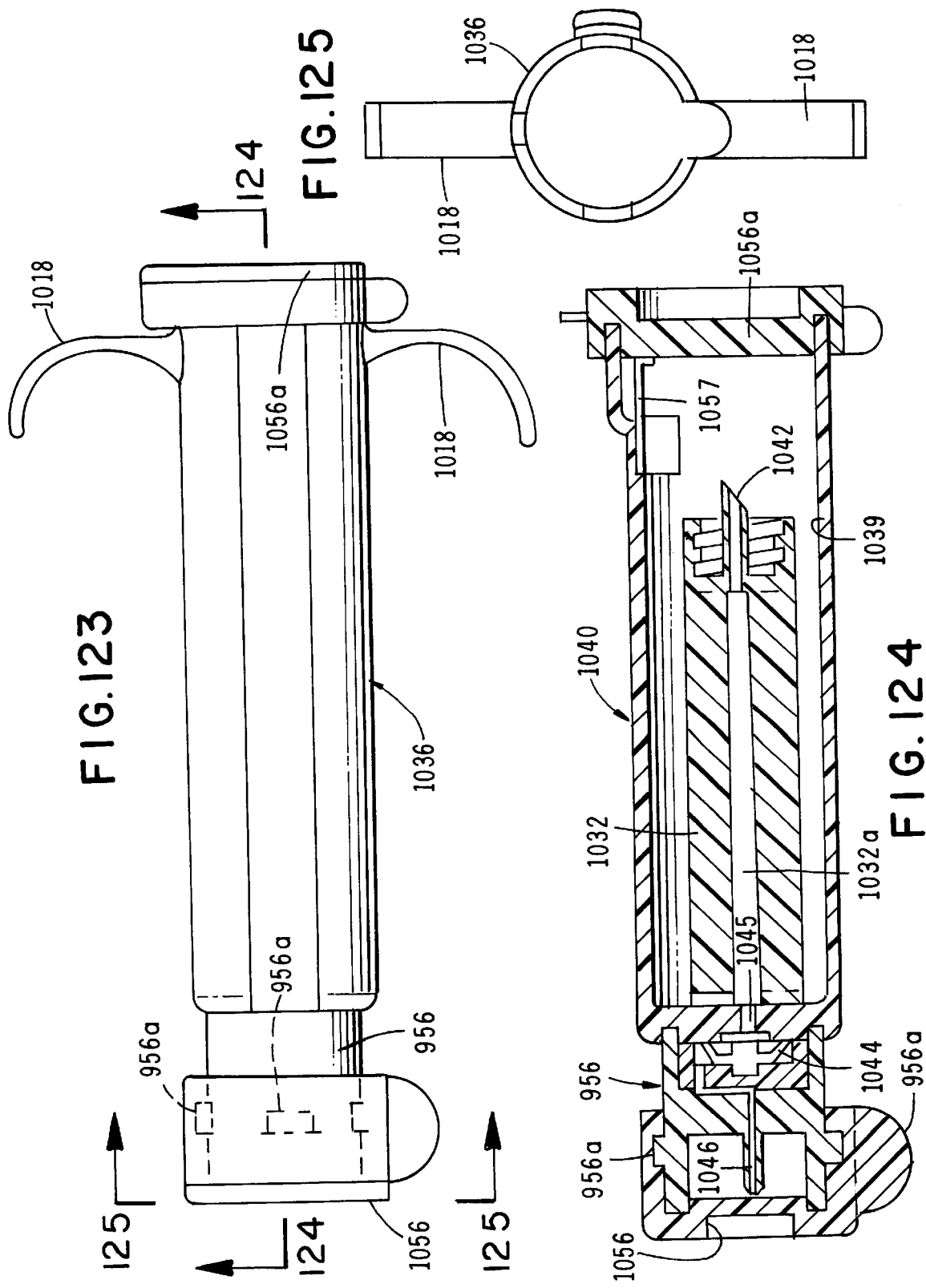

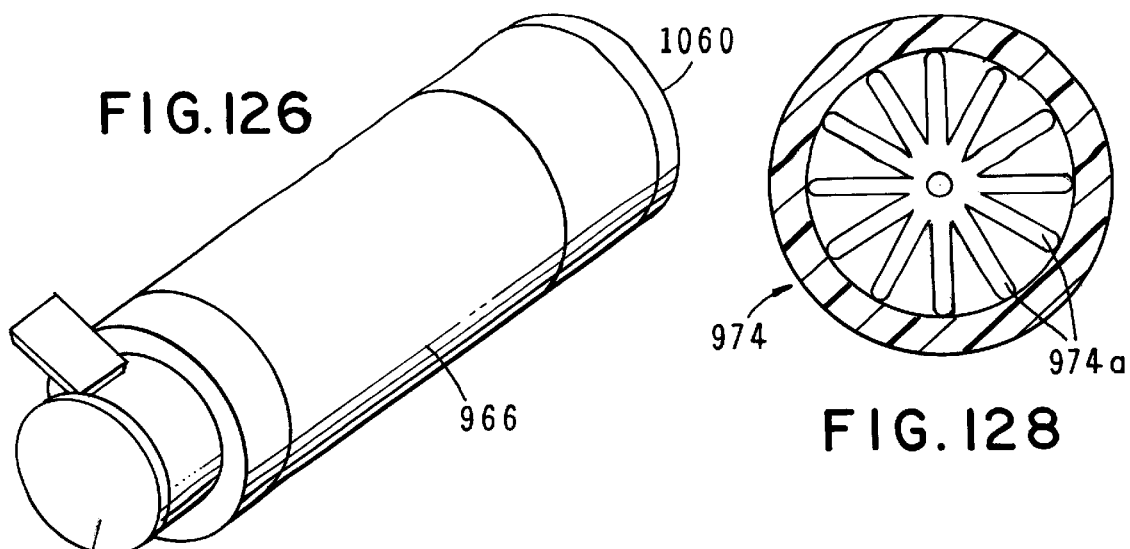
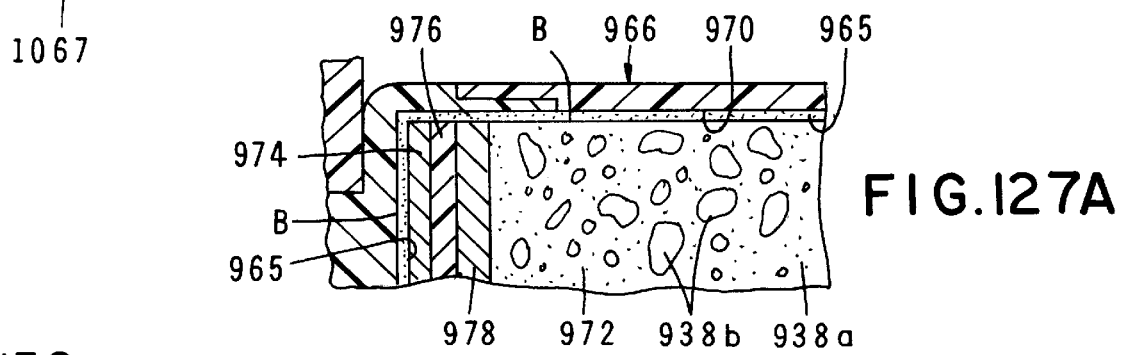
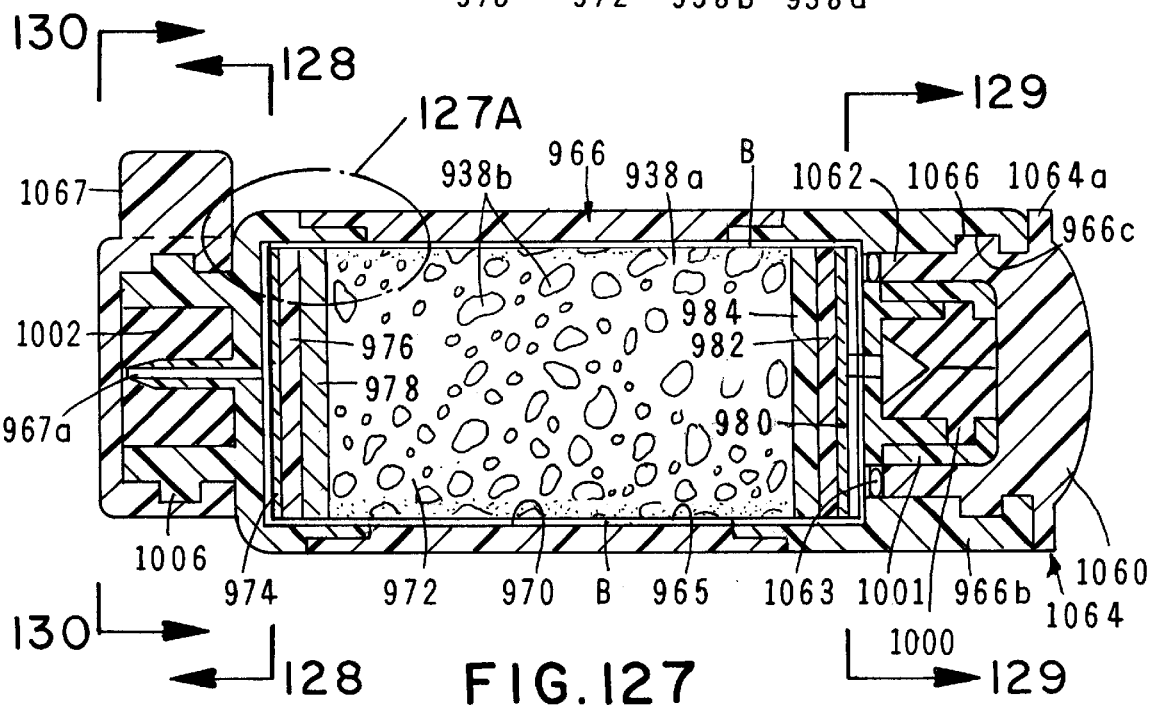

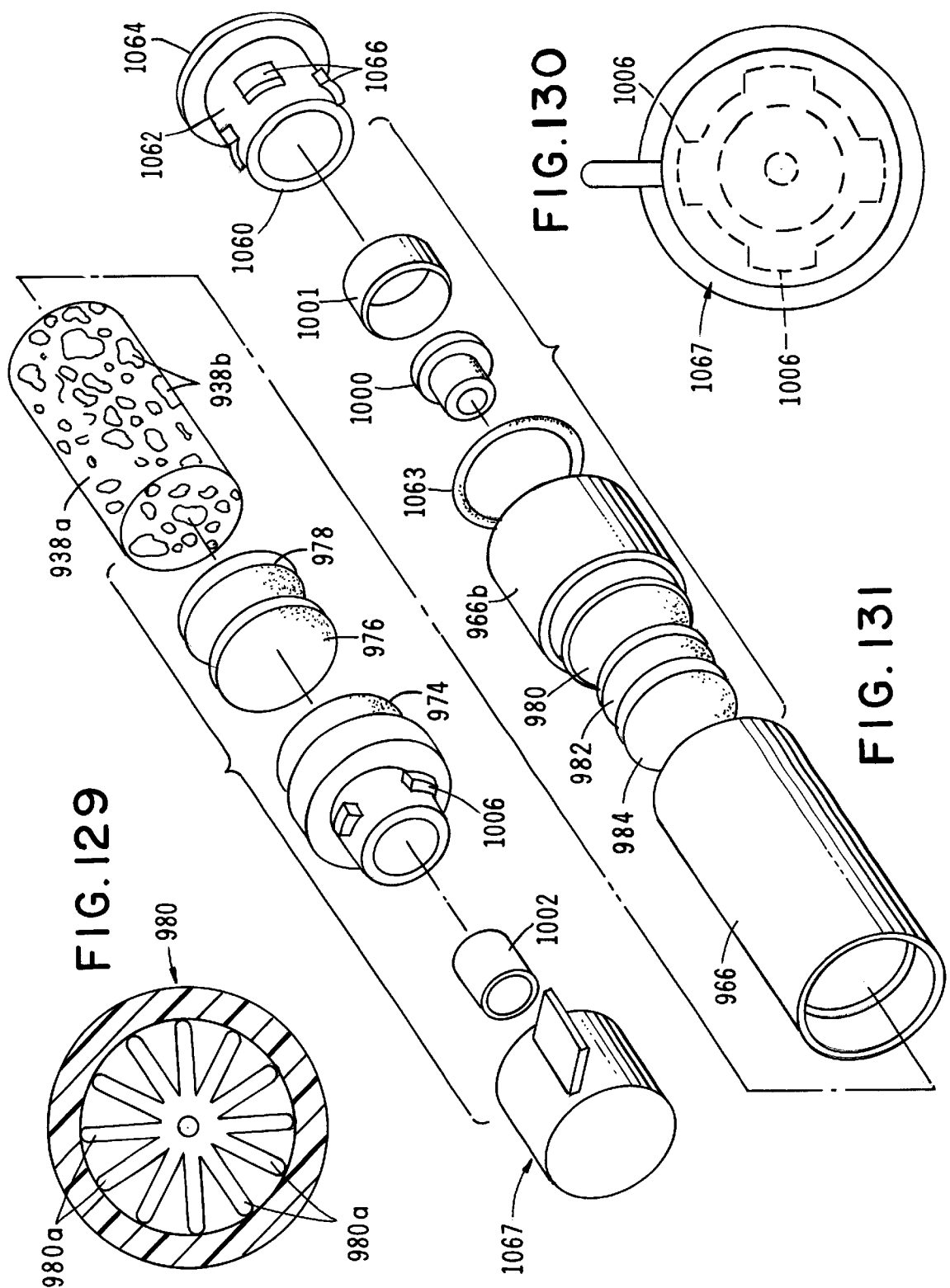

FLUID DELIVERY APPARATUS WITH RESERVOIR FILL ASSEMBLY

This is a Continuation-In-Part of copending application Ser. No. 09/363,288 filed Jul. 28, 1999 which is a Divisional application of application Ser. No. 09/017,047 filed Feb. 2, 1998 now U.S. Pat. No. 5,962,794 which is a Continuation-In-Part application of application, Ser. No. 08/718,686 filed Sep. 24, 1996 now U.S. Pat. No. 5,721,382 which is a Continuation-In-Part of application, Ser. No. 08/432,220, filed May 1, 1995 now abandoned.

BACKGROUND OF THE INVENTION

Field of the Invention

The present invention relates generally to fluid delivery devices. More particularly, the invention concerns an improved apparatus, including a fluid dispenser having visual flow indicator means, for infusing medicinal agents into an ambulatory patient at specific rates over extended periods of time and a novel reservoir fill assembly for controllably filling the reservoir of the fluid dispenser.

DISCUSSION OF THE INVENTION

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a base define a fluid chamber that contains the fluid which is to be dispensed. The elastomeric film membrane controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/718,686 filed by the present inventors on Sep. 24, 1996 also describes various alternate constructions and modified physical embodiments of the invention including the provision of a novel fluid actuated indicator means for visually indicating fluid flow from the device. This co-pending application is also hereby incorporated by reference in its entirety as though fully set forth herein.

The apparatus of the present invention can be used with minimal professional assistance in an alternate health care environment, such as the home. By way of example, devices of the invention can be comfortably and conveniently removably affixed to the patient's clothing or to the patient's body and can be used for the continuous infusion of antibiotics, hormones, steroids, blood clotting agents, analgesics including morphine, and like medicinal agents. Similarly, the devices can be used for I-V chemotherapy and can accurately deliver fluids to the patient in precisely the correct quantities and at extended microfusion rates over time.

SUMMARY OF THE INVENTION

It is an object of the present invention to provide an apparatus for delivering fluids at a precisely controlled rate which comprises a fluid dispensing component having a fluid reservoir for containing the fluids to be delivered and a reservoir fill component which can be removably interconnected with the fluid dispensing component. More particularly, it is an object of the invention to provide such an apparatus in which the reservoir fill component can be used to controllably fill the reservoir of the dispensing component and in which the dispensing component can be used for the precise infusion of pharmaceutical fluids to an ambulatory patient at controlled rates.

It is another object of the invention to provide an apparatus of the aforementioned character which includes adding means for adding to the fluids delivered to the dispensing component various additives, such as drugs and other beneficial agents.

Another object of the invention is to provide an apparatus that is highly reliable and easy-to-use by lay persons in a non-hospital environment.

Another object of the invention is to provide an apparatus which can be factory prefilled with a wide variety of medicinal fluids or one which can readily be filled in the field shortly prior to use using the novel reservoir fill component which can be removably interconnected to the lower surface of the base of the fluid dispenser.

Another object of the invention is to provide an apparatus as defined in the preceding paragraph in which the reservoir fill assembly is uniquely designed to accept a vial component of conventional construction which is factory filled with the medicinal fluid to be delivered to the patient.

A further object of the invention is to provide an accurate and highly reliable fluid delivery device which can be manufactured inexpensively in large volume by automated machinery.

Another object of the invention is to provide a device of the character described in which the dispenser component embodies a highly novel fluid flow indicator that provides a readily discernible visual indication of fluid flow status through the device.

Another object of the invention is to provide a device of the character described in which the dispenser component includes a novel infusion means, or delivery line assembly, which can be conveniently stored within a forward compartment of the housing of the dispenser.

Another object of the present invention is to provide an apparatus of the aforementioned character in which the aforementioned reservoir fill assembly comprises a container subassembly which includes either a conventional factory-prefilled vial or alternatively a container that can be filled in the field with wide variety of medicinal fluids.

Another object of the present invention is to provide a fill assembly of the type described in the preceding paragraph in which the container of the container subassembly is partially received within a novel adapter subassembly that can readily be removably interconnected with the fluid dispensing device.

Another object of the invention is to provide an apparatus as described in the preceding paragraphs which includes locking means for locking the container subassembly to the adapter subassembly following filling of the fluid reservoir of the fluid dispenser.

Another object of the invention is to provide a novel reservoir fill assembly for use with the fluid dispenser subassembly of the apparatus which is easy to use, is inexpensive to manufacture, and one which maintains the container in a substantially aseptic condition until time of use.

Other objects of the invention are set forth in U.S. Pat. No. 5,205,820 which is incorporated herein and still further objects will become more apparent from the discussion which follows.

By way of summary, the fluid delivery apparatus of the present form of the invention comprises two cooperating assemblies, namely a fluid dispenser and a reservoir fill assembly which can be removably coupled with the lower surface of the base of the fluid dispenser for filling the fluid reservoir of the fluid dispenser. The fluid dispenser, which readily lends itself to automated manufacture, is generally similar to that described in U.S. Pat. No. 5,721,382 and includes a base and a stored energy means comprising at least one distendable elastomeric membrane which cooperates with the base to form a fluid reservoir. In one form of the invention, the fluid dispenser includes a highly novel fluid flow indicator means which comprises a mechanical fluid flow indicator that provides a clear visual indication of normal fluid flow and absence of fluid flow from the fluid reservoir. In another form of the invention, the fluid dispenser includes a novel infusion apparatus which can be conveniently stored within a forward compartment of the housing of the fluid dispenser.

BRIEF DESCRIPTION OF THE DRAWINGS

FIG. 1 is a generally perspective, bottom view of one form of the fluid dispenser of the invention.

FIG. 2 is an enlarged bottom plan view of the device shown in FIG. 1.

FIG. 3 is a cross-sectional view taken along lines 3—3 of FIG. 2.

FIG. 4 is an enlarged side-elevational view of the device shown in FIG. 1, partly broken away to show internal construction.

FIG. 4A is a cross-sectional exploded view of the dispenser connector element and umbrella valve of the fluid dispenser which controls fluid flow toward the reservoir of the dispenser.

FIG. 4B is a view taken along lines 4B—4B of FIG. 4A.

FIG. 5 is a cross-sectional view of the removable cover which seals the inlet port of the fluid delivery apparatus.

FIG. 6 is a generally perspective view of the adapter portion of the reservoir fill assembly of the apparatus of the invention.

FIG. 16 is an enlarged, cross-sectional, exploded view of the rear portion of the reservoir fill assembly of the apparatus of the invention.

FIG. 17 is an enlarged, fragmentary, cross-sectional view of the forward portion of the dispensing unit illustrating the construction of one form of the flow indicator means and flow control means of the invention.

FIG. 18 is a generally perspective, exploded view of the downstream portion of one form of the fluid dispensing apparatus of the invention showing the flow indicator means and a portion of the flow control means.

FIG. 19 is a generally perspective, exploded view of one form of the fluid flow control assembly illustrating its laminate construction.

FIG. 28 is a cross-sectional view similar to FIG. 23 but showing the indicator means as it appears when there is a blockage downstream of the indicator means that prevents normal fluid flow.

FIG. 29 is a fragmentary plan view of the symbol that is viewable by the user when the apparatus is in the configuration shown in FIG. 28.

FIGS. 30 and 30A comprise, when taken together, an enlarged, cross-sectional view of an alternate form of the apparatus of the invention which includes a dual vial reservoir fill assembly.

FIG. 31A is a fragmentary top plan view of a portion of one of the pusher sleeves of the apparatus shown in FIG. 30A.

FIG. 31B is a fragmentary top plan view of a portion of the other pusher sleeve of the apparatus shown in FIG. 30A.

FIG. 32 is an enlarged, exploded, cross-sectional view of an alternate form of the dispenser connector and fill assembly connector of the invention.

FIG. 33A is an enlarged, exploded, cross-sectional view of an alternate form of fill assembly cannula construction usable with one of the vial subassemblies thereof FIG. 33B is an enlarged, cross-sectional view of the area identified in FIG. 30 by the numeral 33B.

FIG. 35 is a generally perspective view of one of the locking tabs of the locking means of this latest form of the invention.

FIG. 36 is a cross-sectional view taken along lines 36—36 of FIG. 34.

FIG. 37 is a view taken along lines 37—37 of FIG. 34.

FIG. 38 is a view taken along lines 38—38 of FIG. 34.

FIG. 39 is a cross-sectional view taken along lines 39—39 of FIG. 34.

FIG. 40 is a view taken along lines 40—40 of FIG. 34.

FIG. 48 is an enlarged, cross-sectional, exploded view of the coupler mechanism of this latest form of the invention.

FIG. 49 is an exploded, cross-sectional view of an alternate form of coupling mechanism for coupling together the dispenser component and the reservoir fill component.

FIG. 50 is an exploded cross-sectional view of still another form of coupling mechanism for coupling together the dispenser component and the reservoir fill component thereof FIG. 51 is a generally perspective, exploded view of the alternate form of reservoir fill assembly of the apparatus of the invention shown in FIG. 46.

FIG. 52 is a generally perspective, fragmentary view of the forward end of the reservoir fill assembly shown in FIG. 51 illustrating the construction of the closure caps of the assembly.

FIG. 53 is a cross-sectional view of yet another form of the reservoir fill assembly of the apparatus of the invention.

FIG. 54 is a cross-sectional view taken along lines 54—54 of FIG. 53.

FIG. 60 is an exploded, generally perspective, fragmentary view similar to FIG. 21 illustrating an alternate form of dispenser fluid flow control means.

FIG. 60A is an enlarged, cross-sectional view of a generally tubular shaped, elastomeric seal which, as shown in FIG. 60, is disposed proximate a rate control wafer which forms a part of the dispenser flow control means of this latest embodiment of the invention.

FIG. 60B is an enlarged, cross-sectional view of the elastomeric seal shown in FIG. 60A, but housing a novel rate control frit which forms a part of an alternate form of the dispenser flow control means of the invention.

FIG. 63 is a greatly enlarged, fragmentary, cross-sectional view similar to FIG. 23 further illustrating the alternate form of flow control means of the invention shown in FIGS. 60 and 60B.

FIG. 64 is a side-elevational view of one form of the infusion means or delivery line assembly of the apparatus of the invention for delivering fluid from the fluid dispenser to the patient.

FIG. 65 is a top view of the delivery line assembly shown in FIG. 64.

FIG. 66 is a greatly enlarged, cross-sectional view of the connector fitting of the delivery line assembly which houses the rate control frit of the dispenser fluid flow control means of the invention.

FIG. 67 is an exploded, side-elevational view similar to FIG. 4 but showing an alternate form of dispenser component of the present invention and being partly broken away to illustrate alternate reservoir filling means comprising a luer fitting type connector for use in filling the reservoir of the dispenser component.

FIG. 68 is a view taken along lines 68—68 of FIG. 67 showing the fluid flow passageways of the connector.

FIG. 73 is a front view of the apparatus illustrated in FIG. 72 showing the delivery line assembly storage compartment of the dispenser in an open configuration.

FIG. 78 is an exploded, generally perspective front view of the support structure of the fluid delivery apparatus of the form of the invention shown in FIGS. 69 and 70.

FIG. 79 is an exploded, generally perspective, rear view of the components shown in FIG. 78.

FIG. 82 is a generally perspective exploded view of one form of the reservoir fill assembly of the invention.

FIG. 83 is a generally perspective, bottom view of one form of the fluid dispenser of the invention showing the reservoir fill assembly connected thereto.

FIG. 95 is a generally perspective, bottom view of an alternate form of the fluid dispenser of the invention showing the reservoir fill assembly connected thereto.

FIG. 96 is a cross-sectional view of the alternate form of the fluid dispenser shown in FIG. 95 but showing the reservoir fill assembly in a starting position prior to filling the reservoir of the dispensing component.

FIG. 99 is an enlarged cross-sectional view taken along lines 99—99 of FIG. 97.

FIG. 101 is a front view of the fluid dispenser showing flow indicator indicia indicating no flow of fluid through the apparatus.

FIG. 102 is a front view of the fluid dispenser showing the flow indicator indicia indicating fluid flow through the apparatus.

FIG. 103 is a generally perspective view of an alternate form of fluid dispenser component of the present invention.

FIG. 105 is a generally perspective view of an alternate form of fill assembly of the invention for use with the fluid dispensing component shown in FIG. 103.

FIG. 106 is a generally perspective view of the forward portion or cap assembly of the fill assembly shown in FIG. 105.

FIG. 106A is an alternate form of the forward portion or cap assembly of the fill assembly shown in FIG. 105.

FIG. 106B is still another form of forward portion of the fill assembly shown in FIG. 105.

FIG. 106C is yet another embodiment of the forward portion of the fill assembly shown in FIG. 105.

FIG. 106D is yet another form of the forward portion of the fill assembly shown in FIG. 105.

FIG. 108 is an enlarged, cross-sectional view of the apparatus shown in FIG. 7 illustrated mated with the fluid delivery apparatus.

FIG. 109 is a cross-sectional view taken along lines 109—109 of FIG. 108.

FIG. 110 is a cross-sectional view taken along lines 110—110 of FIG. 108.

FIG. 111 is a cross-sectional, exploded view showing the connector portion of the fluid delivery apparatus in fragmentary form and showing the reservoir fill assembly in exploded view.

FIG. 111A is a greatly enlarged, cross-sectional view of the area designated in FIG. 111 as 111A.

FIG. 112 is a generally perspective, exploded view of the alternate form of reservoir fill assembly shown in FIG. 108.

FIG. 113 is a side-elevational, cross-sectional view of the fill assembly shown in FIG. 112.

FIG. 114 is a generally perspective, exploded view of the fill assembly shown in FIG. 113.

FIG. 115 is a generally perspective, exploded view of an alternate form of reservoir fill assembly of the invention.

FIG. 116 is a cross-sectional view of the unfilled fluid container component of the assembly shown in FIG. 115.

FIG. 116A is a greatly enlarged, cross-sectional view of the area designated in FIG. 116 as 116A.

FIG. 117 is a side-elevational view, partly in cross section of the assembly shown in FIG. 116 and illustrating the manner of filling of the component with the fluid to be introduced into the reservoir of the fluid delivery device.

Figure 115:
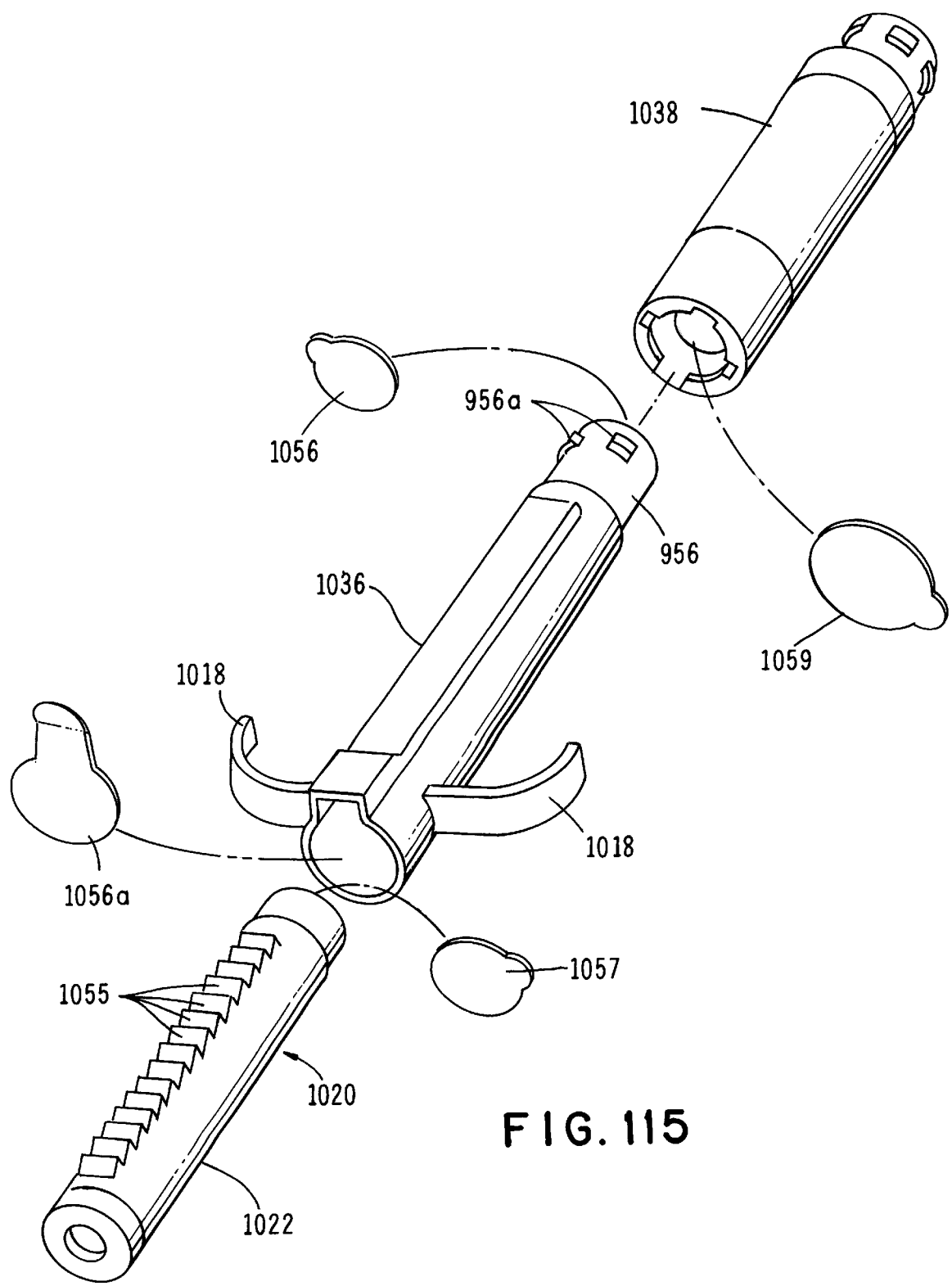
Figure 116:
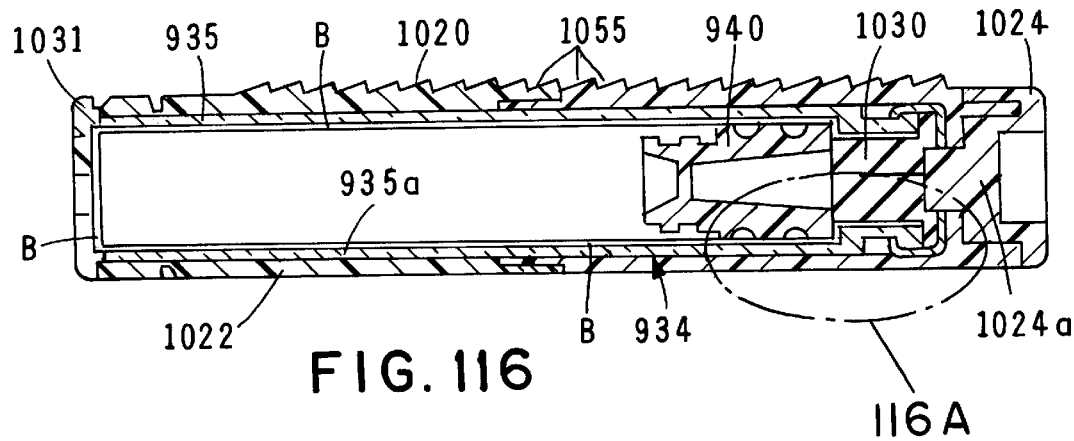
Figure 116A:
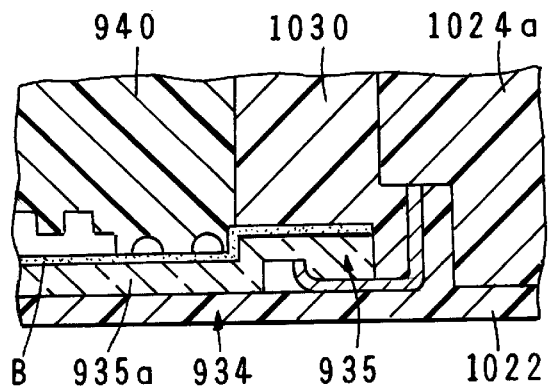

FIG. 118 is a cross-sectional view of the reservoir fill assembly shown in FIG. 115 with the component parts thereof in a mated relationship.

FIG. 119 is a cross-sectional view taken along lines 119—119 of FIG. 118.

FIG. 120 is a cross-sectional view taken along lines 120—120 of FIG. 118.

FIG. 121 is a generally perspective view of still another form of reservoir fill assembly of the present invention.

FIG. 122 is a generally perspective, exploded view of the assembly shown in FIG. 121.

FIG. 123 is a side-elevational view of the assembly shown in FIG. 121.

FIG. 124 is a cross-sectional view taken along lines 124—124 of FIG. 123.

FIG. 125 is a view taken along lines 125—125 of FIG. 123.

FIG. 126 is a generally perspective view of an alternate form of the immobilized drug vial assembly of the reservoir fill assembly of the apparatus of the invention.

FIG. 127 is a cross-sectional view of the immobilized drug vial assembly shown in FIG. 126.

FIG. 127A is a greatly enlarged, cross-sectional view of the area designated as 127A in FIG. 127

FIG. 128 is a cross-sectional view taken along lines 128—128 of FIG. 127.

FIG. 129 is a cross-sectional view taken along lines 129—129 of FIG. 127.

FIG. 130 is a view taken along lines 130—130 of FIG. 127.

FIG. 131 is a generally perspective, exploded view of the immobilized drug vial assembly shown in FIG. 126.

DESCRIPTION OF THE INVENTION

Figure 7:
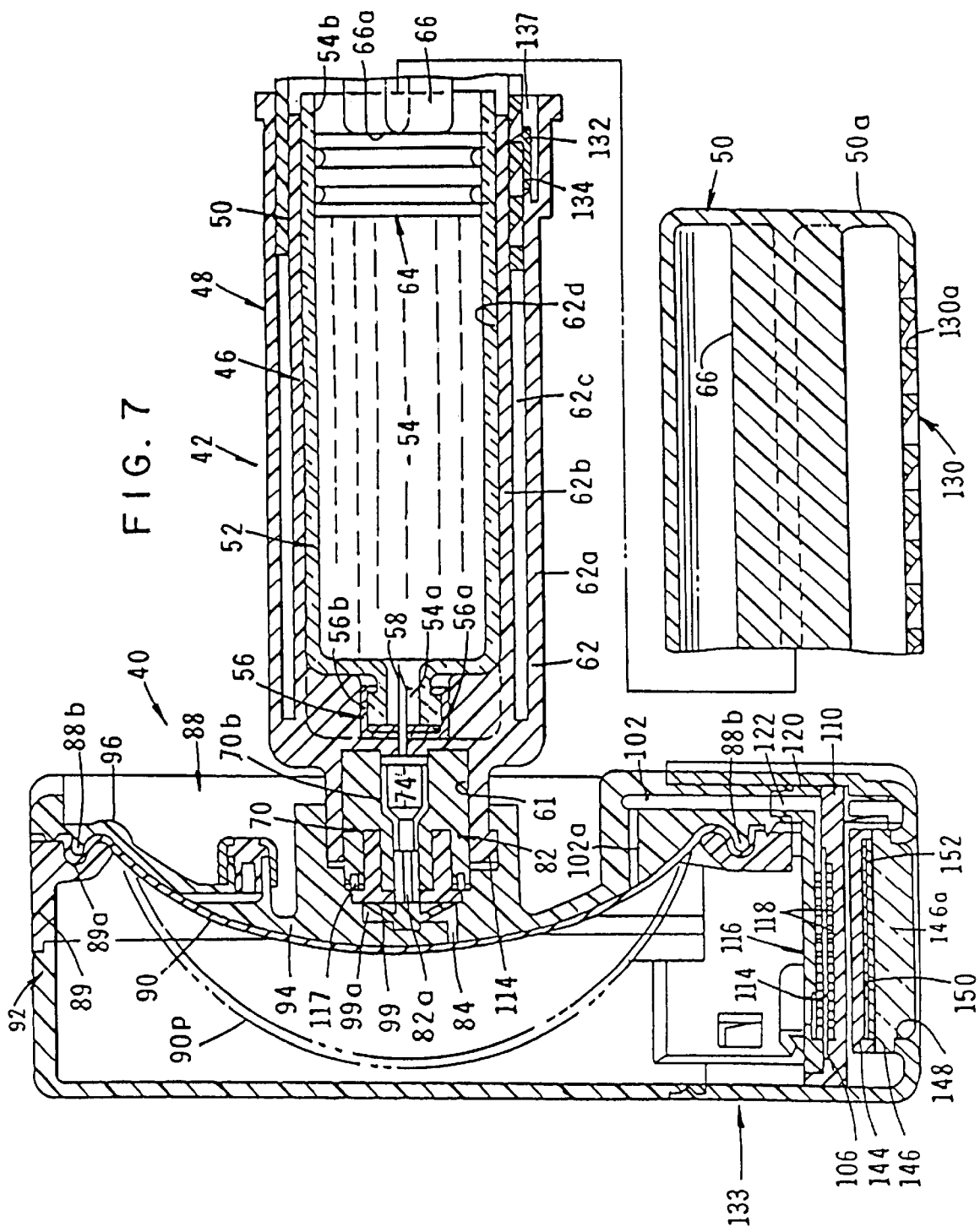
FIG. 7 is an enlarged, cross-sectional view of the fluid dispenser of the invention shown operably mated with one form of the reservoir fill assembly.
Figure 8:
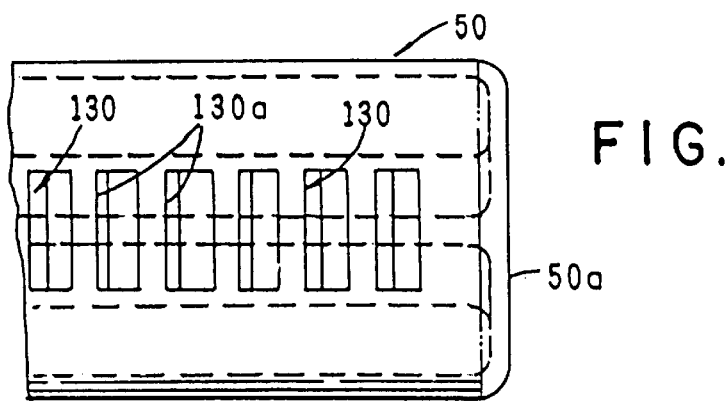
FIG. 8 is a fragmentary top plan view of a portion of the adapter sleeve of the reservoir fill assembly showing the locking teeth formed thereon.

Referring to the drawings and particularly to FIGS. 1 through 7, one form of the apparatus of this latest form of the present invention is there illustrated. As best seen in FIG. 7, the apparatus here comprises two major cooperating assemblies, namely a fluid dispensing apparatus or fluid dispenser 40 and a reservoir fill assembly 42 which can be operably coupled with fluid dispenser 40. As will be described in greater detail hereinafter, dispenser 40 is made up of three major cooperating subassemblies namely, a reservoir subassembly, a flow rate control subassembly, and a flow indicator subassembly.

Turning particularly to FIGS. 9 through 16, the novel reservoir fill assembly 42 of the invention can be seen to also comprise three major components, namely a container subassembly 46 (FIG. 16), an adapter subassembly 48 (FIG. 9) and an adapter or pusher sleeve 50 (FIG. 16). Container subassembly 46 includes a container such as a vial 52 which contains the medicinal fluid with which the reservoir of the dispensing apparatus is to be filled. Adapter subassembly 48 functions to interconnect the fill assembly with the medicament dispenser in the manner presently to be described so that fluid can be transferred from container 52 to the reservoir of the dispenser component.

Figure 9:
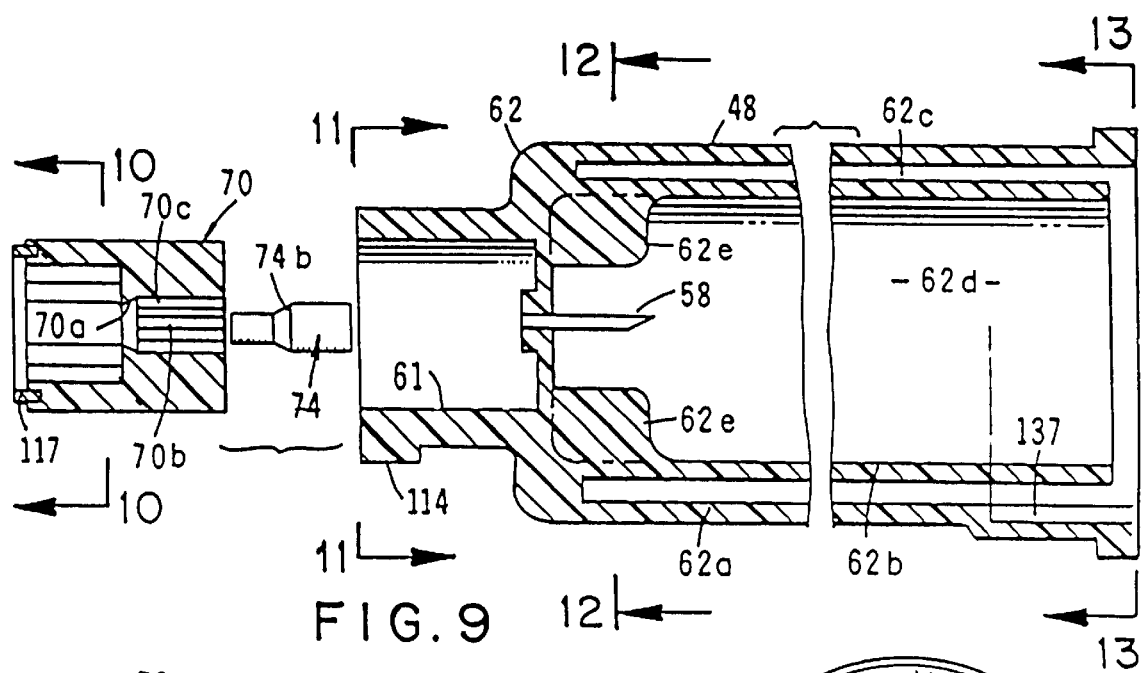
FIG. 9 is an enlarged, cross-sectional, exploded view of the adapter subassembly of the reservoir fill assembly.

As best seen in FIG. 16, container 52 includes a fluid chamber 54 having first and second open ends 54a and 54b. First open end 54a is sealably closed by closure means, here provided in the form of septum assembly 56 which includes a pierceable septum 56a and a clamping ring 56b for connecting the septum to the container proximate open end 54a. Septum 56a is pierceable by the cannula means or cannula 58 of the adapter subassembly 48. Septum 56a and cannula 58 form a part of the fill flow control means of the invention for controlling fluid flow toward the dispenser component 40. As shown in FIG. 9, cannula 58 is mounted centrally of an end wall 60 of body 62 of the adapter subassembly.

To expel fluid from fluid chamber 54 of the vial assembly and into cannula 58 of the adapter subassembly and thence into the fluid reservoir of the dispenser unit, displacement means are provided. This displacement means here comprises a plunger 64 which is telescopically movable within chamber 54 by pusher sleeve subassembly 50. To accomplish this movement, sleeve assembly 50 is provided with pusher means shown here as a pusher rod 66 which is integrally formed with end wall 50a of sleeve 50 (see also FIG. 7).

Referring particularly to FIGS. 7 and 9, it is to be noted that body 62 of adapter subassembly 48 uniquely includes outer and inner, generally cylindrically shaped walls 62a and 62b which define therebetween an elongated annular space 62c and within which sleeve component 50 is slidably received. As shown in FIG. 7, container assembly 46 is closely receivable within a chamber 62d formed internally of wall 62b of the adapter subassembly and can be urged forwardly of chamber 62d by inward telescopic movement of sleeve 50 into space 62c. More particularly, as indicated in FIG. 7, the inboard end 66a of pusher rod 66 engages plunger 64 and urges it inwardly of reservoir 54 as sleeve 50 is moved inwardly of annular space 62c.

Figure 10:
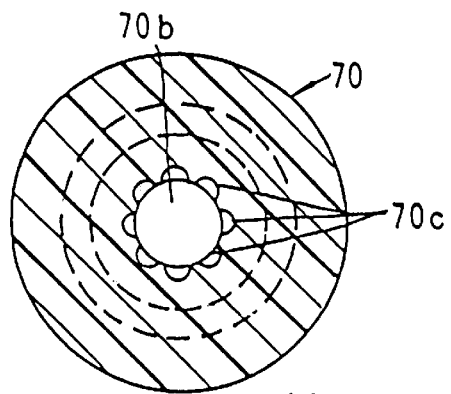
FIG. 10 is a cross-sectional view taken along lines 10—10 of FIG. 9.
Figure 11:
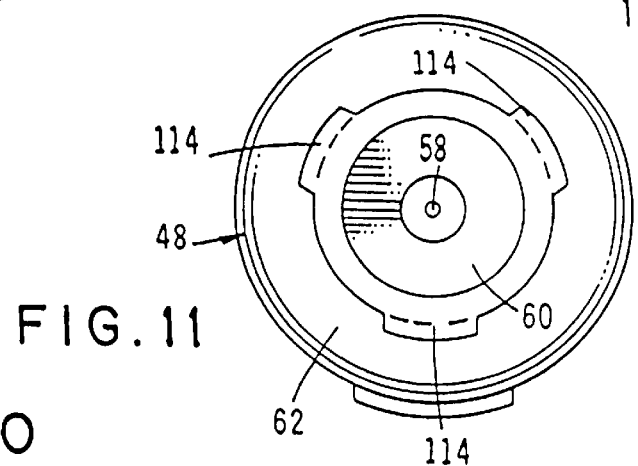
FIG. 11 is a view taken along lines 11—11 of FIG. 9.
Figure 12:
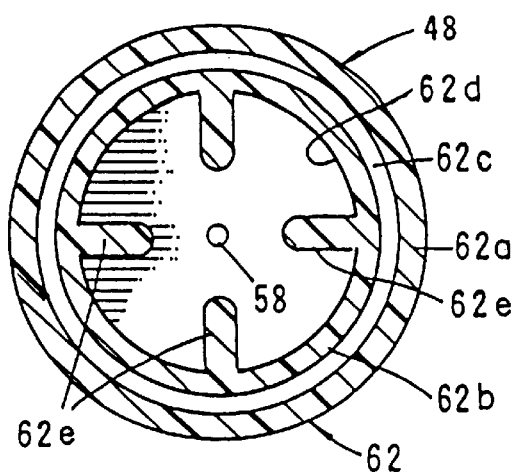
FIG. 12 is a cross-sectional view taken along lines 12—12 of FIG. 9.
Figure 13:
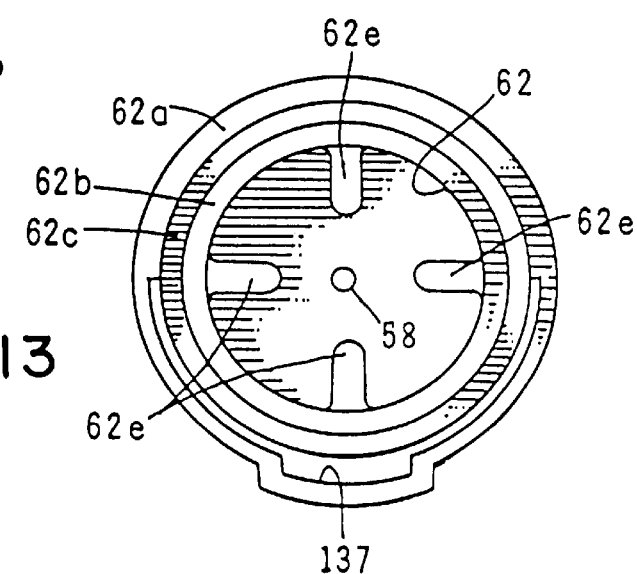
FIG. 13 is a view taken along lines 13—13 of FIG. 9.
Figure 14:
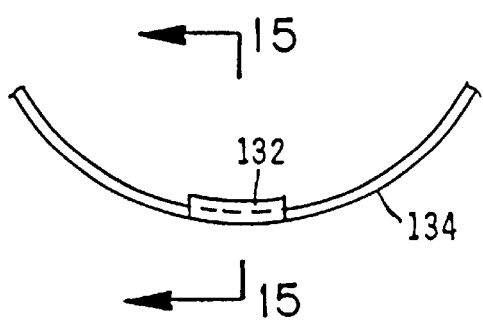
FIG. 14 is an end view of the locking tab portion of the locking means of the invention for locking the pusher sleeve subassembly of the reservoir fill assembly to the adapter component thereof
Figure 15:
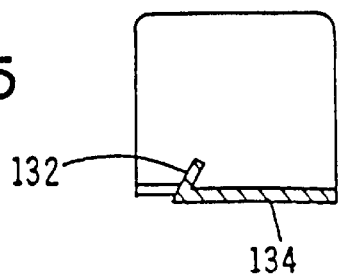
FIG. 15 is a cross-sectional view taken along lines 15—15 of FIG. 14.

During the initial mating of sleeve 50 with adapter subassembly 48, the resistance of the fluid within chamber 54 will resist movement of plunger 64 inwardly of reservoir 54 so as to cause the entire vial cartridge assembly to initially move inwardly of chamber 62d to a position wherein septum 56a is engaged by cannula 58 of the adapter subassembly. As shown in FIGS. 12 and 13 guide ribs 62e formed interiorly of chamber 62d, guide the neck portion of the vial toward cannula 58. A continued inward force on sleeve 50 will cause cannula 58 to pierce septum 56a in the manner shown in FIG. 7, thereby opening fluid communication between reservoir 54 of vial 52 and the internal fluid passageway of cannula 58. Once septum 56a has been pierced, pusher rod 66 will urge plunger 64 forwardly of reservoir 54 from a first location proximate open end 54b to a second location proximate end 54a. As plunger 64 moves forwardly of reservoir 54, fluid within the reservoir will be caused to flow into the central fluid passageway of cannula 58 and toward additional components of the flow control means of the invention which controls fluid flow toward the fluid dispenser component 40. These further flow control means include valve means comprising a support assembly of the character shown in FIG. 9 and generally designated by the numeral 70. Valve support assembly 70 is held within a counterbore 61 formed in body 62 and in close proximity with wall 60 of adapter subassembly 48 by any suitable means such as sonic welding. Member 70 includes a valve seat 70a and a centrally disposed fluid passageway 70b which is defined by a plurality of circumferentially spaced fluid flow grooves 70c (FIG. 10). Disposed within passageway 70b is a check valve 74 which also forms a part of the valve means for controlling fluid flow from cannula 58 toward the fluid reservoir of the dispenser assembly. Check valve 74 is designed to permit fluid flow toward dispenser 40 but blocks fluid flow in the opposite direction. As shown in FIG. 9, check valve 74, which is of conventional construction, includes a body portion 74a and a seat portion 74b which sealably engages seat 70a when valve 74 is in a closed position. The construction and operation of valve 74 is well understood by those skilled in the art and the manner of opening the valve during the filling step will presently be described.

Prior to use, the adapter subassembly component 48 of the reservoir fill assembly 42 is maintained in a protected and substantially sterile configuration by tear-away end caps 76 and 78 (see FIG. 6). As indicated in FIG. 6, tear-away end cap 76 is receivable over and closes the forward end of adapter subassembly 48, while tear-away end cap 78 is received over and closes the rearward open end portion of adapter subassembly 48. Similarly, as shown in FIGS. 4 and 5, a tear-away cap 80 is received over and closes the dispenser connector subassembly 82 and inlet 84 of the dispenser assembly 40. Cap 80 maintains the dispenser connector and fluid inlet passageway of the device in a closed and substantially sterile condition.

Turning again to FIGS. 1 through 4, the fluid dispenser assembly 40 of the apparatus of this form of the invention is similar in many respects to that described in Serial No. 08/718,686 and includes a housing assembly comprising a base 88, a capture ring 89, a stored energy source, or distendable membrane 90 and a cover 92 for enclosing the stored energy source, the capture ring and the base. The base 88 includes an ullage defining protuberance 94 and a membrane capture portion 96. Disposed between base 88 and cover 92 is the membrane capture ring 89 which has a bottom opening 89a which receives protuberance 94 of base 88 (see FIG. 3).

Referring particularly to FIGS. 3, 4, and 7, base 88 comprises, in addition to the distendable member engaging protuberance, or ullage 94, the previously identified dispenser connector subassembly 82, to which the reservoir fill assembly 42 is interconnected in the manner shown in FIG. 7. Base 88 also includes an upstanding tongue 88b which extends about the perimeter of the base and is closely receivable within groove 89b formed in the capture ring 89 (FIG. 3). When the base 88 and the membrane capture ring 89 are assembled in the manner shown in FIG. 3, the periphery of distendable membrane 90 will be securely clamped within groove 89b by tongue 88b. After the parts are thus assembled, base 88 is bonded to capture ring 89 by any suitable means such as sonic bonding which also functions to simultaneously trim membrane 90. This done, cover 92 is mated with capture ring 89 in the manner shown in the drawings and is suitable bonded in place. Cover 92 can, if desired, be constructed from a substantially transparent plastic material which is impermeable to fluids, including gases.

During the reservoir filling step, the details of which will presently be described, fluid under pressure will flow into inlet passageway 84 of the fluid dispenser via an umbrella valve 99 and thence into a reservoir 100 which is formed between protuberance 94 and distendable membrane 90p which is shown in phantom lines in FIG. 7. As the fluid under pressure flows into the reservoir, it will cause membrane 90 to distend outwardly from protuberance 94 in the manner shown by the phantom lines in FIG. 7. While the stored energy means can be in the form of a single prestressed or unstressed isotropic, elastomeric distendable membrane, such as membrane 90, it can also be constructed as a laminate assemblage made up of a plurality of initially generally planar distendable elements of films. Such construction is described in Ser. No. 08/718,686, which application is incorporated herein by reference. During the infusion step, internal stresses formed in membrane 90 will cause it to move toward protuberance 94 and fluid within reservoir 100 will be uniformly and controllably forced outwardly through a passageway 102a and then through a passageway 102 formed in base 88 (FIG. 7) in a direction toward the fluid flow indicator means of the invention.

Turning to FIGS. 7, 17, 18 and 19, the important dispenser flow control means of the dispenser component of the present form of the invention is there shown. This means, which is disposed externally of reservoir 100, functions to control fluid flow outwardly of the device. In the embodiment of the invention shown in FIGS. 18 and 19, the dispenser flow control means 106, which includes a fluid flow rate control means, is closely received within a cavity 108 formed in a support means, shown here as a membrane support structure 110. The downstream wall 112 of cavity 108 is provided with fluid distribution means comprising a multiplicity of circumferentially spaced, manifolding stand-off elements 114 against which assembly 106 is held in engagement by a disc-like member 116 (FIG. 21) which is receivable within recess 108 in the manner shown in FIG. 17. Member 116 is provided with fluid collection means shown here as a multiplicity of circumferentially spaced, manifolding stand-offs 118 (FIG. 21) which engage assembly 106 when member 116 is in position within cavity 108 (see FIG. 17). More particularly, when member 116 is in place within cavity 108, the fluid flow control means is bonded at its circumference to member 110 and securely positioned between stand-offs 114 and 118 which cooperate to define a multiplicity of concentric and radial extending fluid passageways, which function to direct flow through the fluid flow control means. A vent patch 111 vents to atmosphere any air trapped within the fluid passageways (FIG. 21).

As best seen in FIG. 19, the flow control means here comprises a laminate construction made up of layers 106a, 106b, 106c, 106d, 106e, and 106f. More particularly, layer 106a comprises first filter for initially filtering the fluid, while layer 106b comprises a second filter for providing a second, more refined, filtering of the fluid. Layer 106c is here shown as a first flow rate control membrane for controlling flow at a first rate. Layer 106e is a second flow rate control membrane for controlling flow at a second rate. Disposed intermediate rate control membranes or layers 106c and 106e is a distribution means or porous distribution layer for distributing the fluid flowing through membrane 106c across the surface of membrane 106e. Layer 106f comprises a porous support member for supporting membrane 106e. Reference should be made to copending Ser. No. 08/718,686 for a more detailed description of the operation of the flow control means and for a discussion of the materials suitable for constructing various components of the flow control means.

Figure 21:
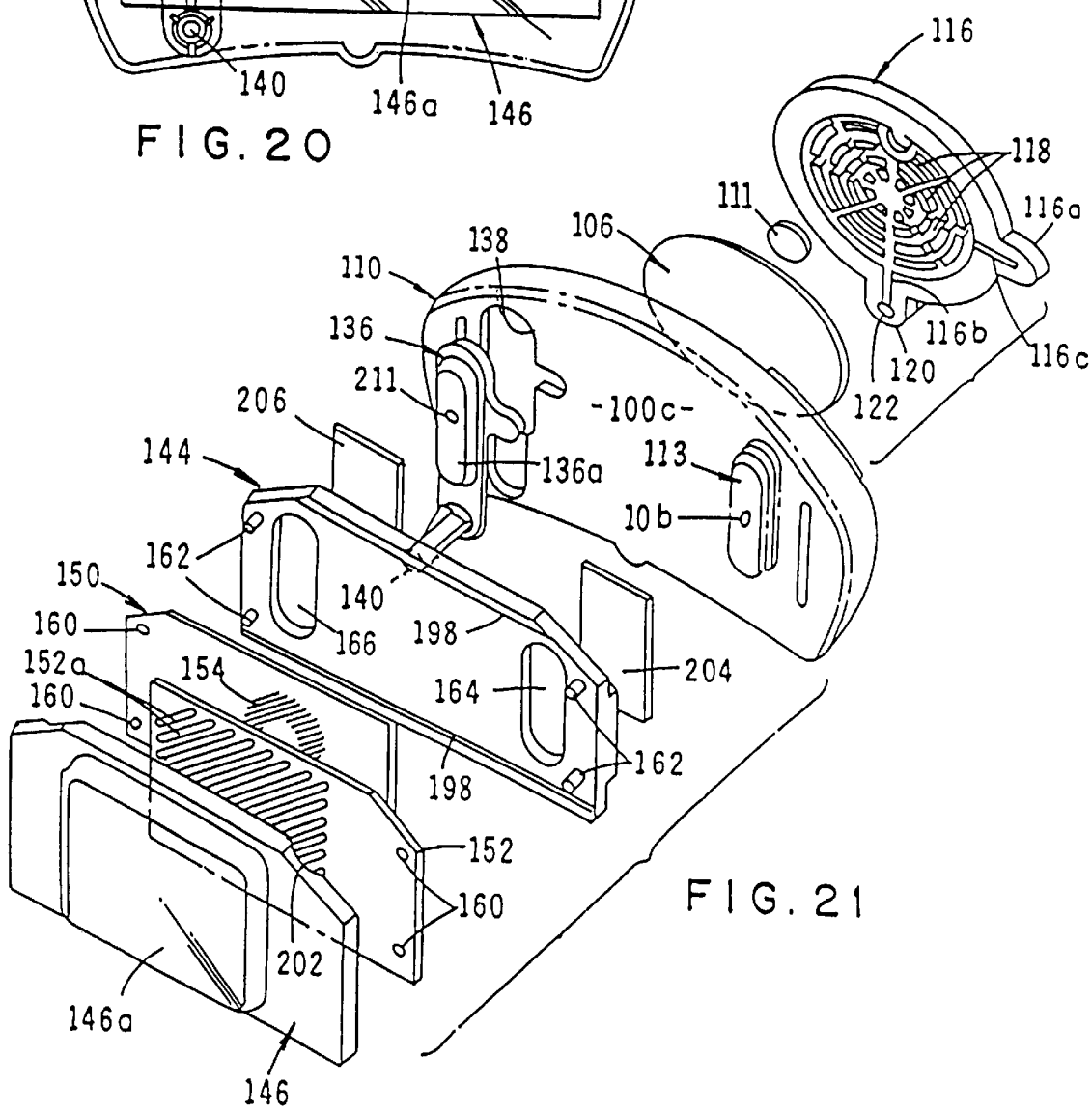
FIG. 21 is a generally perspective exploded view of one form of forward housing portion of the apparatus of the invention showing the flow indicator means and a portion of the flow control means.

As best seen in FIG. 21, member 116 includes a downwardly extending fluid inlet leg or segment 120 which is provided with a fluid passageway 122. Passageway 122 is adapted to communicate with cavity 108 when member 116 is mated with support structure 110. Formed on either side of the central portion of the support structure 110, are wing-like protuberances 124 that are received within spaced-apart, arcuate-shaped cavities (not shown) formed in the base 88. Also formed in base 88 is a socket 128 which closely receives the inboard end of segment 120 (FIG. 17). Located proximate the upper edge of support structure 110 are spaced-apart capture grooves 132, which attach an indicator cover 133 to structure 110. Indicator cover 133, is, in turn, connected to cover 92 by any suitable means in the manner best seen in FIG. 17. Copending Ser. No. 08/718,686 provides further details concerning the construction of indicator cover 133 and its attachment to cover 92.

Figure 20:
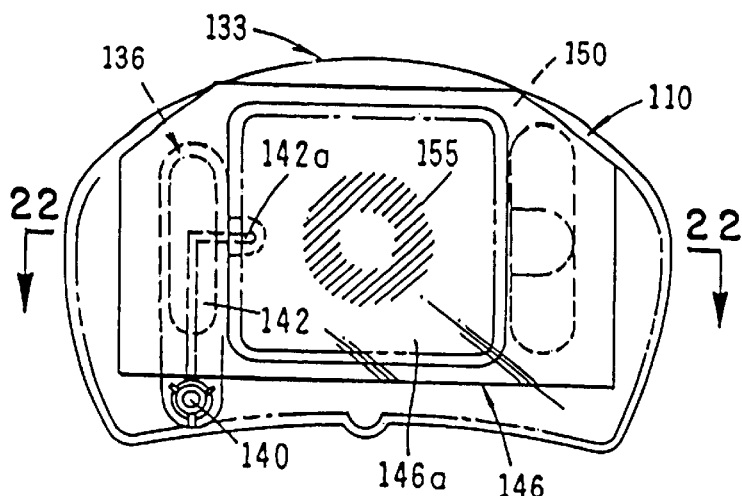
FIG. 20 is a front view of the housing portion of the flow indicator means of the invention.

As shown in FIG. 17, when the fluid flow control subassembly is mated with the reservoir assembly, fluid inlet passageway 122 of member 116 is placed in fluid communication with reservoir 100 via passageways 102 and 102a. With this construction, when fluid is forced into passageway 102a by the stored energy means, the fluid will flow into passageway 102, then into passageway 122 of member 116, and finally into chamber 108 formed in member 110 via the fluid passageway 116b. As the fluid under pressure flows into the upstream portion of chamber 108 behind flow control assembly 106, it will be distributed by stand-offs 118 so that it will uniformly flow through assembly 106 and toward the fluid outlet port of the flow control subassembly. As best seen in FIG. 21, the outlet port here comprises a uniquely shaped assembly 136 which is receivable in a cavity 138 formed in the back or downstream wall 100c of substrate 110. Assembly 136 includes a fluid outlet 140 and an internal chamber 142 having an actuator fill port 142a (FIG. 20), the purpose of which will presently be described.

Considering next the very important flow indicator means of the invention. This novel means visually distinguishes among three conditions of operation, namely normal fluid flow, fluid flow blockage or occlusion, and reservoir empty. Turning to FIG. 18, the flow indicator means here comprises an indicator base or platform 144 and a support or lens plate 146. As shown in FIG. 17, platform 144 and plate 146 are housed within indicator cover 133. As seen in FIG. 21, plate 146 has a viewing lens portion 146a which indexes with an opening 148 provided in indicator cover 133.

Figure 24:
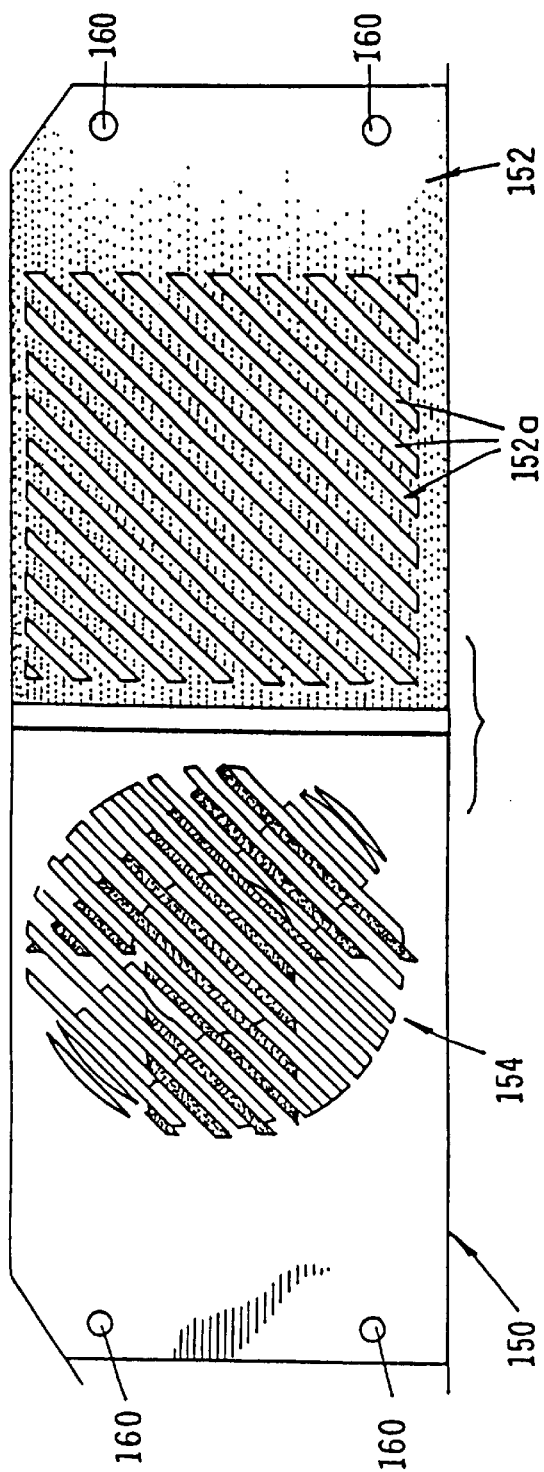
FIG. 24 is an enlarged plan view of the indicia carrying thin films of the flow indicator means of the apparatus of the invention.

Disposed between platform 144 and lens plate 146 are first and second indicia-carrying means shown here as thin films. These films, which are identified in FIGS. 18 and 21 as 150 and 152, are in intimate contact and are constructed from a substantially transparent, flexible polymer material such as mylar. The downstream surface of the inferior or first film 150 is printed with three integrated symbols 154 (FIG. 24), namely a blue circle 155 (FIG. 25), a green arrow 157 (FIG. 27), and a red X 159 (FIG. 29), each consisting of diagonal strips of color printed in an alternating pattern (blue, green, red, blue, green red, and so on). The superior or second film 152 serves as a "mask" over the inferior film 150 and is printed with a pattern of diagonal alternating clear and opaque strips 152a that occur in a 1:2 ratio. The printed ratio of the superior "mask" allows only one colored symbol to appear at a time when viewed through viewing lens 146a in plate 146. The inferior and superior films are provided at their opposite ends with apertures 160 which receive retention pins 162 provided on platform 144 (FIG. 21) which permit attachment of the film to platform 144 in a manner such that the non-patterned portion of both the superior and inferior films are maintained in index. With this construction, each thin film is able to move in opposing directions parallel to the film plane with its range of motion limited to one axis in the film plane by edge guides 198 provided on platform 144 (FIG. 21). As the films move, the visible symbol pattern changes due to the transverse displacement of the patterns imprinted thereon.

Figure 23:
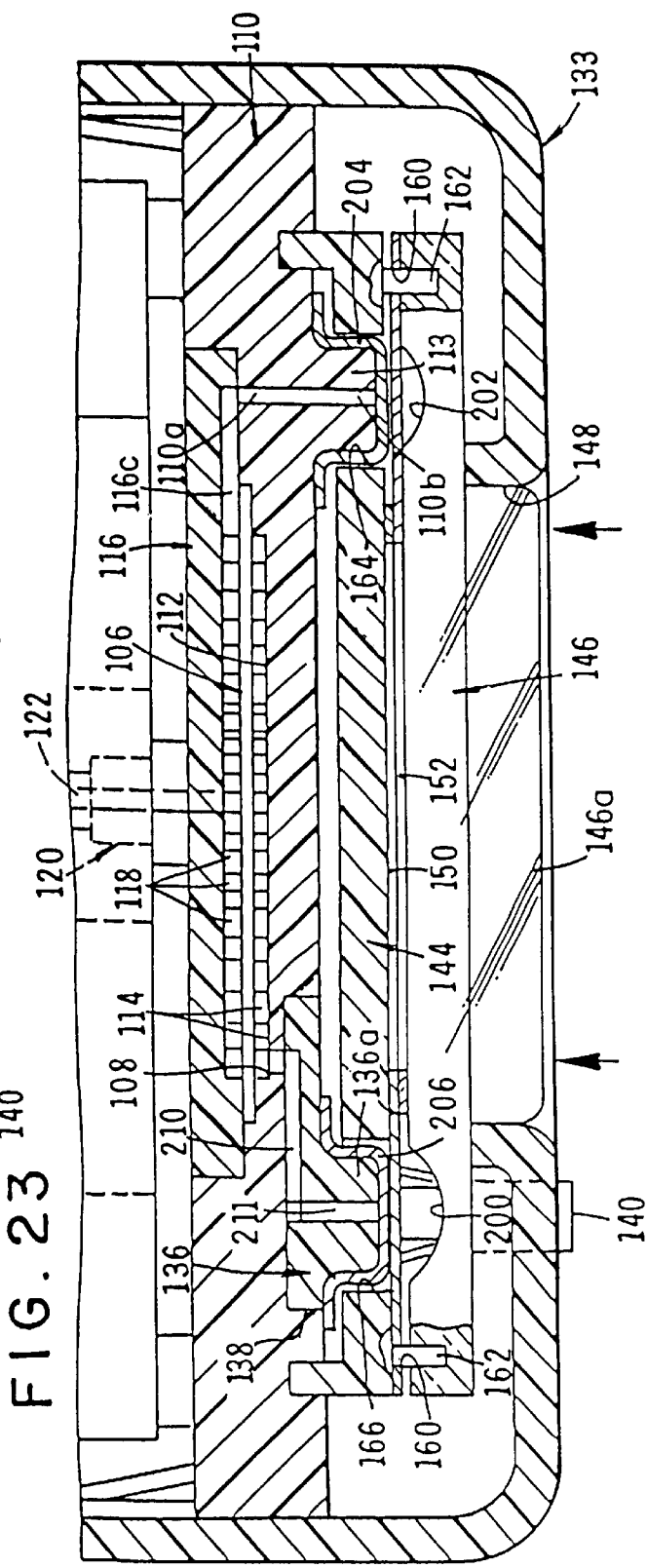
FIG. 23 is a cross-sectional view showing the indicator means of the invention in its starting configuration.
Figure 26:
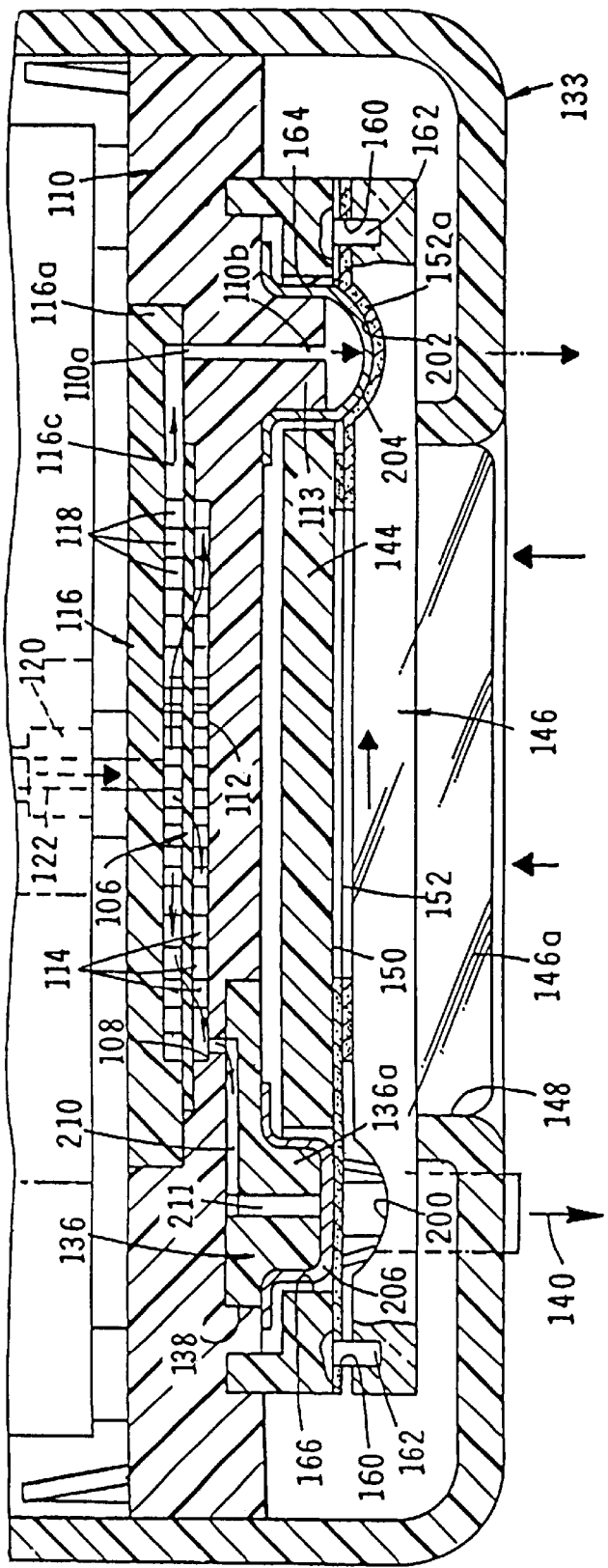
FIG. 26 is a cross-sectional view similar to FIG. 23 but showing the indicator means as it appears when fluid is flowing through the apparatus in a normal fashion.

Referring particularly to FIGS. 18, 23, and 26, it can be seen that support plate 146 is provided with transversely spaced, channel-like depressions 200 and 202 which index with slots 166 and 164 formed in platform 144 respectively when the components are assembled in the manner shown in the drawings. Aligned with the upstream side of slots 164 and 166 are mechanical actuator means, here provided as mechanical actuators or elastomeric elements 204 and 206. More particularly, the first actuator element 204 aligns with slot 164 and the second actuator element 206 aligns with slot 166.

Figure 27:
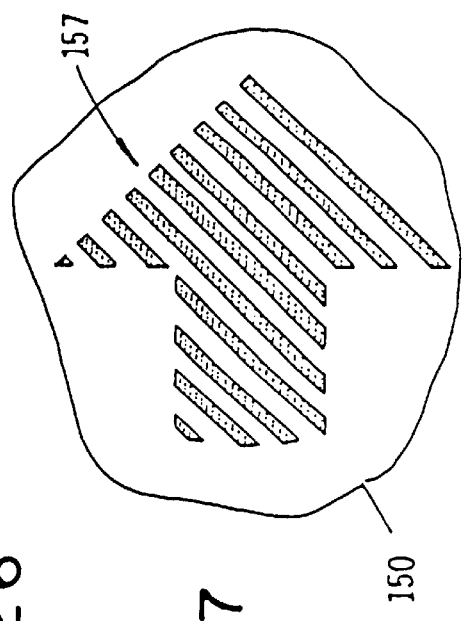
FIG. 27 is a fragmentary plan view of the symbol that is viewable by the user when the apparatus is in the configuration shown in FIG. 26.

In a manner presently to be described, the mechanical actuator means are deflected from their initial configuration whenever there is sufficient fluid pressure present within the fluid flow path to cause their outward deflection toward thin films 150 and 152. During operation the first mechanical actuator element 204 is deflected by fluid pressure of reservoir 100. More particularly, when there is sufficient fluid pressure in the fluid reservoir and fluid is being delivered by the stored energy means of the device, the first mechanical actuator means is deflected outwardly so as to urge the non-patterned portion 152a of indicator film 152 into expansion channel 202 (FIG. 26). As the film arches into channel 202, the printed portion of the film is transversely displaced a specific distance. This film displacement re-aligns the printed symbol patterns on the inferior film 150 with the mask pattern on the superior film 152 and results in a change of the symbol (in this case an arrow as shown in FIG. 27) that is visible through the support plate view aperture 146a.

As can be observed by referring to FIGS. 28 and 29, both the first and second mechanical elastomeric actuator elements 204 and 206 are inflated and deflected outwardly toward their respective extension channels when the device is filled and primed but not in a state of delivery or when there is a buildup of fluid pressure during delivery that is caused by blockage of the delivery line downstream from second mechanical actuator element 206. While element 204 can be deflected by normal line pressure, element 206 is deflected only by pressure buildup resulting from the downstream blockage. When both mechanical actuators are deflected outwardly in the manner shown in FIG. 28, both the superior and inferior films are displaced transversely to a second position revealing a second symbol, as for example, an X as viewed through the viewing aperture of the support plate (see FIGS. 28 and 29).

Figure 25:
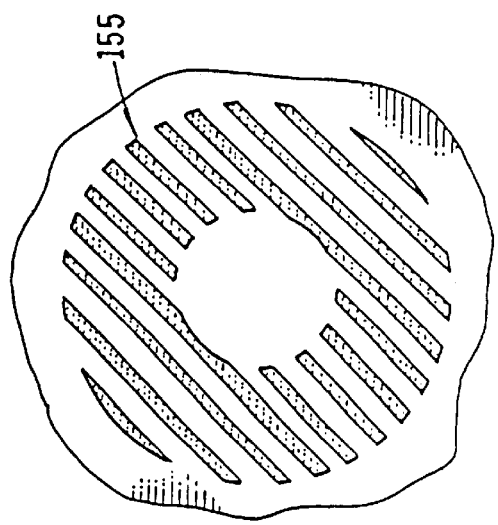
FIG. 25 is a fragmentary plan view of the symbol that is viewable by the user when the apparatus is in the configuration shown in FIG. 23.

A third alignment of symbol patterns as shown in FIGS. 23 and 25 is visible when the device is in an unfilled state or when the delivery line is open, the reservoir is empty and fluid delivery to the patient has been completed. In this case, there is no fluid pressure in the line on either the upstream or downstream side of the flow control means and thus both the first and second mechanical actuator elements are in a non-deflected position. In this condition, the inferior and superior films are not transversely displaced and thus exhibit a third combination of patterns resulting in a third symbol as, for example, a circle being visible through the viewing aperture of the support plate (see FIG. 25). Actuating elements 204 and 206 can be precisely tailored to deflect under various pressures thereby permitting great apparatus versatility.

Figure 22:
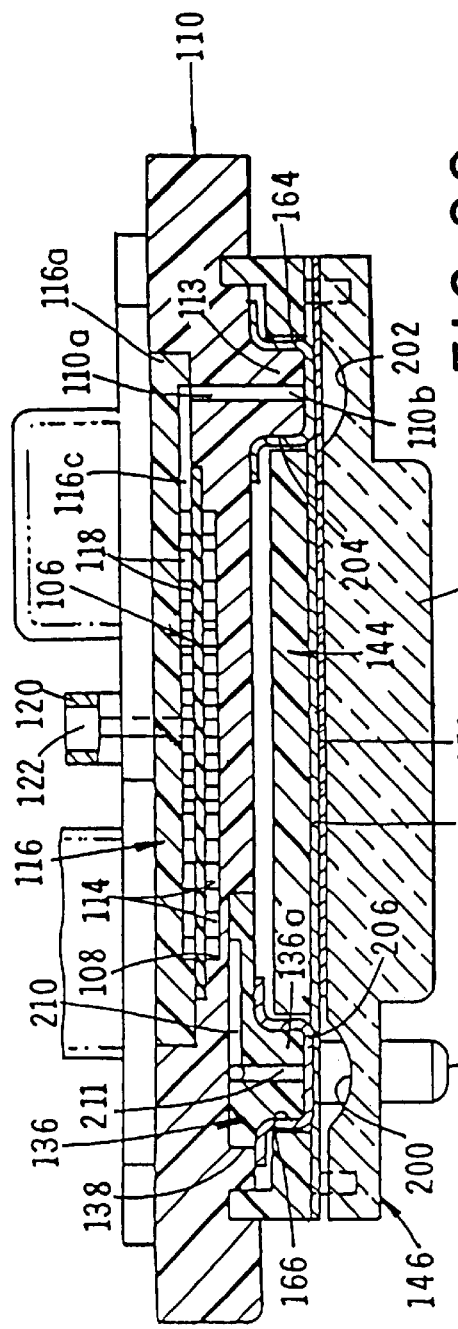
FIG. 22 is a cross-sectional view taken along lines 22—22 of FIG. 20.

In considering the method of operation of the device and the manner in which fluid flow through the device, reference should be made particularly to FIGS. 7 and 17. During the filling step, the fluid to be dispensed is introduced into reservoir 100 using the reservoir fill assembly 42. More particularly, fluid from container 52 will flow past the valve means of assembly 42, past umbrella valve 99 which is housed in an outlet port 99a and into reservoir 100 via inlet passageway 84. After filling and during the fluid dispensing step, the prestressed membrane 90 will tend to return toward a less distended configuration causing fluid within the reservoir to flow outwardly of reservoir 100, into passageway 102a and then into passageway 102. The fluid under pressure will next flow into passageway 122 of the inlet port of disc-shaped member 116. A portion of the fluid entering cavity or chamber 108 can by pass the fluid flow control assembly 106 and flow directly toward an ear-shaped extension 116a (FIG. 21) provided on member 116 via flow passageways 116b and 116c (see also FIG. 22). From passageway 116c, the fluid will flow under pressure into a passageway 110a formed in substrate 110 and toward passageway outlet 110b (FIG. 26). It is to be noted that passageway 110a extends through a protuberance 113 formed on substrate 110. This construction permits the fluid flowing into ear-shaped protuberance 116a to flow through passageway 110a and impinge directly upon flow indicator element 204 which sealably engages the protuberance, causing it to deform outwardly in a manner to force portion 152a of indicator film 152 to arch into expansion channel 202 (FIG. 26). This, in turn, will cause transverse displacement of indicator film 152 in the manner previously described.

As indicated in FIG. 28, fluid flowing through passageway 122 of disc-shaped member 116 will also be distributed over the upstream face of the flow control assembly 106 by the fluid distribution means, or protuberance 118 and will pass through the membrane at a predetermined controlled rate. The fluid flowing through the flow control means will be collected by the fluid collection means or protuberances 114 and then will flow into a passageway 210 (FIG. 28). The fluid will then flow outwardly of the device through fluid outlet 140 to which an appropriate infusion line can be connected. It is to be observed that a portion of the fluid flowing into outlet port assembly 136 is free to flow through passageway 211 provided in a protruding portion 136a thereof. If there is a blockage which prevents continued free fluid flow outwardly of the device through outlet 140 fluid, under pressure, will impinge upon indicator element 206 causing it to deflect outwardly in the manner shown in FIG. 28. This outward deflection of element 206 will urge a portion of indicator film 150 into receiving channel 200 of the lens plate causing transverse movement of film 150 so as to reposition film 150 relative to film 152. Should fluid flow into passageway 211 cease, indicator element 206 will return to its at rest position as will film 150. Similarly, if fluid flow from the reservoir ceases, film 152 will also return to its at rest position thereby once again causing the "O" symbol to be viewable through the viewing lens.

At the time of use of the apparatus of the invention, and with the adapter assembly 48 in the sealed condition shown in FIG. 6, closure cap 76 is first removed from the assembly. This done, the assembly can be mated with the dispenser apparatus 40 in the manner shown in FIG. 7 and lockably interconnected therewith by connector means which here comprises a bayonet type connector arrangement of the character best seen in FIGS. 2, 9, and 11. More particularly, as shown in FIG. 2, the connector boss on base 88 of the dispenser unit 40 is provided with a dispenser connector comprising a plurality of circumferentially spaced-apart tab receiving slots 88a. Similarly, the inboard end of the adapter subassembly 48 is provided with an adapter connector comprising a plurality of circumferentially spaced apart locking ears 114 (FIGS. 9 and 11) which are adapted to be received within slots 88a. With this construction, after locking ears 114 have been received within slots 88a, rotation of adapter subassembly 48 relative to the dispensing means will bring ears 114 into locking engagement with the dispenser unit thereby operably interconnecting the reservoir fill assembly with the dispenser unit 40. To enable smooth rotation of the adapter subassembly relative to the dispenser unit, an antilock elastomeric ring 117 is formed on the front face of member 70 (FIG. 9).

During mating of the adapter assembly 48 with the dispenser unit 40, a generally cross-shaped extension 82a provided on connector subassembly 82 functions as a valve operating means to move valve 74 of the valve means away from seat 70a. During mating, elastomeric ring 117 sealably engages connector subassembly 82 to form a substantially leak-tight seal.

With adapter subassembly 48 suitably mated with the dispenser apparatus 40, cap 78 is removed from the inboard end of adapter assembly 48 (FIG. 6) and the first end of vial assembly 46 is inserted into chamber 62d of adapter subassembly 48. With the vial cartridge assembly inserted into chamber 62d sleeve 50 is then mated with adapter assembly 48 in the manner shown in FIG. 7 by inserting the leading edge of the pusher sleeve into annular space 62c. A forward movement of the pusher sleeve into annular space 62c will cause pusher rod 66 to move into pressural engagement with plunger 64. As previously mentioned, the fluid within chamber 54 of the vial assembly will resist inward movement of plunger 64 causing the entire vial assembly to move forwardly within chamber 62d to the position where cannula 58 of the adapter subassembly interengages pierceable septum 56a of the container assembly. As previously mentioned, cannula 58 and septum 56a comprise a part of the flow control means of the invention. A continued inward force on the pusher sleeve 50 will cause hollow cannula 58 to pierce septum 56a thereby opening fluid communication between chamber 54 of vial 52 and passageway 70b of valve support assembly 70. Exertion of a continued inward pressure on pusher sleeve 50 will cause plunger 64 to move forwardly of vial chamber 54 causing the fluid contained within chamber 54 to flow into hollow cannula 58 and past check valve 74 of the flow control means of the invention. Because valve member 74 of the adapter subassembly has been moved away from seat 70a by extension 82a, fluid will flow into bypass flow channels 70c formed in member 70. The fluid under pressure will next flow into a chamber 99a formed in base 88. Disposed within chamber 99a is an umbrella valve 99 which also forms a part of the flow control means of the invention and is of a conventional construction well known to those skilled in the art. Umbrella valve 99 permits fluid flow toward passageway 84 but blocks flow in the opposite direction. As the fluid under pressure flows through inlet passageway 84, the stored energy means, or member 90 will be further distended causing additional internal stresses to be built up within the member, which stresses tend to return the member toward its less stressed starting configuration. With reservoir 100 thusly filled, valve member 99 will prevent fluid flow in a direction toward the reservoir fill assembly 42.

Turning particularly to FIGS. 7, 8, 14 and 15, it is to be noted that pusher sleeve 50 is provided with a plurality of longitudinally spaced, upstanding teeth 130 (FIG. 8) which form a part of the locking means of the invention for locking sleeve 50 to the adapter assembly after filling of reservoir 100 has been accomplished. As sleeve 50 is inserted into annular space 62c, teeth 130 will slide under an inwardly extending tab 132 provided on a locking clip 134 which also forms a part of the locking means and which is carried within a relief 136 formed in adapter assembly 48 in the manner shown in FIG. 9. When sleeve 50 is fully inserted into annular space 62c, tab 132 will lockably engage rearward most tooth 130a (FIG. 8) preventing withdrawal of the sleeve from space 62c.

Following the filling step, the adapter assembly 48 can be counterrotated in a manner to be disconnected from the dispenser unit 40 and the closure cap 80 once again placed over subassembly 82 to maintain the subassembly in a protected substantially sterile condition.

At any time after the reservoir filling step, the fluid contained within reservoir 100 can be delivered to the patient by affixing the dispenser unit to the patient using suitable interconnection means. With the unit affixed to the patient, opening of the infusion line will permit the stored energy means or member 90 to move toward its first, less distended configuration thereby controllably urging fluid flow outwardly of the device via outlet portion 140.

As previously mentioned, various fluids can be dispensed from reservoir 100 including, by way of example, beneficial agents such as medicaments of various types, drugs, pharmaceuticals, hormones, antibodies, biologically active materials, elements, chemical compounds, or any other suitable materials used in diagnostic cures, medication, treatment or preventing of diseases, or maintenance of the good health of the patient.

Figure 41:
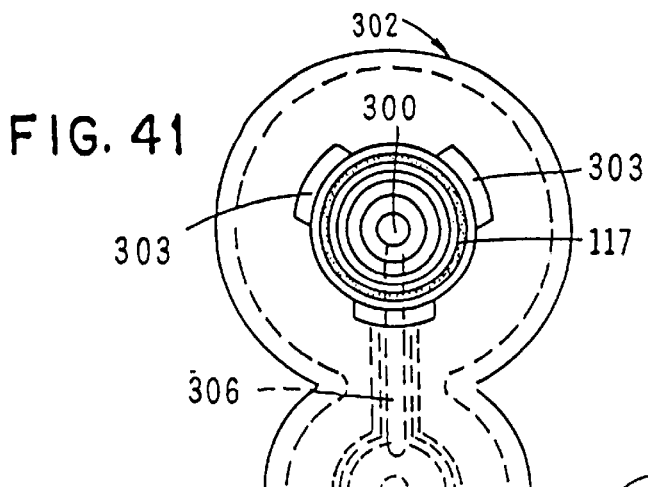
FIG. 41 is a view taken along lines 41—41 of FIG. 34.

Referring next to FIGS. 30 through 41, alternate embodiments of the dispensing apparatus of the invention are there shown. As before, the apparatus comprises a fluid dispenser and a cooperating reservoir fill assembly. The alternate embodiments shown in FIGS. 30 and 41 are similar in many respects to the embodiments in FIGS. 1 through 12 and like numbers are used in these latter drawings to identify like components. In FIG. 30, one form of alternate embodiment is shown fully assembled with the reservoir fill component operably connected to the fluid dispenser component. The fluid dispenser component, which is identified in FIG. 30 by the numeral 40, is identical in construction and operation to the dispenser component previously described in connection with FIGS. 1 through 29.

Figure 34:
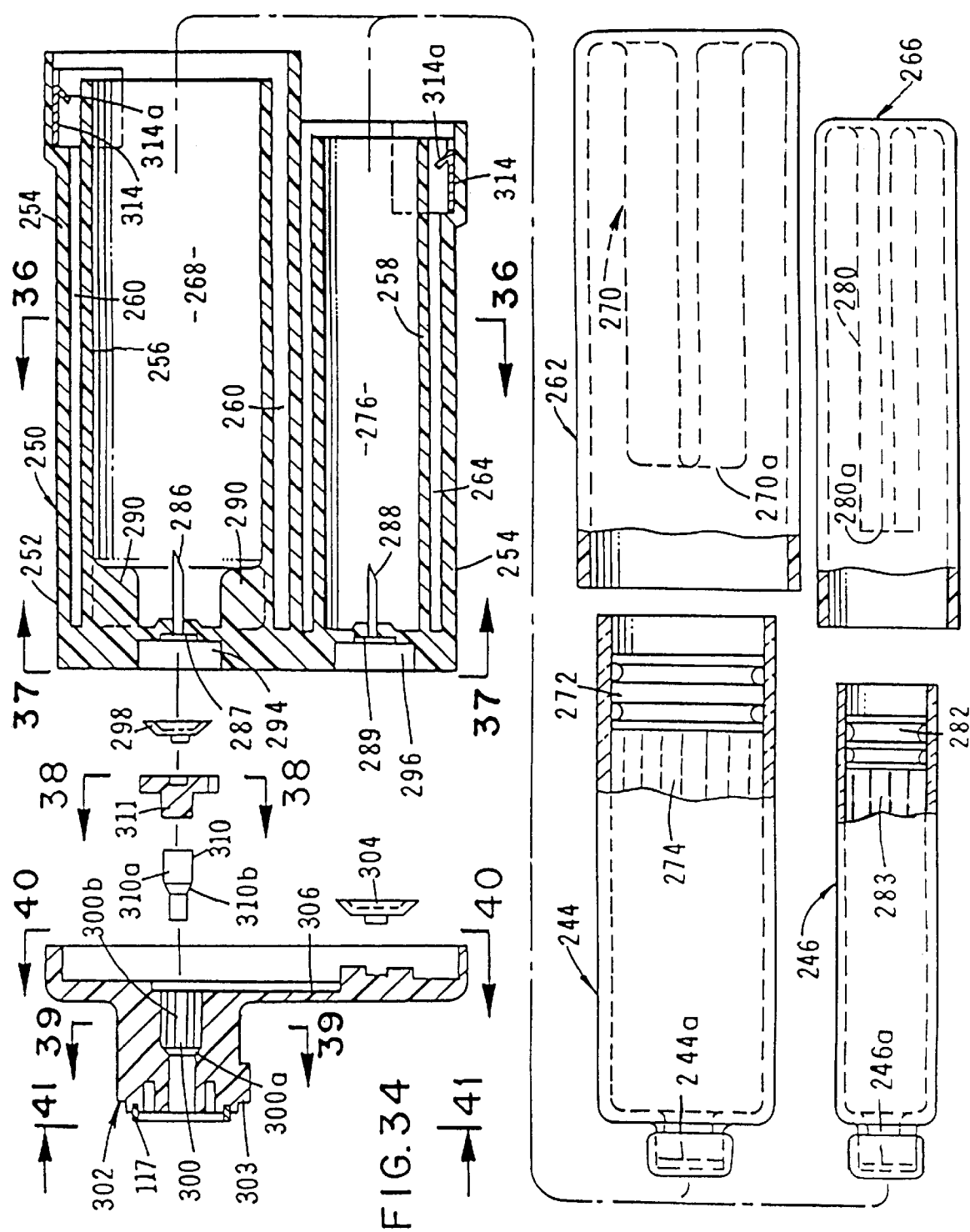
FIG. 34 is an exploded, cross-sectional view of the reservoir fill assembly of this latest form of the invention.

The major difference between the apparatus of this latest form of the invention and that shown in FIGS. 1 through 29 resides in the fact that the reservoir fill assembly, which is generally designated by the numeral 242, comprises multiple container assemblies 244 and 246 which are receivable within a differently configured adapter assembly 250 (FIG. 30). Referring particularly to FIGS. 30, 30A, 34, and 36, it is to be noted that body 252 of adapter subassembly 250 includes an outer wall 254 and radially spaced apart inner, generally cylindrically shaped walls 256 and 258 (FIGS. 34 and 36).

Walls 254 and 256 define therebetween an elongated annular space 260 within which a first sleeve component 262 is telescopically received (FIG. 30A). Similarly, walls 254 and 258 define therebetween an elongated annular space 264 within which a second sleeve component 266 is received. As shown in FIG. 30, container assembly 244 is closely receivable with a chamber 268 formed internally of wall 256 of the adapter subassembly and can be urged forwardly of chamber 268 by inward telescopic movement of sleeve 262 into space 260. As was the case in the earlier described embodiment, the inboard end 270a of pusher rod 270 engages a first plunger 272 and urges it inwardly of a container reservoir 274 as sleeve 262 is moved inwardly of annular space 260 (FIG. 30A). In a similar fashion, container assembly 246 is closely receivable within a chamber 276 formed internally of wall 258 and can be urged forwardly of chamber 276 by inward telescopic movement of sleeve 266 into space 264. During mating of the second container assembly with the adapter assembly, the inboard end 280a of a pusher rod 280 engages a second plunger 282 and urges it inwardly of a container reservoir 283 as sleeve 266 is moved inwardly of annular space 264 (FIG. 30A).

During the initial mating of sleeves 262 and 266 with adapter subassembly 250, the resistance of the fluid within the containers of the container assemblies or vial cartridges will resist movement of plungers 272 and 282 inwardly of their respective reservoirs so as to cause the vial cartridges to initially move inwardly of their respective chambers to a position wherein a septum 244a of container assembly 244 is engaged by a first cannula 286 of the adapter subassembly and a septum 246a of container assembly 246 is engaged by a second cannula 288 of the adapter subassembly (see also FIG. 33B). As shown in FIG. 36, guide ribs 290 formed interiorly of chamber 268, guide the neck portion of vial assembly 244 toward cannula 286. A continued inward force on sleeves 262 and 266 will cause cannulas 286 and 288 to pierce their respective septums 244a and 246a in the manner shown in FIG. 30, thereby opening fluid communication between the reservoirs of the vial assemblies 244 and 246 and the internal fluid passageway of cannulas 286 and 288.

Once each of the septums has been pierced, the pusher rods of the pusher sleeves 262 and 266 will urge plungers 272 and 282 forwardly of their respective reservoirs causing the fluid within the reservoirs to flow into the central fluid passageways of cannulas 286 and 288 and, via generally "X" shaped passageway 287 and 289 (FIG. 37), toward valve support chambers 294 and 296 formed in body 252 (FIG. 34). Disposed within chamber 294 is a first umbrella valve 298 which is of conventional construction. Umbrella valve 298 permits fluid flow from chamber 294 toward a fluid passageway 300 which is formed in a cover member 302 which is connected to adapter body 252 by any suitable means to form the construction shown in FIG. 30. However, valve 298 is constructed so as to block fluid flow in an opposite direction. Disposed within chamber 296 is a second umbrella valve 304 which permits fluid flow toward a fluid passageway 306 formed in cover 302 but blocks fluid flow in the opposite direction (see FIG. 30). As before, umbrella valves 298 and 304 comprise portions of the flow control means of the invention.

Formed within passageway 300 which is in communication with passageway 306 is a valve seat 300a and a plurality of circumferentially spaced fluid flow grooves 300b (FIGS. 34, 39, and 40). Disposed within passageway 300 is a valve means shown here as a check valve 310 for permitting fluid flow from cannula 286 and fluid passageway 300 toward the fluid reservoir of the dispenser assembly but blocking fluid flow in the opposite direction. Located between check valve 310 and umbrella valve 298 is a valve retainer member 311 which maintains the umbrella valve in position (see also FIG. 38). As shown in FIG. 34, check valve 310, which is of conventional constriction, includes a body portion 310a and a seat portion 310b which sealably engages seat 300a when valve 310 is in a closed position. Valve 310 also forms a part of the flow control means of the invention for controlling the flow of fluid toward the dispenser component.

Figure 42:
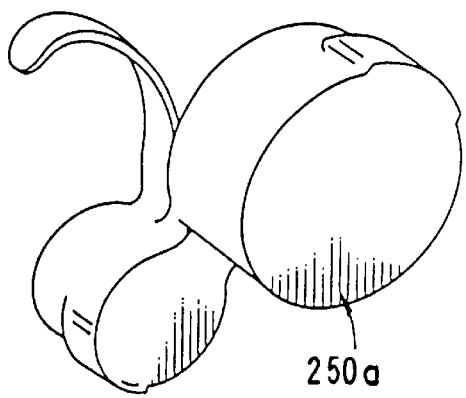
FIG. 42 is a generally perspective view of the closure cap embodiment of the present component of the invention for sealably closing the adapter component of the reservoir fill assembly of the invention shown in FIG. 30A.

It is to be understood that container assemblies 244 and 246 can be filled with various fluids including diluents as well as a wide variety of beneficial agents. Accordingly, following interconnection of the fill assembly with the dispenser component in the manner previously described, the multi-vial reservoir fill assembly of this latest form of the invention can advantageously be used to sequentially fill, or partially fill, the reservoir of the fluid dispenser with fluids contained within the container assemblies for sequential delivery to the patient. Alternatively, the fill assembly can be used to simultaneously fill the fluid dispenser with the fluids contained within container assemblies 244 and 246 thereby creating a fluid mixture which can be delivered to the patient overtime. Referring to FIGS. 34 and 41, it is to be noted that cover 302 is provided with locking tabs 303 which mate in bayonet locking fashion with slots 88a formed in the base of the dispenser component. Prior to use of the adapter subassembly, the open ends thereof are closed by a tear-away cap 250a of the character shown in FIG. 42.

Turning particularly to FIGS. 31A, 31B and 35, it is to be noted that pusher sleeves 262 and 266 are provided with a plurality of longitudinally spaced, upstanding teeth 312 which form a part of the locking means of the invention for locking sleeves 262 and 266 to the adapter assembly after the filling of the reservoir of the fluid dispenser. As the sleeves are inserted into annular 48 ( spaces 260 and 264, teeth 312 will slide under an inwardly extending tab 314a provided on a pair of locking clips 314 which are of the character shown in Figures 30A and 35 and which also form a part of the locking means of the invention. Clips 314 are carried within reliefs 316 and 318 formed in the adapter assembly in the manner shown in FIG. 30A. When the two sleeves are fully inserted into their respective annular spaces, tabs 314a will lockably engage rearward most tooth 312a on the sleeves thereby preventing withdrawal of the sleeves from the annular spacer.

As before, following the filling step, the adapter assembly 250 can be disconnected from the dispenser unit 40 and the closure cap 80 is once again placed over subassembly 82 to maintain the subassembly in a protected substantially sterile condition.

Turning to FIG. 32, an alternate form of coupler mechanism of the invention is there illustrated. The primary difference between this latest form of the invention and those previously described herein resides in the fact that the cover 302a of the adapter assembly of the reservoir fill component is provided with a slit septum 318 in place of the valve means or valve 310. With this construction, in order to enable mating of the reservoir fill assembly with the dispenser unit, the dispenser unit is provided with a blunt end cannula 320 which is adapted to pierce slit septum 318.

Referring next to FIG. 33A, still another form of reservoir fill assembly of the invention is there illustrated. This fill assembly is identical in construction and operation to that shown in FIGS. 34 through 40 save that septum 244a of the container subassembly 244 has been replaced by a slit septum 320 and piercing cannula 286 has been replaced by a blunt end cannula 322. Use of the blunt end cannula 322 and the slit septum 320 in connection with the transfer of fluid from larger container assembly 244 somewhat simplifies the manufacture of the cover member and reduces the cost thereof.

Figure 43:
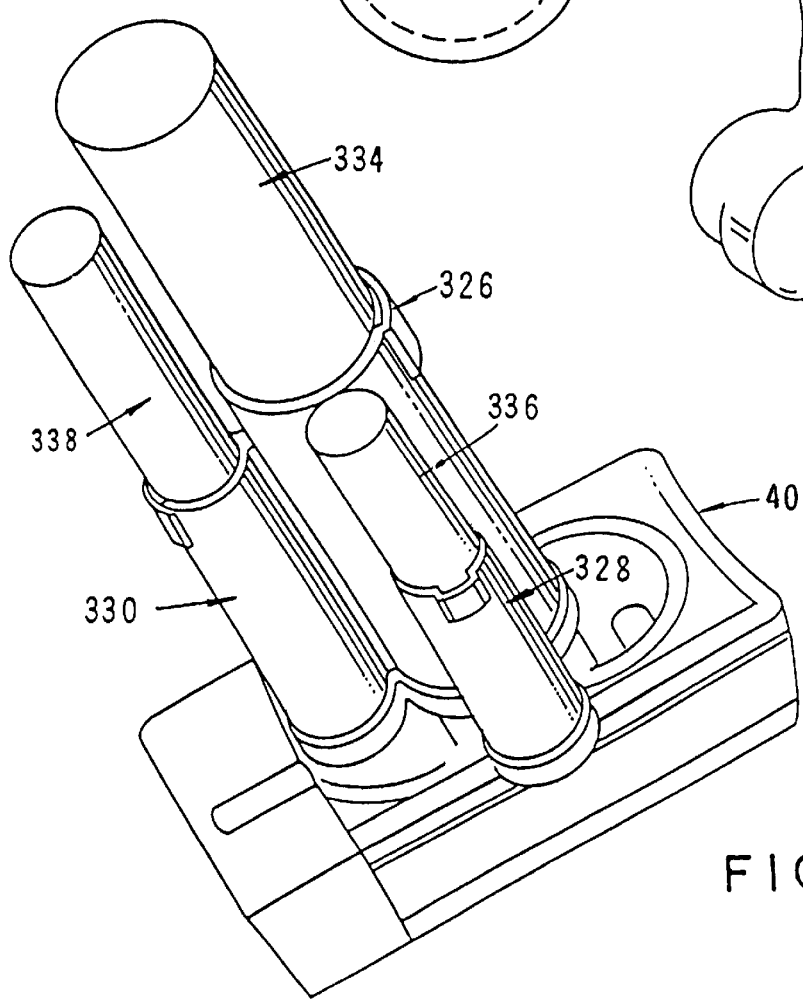
FIG. 43 is a generally perspective view of another embodiment of the fluid delivery apparatus of the invention.
Figures 44, 45:
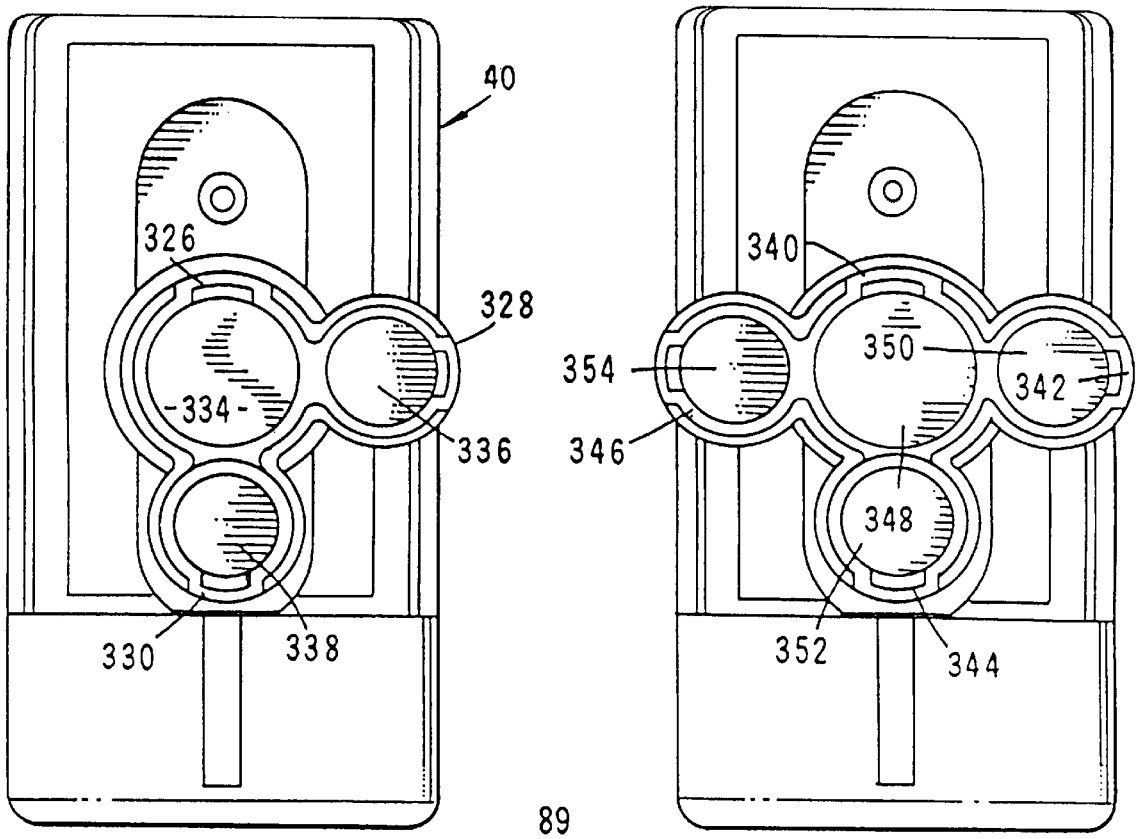
FIG. 44 is a bottom plan view of the embodiment of the invention shown in FIG. 43.
FIG. 45 is a bottom plan view of still another form of the apparatus of the invention.
Figure 47:
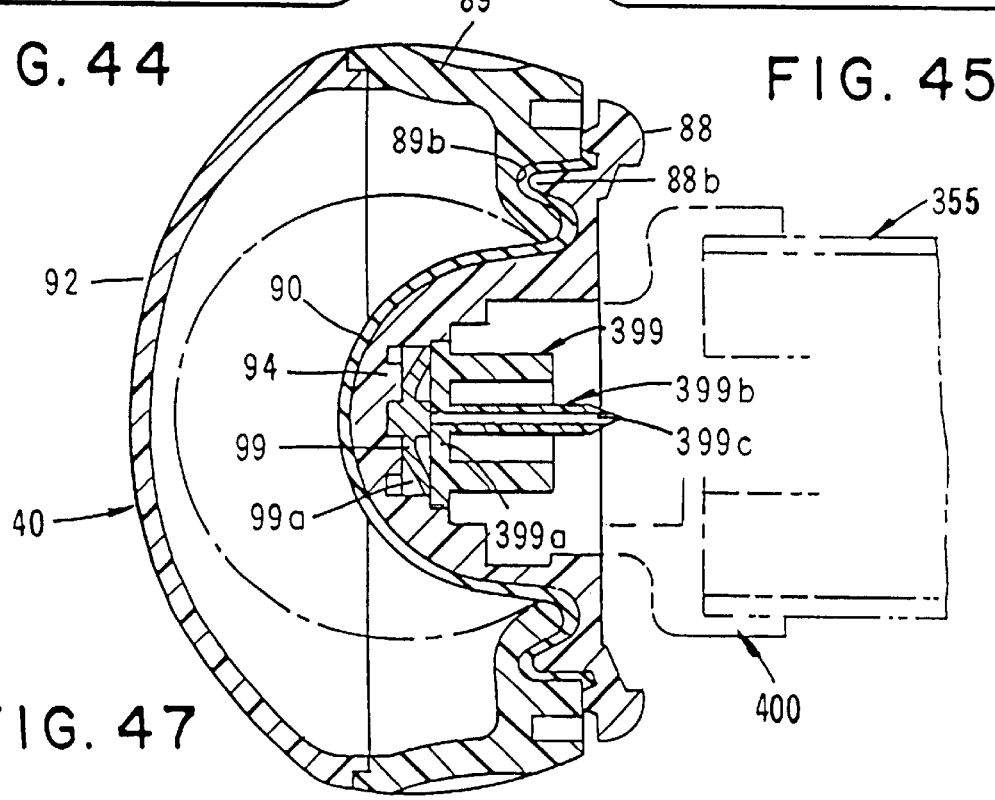
FIG. 47 is a cross-sectional view taken along lines 47—47 of FIG. 46.

Turning next to FIGS. 43, 44 and 45, additional alternate forms of the fluid delivery apparatus are there shown. More particularly, FIGS. 43 and 44 show a reservoir fill assembly which has the capability of filling the fluid reservoir of the fluid dispenser 40 with fluid from three separate container assemblies. As best seen in FIGS. 43 and 44, one form of this latest embodiment of the invention includes first, second and third circumferentially spaced adapter components 326, 328 and 330, each of which contains a separate container assembly. These adapter components are similar in construction and operation to those previously described herein and are adopted to slidably receive pusher sleeves 334, 336 and 338 respectively which are also of similar construction and operation to those previously described.

FIG. 45 illustrates a reservoir fill assembly which has the capability of filling the fluid reservoir of the fluid dispenser with fluids from four container assemblies which assemblies are housed within circumferentially spaced adapter components 340, 342, 344, and 346 and are operated by pusher sleeves 348, 350, 352 and 354 respectively. Once again, these container assemblies, adapter components, and pusher sleeves are of similar construction and operation to those previously described herein.

Figure 46:
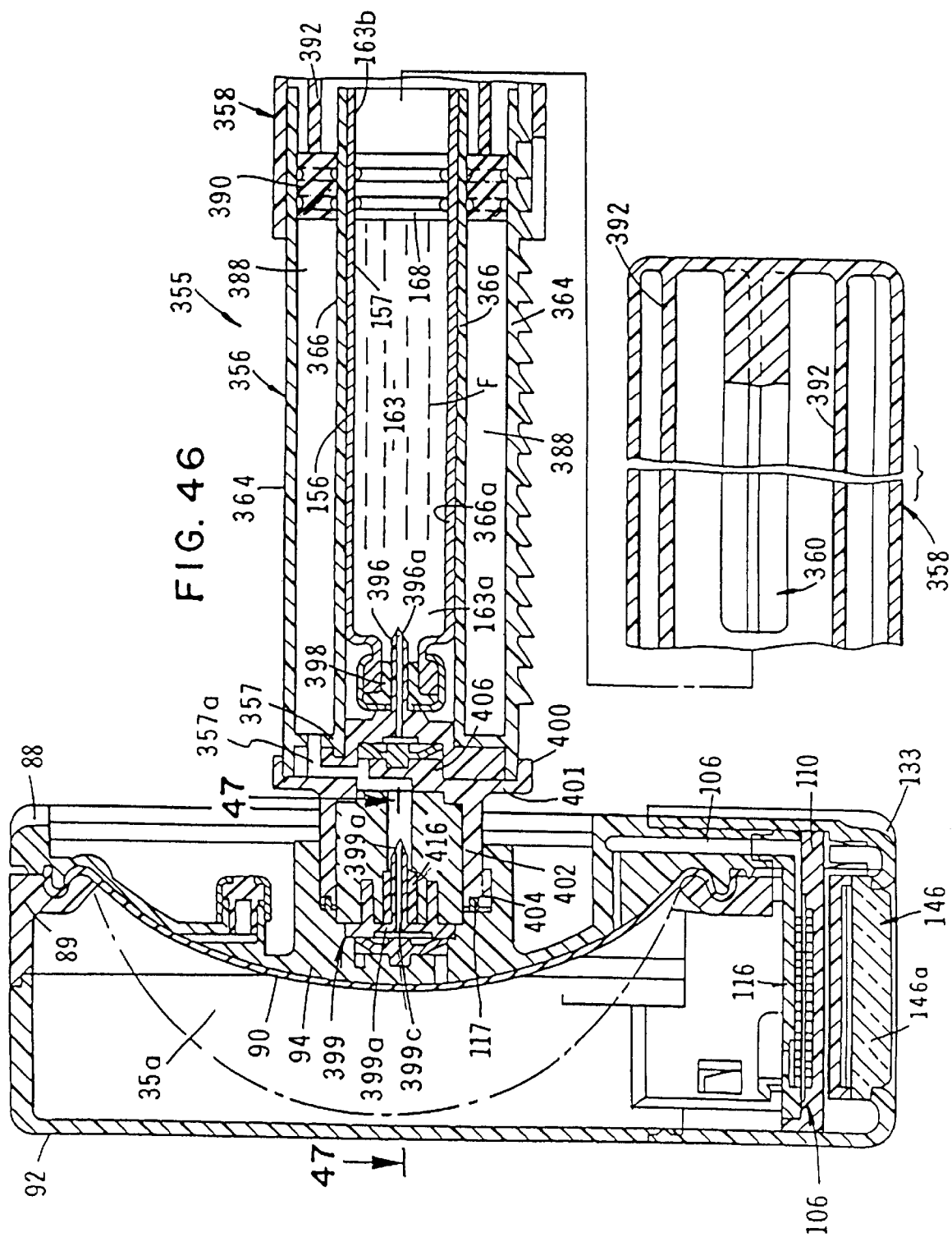
FIG. 46 is a cross-sectional view of another form of the fluid dispenser of the invention showing the dispenser component operably mated with an alternate form of reservoir fill assembly.
Figure 55:
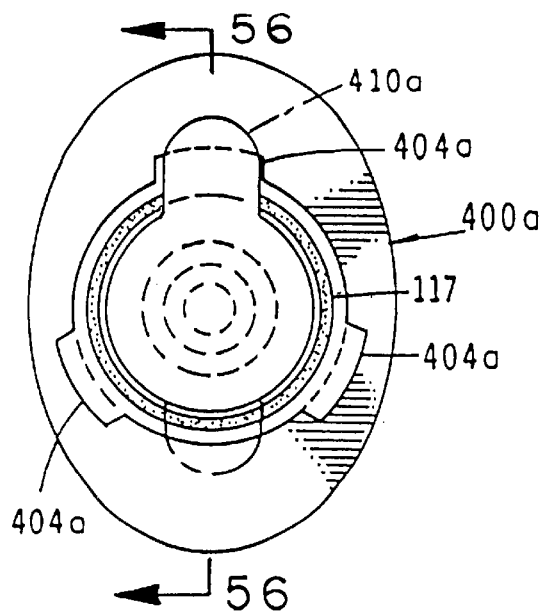
FIG. 55 is a view taken along lines 55—55 of FIG. 53 partly broken away to show internal construction.

Turning next to FIG. 46, another embodiment of the present invention is there shown. In this latest embodiment, the fluid dispenser component is quite similar to that previously described as is the fill assembly. Accordingly, where appropriate, like members are used to designate like components. Once again, this latest embodiment of the reservoir fill assembly, which is generally designated by the numeral 355 comprises three major components, namely a container subassembly 156 which is substantially identical to that previously described, an adapter subassembly 356 which is of slightly different construction from that previously described, and an adapter or pusher sleeve 358 which is also similar to that previously described. As before, container subassembly 156 includes a container such as a vial 157 which contains the medicinal fluid "F" with which the reservoir of the dispensing apparatus is to be filled. As in the earlier described embodiments, the adapter subassembly 356 functions to interconnect the reservoir fill assembly with the fluid dispenser 40 in a manner such that fluid can be transferred from container 157 to the reservoir of the fluid dispenser here generally designated by the numeral 359. This fluid transfer is accomplished by urging sleeve 358 forwardly over the adapter subassembly in the manner indicated in FIG. 46. More particularly, to expel fluid from fluid chamber 163 of container 157 and into reservoir of the dispenser component, a plunger 168 is telescopically movable within chamber 163 by pusher sleeve subassembly 358 which includes pusher means shown here as a pusher rod 360 which, as before, is integrally formed with end wall of the sleeve.

It is to be noted that adapter subassembly 356 of this latest embodiment of the invention includes an outer, generally cylindrically shaped wall 364 and an inner, generally cylindrically shaped wall 366 which define therebetween an elongated annular space 388 within which an annular shaped sealing ring 390 is moved longitudinally by an inner wall 392 of pusher sleeve 358. Annular space 388 comprises a diluent reservoir for containing a suitable diluent. Container assembly 156 is closely receivable within a chamber 366a formed internally of wall 366 of the adapter subassembly and can be urged forwardly of chamber 366a by inward movement of sleeve 358 relative to adapter assembly 356.

Following interconnection of the reservoir fill assembly with the dispenser unit, in the manner shown in FIG. 46, a continued exertion of an inward force on sleeve 358 will cause cannula 396 of the adapter subassembly 356 to pierce septum 398 of the container subassembly in the manner shown in FIGS. 46. This action opens fluid communication between reservoir 163 of vial 157 and the internal fluid passageway 396a of cannula 396. Once septum 398 has been pierced, pusher rod 360 will urge plunger 168 forwardly of reservoir 163 from a first location proximate open end 163b to a second location proximate end 163a. As plunger 168 moves forwardly of reservoir 163, fluid within the reservoir will be caused to flow into cannula passageway 396a for delivery toward the reservoir of the fluid dispenser via a hollow cannula assembly 399 (FIG. 48). During the reservoir filling step the medicinal agent carried within reservoir 163 of vial 157 will be delivered to the reservoir of the dispenser component as will the diluent contained within space 388 with the diluent being intermixed with the medicinal agent as the fluid flows into the dispenser reservoir.

Figure 59:
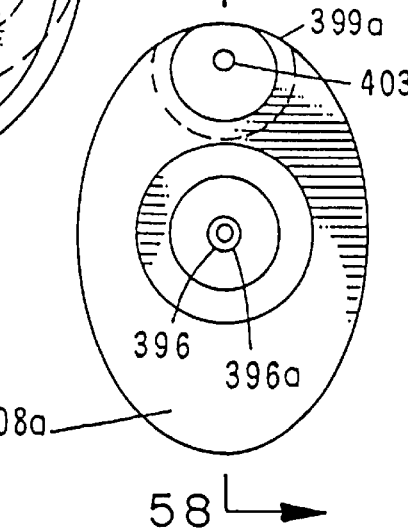
FIG. 59 is a view taken along lines 59—59 of FIG. 58.
Figure 58:
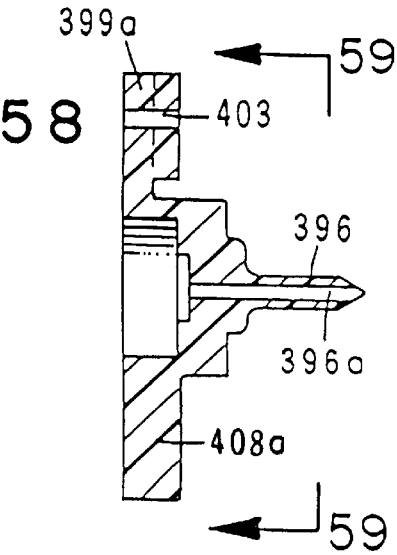
FIG. 58 is a cross-sectional view taken along lines 58—58 of FIG. 59.
Figure 62:
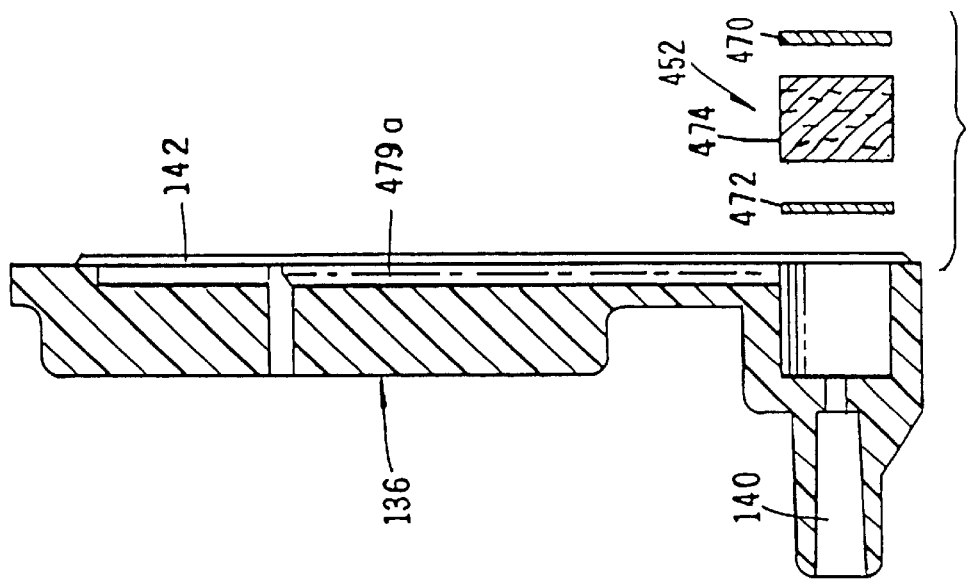
FIG. 62 is an enlarged, cross-sectional view taken along lines 62—62 of FIG. 60 showing the flow control elements exploded from housing within which they are mounted.

A cover member 400 is connected to wall 364 of the adapter body by any suitable means such as sonic bonding. Cover 400 includes a flanged plate portion 401 and a generally cylindrically shaped extension 402 integrally formed with plate 401. Formed proximate the outboard end of extension 402 are connector means shown here as circumferentially spaced locking tabs 404. Plate 401 of cover 400 includes a generally circular shaped internal recess 406 which receives a cannula support plate 408 of cannula assembly 399 which plate supports cannula 396 (FIGS. 59 and 58). Wall 357 of adapter 355 is provided with a passageway 357a which functions to permit the flow of diluent from space 388 toward cannula 399b (FIG. 46).

Prior to use, the adapter assembly can be appropriately sealed by a tear-away cap. Following removal of this cap, the reservoir fill assembly can be lockably mated with the fluid dispenser in the manner previously described by inserting tabs 404 into the openings provided in the dispenser base of the fluid dispenser.

As shown in FIG. 46, the fluid dispenser of this latest form of the delivery apparatus is quite similar to that shown in FIGS. 1 through 7. However in this latest fluid dispenser construction, the extension 82a of dispenser connector 82 has been replaced with hollow cannula assembly 399 which includes a cannula support plate 399a and a cannula 399b having a fluid passageway 399c. Similarly, valve member 58 has been replaced by a slit septum 416 which is readily pierceable by cannula 399b.

It is to be understood that the same type of coupling mechanism depicted in FIGS. 1 through 7 can be used in the dispenser embodiment shown in FIG. 46. For example, as shown in FIG. 50 where like numbers are used to identify like components, the same type of dispenser connector 82 with extension 82a could be used in conjunction with a valve member such as valve member 74 shown in FIGS. 7 and 50.

Additionally, as shown in FIG. 49 where like numbers are used to identify like components, the dispenser connector could be provided with a slit septum 420 and the fill reservoir connector could be provided with a cannula assembly 422 which comprises a cannula support 422a and a blunt end hollow cannula 422b. A tear-away cover 423 is here used to protect cannula 422b.

Referring to FIGS. 51 through 59, another embodiment of the present invention is there shown. In this latest embodiment, the fluid dispenser component is very similar to that shown in FIG. 46 as is the fill assembly. Accordingly, where appropriate, like members are used to designate like components. The fill assembly of this latest form of the invention, which is generally designated by the numeral 355a comprises three major components, namely a container subassembly 156 which is substantially identical to that previously described, and an adapter subassembly 356a which is of a slightly different construction from that previously described, and an adapter or pusher sleeve 358a which is also similar to that shown in FIG. 46. As before, container subassembly 156 includes a container such as a vial 157 which contains the medicinal fluid "F" with which the reservoir of the dispensing apparatus is to be filled. As in the earlier described embodiments, the adapter subassembly 356a functions to interconnect the reservoir fill assembly with the fluid dispenser in a manner such that fluid can be transferred from container 157 to the reservoir of the fluid dispenser 359. This fluid transfer is accomplished by urging sleeve 358a forwardly over the adapter subassembly in the manner indicated in FIG. 53. More particularly, to expel fluid from fluid chamber 163 of container 157 and into the reservoir of the dispenser component, a plunger 168 is telescopically movable within chamber 163 by pusher sleeve subassembly 358a which includes pusher means shown here as a pusher rod 360a which, as before, is integrally formed with the end wall of the sleeve.

Referring particularly to FIGS. 51, 53, and 54, it is to be noted that adapter subassembly 356a of this last embodiment of the invention includes an outer, generally elliptical shaped wall 364a and an inner, generally cylindrically shaped wall 366 which define therebetween an elongated annular-like space 388a within which an elliptically shaped sealing ring 390a is moved longitudinally by an inner wall of pusher sleeve 358a. Container assembly 156 is closely receivable within a chamber 366a formed internally of wall 366 of the adapter subassembly and can be urged forwardly of chamber 366a by inward movement of sleeve 358a relative to adapter assembly 356a.

Following interconnection of the reservoir fill assembly with the dispenser unit, a continued exertion of an inward force on sleeve 358a will cause cannula 396 of the adapter subassembly 356a to pierce septum 398 of the container subassembly in the manner shown in FIG. 53 (see also FIGS. 58 and 59). This action opens fluid communication between reservoir 163 of vial 157 and the internal fluid passageway 396a of cannula 396. Once septum 398 has been pierced, pusher rod 360a will urge plunger 168 forwardly of reservoir 163 from a first location proximate open end 163b to a second location proximate end 163a. As plunger 168 moves forwardly of reservoir 163, fluid within the reservoir will be caused to flow into cannula passageway 396a for delivery toward the reservoir of the fluid dispenser via a hollow cannula assembly 399. During this reservoir filling step, as ring 390a moves forwardly of space 388a, the diluent contained within space 388a will be urged to flow toward the hollow cannula of the dispenser component and will be intermixed with the medicinal fluid contained within vial 157.

Figure 56:
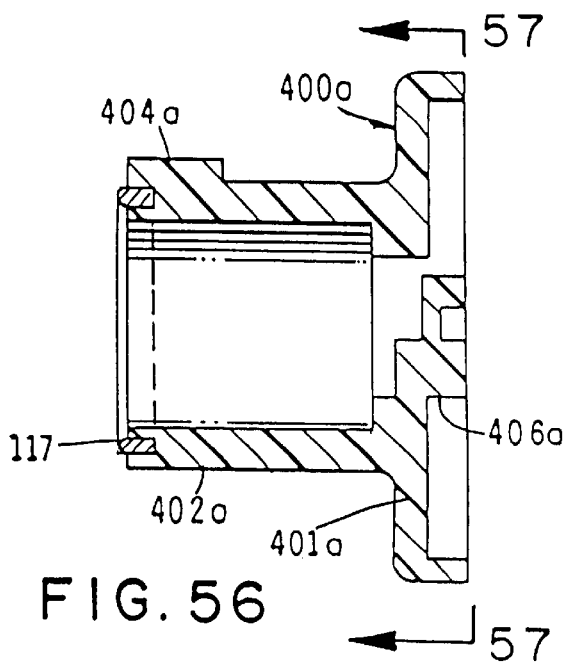
FIG. 56 is a cross-sectional view taken along lines 56—56 of FIG. 55.
Figure 57:
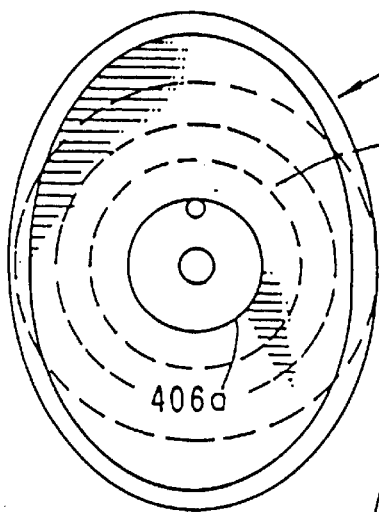
FIG. 57 is a view taken along lines 57—57 of FIG. 56.

As best seen in FIGS. 51, 52, 53 and 55, a cover member 400a is connected to wall 364a of the adapter body by any suitable means such as sonic bonding. Cover 400a includes a flanged plate portion 401 a and a generally cylindrically shaped extension 402a integrally formed with plate 401 a. Formed proximate the outboard end of extension 402a are connector means shown here as circumferentially spaced locking tabs 404a. Plate 401a of cover 400a includes a generally circular shaped internal recess 406a which receives a cannula support plate 408a of cannula assembly 399 which plate supports cannula 396 (FIGS. 56 and 58). Plate 408a is provided with a fluid passageway 403 which indexes with a passageway 405a formed in wall 405 of adapter 356a. Passageways 403 and 405a permit flow of the diluent contained within space 388a toward the dispenser component due to the urging of ring 390a.

Prior to use, the adapter assembly is sealed by a peel-away seal 410 and a tear-away cap 412 (FIG. 52). Following removal of seal 410 and cap 412, the reservoir fill assembly can be lockably mated with the fluid dispenser in the manner previously described by inserting tabs 404a into the openings provided in the dispenser base of the fluid dispenser.

Turning to FIGS. 60 through 63, an alternate form of the dispenser component with alternate dispenser flow control means is there shown. As before, these alternate dispenser flow control means function to control fluid flow outwardly of the device. In the embodiment of the invention shown in FIGS. 60, 60A, 61, and 62, the dispenser flow control means comprises a first flow control means 450 and a second back-up flow control means 452. First flow control means 450 includes a fluid flow rate control wafer 450a, which is closely received within a cavity 454 formed in a support means, shown here as a membrane support structure 456. Support structure 456 is similar in many respects to the earlier described structure 110 (FIG. 18) but the fluid distribution means which comprises a multiplicity of circumferentially spaced, manifolding stand-off elements 114 has been replaced by cavities 454 and 458. Wafer 450a is held in position within cavity 454 by a tube-like, elastomeric member 440 (FIGS. 60 and 60A) which is receivable within a recess 462 formed in a boss 464 provided on a disc-like member 466 (FIG. 60). Member 466 is similar in many respects to member 116 which is shown in FIG. 21. However, the manifolding stand-offs 118 provided on member 116 have been replaced in member 466 with boss 464 which is provided with cavity 462 (see FIG. 60). When member 466 is in place within cavity 458 of structure 456, wafer 450a is securely positioned between elastomeric sleeve 440 and the bottom wall of cavity 454. As before, a vent patch 111 vents to atmosphere any air trapped within the fluid passageways of the device via a vent "V".

Figure 61:
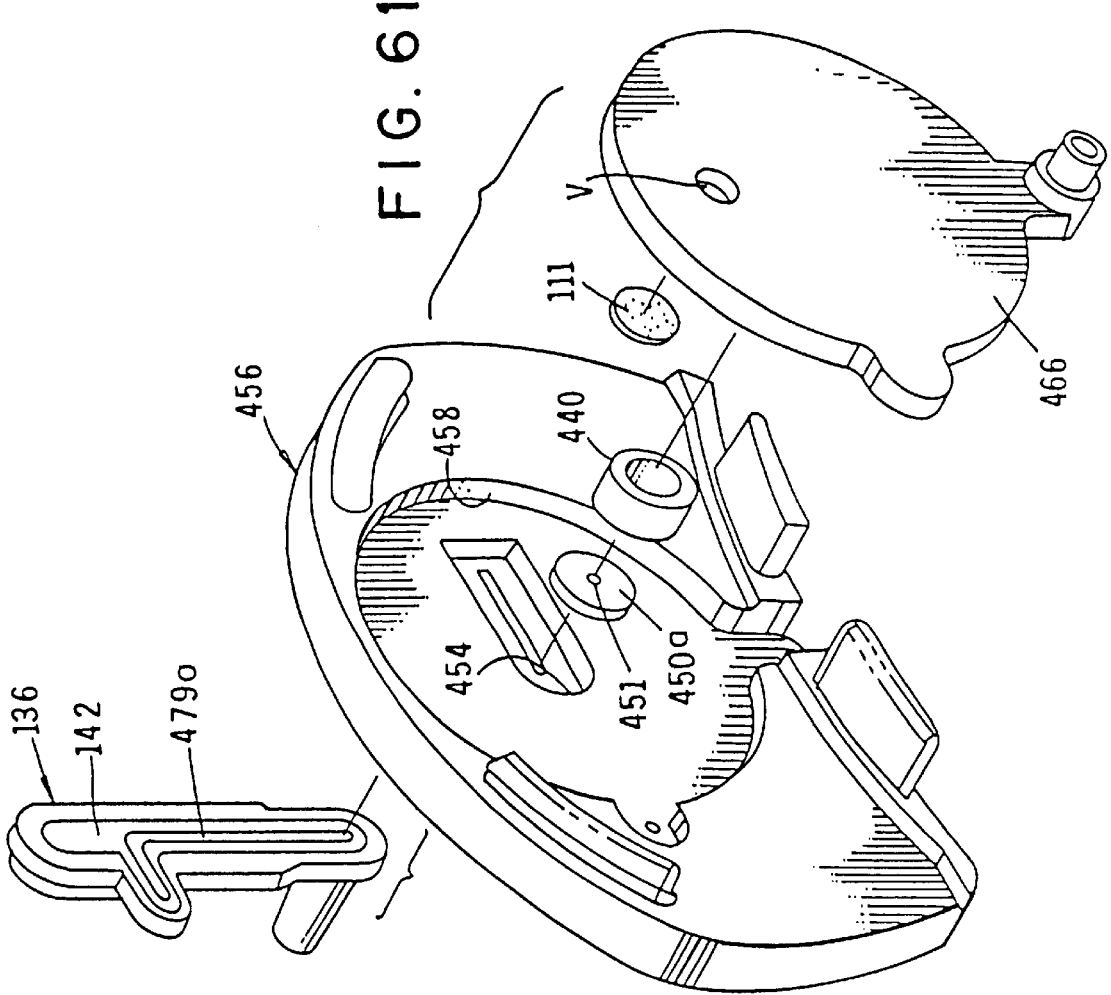
FIG. 61 is an exploded, generally perspective, fragmentary view similar to FIG. 60 but further illustrating the alternate form of dispenser flow control means of this latter form of the invention.

As best seen in FIGS. 60 and 61, first flow control means 450 comprises the rate control wafer 450a which has a single laser drilled aperture 451 which controls fluid flow toward an assembly 136, which assembly is identical to that previously described and shown in FIG. 21. Because of the similarity of this latest embodiment of the invention to that shown in FIGS. 18 through 23, like numbers have been used in FIGS. 60 through 62 to identify like components. Laser drilled wafer 450 can be constructed of metal, ceramic or like material and functions to precisely control fluid flow toward assembly 136 at a very precise rate. The second, or back-up flow control means 452, here comprises an assemblage made up of first and second filters 470 and 472 and a flow rate control porous frit 474 disposed intermediate filters 470 and 472. Once again, reference should be made to co-pending Serial No. 08/718,686 for a more detailed discussion of the various materials suitable for constructing various components of this alternate dispenser flow control means of the invention as described in the preceding paragraphs.

As best seen in FIG. 60, member 466 includes a downwardly extending fluid inlet leg or segment 478 which is provided with a fluid passageway 122. As previously discussed, passageway 122 is adapted to communicate with reservoir 100 of the dispenser via passageway 102 and 102a which member 466 is mated with support structure 110.

With this construction, when fluid is forced into passageway 102a by the stored energy means, the fluid will flow into passageway 102, then into passageway 122 of member 466 and finally into chamber 462 formed in boss 464. The fluid under pressure will then flow through rate control wafer 450a and toward the fluid outlet port of the flow control subassembly. As before, the outlet port comprises the uniquely shaped assembly 136 which is receivable in a cavity 138 formed in the back or downstream wall 456a of a substrate 456. Assembly 136 includes a fluid outlet 140 and an internal chamber 142.

Fluid flowing from chamber 142 toward outlet 140 via passageway 479a (FIGS. 61 and 62) will flow through the second flow control means or filters 470 and 472 and porous member or frit 474. With the novel construction thus described, should the first flow control means 450 for any reason fail to operate properly, the second back-up flow control means 452 will properly and precisely control fluid flow outwardly of the device via outlet port 140.

FIGS. 60B and 63 show still another alternate form of dispenser flow control means of the invention. This alternate flow control means is identical to that described in connection with FIGS. 60, 60A, 61 and 62 save that a porous rate control frit 482 is provided internally of elastomeric sleeve 440. Frit 482 cooperates with apertured wafer 450a to precisely control the rate of fluid flow toward chamber 142 of insert 136.

Referring to FIGS. 64, 65, and 66, one form of infusion means of the apparatus of the invention for delivering fluid from the dispenser component to the patient is there illustrated and generally designated by the numeral 486. This infusion means, or delivery line assembly, includes a connector fitting 488 which functions to interconnect the delivery line assembly with outlet 140 of the dispenser component of the apparatus of the invention. Connector 488 is of a character well known to those skilled in the art and has a tapered connector surface 488a or the character shown in FIG. 66 to enable the connector to be press fit into the outlet of the dispenser component. A long length of tubing 490 interconnects connector 488 with a luer fitting 492 which is of a conventional construction and which receives a luer cap 494. Intermediate the ends of length of tubing 490 is a coiled section 490a (See FIG. 6). Also disposed intermediate the ends of length of tubing 490 is a gas vent and filter 496 which is also of a conventional construction well known to those skilled in the art and readily commercially available from various sources. Disposed between connector 488 and gas vent and filter 496 is a tubing clamp 498 which is also of a character well known to those skilled in the art and functions to block fluid flow through tubing 490.

Disposed within connector 488 is still another form of dispenser flow control means of the present invention. This flow control means is similar to that shown in FIG. 60B and comprises an elastomeric sealing sleeve which is disposed within a cavity 502 formed within the body portion of connector member 488. Positioned within elastomeric sleeve 500 is the latest form of flow rate control means which here comprises first and second filters 504 and 506 and a porous rate control frit 508 disposed therebetween.

It is to be understood that the infusion means or delivery line assembly shown in FIGS. 64, 65, and 66 can be used with any embodiment of the fluid dispenser component of the invention shown in the drawings and previously described herein. Accordingly, use of this novel infusion means can provide secondary flow control to the flow control offered by the flow control means embodied in any specific embodiment of the invention previously described herein.

Turning to FIGS. 67 and 68, still another form of the fluid dispenser component of the apparatus of the present invention is there illustrated. This device is similar in most respects to the device shown in FIGS. 1 through 29 and like numerals are used in FIGS. 67 and 68 to identify like components. The major difference between this latest form of the dispenser component of the invention and that shown in FIG. 4 resides in the provision of the secondary means for filling the reservoir of the device. This secondary filling means comprises a luer connector 510 which is interconnected with the base of the dispenser component in the manner shown in FIG. 67. Disposed between luer connector 510 and a passageway 512 leading to the fluid reservoir of the device is valve means shown here as a conventional umbrella valve 514. A cover 516 is used to close the inlet end 510a of luer connector 510. As shown in FIG. 68, luer connector 510 is provided with inlet flow passageways 518 which are disposed in the crossing relationship shown in FIG. 68. This construction permits fluid flowing into inlet port 510a to flow through passageways 518 into a chamber 520 which houses umbrella valve 514 and then into the reservoir of the unit via passageway 512. As before umbrella valve 514 functions to permit fluid flow toward the reservoir but effectively blocks fluid flow in the opposite direction.

Referring to FIGS. 69 through 81, yet another embodiment of the present invention is there shown. In this latest embodiment, which is generally designated by the numeral 530, the fluid dispenser component is, once again, very similar to those previously described herein. Accordingly, where appropriate, like members are used in FIGS. 69 through 81 to designate like components. The reservoir fill assembly of this latest form of the invention, which is generally designated in the drawings by the numeral 42 is identical to that shown in FIGS. 7 through 16 and is as previously described herein in connection with those figure drawings.

The fluid dispenser component of this latest form of the invention, while being of similar configuration to that shown in FIGS. 1 through 7, does not include the flow indicator means shown in FIGS. 1 through 7. Rather, this latest form of the dispenser component includes a somewhat different infusion means, and importantly includes novel storage means for storing the infusion means designated in FIG. 69 by the numeral 531.

Figure 69:
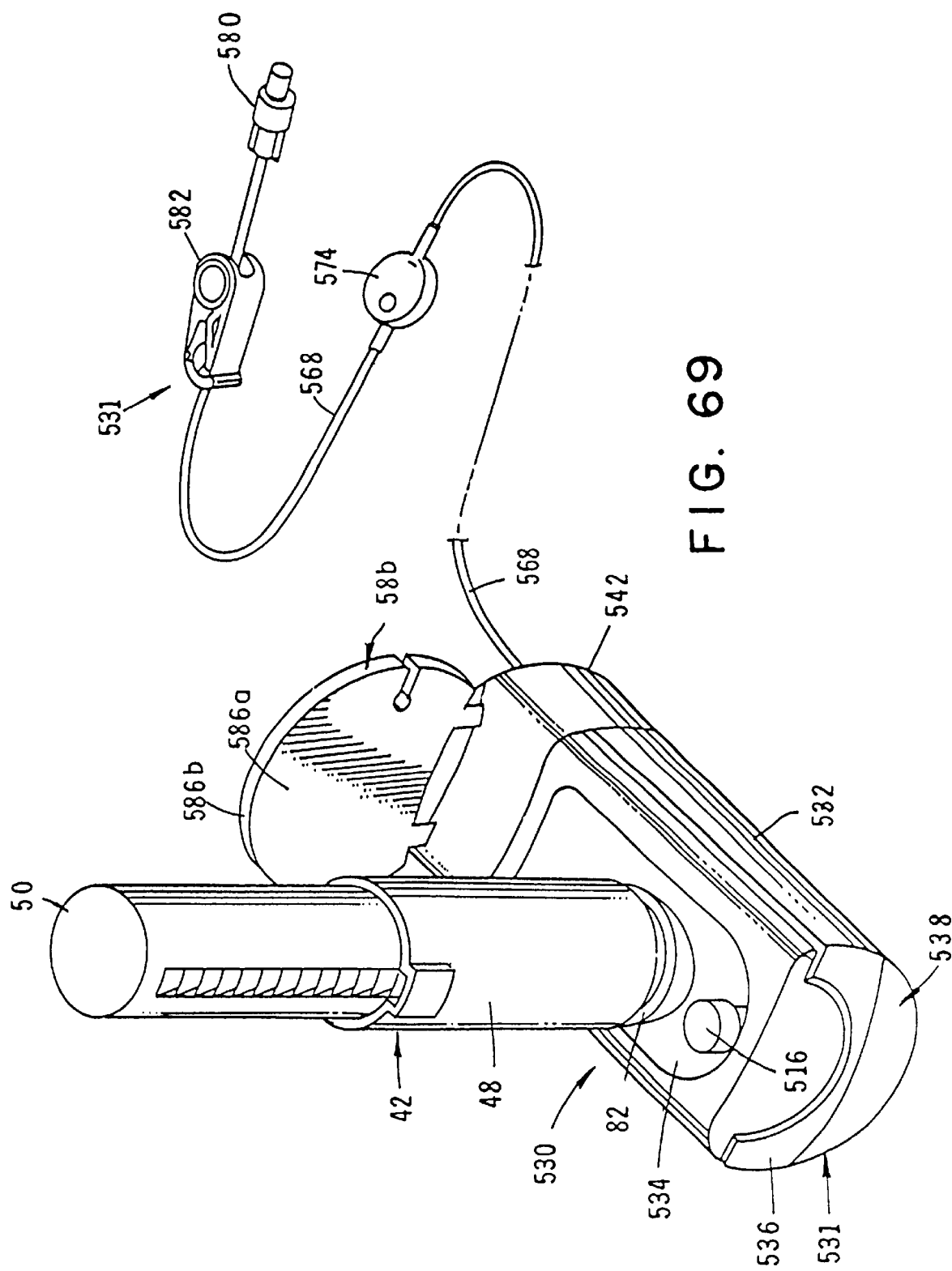
FIG. 69 is a generally perspective bottom view of still another form of the apparatus of the invention having a delivery line assembly stored within a forward compartment of the dispenser housing.
Figure 70:
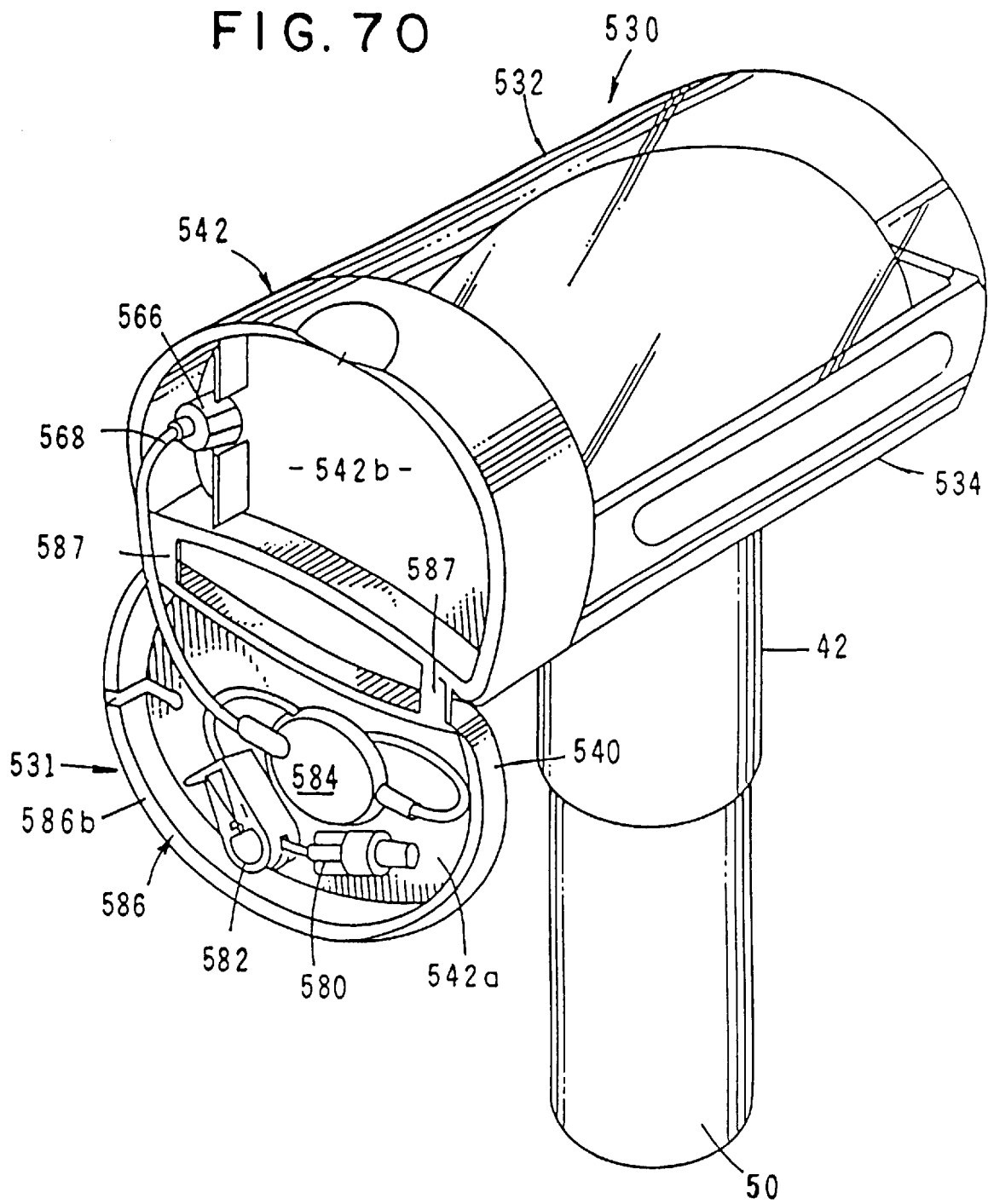
FIG. 70 is a generally perspective top view of the form of the invention illustrated in FIG. 69 better illustrating the configuration of the delivery line assembly and storage compartment of the dispenser.
Figure 71:
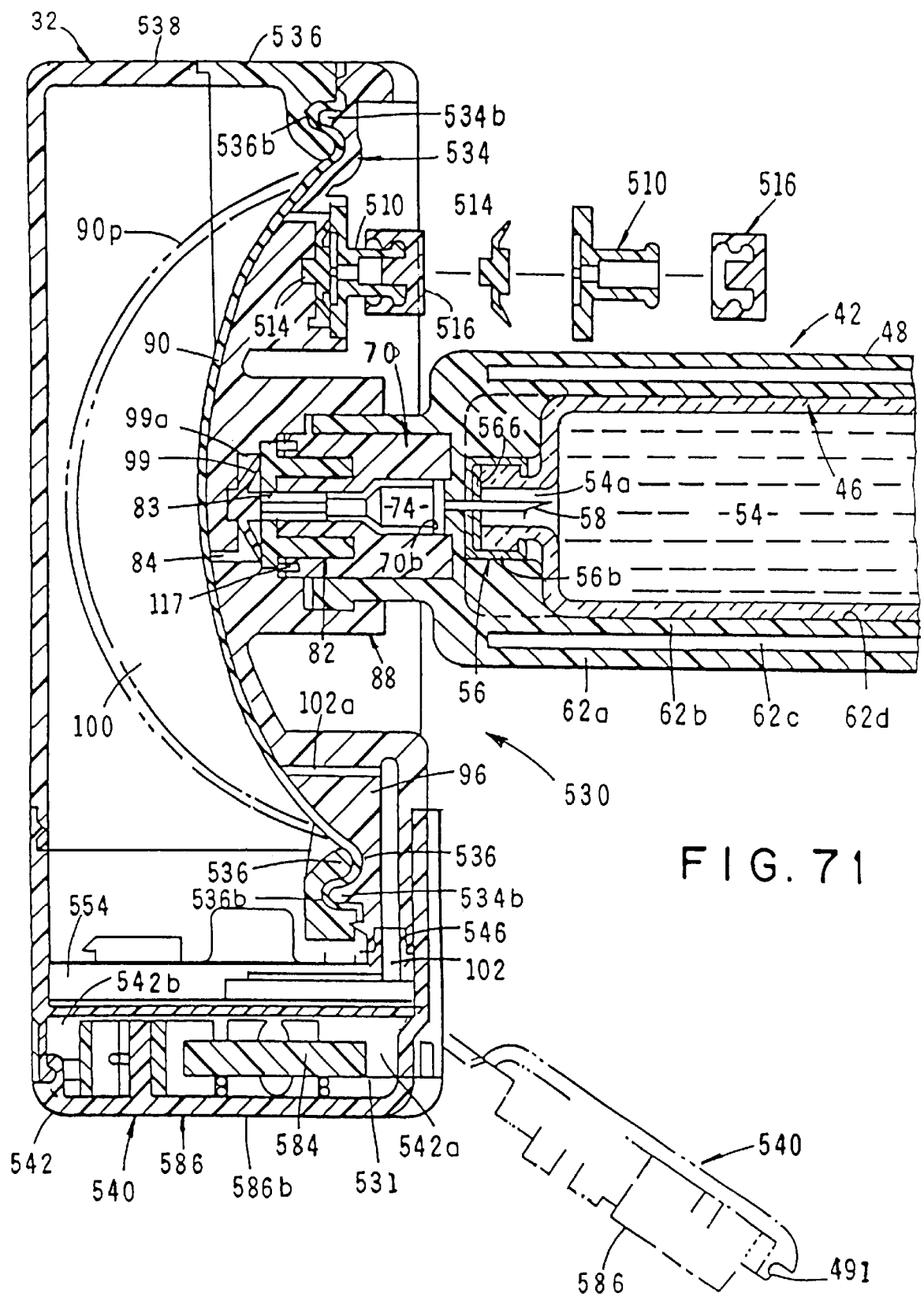
FIG. 71 and 71A, when considered together, comprise a greatly enlarged, cross-sectional view of the apparatus illustrated in FIG. 69 showing the manner of interconnection of the alternate form of dispenser component with the reservoir fill assembly.
Figure 71A:
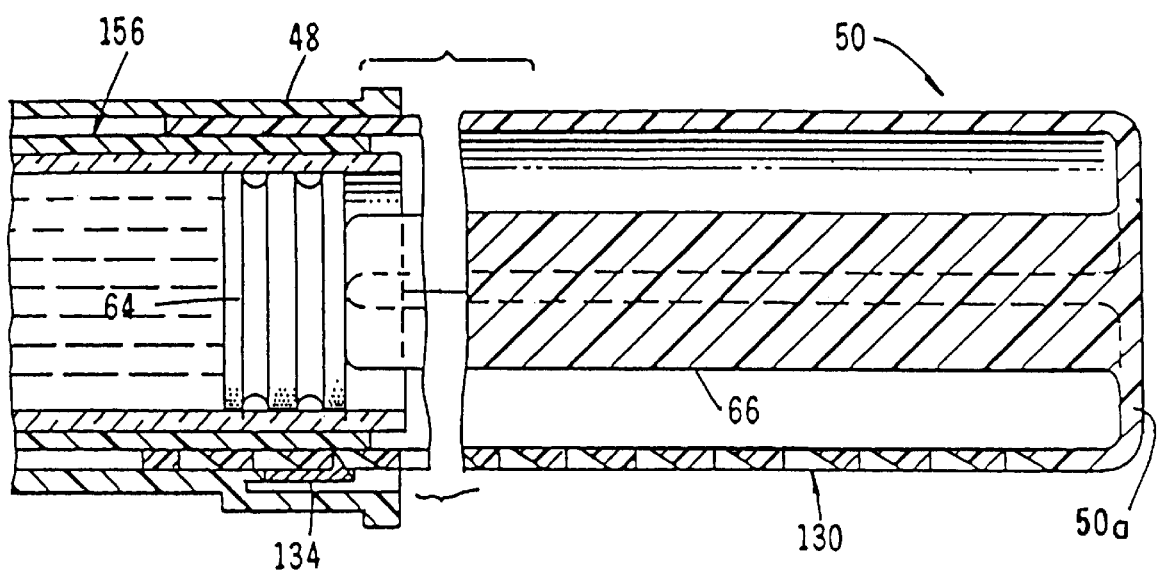

Turning particularly to FIGS. 69, 70, and 71, the fluid dispenser assembly of the apparatus of this latest form of the invention, which is designated as 532, includes a housing assembly comprising a base 534, a capture ring 536, a stored energy source, or distendable membrane 90 (FIG. 71) and a cover 538 for enclosing the stored energy source, the capture ring and the base. As shown in FIG. 71, base 534 includes an ullage defining protuberance 94 and a membrane capture portion 96. Disposed between base 534 and cover 538 is the membrane capture ring 536 which has a bottom opening 536a which receives protuberance 94 of base 534.

Referring particularly to FIGS. 69 and 71, base 534 comprises, in addition to the distendable member engaging protuberance, or ullage 94, the previously identified dispenser connector subassembly 82, to which the reservoir fill assembly 42 is interconnected in the manner shown in FIG. 71. Base 534 also includes an upstanding tongue 534b which extends about the perimeter of the base and is closely receivable within a groove 536b formed in the capture ring 536 (FIG. 71). When the base and the membrane capture ring are assembled in the manner shown in FIG. 71, the periphery of distendable membrane 90 will be securely clamped within groove 536b by tongue 534b. After the parts are thus assembled, base 534 is bonded to capture ring 536 by any suitable means such as sonic bonding which also functions to simultaneously trim membrane 90.

During the reservoir filling step, which is as was previously described in connection with the earlier embodiments, fluid under pressure will flow into inlet passageway 84 of the fluid dispenser via an umbrella valve 99 and thence into a reservoir 100 which is formed between protuberance 94 and distendable membrane 90p which is shown in phantom lines in FIG. 71. Umbrella valve 99 forms a part of the fill flow control means of the invention. As the fluid under pressure flows into the reservoir, it will cause membrane 90 to distend outwardly from protuberance 94 in the manner shown by the phantom lines in FIG. 71.

As previously stated, an important feature of this latest embodiment is the provision of the novel storage means provided proximate the forward end of the housing of the dispenser component. This storage means, which as shown in FIGS. 70, and 71 and is generally designated therein by the numeral 540. This important storage means comprises a part of the cover means of the invention which includes a portion of cover 538.

Figure 72:
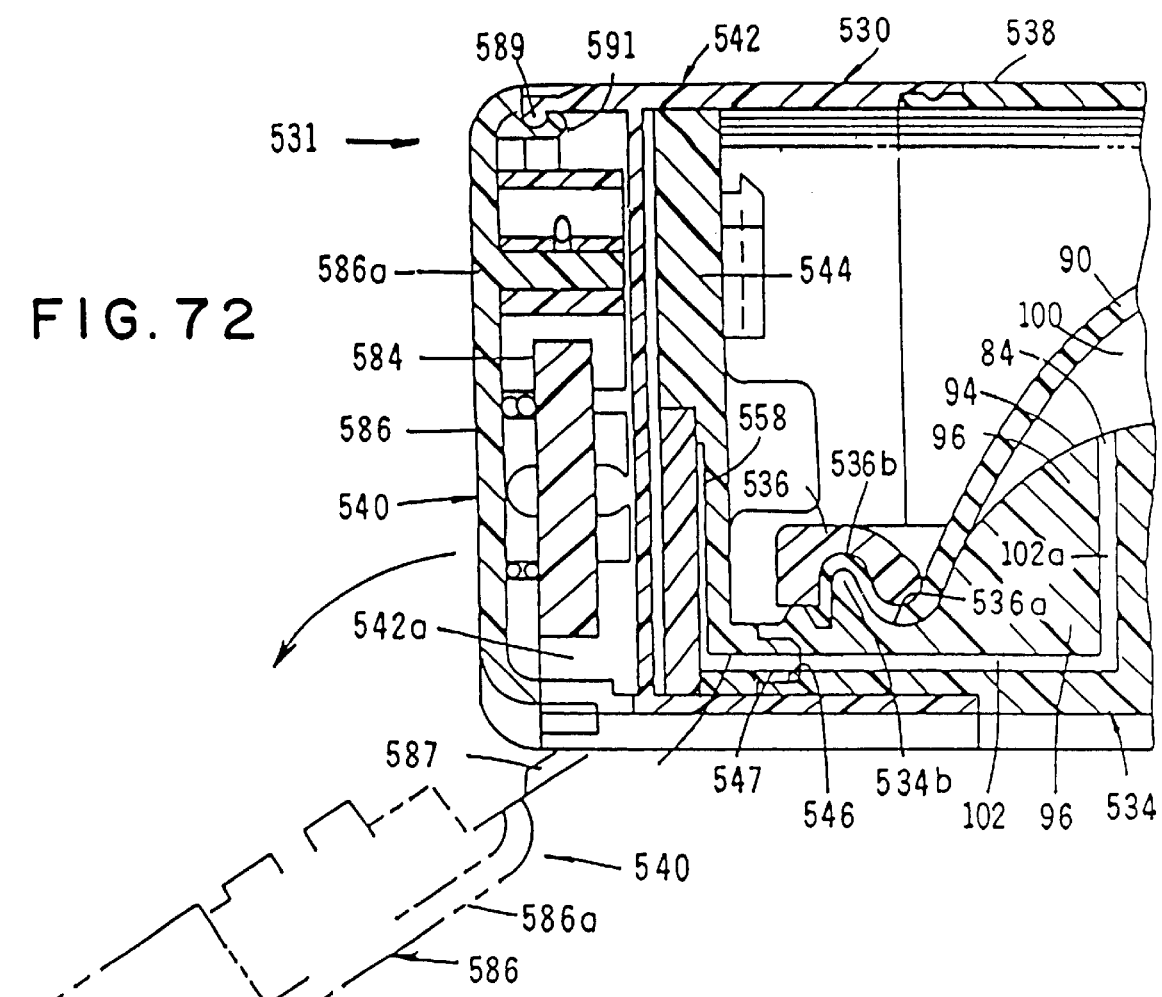
FIG. 72 is an enlarged, fragmentary, cross-sectional view of the forward portion of the form of the dispenser component shown in FIG. 69.

The cover means also includes a housing assembly 542 (FIG. 72) which is interconnected with cover 538 and base 534. Housing assembly 542 functions to close the forward or delivery end of the dispenser component. As best seen in FIG. 72, housing assembly 542 includes a first or forward compartment 542a and a second, or rearward compartment 542b. Rearward compartment 542b houses a support structure 544, the construction of which is illustrated in FIGS. 78 and 79. As there shown, support structure 544 includes an outwardly extending, generally cylindrically shaped, fluid inlet element 546 within which is provided a fluid passageway 548 (FIG. 79). When support structure 544 is mated with base assembly 534, passageway 548 will communicate with reservoir 100 via passageways 102 and 102a (see also FIG. 7). As before, base assembly 534 has a centrally disposed, socket-like recess 547 that closely receives inlet element 546 when structure 544 is mated with base assembly 534 in the manner shown in the drawings.

Figure 74:
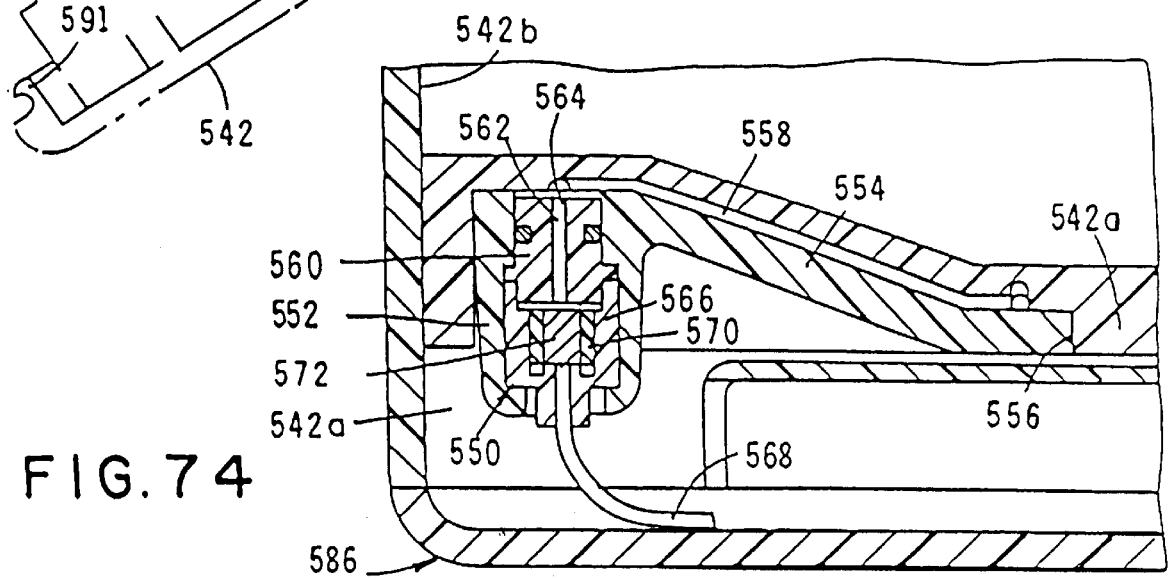
FIG. 74 is a cross-sectional view taken along lines 74—74 of FIG. 73.
Figure 75:
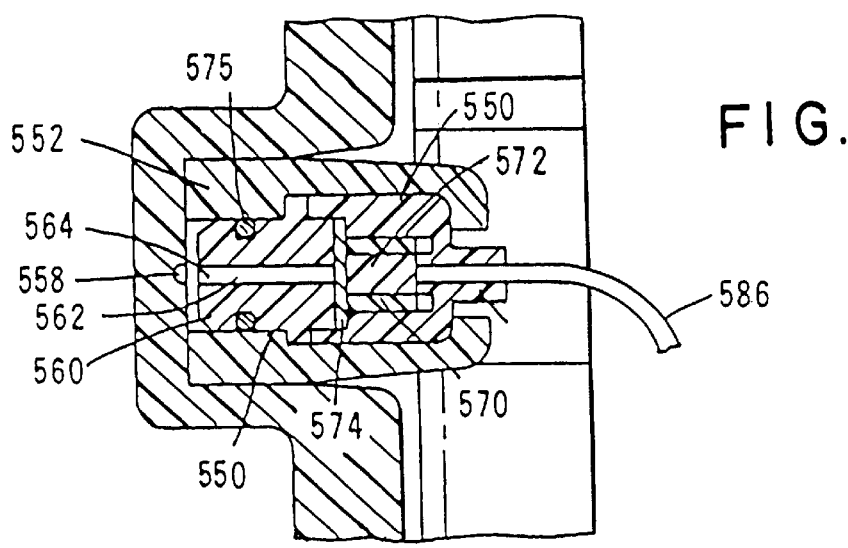
FIG. 75 is a cross-sectional view taken along lines 75—75 of FIG. 73.

The flow control means of this latest form of the invention for controlling the rate of fluid flow of fluid from the device here comprises a novel dispenser flow control assembly 550 of the character shown in FIGS. 74 and 75. This dispenser flow control means includes a rate control assembly which is mounted within a socket like portion 552 formed in an insert 554 which is received within cavity 556 formed in the forward wall 544a of support structure 544 (see FIG. 78). Insert 554, in cooperation with a fluid passageway 558 formed in support structure 544, functions to provide a fluid flow path between reservoir 100 and the flow control assembly 550. More particularly, assembly 550 here comprises a quick disconnect housing 560 which has a central fluid passageway 562 having an inlet 564 which communicates with passageway 558 in the manner shown in the drawings.

Figure 76:
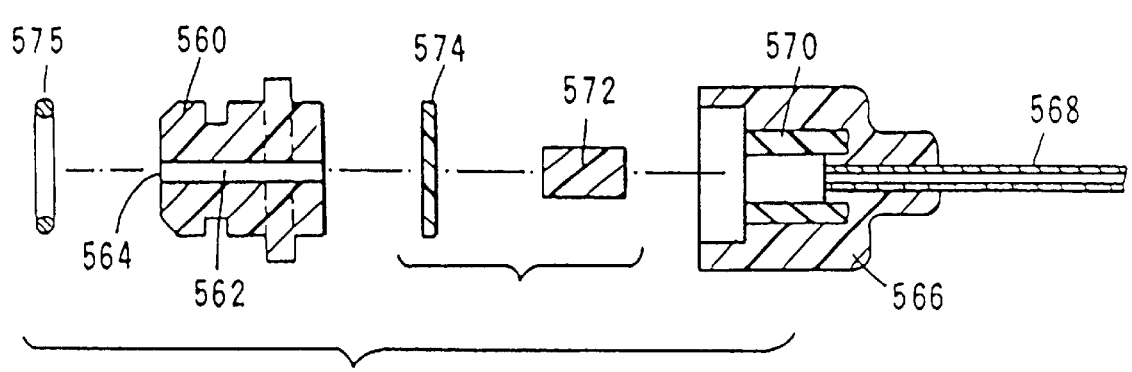
FIG. 76 is an enlarged, exploded, cross-sectional view of the dispenser flow control means of this latest form of the invention.
Figure 77:
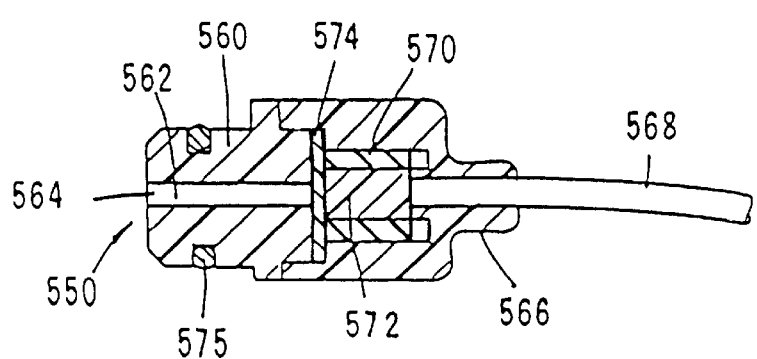
FIG. 77 is a view of the dispenser flow control means illustrated in FIG. 76 showing the flow control means in an assembled configuration.

Interconnected with quick disconnect housing 560 is a delivery line housing 566 to which a delivery line 568 is sealably connected (FIGS. 76 and 77). Disposed within housing 566 is an elastomeric compression ring 570 which sealably receives the dispenser flow rate control means of this form of the invention, which means here comprises a generally cylindrically shaped rate control frit 572. Also forming a part of the dispenser flow control means of this latest embodiment is filter means, here shown as a filter element 574 which is disposed between frit 572 and quick disconnect housing 560 (FIG. 76).

When insert 554 is in position within cavity 556 in the manner shown in FIG. 72, quick connect socket portion 552 extends into forward chamber 542a of the storage means. With this construction, the flow control means can be placed in fluid communication with the fluid reservoir of the dispenser by inserting quick disconnect housing 560 into socket portion 552 and then turning it in a conventional fashion to securely lock it in position. To prevent leakage of fluid between housing 560 and socket portion 552 and elastomeric O-ring 575 is provided in housing 560 (FIGS. 76 and 77).

Connected to the flow control means is the fluid delivery or infusion means of the invention. This latter means, which comprises delivery line assembly 531, is uniquely removably stowed within first or forward compartment 542a of the storage means. As best seen in FIGS. 69 and 70, the infusion means here comprises a luer assembly 580 and a line clamp 582 both of which are of conventional construction. Previously identified delivery line 568 is interconnected with luer assembly 580 in the manner shown in FIG. 73. Disposed between the flow control means and luer assembly 580 is a vent means shown here as a conventional gas vent assembly 584 for venting gases trapped within the system to atmosphere.

Forward compartment 542a is formed within an access door 586 which is connected to that portion of the rearward portion of housing 542 which defines rearward compartment 542b, by hinge means here shown as a part of living hinge elements 587. With this arrangement, door 586 can be pivoted relative to base 534 from the closed position shown by the solid lines in FIG. 72 to the open position show by the phantom lines in FIG. 72. Door 586, which forms a part of the storage means, includes a front face 586a which in cooperation with an interconnected circumscribing wall 586b, forms forward compartment 542a (FIGS. 72 and 73). Latching means, shown here as comprising an arcuate protuberance 589 formed on housing 542, and an arcuate locking tab 591 formed on door 586, cooperate to latchably maintain the door in a normally closed condition (FIG. 72). With this novel arrangement, the infusion means of the invention can remain securely stowed within compartment 542a until time of use.

Figure 80:
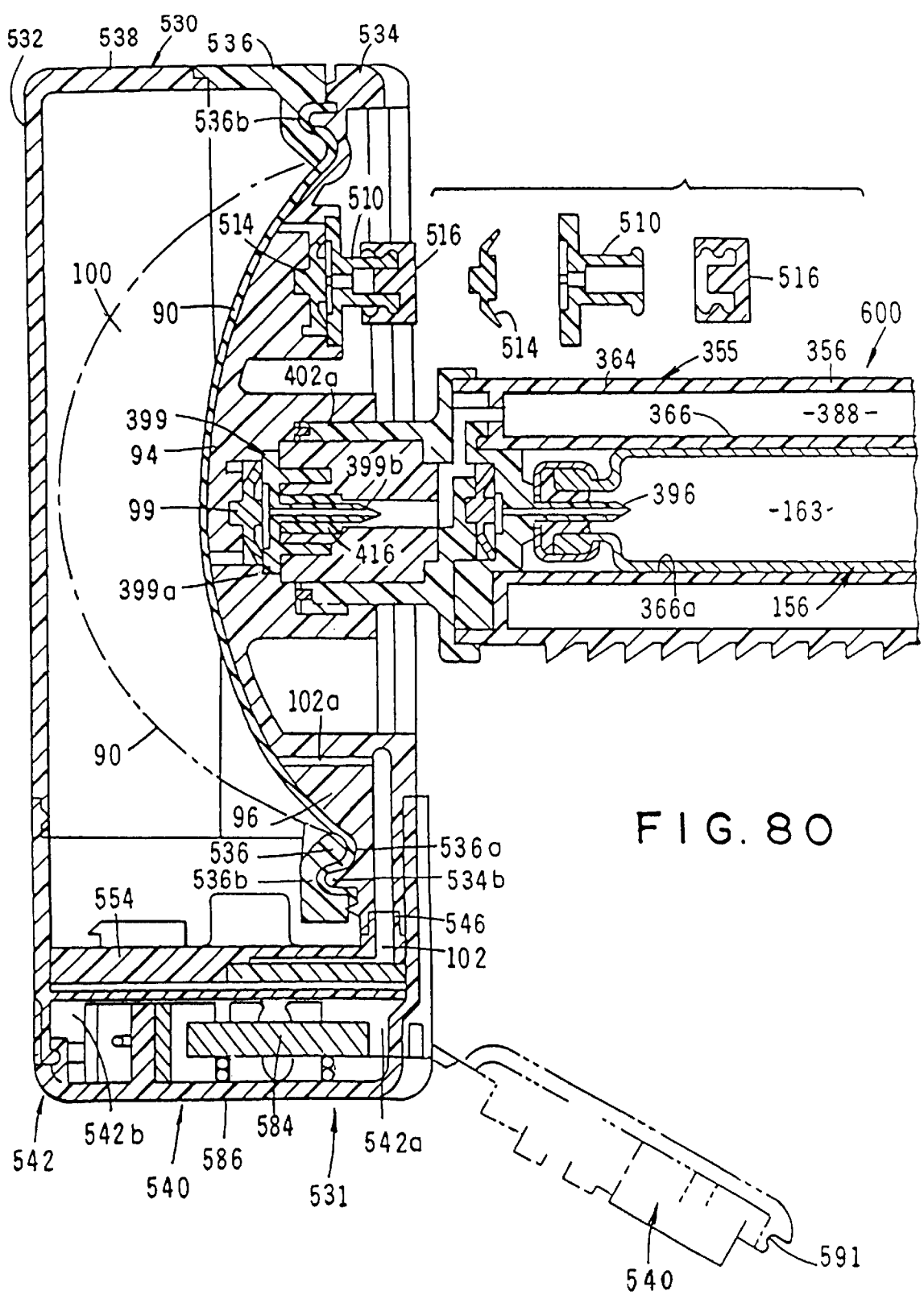
FIG. 80 and 80A, when considered together, comprise an enlarged, side-elevational, cross-sectional view similar to FIG. 71 but showing still another form of the apparatus of the invention.
Figure 80A:
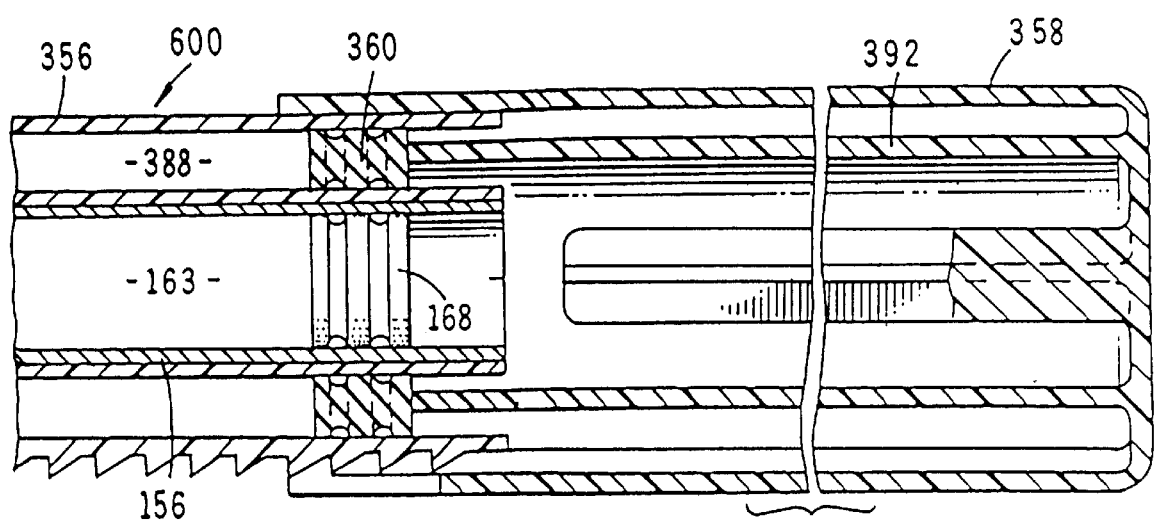
Figure 81:
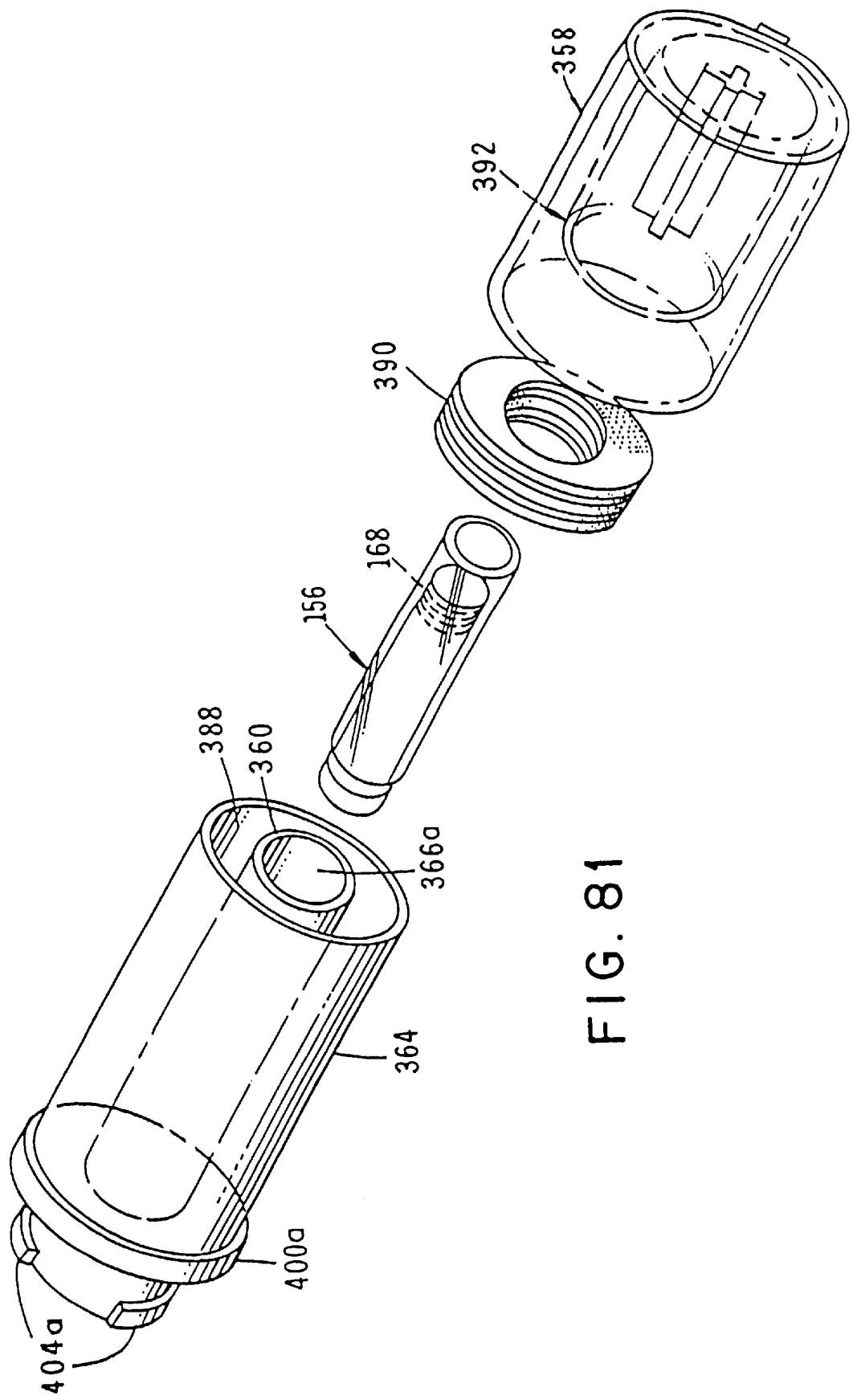
FIG. 81 is a generally perspective, exploded view of the reservoir fill assembly of the apparatus illustrated in FIG. 80.

Turning next to FIGS. 80 and 81, still another form of the apparatus of the invention is there shown and generally identified by a numeral 600. This form of the apparatus is quite similar to that illustrated in FIGS. 45 and 46 and like numbers are used to identify like components.

As shown in FIG. 80, in this latest embodiment, the fluid dispenser component is quite similar to that shown in FIGS. 69 through 71. Similarly, this latest embodiment of the reservoir fill assembly is identical to that shown in 46 and therefore is generally designated by the numeral 355. As before the reservoir fill assembly comprises three major components, namely a container subassembly 156, an adapter subassembly 356, and an adapter or pusher sleeve 358. The reservoir fill assembly 355 operates in the same manner as previously described herein in connection with the FIG. 46 and couples with the dispenser component in precisely the same manner.

It is to be noted that, as before, the adapter subassembly 356 of this latest embodiment of the invention includes an outer, generally cylindrically shaped wall 364, and an inner, generally cylindrically shaped wall 366, which define therebetween an elongated annular space 388 within which an annular shaped sealing ring 390 is moved longitudinally by an inner wall 392 of pusher sleeve 358. As in the earlier described embodiment, annular space 388 comprises a diluent reservoir. Container assembly 156 is closely receivable within a chamber 366a formed internally of wall 366 of the adapter subassembly and can be urged forwardly of chamber 366a by inward sliding movement of sleeve 358 relative to adapter assembly 356.

As shown in FIG. 80, the fluid dispenser of this latest form of the delivery apparatus is very similar to that shown in FIGS. 68 through 71. However, in this latest construction, as was the case in the embodiment shown in FIG. 46, the extension 82a of dispenser connector 82 has been replaced with hollow cannula assembly 399 which includes a cannula support plate 399a and a cannula 399b having a fluid passageway of the character previously described in connection with the embodiment of FIG. 46. Similarly, valve member 58 has been replaced by a slit septum 416 which is readily pierceable by cannula 399b. (See also FIG. 46 and the discussion relating thereto.) It is to be understood that the same type of coupling mechanism depicted in FIGS. 1 through 7 can be used in the dispenser embodiment shown in FIG. 80.

Additionally, as shown in FIG. 49, the dispenser connector could be provided with a slit septum 420 and the fill reservoir connector could be provided with a cannula assembly 422 which comprises a cannula support 422a and a blunt end hollow cannula 422b.

Referring next to FIGS. 82 through 85, one form of the apparatus of the present invention is there illustrated. As best seen in FIGS. 82 and 83, the apparatus here comprises two major cooperating assemblies, namely a fluid dispensing apparatus or fluid dispenser 620 and a reservoir fill assembly 622 which can be operably coupled with fluid dispenser 620. As will be described in greater detail hereinafter, dispenser 620 is made up of two major cooperating subassemblies namely, a reservoir subassembly and an infusion means for infusing medicinal fluids into the patient.

Figures 84, 85:
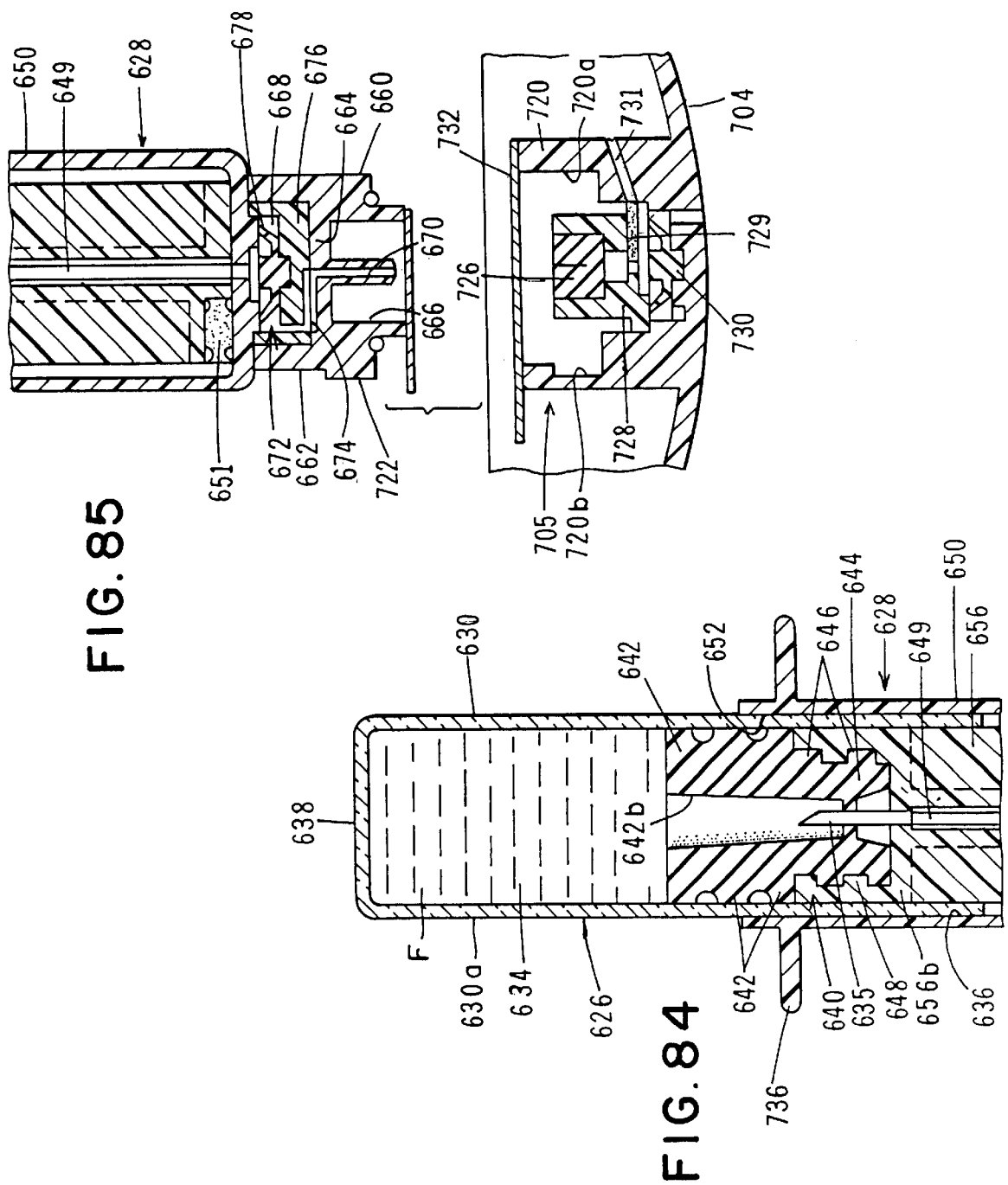
FIG. 84 is a left-side elevational, cross-sectional view of the assembly shown in FIG. 82.
FIG. 85 is a fragmentary, cross-sectional view of the lower portion of the fill adapter assembly ready to be mated with the connector subassembly of the fluid delivery device portion of the apparatus shown in FIG. 82.

Turning particularly to FIGS. 82 and 84, the novel reservoir fill assembly 622 of the invention can be seen to also comprise two major components, namely a container subassembly 626 (FIG. 82) and an adapter subassembly 628. Container subassembly 626 includes a container 630 which contains the medicinal fluid with which the reservoir of the dispensing apparatus is to be filled. When interconnected with the dispensing apparatus, the adapter subassembly 628 permits transfer from container 626 to the reservoir 632 of the dispenser component.

As best seen in FIG. 84, container 630 includes a body portion 630a, having a fluid chamber 634 for containing an injectable fluid "F". Body portion 630 is provided with a first open end 636, and a second closed end 638. First open end 636 is sealably closed by closure means here provided in the form of a plunger assembly 640. Plunger assembly 640 comprises an elastomeric plunger 642 and a connector means, or connector 644 which functions to interconnect the container assembly with the adapter assembly. Plunger assembly 640 is telescopically movable within chamber 634 of container subassembly 626 from a first location proximate first open end 636 to a second location proximate second closed end 638.

Connector 644 includes threads 646 which can be threadably connected to threads 648 provided on adapter assembly 628. Connector 644 also includes a pierceable central wall 644a which is pierceable by an elongated cannula 635 of the adapter assembly, which cannula comprises a part of the first flow control means of an adapter assembly for controlling fluid flow toward the fluid dispenser. Cannula 635 is insert molded into a pusher means and includes a central fluid flow passageway 649. Connector 644 is connected to plunger 642 in the manner shown in FIG. 84 so that as plunger 642 is moved toward closed end 638, in a manner presently to be described, connector 644 and plunger 642 will move as a unit. To prevent leakage of fluid past plunger 642, the plunger is provided with rings 642a which are of a diameter slightly greater than the inside diameter of container body 630a. Plunger 642 also includes a central fluid passageway 642b which is in open communication with fluid chamber 634.

Adapter assembly 628 comprises a hollow housing 650 having a first open end 652 and a second closed end 654. Container assembly 626 is telescopically receivable within open end 652 of housing 650 in the manner shown in FIG. 84 so that the housing can be moved from the first extended position shown in figure 84 to a second container encapsulation position wherein container 630 is substantially encapsulated within housing 650. Provided interiorly of the adapter subassembly is the previously mentioned pusher means which is shown here as a pusher body 656. Pusher body 656, which is generally cross shaped in configuration and functions to support cannula 635 and to move plunger 642 within fluid chamber 634 from the first forward position shown in FIG. 84 to a second position wherein it is disposed proximate end wall 638. Pusher body 656 also includes a head portion 656b within which threads 648 are formed. End wall 654 of housing 650 is provided with a fluid outlet 654a which comprises a part of the second flow control means of the invention for permitting fluid flow toward the delivery apparatus of the invention.

Also forming a part of the adapter assembly of the invention is a closure cap assembly 660 (FIG. 85) which is connected to body portion 650 in the manner shown in FIG. 84. Cap assembly 660 includes a generally cylindrical exterior wall defining a band-like portion 662 and an internal dividing wall 664 which cooperates with wall 662 to form first and second chambers 666 and 668. Connected to wall 664 and extending into chamber 666 is a cannula 670, the purpose of which will presently be described. Disposed within chamber 668 is one of the valving means of the invention which here comprises a conventional umbrella type valve assembly 672 which functions to control fluid flow from passageway 649 toward the central fluid passageway of cannula 670 via a passageway 674 formed in dividing wall 664. Valve assembly 672 is of a conventional configuration having a central hub-like portion which is received within a central bore provided in a support plate 676 and a circumferentially extending, resiliently deform74 able, umbrella shaped flow control skirt 678 which is deflected outwardly by fluid flowing through passageway 649 so as to permit flow into passageway 674 of dividing wall 676.

Figures 89, 90:
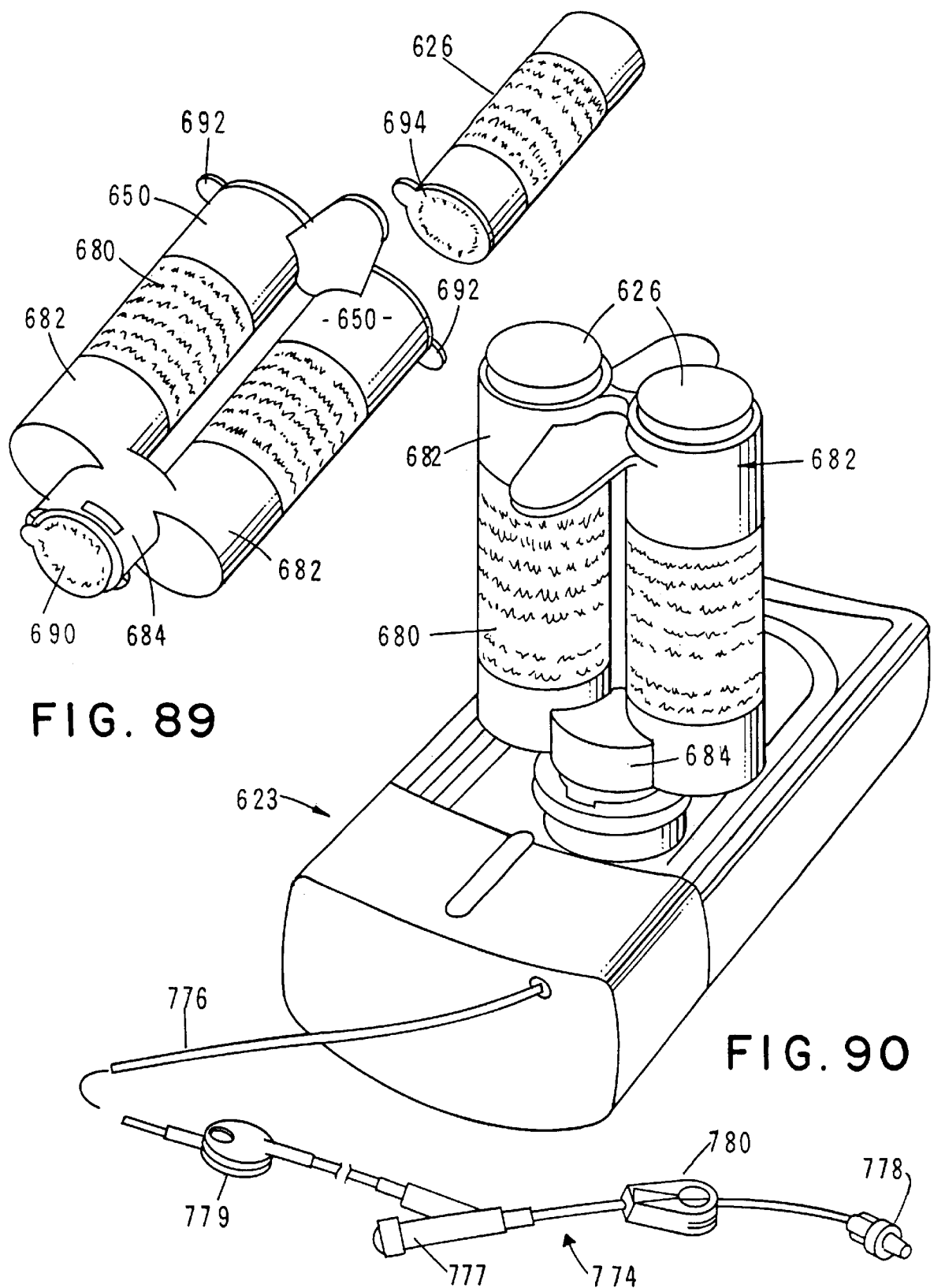
FIG. 89 is a generally perspective, exploded view of an alternate form of the reservoir fill assembly.
FIG. 90 is a generally perspective view of the alternate form of reservoir fill assembly mated with the fluid delivery apparatus.

Turning next to FIGS. 89 and 90, an alternate form of adapter assembly is there shown and generally identified by a numeral 680. Adapter assembly 680 is similar in construction to assembly 628, but includes a pair of interconnected, side-by-side hollow bodies 682, each of which is of the same general construction as the previously described hollow body 650. Each of the hollow bodies 682 has an outlet which permits fluid flow toward an umbrella type valve which is identical to valve 672. Fluid flowing through either of the valves 672 will flow into a central fluid passageway formed in a central connector 684 which interconnects the two hollow housings 682 and then on to the fluid delivery device 620.

As depicted in FIG. 89, adapter assembly 680 is adapted to receive a pair of container assemblies 626 which are of the character previously described. Each of the container assemblies can contain an injectable medicament of either the same or a different character for introduction into the reservoir of the particular delivery assembly which is selected to deliver the medicament to the patient.

Prior to use, the adapter assembly components 632 and 684 of the reservoir fill assembly is maintained in a protected and substantially sterile configuration by tear-away end caps 690 and 692 (see FIG. 89). As indicated in FIGS. 82 and 89, a tear-away end cap 690 is receivable over and closes the forward end of adapter assembly 680, while tear-away end cap 692 is received over and closes the rearward open end portion of bodies 650. Similarly, as shown in FIGS. 82 and 89, a tear-away cap 694 is received over and closes the open ends of the container assemblies 626.

Turning again to FIGS. 82 through 85, the fluid delivery or dispenser assembly 620 of the apparatus of this form of the invention is similar in some respects to that described in incorporated by reference Patent No. 5,721,382 and includes a housing assembly comprising a base 698, a capture ring 699, a stored energy source, or distendable membrane 700 and a cover 702 for enclosing the stored energy source, the capture ring and the base. Base 698 includes an ullage defining protuberance 704 and a membrane capture portion 706. Disposed between base 698 and cover 702 is the membrane capture ring 699 which has a bottom opening 699a which receives protuberance 704 of base 698 (see FIG. 84).

As shown in FIGS. 84 and 85, base 698 comprises, in addition to the distendable member engaging protuberance, or ullage 704, a novel dispenser connector subassembly 705, to which the reservoir fill assembly 622 is interconnected in the manner shown in FIG. 83. Base 698 also includes an upstanding tongue 698b which extends about the perimeter of the base and is closely receivable within a groove 699b formed in the capture ring 699 (FIG. 84). When the base 698 and the membrane capture ring 699 are assembled in the manner shown in figure 84, the periphery of distendable membrane 700 will be securely clamped within groove 699b by tongue 698b. After the parts are thusly assembled, base 698 is bonded to capture ring 699 by any suitable means such as sonic bonding which also functions to simultaneously trim membrane 700. This done, cover 702 is mated with capture ring 699 in the manner shown in the drawings and is suitably bonded in place. Cover 702 can, if desired, be constructed from a substantially transparent plastic material which is impermeable to fluids, including gases.

During the reservoir filling step, the details of which will presently be described, fluid under pressure will flow into inlet passageway 710 of the fluid dispenser via a conventional umbrella valve 730 and thence into reservoir 632 which is formed between protuberance 704 and the stored energy membrane 700. As the fluid under pressure flows into the reservoir, it will cause membrane 700 to distend outwardly from protuberance 704 so as to build up internal stresses within the membrane. While the stored energy means can be in the form of a single prestressed or unstressed isotropic, elastomeric distendable membrane, such as membrane 700, it can also be constructed as a laminate assemblage made up of a plurality of initially generally planar distendable elements of films. Such construction is described in Patent No. 5,721,382, which application is incorporated herein by reference. During the infusion step, the internal stresses formed in membrane 700 will cause it to move toward protuberance 704 and fluid within reservoir 632 will be uniformly and controllably forced outwardly through a passageway 714 and then through a passageway 716 formed in base 698 in a direction toward the infusion means of the invention.

In using the apparatus of this form of the invention, seal cap 694 is removed from container assembly 626 and the open end of container 630 is inserted into the open end of adapter body 650 in the manner shown in FIG. 84. As connector member 644 is threadably interconnected with pusher 656 cannula 635 will pierceably engage and penetrate central wall 644a of the connector thereby opening fluid communication between fluid chamber 634 of the container assembly and passageway 649 of the pusher assembly member 656. Once wall 644a has been penetrated, an inward force exerted on container assembly 626 will cause body 656 to urge plunger 642 inwardly of container reservoir 634 from a first location proximate open end 636 to a second location proximate closed end 638. As plunger 642 moves inwardly, fluid within reservoir 634 will be free to flow into the central fluid passageway of cannula 635 and toward adapter assembly passageway 649. Any gases trapped within passageway 649 will vent to atmosphere via a hydrophobic vent element 651 which connects passageway 649 with an elongated annular passageway formed between the outer surface of container 630 and the inner surface of housing 650. Gases flowing into passageway 733 will leak past container 630 to atmosphere.

To interconnect the reservoir fill assembly with the fluid delivery apparatus 620, the forward end of the adapter assembly is inserted into a hub like portion 720 which comprises a part of connector assembly 705 and defines a receiving chamber 720a. Portion 720 is integrally formed with protuberance 704 (FIG. 85) and includes circumferentially spaced openings 720b which are adapted to receive bayonet type connector ears 722 formed on cap assembly 660 (FIGS. 84 and 85). Relative rotation of the fill assembly 622 and the fluid delivery apparatus 620 will securely interconnect the components in the manner shown in FIG. 84. As indicated in FIG. 84, as the fill assembly is mated with the delivery component, cannula 670 of the adapter assembly will pierce a pierceable septum 726 which is mounted within septum mounting component 728 which is disposed within hub 720 that forms a part of the connector assembly 705 (see FIG. 85). Also disposed within hub 720 is a vent means shown here as a hydrophobic vent element 729 and delivery component valving means for controlling fluid flow toward inlet 710. This delivery component valving means here comprises a conventional umbrella type check valve 730 which permits fluid flow from cannula 670 toward passageway 710, but blocks fluid flow in the opposite direction. Valve 730 is similar in construction and operation to the previously described umbrella valve 672.

After the peelable end cap 732 (FIG. 85) of the fluid delivery assembly 620 has been removed and the fill assembly 622 has been mated therewithin, the assemblage thus formed can be interconnected with the delivery assembly in the manner previously described. Fluid can be expelled from the fluid chamber 634 of the container assembly into the fluid reservoir 632 of the fluid delivery apparatus 620. This step is accomplished by urging container 630 into the annular space 733 defined by the interior wall of hollow housing 650 and the exterior surface of adapter body 656. This is accomplished by gripping finger engaging ears 736 (FIG. 84) and then urging the container 630 inwardly with the thumb. During the filling step, any air trapped within passageway 649 will be vented to atmosphere via vent element 651 and annular space 733. Similarly, any air trapped within septum mounting component 728 will be vented to atmosphere via a hydrophobic vent element 729 and a vent passageway 731 formed in connector assembly 705.

A s shown in FIG. 84, the fluid dispenser also includes fluid recovery means for recovering fluid from reservoir 632. This important means, which enables recovery at any time of fluid contained within the reservoir, here comprises a septum 737 housed within a chamber 737a formed in protuberance 704. Septum 737 is pierceable by a cannula of a conventional syringe assembly that can be used to remove fluid from the reservoir.

As previously mentioned, after the reservoir filling step and during the fluid dispensing step, the prestressed membrane 700 will tend to return toward a less distended configuration causing fluid within reservoir 632 to flow outwardly of the reservoir into passageway 714 and then into passageway 716. The fluid under pressure will next flow into passageway 740 of the inlet port of disk shaped member 742 (see FIGS. 87, 88, 91 and 92). Member 742 is similar in construction and operation member 466 shown in FIG. 62 and mates with a support structure 746 which is similar in form to support structure 456 (FIG. 61).

Figure 86:
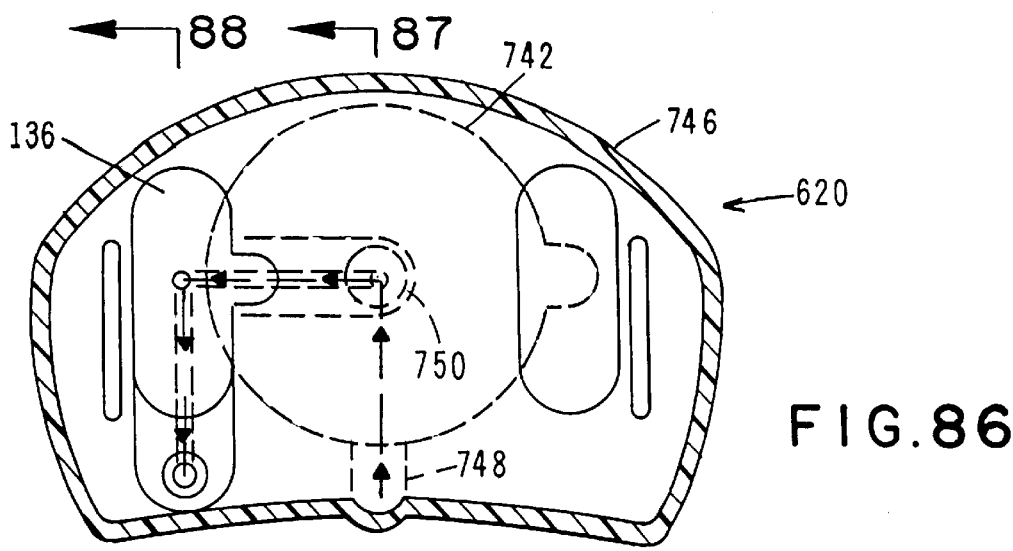
FIG. 86 is a cross-sectional view taken along lines 86—86 of FIG. 84.

Like member 466, member 742 includes a downwardly extending fluid inlet leg or segment 748 (FIG. 86) which is provided with the previously identified fluid passageway 740. As shown in FIG. 84, passageway 740 is adapted to communicate with reservoir 632 of the dispenser via passageways 714 and 716 when member 742 is mated with support structure 746 in the manner indicated in FIGS. 84 through 88.

Figure 91:
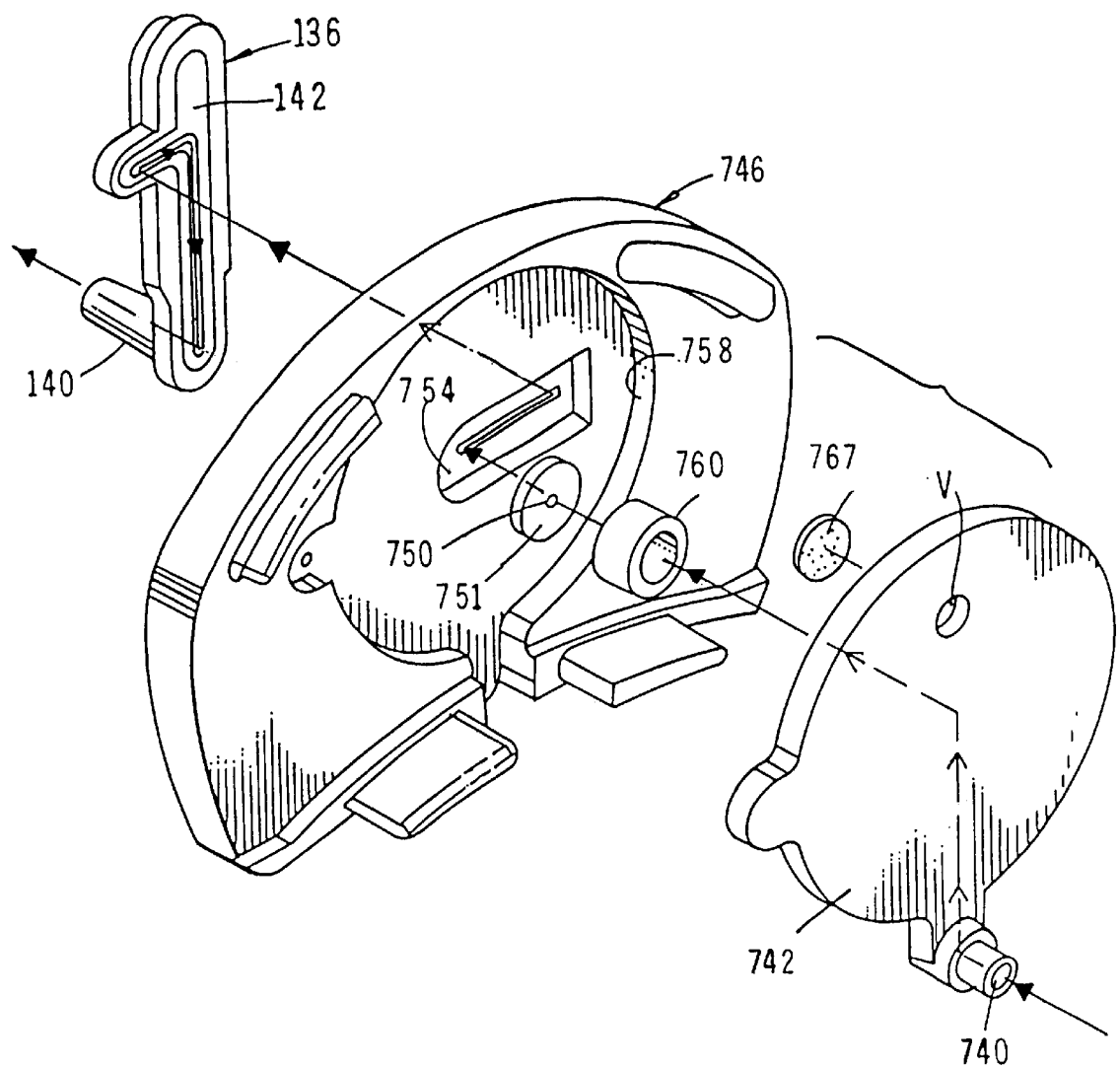
FIG. 91 is a generally perspective, exploded rear view of the forward portion of the fluid dispenser which houses the flow rate control means of the invention.
Figure 92:
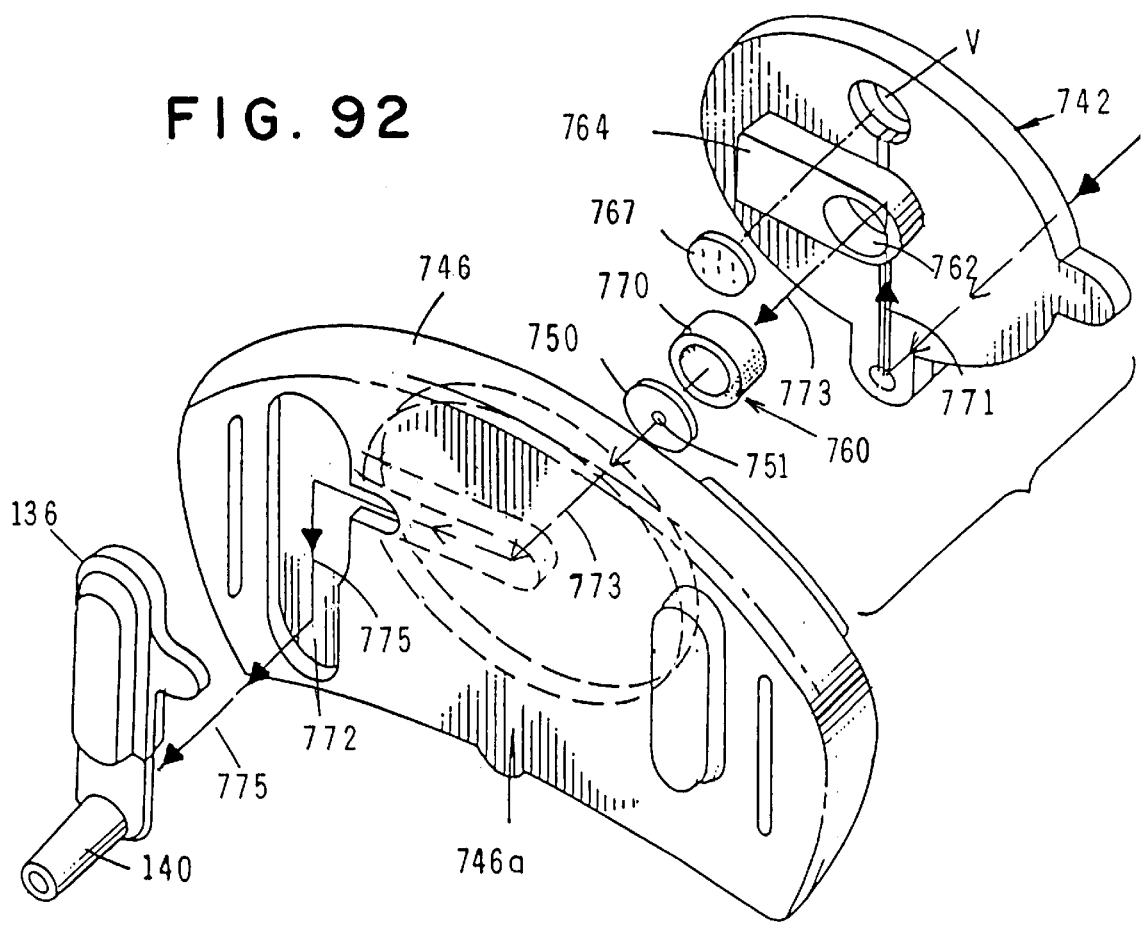
FIG. 92 is a generally perspective, exploded front view of the forward portion of the fluid dispenser.
Figure 92A:
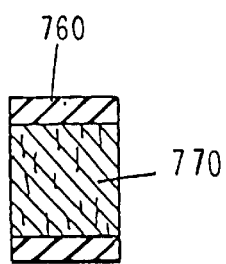
FIG. 92A is an enlarged cross-sectional view of the rate control frit shown in FIG. 92.

Turning to FIGS. 91 and 92, an alternate form of dispenser flow control means is there shown. As before, these alternate dispenser flow control means function to control fluid flow outwardly of the device. The embodiment of the invention shown in FIGS. 91 and 92 is similar to that shown in FIGS. 60, 60A, 61, and 62, and also comprises a first and second flow control means. First flow control means includes a fluid flow rate control wafer 750, which is closely received within a cavity 754 of support structure 746. Support structure 746 is similar in many respects to the earlier described structure 110 (FIG. 18) but the fluid distribution means which comprises a multiplicity of circumferentially spaced, manifolding stand-off elements 114 has been replaced by cavities 754 and 758. Wafer 750 is held in position within cavity 754 by a tube-like, elastomeric member 760 (FIGS. 91, 92, and 92A) which is receivable within a recess 762 formed in a boss 764 provided on a disc-like member 742 (FIG. 92). Member 742 is similar in many respects to member 116 which is shown in FIG. 21. However, the manifolding stand-offs 118 provided on member 116 have been replaced in member 742 with boss 764 which is provided with cavity 762. When member 742 is in place within cavity 758 of structure 746, wafer 750 is securely positioned between elastomeric sleeve 760 and the bottom wall of cavity 754. As before, a vent patch 767 vents to atmosphere any air trapped within the fluid passageways of the device via a vent "V".

As best seen in FIGS. 91 and 92, the rate control wafer 750 which has a single laser drilled aperture 751 which controls fluid flow toward an assembly 136, which assembly is identical to that previously described and shown in FIG. 21. Because of the similarity of this latest embodiment of the invention to that shown in FIGS. 18 through 23, like numbers have been used in FIGS. 91 and 92 to identify like components. Laser drilled wafer 750 can be constructed of metal, ceramic or like material and functions to precisely control fluid flow toward assembly 136 at a very precise rate. The second, or back-up flow control means here comprises a porous rate control frit 770 (FIGS. 92A) Reference should be made to co-pending Serial No. 09/017,047 for a more detailed discussion of the various materials suitable for constructing various components of this alternate dispenser flow control means of the invention as described in the preceding paragraphs.

Figure 88:
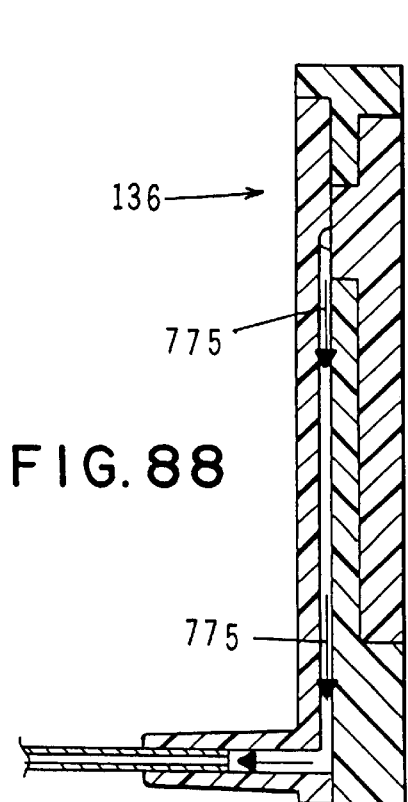
FIG. 88 is a cross-sectional view taken along lines 88-88 of FIG. 86.
Figure 87:
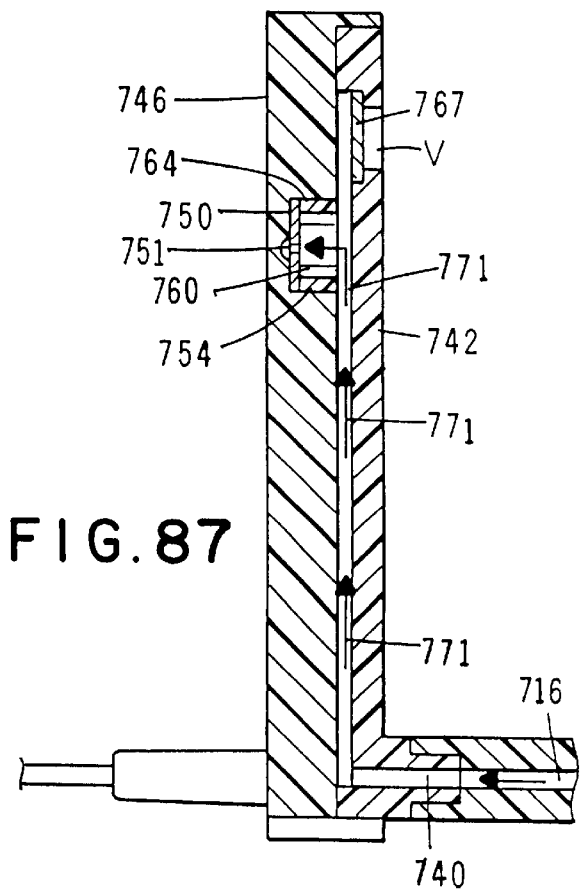
FIG. 87 is a cross-sectional view taken along lines 87—87 of FIG. 86.

With the construction described in the preceding paragraphs, when fluid is forced into passageway 714 by the stored energy means, the fluid will flow into passageway 716, then into passageway 740 of member 742 and finally in the direction of arrows 771 into chamber 762 formed in boss 764 (see FIGS. 87 and 92). The fluid under pressure will then flow through frit 770 toward the fluid outlet port of the flow control subassembly. As previously mentioned, the outlet port comprises the uniquely shaped assembly 136 which is receivable in a cavity 772 formed in the back or downstream wall 746a of a substrate 746. Assembly 136 includes a fluid outlet 140 and an internal chamber 142 (FIG. 91). As indicated in FIGS. 88 and 92, fluid flowing into chamber 772 will flow downwardly in the direction of the arrows 775 toward outlet 140 and into the infusion means of the apparatus.

Referring to FIG. 83, one form of infusion means of the apparatus of the invention for delivering fluid from the dispenser component to the patient is there illustrated and generally designated by the numeral 774. This infusion means, or delivery line assembly, is interconnected with outlet 140 of the dispenser component of the apparatus of the invention in the manner shown in figures 83 and 88. A long length of tubing 776 interconnects outlet 140 with a luer fitting 778 which is of a conventional construction. Intermediate the ends of length of tubing 776 is a gas vent and filter 779 which is also of a conventional construction and a tubing clamp 780 which is also of a character well known to those skilled in the art and functions to block fluid flow through tubing 776 (FIG. 83).

Figures 93, 94:
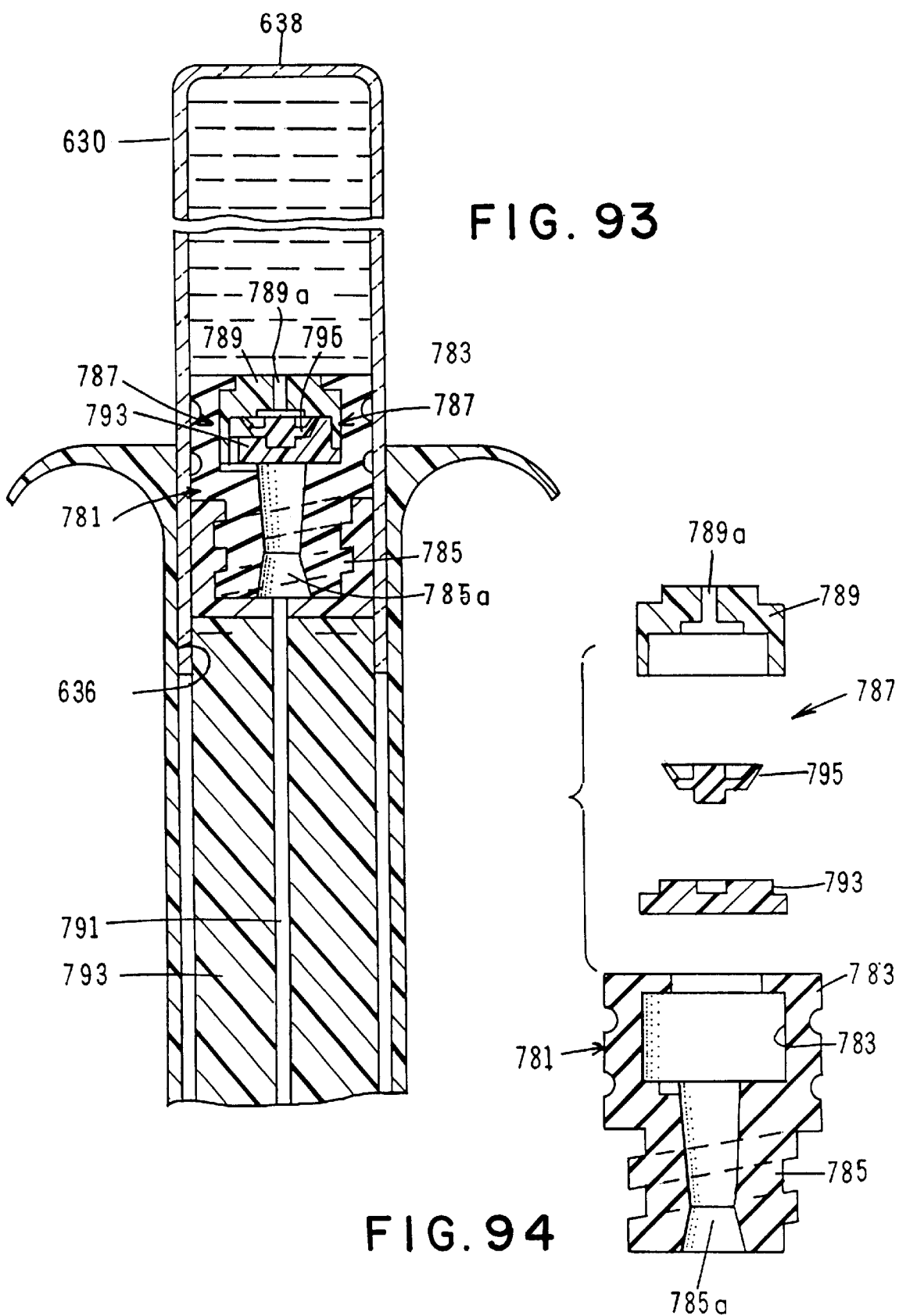
FIG. 93 is a fragmentary, cross-sectional view of an alternate form of container and adapter assembly of the apparatus of the invention.
FIG. 94 is an exploded, cross-sectional view of an alternate form of plunger connector subassembly adapted to house an alternate form of flow control means for controlling fluid flow toward the fluid dispenser assembly.

Referring to FIGS. 93 and 94, an alternate form of reservoir fill assembly is there illustrated. This assembly is generally similar to assembly 622 and like numbers are used in FIGS. 93 and 94 to identify like components. As before, the reservoir fill assembly comprises two major components, namely a container subassembly and an adapter subassembly. The container subassembly includes a container 630 which contains the medicinal fluid with which the reservoir of the dispensing apparatus is to be filled. Container 630 is provided with a first open end 636, and a second closed end 638. First open end 636 is sealably closed by closure means here provided in the form of a plunger assembly 781 which is of a somewhat different construction from plunger assembly 640. This plunger assembly 781 here comprises an elastomeric plunger 783 and a connector means, or connector 785 which functions to interconnect the container assembly with the adapter assembly. As before, the plunger assembly is telescopically movable within container 630 from a first location proximate first open end 636 to a second location proximate second closed end 638.

Unlike connector 644, connector 785 does not include a pierceable central wall which is pierceable by the elongated cannula 634 of the adapter assembly. Rather the central wall has been eliminated and fluid flow from container 630 toward the adapter assembly is controlled by an alternate flow control means, here provided as a valving means housed within plunger 783 in the manner shown in FIGS. 93 and 94. As shown in FIG. 94, plunger 783 includes a central chamber 783a which houses the valving means. This novel valving means here comprises a conventional umbrella type valve assembly 787 which functions to control fluid flow from a passageway 789a formed in valve capture member 789 toward a central fluid passageway 791 formed in the pusher means 793 of the modified adapter assembly of this latest embodiment (FIG. 93). Valve assembly 787 is of a conventional configuration having a central hub-like portion which is received within a central bore provided in a support plate 793 and a circumferentially extending, resiliently deformable, umbrella shaped flow control skirt 795 which is deflected outwardly by fluid flowing through passageway 789a so as to permit flow into passageway 785a of connector 785.

As in the earlier forms of the invention, the alternate form of adapter assembly shown in FIG. 93 has an outlet which permits fluid flow toward an umbrella type valve which is identical to valve 672. Fluid flowing through valve 672 will flow into a fluid passageway formed in a central connector 664 and then into reservoir 632 via a second umbrella valve 730 (see, for example FIG. 84).

Turning now to FIGS. 95 through 102, an alternate form of the fluid delivery apparatus of the present invention is there illustrated. This apparatus is similar in many respects to that shown in FIGS. 82 through 84 and like numerals are used to identify like components. As best shown in FIG. 95, as before the apparatus comprises two major cooperating assemblies, namely a fluid dispensing apparatus or fluid dispenser 800 and a reservoir fill assembly 802 which can be operably coupled with fluid dispenser 800. Reservoir fill assembly 802 is very similar in construction and operation to that previously described herein. Dispenser 800, on the other hand, is made up of three major cooperating subassemblies namely, a reservoir subassembly, a fluid flow indicator means and an infusion means for infusing medicinal fluids into the patient.

As shown in FIG. 96, reservoir fill assembly 802 comprises two major components, namely a container subassembly 626 and an adapter subassembly 804. Container subassembly 626 is identical in construction and operation to that previously described and contains the medicinal fluid with which the reservoir of the dispensing apparatus is to be filled. When interconnected with the dispensing apparatus, the adapter subassembly 804, which is of a slightly different configuration permits fluid transfer from container 626 to the reservoir of the dispenser component.

As best seen in FIG. 96, container 630 includes a body portion 630a, having a fluid chamber 634 for containing an injectable fluid "F". Body portion 630 is provided with a first open end 636, and a second closed end 638. First open end 636 is sealably closed by closure means here provided in the form of a plunger assembly 640.

Adapter assembly 802 comprises a hollow housing 650 having a first o p e n end 652 and a second closed end 654. Container assembly 626 is telescopically receivable within open end 652 of housing 650 in the manner shown in FIG. 96 so that the housing can be moved from the first extended position shown in figure 96 to a second container encapsulation position wherein container 630 is substantially encapsulated within housing 650. Provided interiorly of the adapter subassembly is a pusher means which is of slightly different construction from that previously described. More particularly, the pusher means here comprises a pusher body 806 which is generally cross shaped in configuration and functions to support cannula 810 and to move plunger 640 within fluid chamber 634 from the first forward position shown in FIG. 96 to a second position wherein it is disposed proximate end wall 638.

Needle-like cannula 810, unlike blunt end cannula 644 has a sharp piercing end 810a which is adapted to pierce wall 644a of the plunger assembly to place fluid chamber 634 of the container into fluid communication with an elongated fluid passageway 812 formed in pusher body 806. Passageway 812 communicates with fluid outlet 654a formed in end wall 654 and comprises a part of the second flow control means of the invention for permitting fluid flow toward the delivery apparatus of the invention. Once again, vent means, or hydrophobic element 651 is provided within body 650 to vent to atmosphere gases trapped within passageway 812.

Also forming a part of the adapter assembly of this latest form of the invention is a closure cap assembly 660 having a barrel-like portion which is connected to body portion 650 in the manner shown in FIG. 96. As before, cap assembly 660 includes an internal dividing wall 664 which supports piercing cannula 670. Disposed within cap assembly 660 is one of the valving means of the invention which, as before, comprises a conventional umbrella type valve assembly 672 of the character previously described which functions to control fluid flow from passageway 812 toward the central fluid passageway of cannula 670 via a passageway 674 formed in dividing wall 664.

As indicated in FIG. 96, the fluid delivery or dispenser assembly 800 of the apparatus of this latest form of the invention is similar in many respects to that shown in FIG. 83 and 84 and earlier described herein. More specifically, assembly 800 includes a housing assembly comprising a base 698, a capture ring 699, a stored energy source, or distendable membrane 700 and a cover 702 for enclosing the stored energy source, the capture ring and the base. Base 698 includes an ullage defining protuberance 704 and a membrane capture portion 706. Disposed between base 698 and cover 702 is the membrane capture ring 699 which functions in the manner previously described to capture membrane 700. As before, base 698 comprises dispenser connector subassembly 705, to which the reservoir fill assembly is interconnected in the manner previously described. During the reservoir filling step of this latest form of the invention, fluid under pressure will flow into inlet passageway 710 of the fluid dispenser via a conventional umbrella valve 712 and thence into the reservoir which is formed between protuberance 704 and the stored energy membrane 700. As the fluid under pressure flows into the reservoir, it will cause membrane 700 to distend outwardly from protuberance 704 so as to build up internal stresses within the membrane. During the infusion step, the internal stresses formed in membrane 700 will cause it to move toward protuberance 704 and fluid within the reservoir will be uniformly and controllably forced outwardly through a passageway 714 and then through a passageway 716 formed in base 698 in a direction toward the previously mentioned fluid flow indicator means of this latest form of the invention.

In using the apparatus of this latest form of the invention, the reservoir fill assembly is interconnected with the fluid delivery apparatus in the exact manner previously described by inserting barrel portion 660 into the receiving chamber formed in the base of the reservoir assembly and the reservoir of the fluid delivery apparatus is appropriately filled. During the reservoir filling step any air trapped within passageway 812 will be vented to atmosphere via vent element 651 and annular space 733. Similarly, any air trapped within septum mounting component 728 will be vented to atmosphere via a hydrophobic vent element 729 and a vent passageway 731 formed in connector assembly 705.

After the reservoir filling step and during the fluid dispensing step, the prestressed membrane 700 will tend to return toward a less distended configuration causing fluid within the dispenser reservoir to flow outwardly of the reservoir into passageway 714 and then into passageway 716 (FIG. 96). The fluid under pressure will next flow into passageway 740 of the inlet port of disk shaped member 742 which forms a part of the flow indicator means of the invention. The flow indicator means of this form of the invention is similar to that shown in FIGS. 61 and 62 and includes a support structure 814 which is similar in form to support structure 456 (FIG. 61).

Like member 466 of the earlier embodiment member, 742 includes a downwardly extending fluid inlet leg or segment 748 (see also FIG. 86) which is provided with the previously identified fluid passageway 740. As shown in FIG. 96, passageway 740 is adapted to communicate with the reservoir of the dispenser via passageways 714 and 716 when member 742 is mated with support structure 814 in the manner indicated in FIG. 96. The dispenser flow control means of this latest form of the invention is identical to that described in connection with FIGS. 91 and 92 and function to control fluid flow outwardly of the device.

Figure 100:
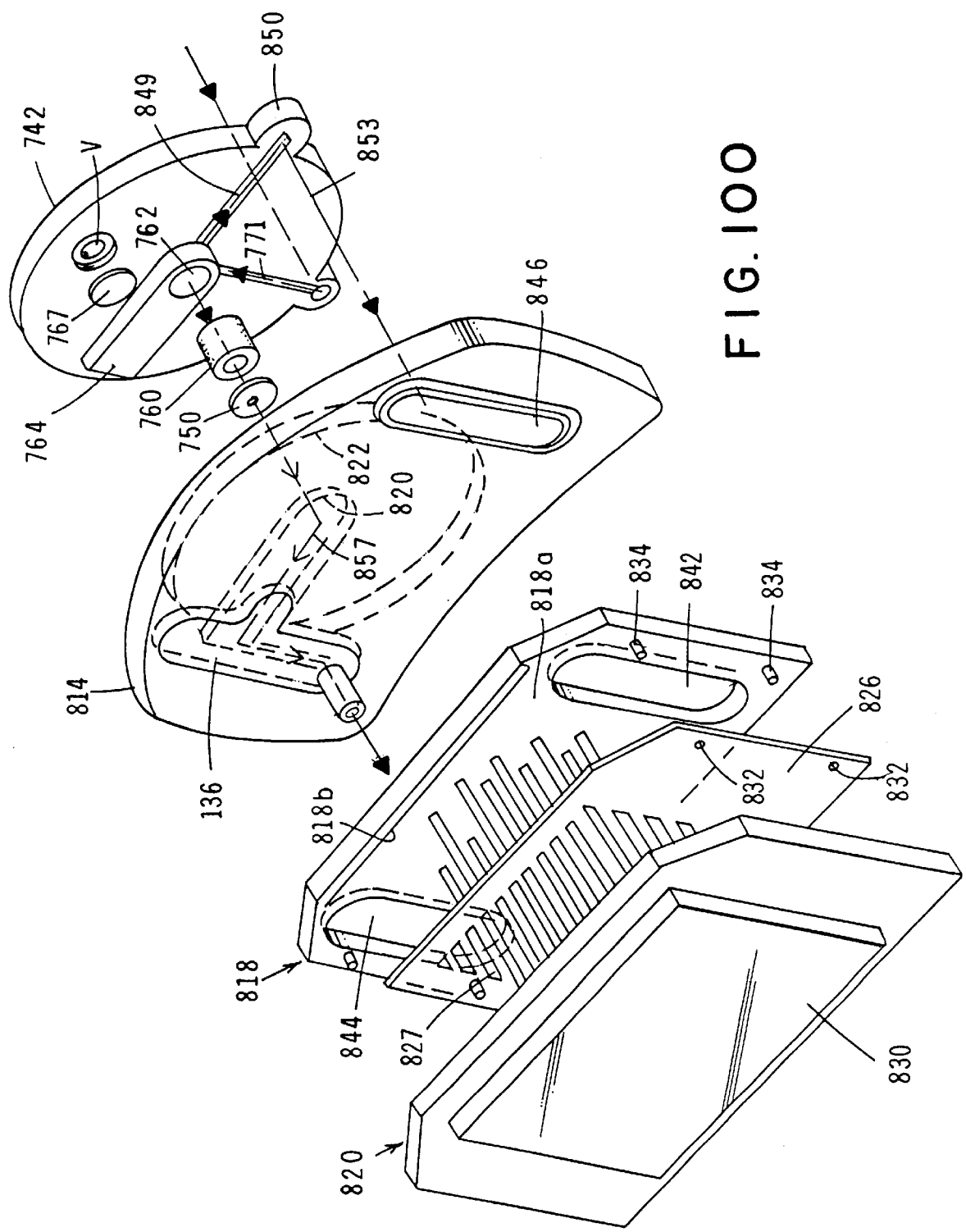
FIG. 100 is a generally perspective, exploded view of the flow indicator means of this latest form of the invention.

As before, the first flow control means includes a fluid flow rate control wafer 750, which is closely received within a cavity 820 formed in support structure 814 (FIG. 100). Support structure 814 is similar in many respects to the earlier described structure 110 (FIG. 18) but the fluid distribution means which comprises a multiplicity of circumferentially spaced, manifolding stand-off elements 114 has been replaced by cavities formed in the support structure. Wafer 750 is held in position within cavity 820 by a tube-like, elastomeric member 760 of the character shown in FIGS. 91, 92 and 92A. When member 742 is in place within a cavity 822 of structure 814, laser drilled wafer 750 is securely positioned between the elastomeric sleeve and the bottom wall of cavity 822. As before, a vent patch 767 vents to atmosphere any air trapped within the fluid passageway of the device via a vent "V".

Turning to FIGS. 91 and 92, an alternate form of dispenser flow control means is there shown. As before, these alternate dispenser flow control means function to control fluid flow outwardly of the device. The embodiment of the invention shown in FIGS. 91 and 92 is similar to that shown in FIGS. 60, 60A, 61, and 62, and also comprises a first and second flow control means. First flow control means includes a fluid flow rate control wafer 750, which is closely received within a cavity 754 support structure 746. Support structure 746 is similar in many respects to the earlier described structure 110 (FIG. 18) but the fluid distribution means which comprises a multiplicity of circumferentially spaced, manifolding stand-off elements 114 has been replaced by cavities 754 and 758. Wafer 750 is held in position within cavity 754 by a tube-like, elastomeric member 760 (FIGS. 91, 92, and 92A) which is receivable within a recess 762 formed in a boss 764 provided on a disc-like member 742 (FIG. 92). Member 742 is similar in many respects to member 116 which is shown in FIG. 21. However, the manifolding stand-offs 118 provided on member 116 have been replaced in member 742 with boss 764 which is provided with cavity 762. When member 742 is in place within cavity 758 of structure 746, wafer 750 is securely positioned between elastomeric sleeve 760 and the bottom wall of cavity 754. As before, a vent patch 767 vents to atmosphere any air trapped within the fluid passageways of the device via a vent "V".

Figure 97:
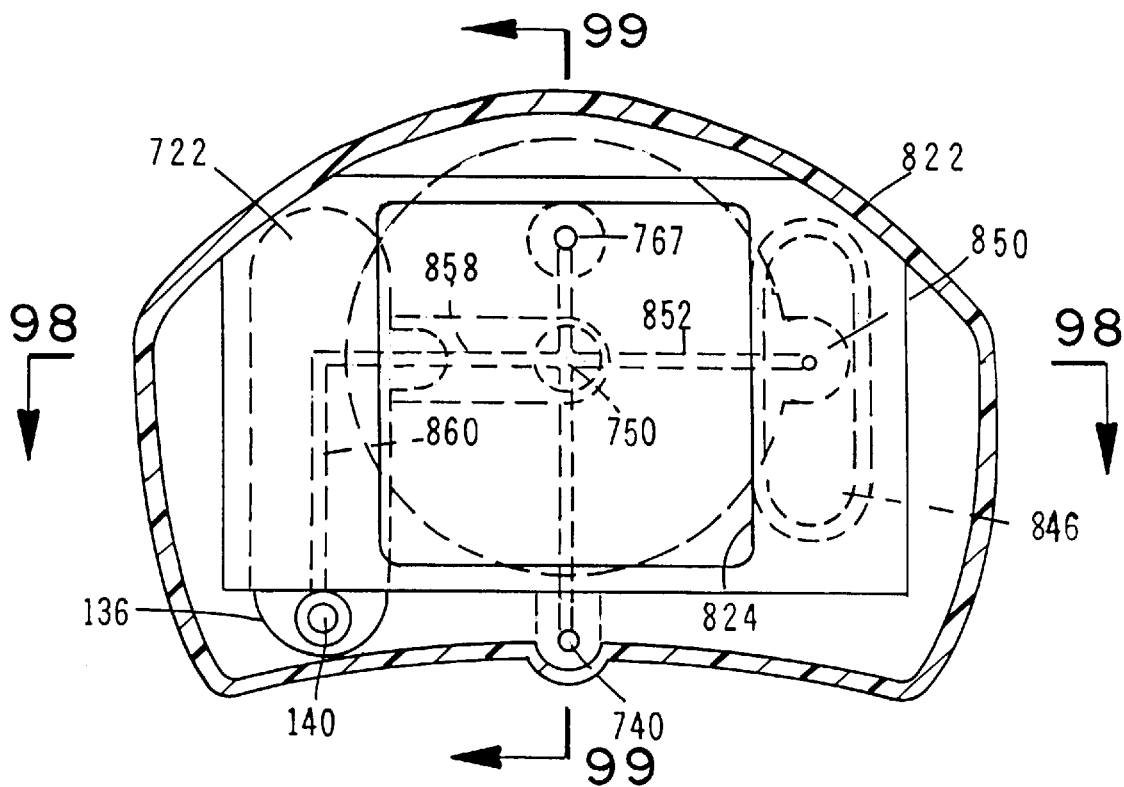
FIG. 97 is a [there is no description for FIG. 97 in your draft]

With the construction described in the preceding paragraphs, when fluid is forced into passageway 714 by the stored energy means, the fluid will flow into passageway 716, then into passageway 740 of member 742 and finally in the direction of arrows 771 into chamber 762 formed in boss 764 (see FIG. 100). The fluid under pressure will then flow through the rate control frit 770 toward the fluid outlet port of the flow control subassembly. Once again, the outlet port comprises the uniquely shaped assembly 136 which is receivable in a cavity 772 formed in the back or downstream wall of support 814 (see FIGS. 92 and 97). As shown in FIGS. 92 and 97, assembly 136 includes a fluid outlet 140 and an internal chamber 142 (FIG. 91). As indicated in FIGS. 88 and 92, fluid flowing into chamber 772 will flow downwardly in the direction of the arrows 775 toward outlet 140 and into the infusion means of the apparatus.

Considering next the flow indicator means of the invention. This novel means is similar in many respects to that shown in FIGS. 19 through 29 and FIGS. 61 through 63 and earlier described herein. As before, the flow indicator means distinguishes among two conditions of operation, namely normal fluid flow and fluid flow stop. Turning to FIG. 100, the flow indicator means here comprises an indicator base or platform 818 and a support or lens plate 820. Platform 818 and plate 820 are housed within indicator cover 822 (FIG. 99). As seen in FIGS. 99 and 101, plate 820 has a viewing lens portion 830 which indexes with an opening 824 provided in indicator cover 822.

Disposed between platform 818 and lens plate 820 is an indicia-carrying means shown here as a thin film 826. Film 826 is in intimate contact with the surface 818a of platform 818 which is printed with two integrated symbols 819 and 821 (FIGS. 101 and 102), namely a blue circle and a green arrow each consisting of diagonal strips of color printed in an alternating pattern. Film 826 serves as a "mask" over the integrated symbols and is printed with a pattern of diagonal alternating clear and opaque strips 827 that occur in a 1:2 ratio. The printed ratio of film 826 allows only one colored symbol to appear at a time when viewed through viewing lens 830 positioned on 820. Film 826 is provided at one of its ends with apertures 832 which receive retention pins 834 provided on platform 818 (FIG. 100) which permit attachment of the film to platform 818 in a manner such that pattern of clear and opaque stripes overlays the alternating patterns printed on plate 818. With this construction, film 826 is able to move in a direction parallel to the film plane with its range of motion limited to one axis in the film plane by edge guides 818b provided on platform 818. As the film moves, the visible symbol pattern changes due to the transverse displacement of the patterns 827 provided on the film.

Figure 98:
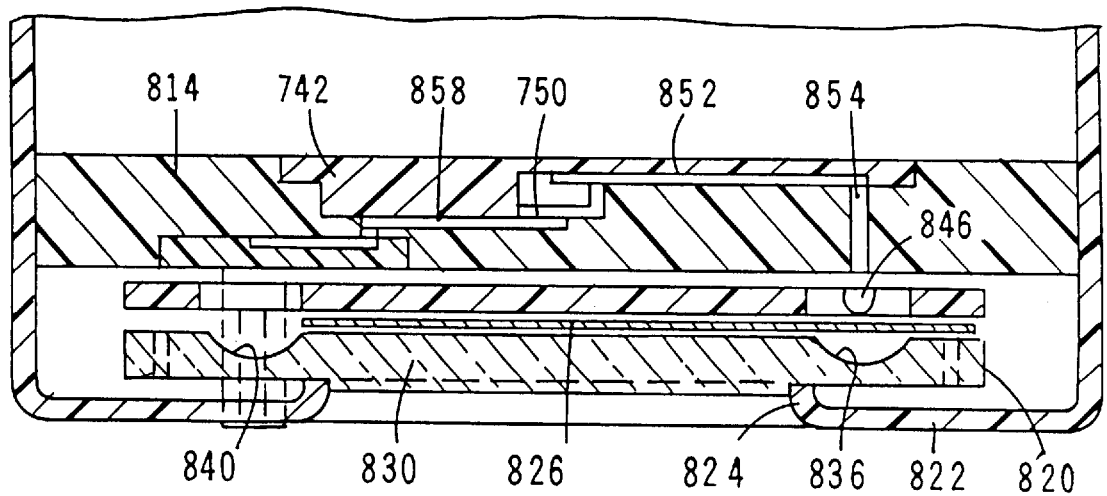
FIG. 98 is an enlarged cross-sectional view taken along lines 98—98 of FIG. 97.

As shown in FIG. 98, support plate 820 is provided with transversely spaced, channel-like depressions 838 and 840 which index with openings 842 and 844 formed in platform 818 respectively when the components are assembled in the manner shown in the drawings. Aligned with the upstream side of slot 838 is a mechanical actuator means, here provided as a mechanical actuator or elastomeric element 846.

As in the earlier described embodiments of the invention, the mechanical actuator means is deflected from its initial configuration whenever there is sufficient fluid pressure present within the fluid flow path to cause its outward deflection toward thin film 826. During operation the mechanical actuator element 846 is deflected by fluid pressure of the reservoir of the dispenser component. More particularly, when there is sufficient fluid pressure in the fluid reservoir and fluid is being delivered by the stored energy means of the device, the mechanical actuator means or elastomeric element 846 is deflected outwardly so as to urge a portion of the indicator film 826 into expansion channel 838 (FIG. 98). As the film arches into channel 838, the film is transversely displaced a specific distance. This film displacement re-aligns the front surface of the support with the mask pattern on film 826 and results in a change of the symbol (in this case an arrow as shown in FIG. 102) that is visible through the support plate view aperture 824.

A second alignment of symbol patterns as shown in FIGS. 23 and 101 is visible when the device is in an unfilled state or when the delivery line is open, the reservoir is empty and fluid delivery to the patient has been completed. In this case, since there is no fluid pressure in the line to deflect the actuator, the film is not deflected and the pattern seen is the zero pattern shown in FIG. 101.

During operation of the device of this latest embodiment, when the prestressed membrane 700 tends to return toward a less distended configuration during the fluid delivery step, fluid within the reservoir will flow outwardly of reservoir, into passageway 714 and then into passageway 716 (FIG. 96). The fluid under pressure will next flow into the inlet passageway 740 formed in disc-shaped member 742. A portion of the fluid entering cavity or chamber 762 can flow in the direction of arrows 849 directly toward an ear-shaped extension 850 (FIG. 100) provided on member 742 via a flow passageway 852 (FIGS. 97 and 98). From extensions 850, the fluid will flow under pressure in the direction of the arrows 853 into pressural engagement with actuator member 846 via passageway 854 (FIGS. 97 and 98) causing it to deflect outwardly into engagement with film 826. This causes the film to deform outwardly in a manner to force a portion of indicator film to arch into expansion channel 838 (FIG. 98). This, in turn, will cause transverse displacement of indicator film 826 in the manner previously described.

As indicated in FIGS. 98 and 100, fluid flowing into chamber 762 will also flow in the direction of the arrows 857 through passageway 858 of member 814 and then into member 136. The fluid will then flow downwardly through a passageway 860 formed in member 136 (FIG. 97) and then outwardly of the device through fluid outlet 140 to which an appropriate infusion line such as line 776 can be connected.

Figure 104:
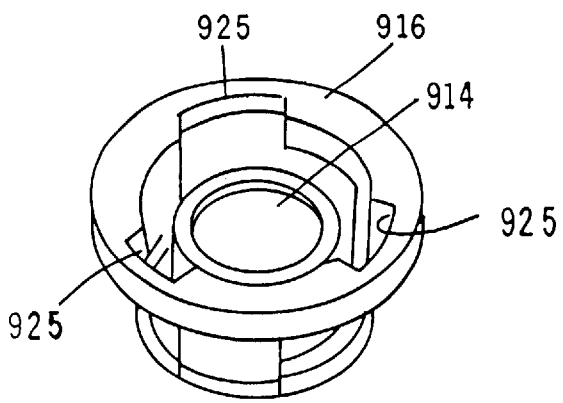
FIG. 104 is a generally perspective view of one form of the adapter component shown in FIG. 103.
Figure 104A:
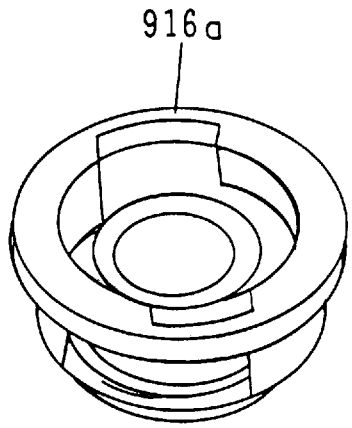
FIG. 104A is an alternate form of an adapter component.
Figure 104B:
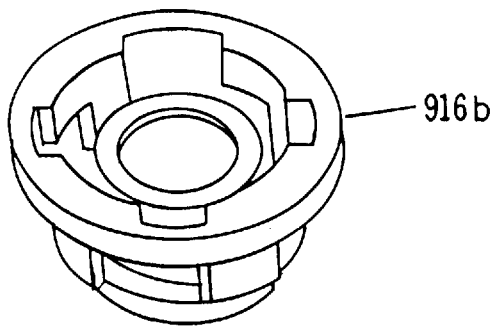
FIG. 104B is still another form of adapter component of the invention.
Figure 104C:
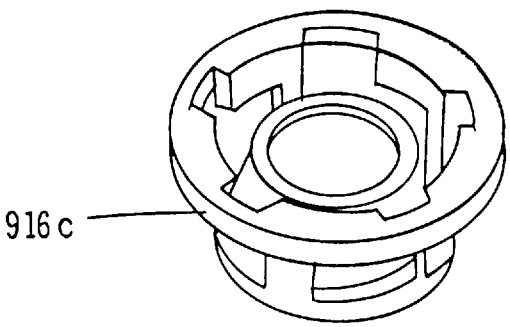
FIG. 104C is yet another form of adapter component of the invention.
Figure 104D:
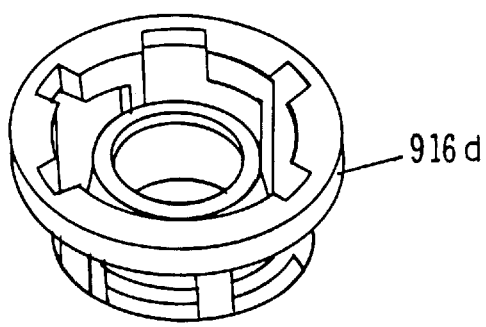
FIG. 104D is still another form of adapter component of the invention usable with the fluid dispenser component shown in FIG. 103.

Turning next to FIGS. 103 and 104, yet another form of the apparatus of the invention is there illustrated. This apparatus is similar in many respects to that shown in FIGS. 95 through 102 and like numbers are used to identify like components. Once again, the apparatus here comprises two major cooperating assemblies, namely a fluid dispensing apparatus or fluid dispenser 900 (FIGS. 103 and 104) and a reservoir fill assembly 902 (FIGS. 105 through 106D) which can be operably coupled with fluid dispenser 900. Dispenser 900 is, in turn, made up of two major cooperating subassemblies namely, a reservoir subassembly 901 (FIG. 103) and an infusion means for infusing medicinal fluids into the patient which is of the character previously described in connection with the apparatus shown in FIGS. 95 through 102.

The reservoir fill assembly 902 of the invention also comprises two major components, namely a container assembly which is identical in construction and operation to previously described container assembly 626 (FIG. 82) and an adapter assembly 904 which is quite similar in construction to adapter assembly 628 save for the provision of differently configured cap assembly.

As before, container assembly 626 is telescopically receivable within open end of the housing of the adapter assembly housing in the manner shown in FIG. 84 so that the housing can be moved from the first extended position shown in FIG. 84 to a second container encapsulation position wherein container 630 is substantially encapsulated within the housing of the adapter assembly.

As previously mentioned, the adapter assembly of this latest form of the invention includes a differently configured closure cap assembly 908 (FIGS. 105 and 106) which is connected to the body portion of the adapter assembly in the manner shown in FIG. 105. Cap assembly 908 includes a generally cylindrical exterior wall defining a barrel-like portion 910 and an outwardly tapering wall 912 which is sealably receivable within a tapered socket-like cavity 914 formed in an adapter coupler 916 provided on fluid dispenser component 900 (FIGS. 103 and 104). Adapter coupler 916 is connected by adhesive bonding or the like to a hublike portion 920 which forms a part of a base assembly 922 and is of the configuration shown in FIG. 103.

During the dispenser reservoir filling step, fluid under pressure will flow from container 630 into the delivery device reservoir 632 which is formed between protuberance 704 and the stored energy membrane 700 (see FIG. 84). As the fluid under pressure flows into the reservoir, it will cause membrane 700 to distend outwardly from protuberance 704 so as to build up internal stresses within the membrane. During the infusion step, the internal stresses formed in membrane 700 will cause it to move toward protuberance 704 and fluid within reservoir 632 will be uniformly and controllably forced outwardly through a passageway 714 and then through a passageway 716 formed in the base in a direction toward the infusion means of the invention.

To interconnect the reservoir fill assembly 902 with the fluid delivery apparatus 900, the forward end or cap assembly portion 908 of the adapter assembly is inserted into cavity 914 of the coupler adapter 916. Formed within coupler adapter 916 are circumferentially spaced tab receiving openings or slots 925 which are adapted to receive bayonet type connector ears or tabs 927 formed on cap assembly 908 (FIGS. 103, 104, 105, and 106). Relative rotation of the fill assembly 902 and the fluid delivery apparatus 900 will securely interconnect the components in the manner previously described. As the fill assembly is mated with the delivery component, tapered wall 912 will sealably engage the wall of cavity 914 and as the adapter assembly is mated with adapter coupler 908 cannula 670 of the adapter assembly will pierce septum 726 of the fluid delivery component so that fluid can be expelled from the fluid chamber of the container assembly into the fluid reservoir of the fluid delivery apparatus 900. This step is accomplished in the manner earlier described by urging container 630 into the adapter assembly housing using the finger engaging ears. After the reservoir filling step and during the fluid dispensing step, the prestressed membrane 700 will tend to return toward a less distended configuration causing fluid within the dispenser reservoir to flow outwardly of the reservoir into passageway 714 and then into passageway 716 (FIG. 96). The fluid under pressure will next flow into passageway 740 of the inlet portion of disk shaped member 742 (see FIGS. 87, 88, 91 and 92).

Turning to FIGS. 106A, 106B, 106C, and 106D, alternate forms of the cap assembly 908 are there shown and designated by the numerals 908a, 908b, 908c and 908d respectively. Cap assembly 908a is provided with two rather than three circumferentially spaced locking tabs 927, while cap assembly 908b is provided with four rather than three circumferentially spaced locking tabs 927. Similarly, cap assembly 908c is provided with five circumferentially spaced locking tabs and cap assembly 908d is provided with six circumferentially spaced locking tabs. These alternate cap assemblies can be selectively affixed to fill assemblies which include container assemblies having containers filled with first, second, third, fourth and fifth differing medicaments.

Referring to FIGS. 104A, 104B, 104C, and 104D, there is shown alternate forms of adapter couplers 916 there designated as 916a, 916b, 916c, and 916d respectively. With the novel construction shown, fill assemblies containing a first medicament, such as morphine sulfate can be provided with a three-tab closure cap assembly 908 and the fluid delivery device can be provided with a three-slot adapter coupler 916. In like manner, fill assemblies containing a second medicament, such as a first antibiotic can be provided with a two-tab closure cap assembly 908a and the fluid delivery device can be provided with a two-slot coupler 916a. Similarly, when the fill assembly contains a third medicament such as a second antibiotic, the fill assembly can be provided with a four-tab closure cap assembly 908b, and the fluid delivery device can be provided with a four-slot coupler 916b. Similarly, fill assemblies containing other medicaments can be provided with five and six-tab closure caps which can be mated with fluid delivery devices having adapter couplers provided with five and six-slots respectively. In this way, potentially serious errors of misadministration of medicaments can be elegantly and positively avoided.

Figure 107:
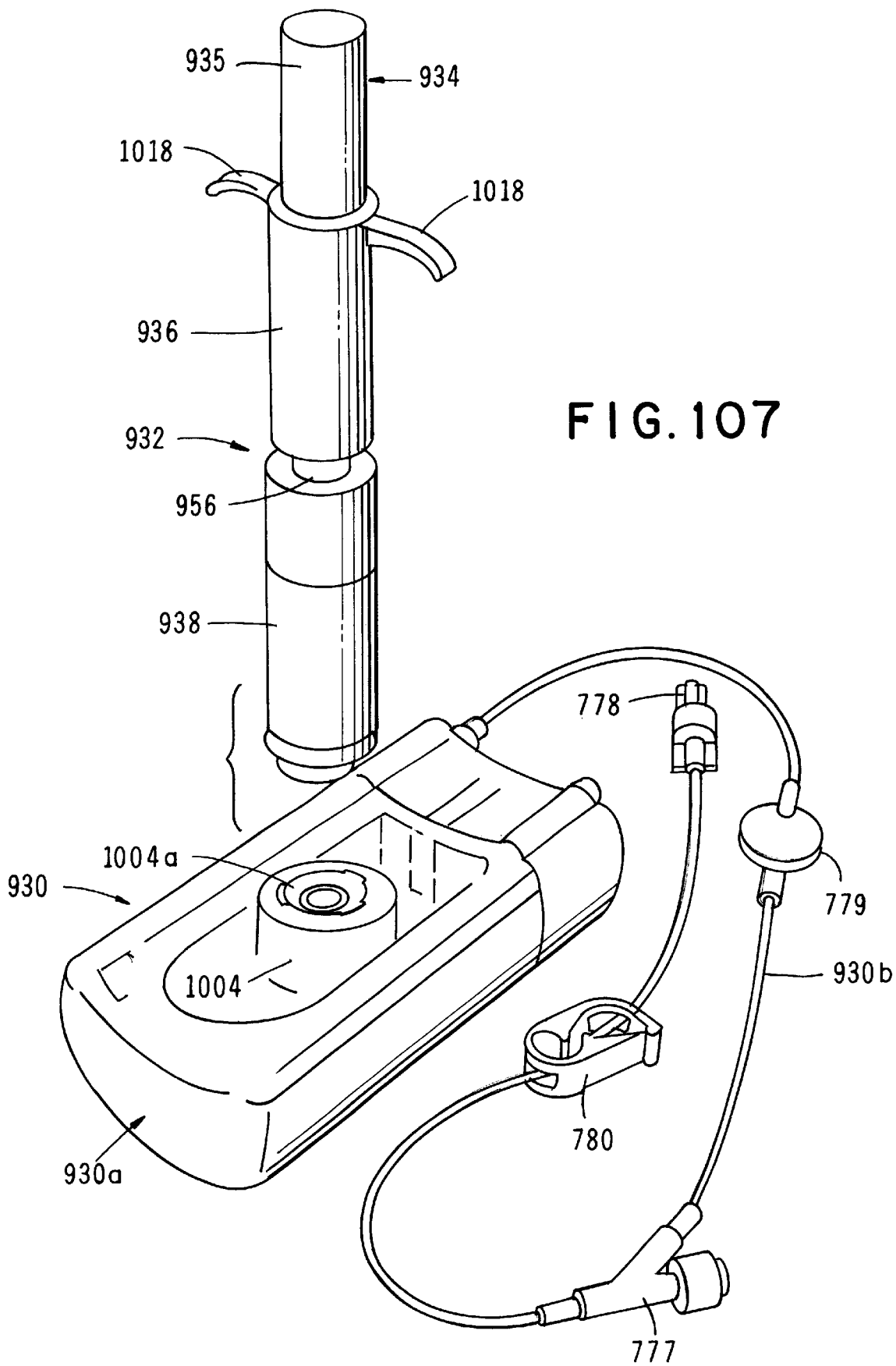
FIG. 107 is a generally perspective exploded view of an alternate form of reservoir fill assembly mated with the fluid delivery apparatus.

Turning next to FIGS. 107 through 114, still another form of the apparatus of the present invention is there illustrated. As best seen in FIGS. 107 and 108, the apparatus once again comprises two major cooperating assemblies, namely a fluid dispensing apparatus or fluid dispenser 930, and a reservoir fill assembly 932 which can be operably coupled with fluid dispenser 930. As in the earlier described embodiments, dispenser 930 is made up of two major cooperating subassemblies namely, a reservoir subassembly 930a and an infusion means 930b for infusing medicinal fluids into the patient. The infusion means is similar to that shown in FIG. 83 and earlier described herein.

Figure 113:
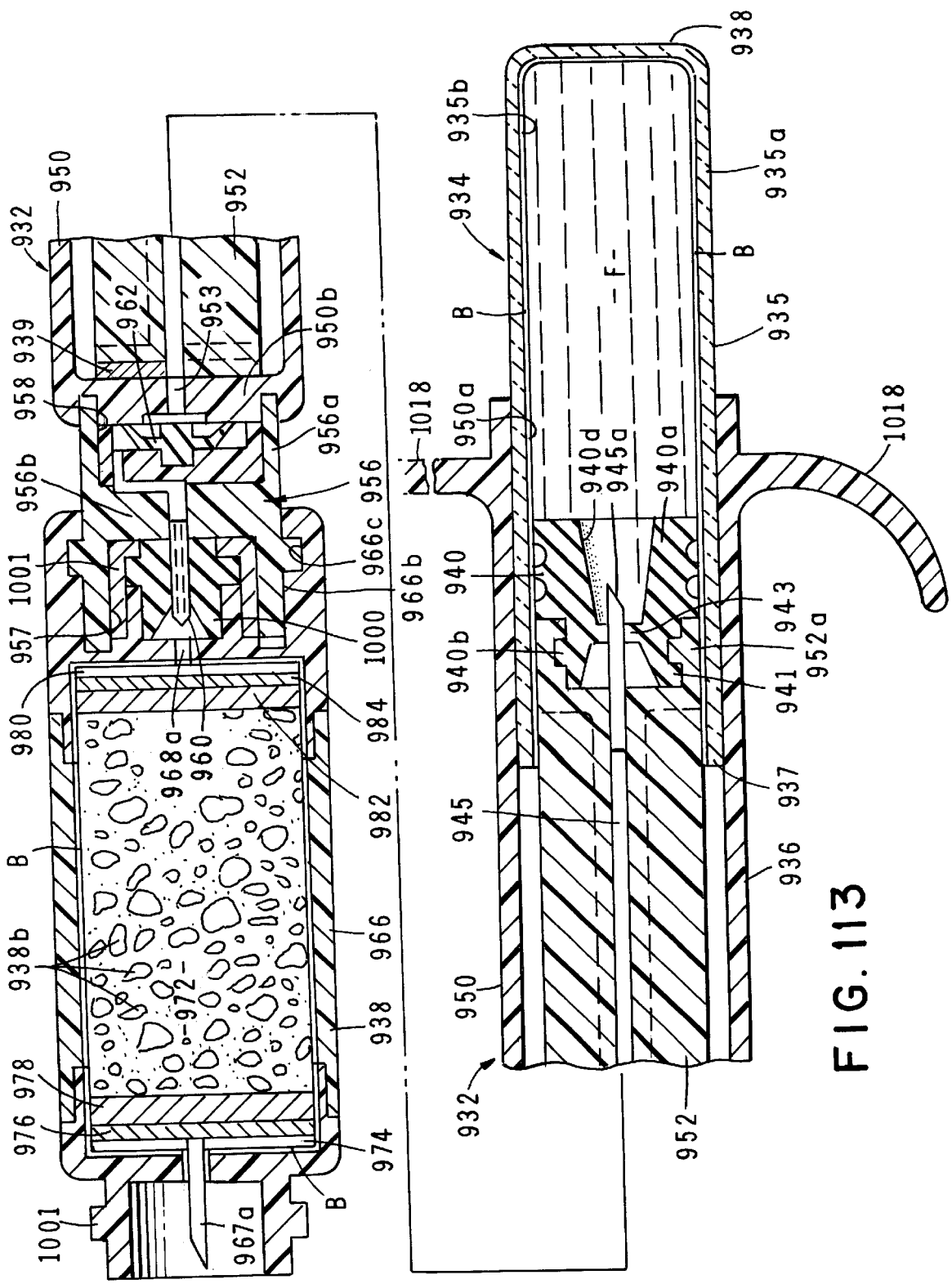

Turning particularly to FIGS. 111 and 113, the reservoir fill assembly 932 of the latest form of the invention uniquely comprises three major components, namely a container subassembly 934 (FIG. 111), an adapter subassembly 936, and an immobilized drug vial assembly 938. Container subassembly 934 includes a container 935 which contains the medicinal fluid agent "F" with which the reservoir of the dispensing apparatus is to be filled. When the immobilized drug vial assembly 938 is interconnected with the dispensing apparatus and when the adapter subassembly 936 is interconnected with the immobilized drug vial assembly in the manner shown in FIG. 108, the fluid "F" can be transferred from container 935 to the reservoir 931 of the dispenser component via the immobilized drug vial assembly.

As best seen in FIG. 111, container 935 includes a body portion 935a, having a fluid chamber 935b for containing an injectable fluid "F". Body portion 935a is provided with a first open end 937, and a second closed end 938. First open end 937 is sealably closed by closure means here provided in the form of a plunger assembly 940. Plunger assembly 940 comprises an elastomeric plunger 940a and a connector means, or connector 940b which functions to interconnect the container assembly with the adapter assembly. Plunger assembly 940 is telescopically movable within chamber 935b of the container subassembly from a first location proximate first open end 937 to a second location proximate second closed end 937a.

Connector 940b includes threads 941 which can be threadably connected to threads 942 provided on adapter subassembly 936. Connector 940b also includes a pierceable central wall 943 which is pierceable by an elongated cannula 945 of the adapter subassembly, which cannula comprises a part of the first flow control means of an adapter subassembly for controlling fluid flow toward the immobilized drug vial assembly and then on to the fluid dispenser. Cannula 945 is insert molded into a pusher means and includes a central fluid flow passageway 945a. Connector 940b is connected to plunger 940a in the manner shown in FIG. 111 so that as the plunger is moved toward closed end 937a, in a manner presently to be described, connector 940b and plunger 940a will move as a unit. To prevent leakage of fluid past plunger 940a, the plunger is provided with rings 940c which are of a diameter slightly greater than the inside diameter of container body 935. Plunger 940a also includes a central fluid passageway 940d which is in open communication with fluid chamber 935b.

Adapter subassembly 936 comprises a hollow housing 950 having a first open end 950a and a second closed end 950b. Container assembly 934 is telescopically receivable within open end 950a of housing 950 in the manner shown in FIG. 113 so that the housing can be moved from the first extended position shown in FIG. 113 to a second container encapsulation position wherein container 935 is substantially encapsulated within housing 950. Provided interiorly of the adapter subassembly is the previously mentioned pusher means which is shown here as a pusher body 952. Pusher body 952, which is generally cross shaped in configuration, functions to support cannula 945 and to move plunger assembly 940 within fluid chamber 935b from the first forward position shown in FIG. 113 to a second position wherein it is disposed proximate end wall 937a. Pusher body 952 also includes a head portion 952a within which threads 942 are formed. End wall 950b of housing 950 is provided with a fluid outlet 953 which comprises a part of the second flow control means of the invention for permitting fluid flow toward the delivery apparatus of the invention.

Also forming a part of the adapter assembly of the invention is a connector or cap assembly 956 (FIG. 111) which is connected to body portion 950 in the manner shown in FIG. 113. Cap assembly 956 includes a generally cylindrical exterior wall defining a band-like portion 956a and an internal dividing wall 956b which cooperates with the exterior wall to form first and second chambers 957 and 958. Connected to wall 956b and extending into chamber 957 is a cannula 960, the purpose of which will presently be described. Mounted within a valve retainer 962a which is disposed within chamber 958 is one of the valving means of the invention which here comprises a conventional umbrella type valve assembly 962 which functions to control fluid flow from passageway 953 toward the central fluid passageway of cannula 960. Valve assembly 962 is of a conventional configuration having a central hub-like portion and a circumferentially extending, resiliently deformable, umbrella shaped flow control skirt which is deflected outwardly by fluid flowing through passageway 953 so as to permit flow into cannula 960.

Considering next the important immobilized drug vial assembly 938, this assembly comprises a generally cylindrically shaped hollow plastic body 966 having first and second ends 966a and 966b (FIG. 111). Body 966 includes apertured walls 967 and 968 which cooperate with the interior wall of the body to define an interior chamber 970 which houses the important adding means or immobilized drug component 972, the character of which will presently be described. Disposed between the immobilized drug component 972 and wall 967 is a distal end fluid collector 974, a distal rate control element 976 and a porous frit 978. Disposed between the immobilized drug component 972 and wall 968 is a proximal end fluid collector 980, a proximal rate control element 982 and a porous frit 984.

As shown in FIG. 109, distal end fluid collector 974 is provided with radially extending fluid collection grooves 974a which function to collect fluid flowing through the immobilized drug component 972 and direct it into the central fluid passageway 967a formed in wall 967. Similarly, proximal end fluid collector 980 is provided with radially extending fluid dispersion grooves 980a which function to disburse fluid flowing through the central fluid passageway 968a formed in wall 968 so as to cause the fluid to be uniformly dispersed into the immobilized drug component via the rate control element 982 and porous frit 984. As the fluid flows through component 972, the additive immobilized therein will be added to the fluid to form the fluid mixture that will ultimately be dispensed to the patient. This fluid mixture will flow through porous frit 978, through rate control element 976 and then toward fluid collector 974 where it will be collected and urged to flow through passageway 967a at a precisely controlled rate.

As previously mentioned, the immobilized drug component 972 cornprises the additive presentation means of the invention which functions to present the additive, such as a drug, to the fluid flowing through the component at a controlled rate as dictated by the rate control element 982 and the frit 984. Component 972 comprises a functional support or substrate 938a which supports the additive 938b. The additive 938b can comprise an element, compound, substance, agent, biologically active material, or other material which can be added, all or in part, to the fluid introduced into component 972 from container subassembly 934. The functional substrate or scaffold can comprise a microporous, mesoporous, macroporous, ordered structure and can be constructed from a polymer, copolymer, an interpolymer, a ceramic, a crystal sponge, a carbon based matrix, a celullosic, glass, plastic biomosaic polymers, azlactone-functional polymer beads, adduct beads, carboxylate-functional polymer beads, gums, gels, filaments and like carriers.

The additives which are supported by the functional support can take various physical forms including liquid, solid, granular, powder, particle, gel, wax, zeolite, hydrocolloid carrier, a gum, a film, tablet, crystalline, emulsions, microcrystalline, microspherical, spray dried compounds and lypohilized compounds and saturants. The additives can be removably connected to and immobilized on, impregnated within or supported by the support means in a number of ways. The additives can be chemically or mechanically attached, affixed or bound directly or indirectly, linked or cross linked, anchored to the surfaces of the support, or surface active agent or they can be absorbed, reaction catalyzed, electrostatically encapsulated, attached by chemical modification or transformation to the carrier surface, polymerized on or through the carrier with or without the use of an interpolymer, localized, entrapped, suspended, deposited, impregnated, coated, or occluded or otherwise removably affixed within voids, cells, tubules, and intersticies formed in the support in the manner shown in FIG. 113.

Similarly, the additives can be added to or intermixed with the liquid flowing through the device by one or more of various mechanisms, including mechanical release, chemical reaction, dissolution, disorbsion, debinding, delinking, bioseparation, diffusion, washing, disintegration, erosion, disassociation, solubilization, leeching, enzymatic cleavage, biological reaction, osmosis, separation from ring opening materials by a ring opening reaction, and other separation means. For a more complete discussion of the construction and operation of the immobilized drug component 972, reference should be made to U.S. Pat. No. 5,279,558 issued to one of the present inventors. U.S. Pat. No. 5,279,558 is incorporated by reference as though fully set forth herein.

Figure 112:
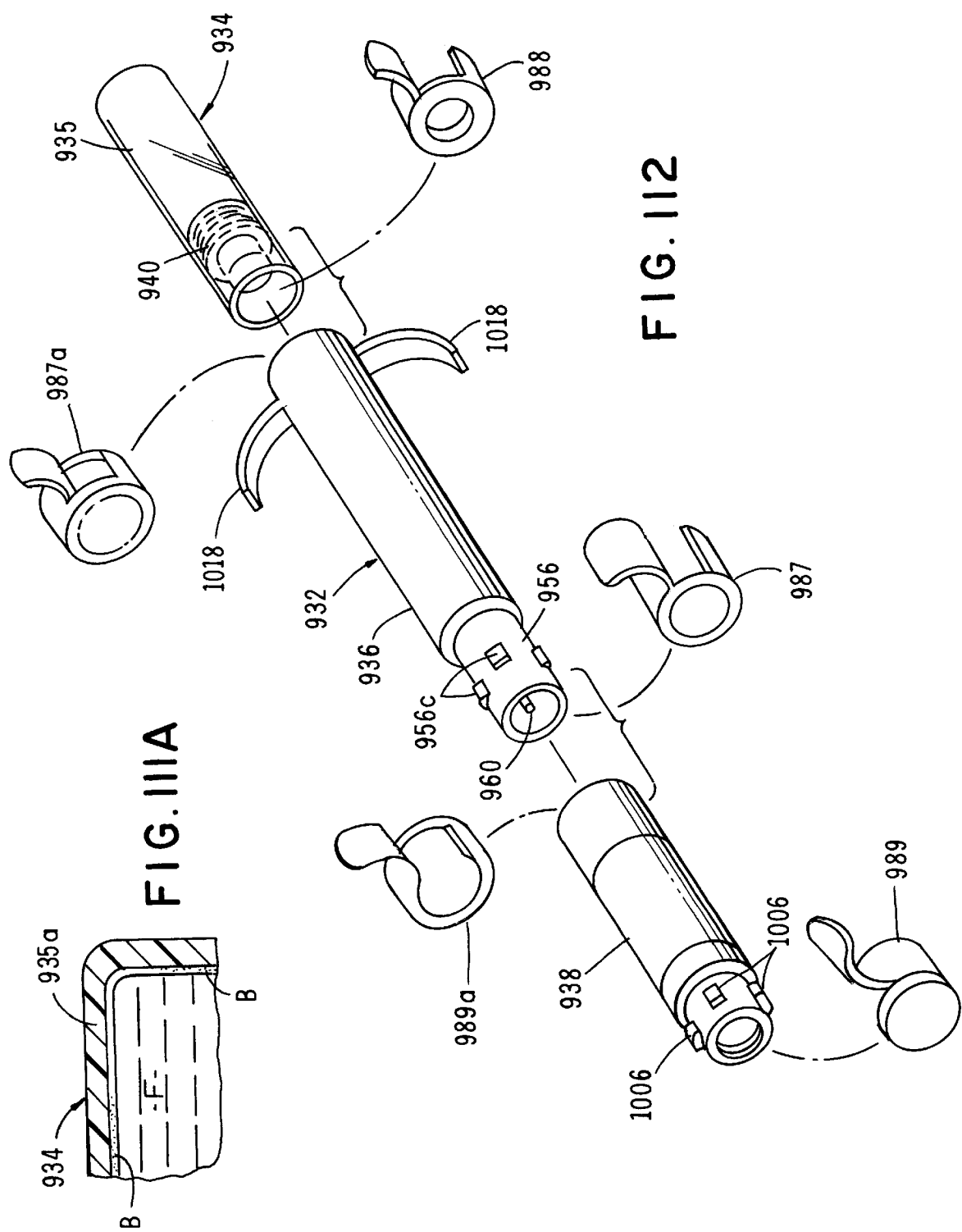

Prior to use, the cooperating components of the reservoir fill assembly are maintained in a protected and aseptic configuration by tear-away end caps of the character shown in FIG. 112. As indicated in FIG. 112, tear-away end caps 987 and 987*a* are receivable over and close the forward and rearward ends of adapter subassembly 936, while a tear-away end cap 988 is received over and closes the open end portion of container 935. Similarly, tear-away caps 989 and 989*a* are received over and close the open ends of immobilized drug vial assembly 938.

Turning again to FIG. 108, the fluid dispenser assembly 930*a* of the apparatus of this form of the invention is similar in some respects to that described in incorporated by reference U.S. Pat. No. 5,721,382 and includes a housing assembly comprising a base 991, a capture ring 992, a stored energy source, or distendable membrane 993 and a cover 994 for enclosing the stored energy source, the capture ring and the base. Base 991 includes an ullage defining protuberance 991*a* and a membrane capture portion 991*b*. Disposed between base 991 and cover 994 is the membrane capture ring 992 which has a bottom opening 992*a* which receives protuberance 991 a of base 991. When the base 991 and the membrane capture ring 992 are assembled in the manner shown in FIG. 108, the periphery of distendable membrane 993 will be securely clamped therebetween.

During the reservoir filling step, fluid under pressure will flow into inlet passageway 996 of the fluid dispenser via a conventional umbrella valve 998 and thence into reservoir 931 which is formed between protuberance 991 a and the stored energy membrane 993. As the fluid under pressure flows into the reservoir, it will cause membrane 993 to distend outwardly from protuberance 991 a so as to build up internal stresses within the membrane. The stored energy means can be in the form of a single prestressed or unstressed isotropic, elastomeric distendable membrane, or can be constructed as a laminate assemblage of the character described in incorporated-by-reference Patent No. 5,721,382. During the infusion step, the internal stresses formed in membrane 993 will cause it to move toward protuberance 991*a* and fluid within the reservoir will be uniformly and controllably forced outwardly into the infusion means of the invention.

Figure 114:
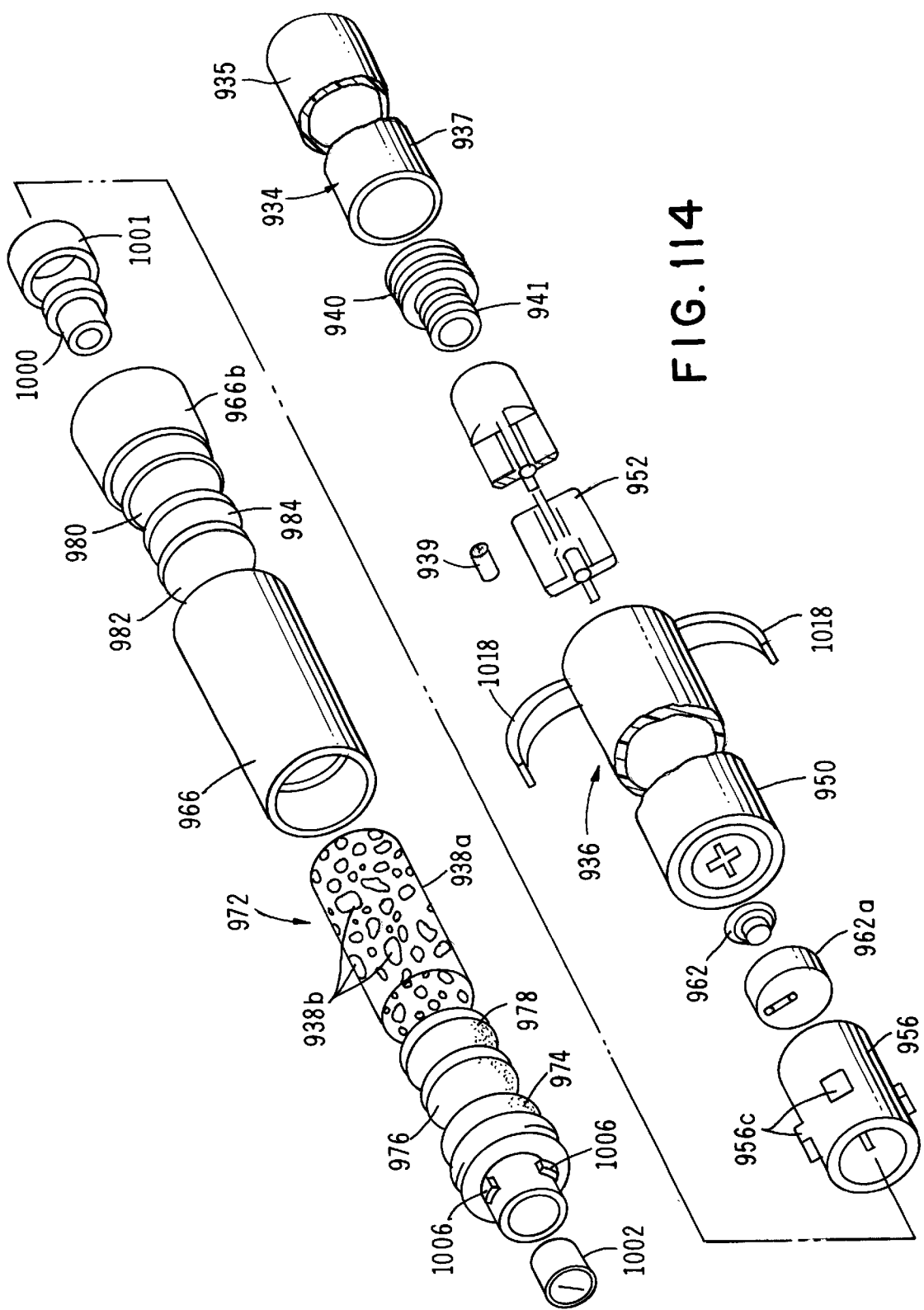

In using the apparatus of this form of the invention, seal cap 988 is removed from container assembly 934 and the open end of the container is inserted into the open end 950*a* of the adapter body in the manner shown in FIG. 113. As connector member 940*b* is threadably interconnected with pusher 952 by relative rotation of the assemblies, cannula 945 will pierceably engage and penetrate central wall 943 of the connector thereby opening fluid communication between reservoir 935*b* of the container assembly and passageway 945*a* of cannula 945. Once wall 943 has been penetrated, an inward force exerted on the container assembly will cause pusher 952 to urge plunger 940 inwardly of the container reservoir. As plunger 940 moves inwardly, fluid within reservoir 935*b* will be free to flow into the central fluid passageway of cannula 945 and toward adapter assembly passageway 953. Any gases trapped within container subassembly 934 will be vented to atmosphere via a porous vent element 939 (FIGS. 113 and 114).

To interconnect the adapter assembly with the immobilized drug vial assembly 938, caps 987 and 987*a* are removed and the forward end of the cap assembly 956 is inserted into opening 966*b* of vial assembly 938 and then rotated to lock bayonet type locking ears 956*c* in place within slots 966*c* formed in end 966*b*. As the parts are mated, cannula 960, which is supported by and extends outwardly from wall 956*b*, will pierce a pierceable septum 1000 contained within a septum cap 1001 disposed within end portion 966*b* of vial assembly 938 thereby permitting fluid flow from reservoir 935*b* into fluid passageway 968*a*. The fluid will then flow into the dispensing grooves 980*a* of fluid collector 980, through rate control element 982, through porous frit 984 and then uniformly through immobilization substrate 938*a* at a controlled rate.

Interconnection of the immobilized drug vial assembly with the fluid dispenser 930 is accomplished by removing the inboard cap 989 along with a protective septum 1002 that is affixed thereto. The proximal end of the vial assembly is then inserted into the receiving chamber 1004*a* of hub-like member 1004 of base 991 of the fluid dispenser. As best seen in FIG. 108, hub-like member 1004 includes circumferentially spaced openings 1004*b* which are adapted to receive bayonet-type connector ears 1006 formed on the proximal end of vial assembly 938. Relative rotation of the vial assembly 938 and the fluid delivery apparatus 930 will securely interconnect the immobilized drug vial assembly and the fluid delivery apparatus in the manner shown in FIG. 108. As indicated in FIG. 108, as the vial assembly 938 is mated with the delivery component, cannula 967*a* of the vial assembly will pierce a pierceable septum 1008 which is mounted within a connector means shown here as the previously identified hub-like member 1004. Also disposed within hub 1004 is valve means for controlling fluid flow toward inlet 996 of reservoir 931. This delivery component valving means here comprises the previously mentioned, conventional umbrella-type check valve 998 which permits fluid flow from cannula 967*a* toward passageway 996, but blocks fluid flow in the opposite direction.

After the inboard peelable end cap 987 of the adapter assembly 932 which includes septum 1012 has been removed (FIG. 112), the assemblage comprising the container assembly 934 and the adapter subassembly 932 can be interconnected with the immobilized drug vial assembly 938 by inserting connector member 956 into open end 966*b* of the vial assembly body so that bayonet-type locking ears 956*c* are received within slots 966*c*. Rotation of the vial assembly will then function to interlock the assemblages together. As the inboard end of the member 956 is inserted into end 966*b*, cannula 960 will pierce a slit septum 1000, which forms a part of the immobilized drug vial assembly thereby opening fluid communication between container reservoir 935*b* and inlet passageway 968*a* of wall 968. By urging container body 935 into the annular space 1016 defined by the interior wall of hollow housing 950 and the exterior surface of pusher member 952 through use of the finger engaging ears 1018 (FIG. 108), plunger 940 will be moved into container 935 causing the fluid "F" to flow into cannula 945. The fluid will then flow past umbrella check valve 962, into cannula 960, into passageway 968*a* and toward proximal end fluid collector 980. Collector 980 collects and disperses the fluid in a manner so that it will uniformly flow through the supporting substrate 938a in the manner previously described. Rate control element 982 and porous frit 984 regulate the flow from collector 980 while rate control element 978 and porous frit 976 regulate the flow of the fluid to the dispensing apparatus.

As shown in FIG. 108, the fluid dispenser also includes fluid recovery means for recovering fluid from reservoir 931. This means, which enables recovery at any time of fluid contained within the reservoir, here comprises a septum 1019 housed within a chamber formed in protuberance 991a. Septum 1019 is pierceable by a cannula of a conventional syringe assembly that can be used to remove fluid from the reservoir in a conventional manner.

Figure 117:
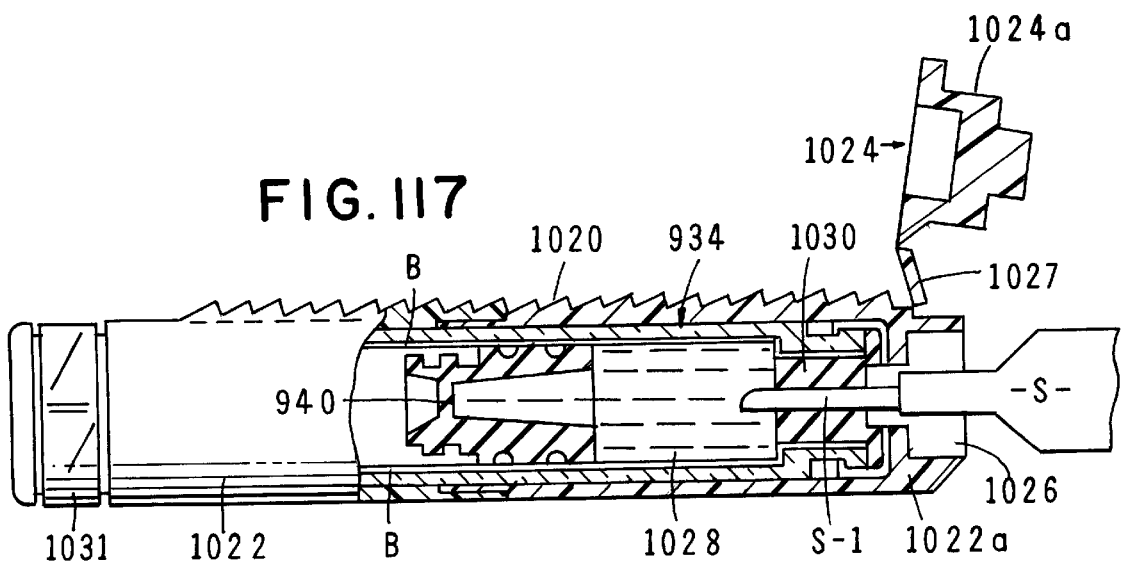

Referring to FIGS. 115 through 125, yet another embodiment of the invention that permits expeditious field filling of the container subassembly with a fluid agent is there illustrated. This latest form of the invention is similar in many respects to that shown in FIGS. 108 through 114 and like numerals are used to identify like components. In this latest embodiment the container assembly is uniquely constructed to enable easy coupling of a fluid containing syringe assembly "S" (FIG. 117) with the container assembly. This novel container assembly, which is designated by the numeral 1020 includes an external sleeve 1022, one end of which is closed by a hingedly connected closure member 1024. As best seen in FIG. 117, closure member 1024 includes a generally cylindrically shaped body portion 1024a that is sealably received within a chamber 1026 defined by end portion 1022a of sleeve 1022. Body portion 1024a is connected to sleeve 1022 by a living hinge 1027 so that the closure member can be moved from the closed position shown in FIG. 116 to the open position shown in FIG. 117. When the closure member is in the open position, the cannula S-1 of syringe "S" can be placed in communication with reservoir 1028 by piercing a septum 1030 in the manner shown in FIG. 117 so that the reservoir can be filled with fluid. As the reservoir fills, plunger assembly 940, which is identical to that described in the previous embodiment, will be moved from the position shown in FIG. 116 to the intermediate position shown in FIG. 117 and then into the position shown in FIG. 118. It is to be noted that gasses displaced by the relative movement of plunger assembly 940 will pass through vent ports formed in a vent patch 1031, which is removed before threadably interconnecting the plunger assembly with the pusher member 1032. With the parts in this position, rotation of the plunger 940 relative to a pusher member 1032 of the adapter subassembly of this latest embodiment will enable the parts to be threadably interconnected in the manner shown in FIG. 118.

With the reservoir fill assembly thus charged with the fluid to be used in filling reservoir 931 of the fluid dispenser component, the adapter subassembly, here identified by the numeral 1036, can be interconnected with the immobilized drug vial assembly 1038 which is substantially identical to the earlier described vial assembly 938. As before, to interconnect the adapter subassembly with the vial assembly 1038, the circumferentially spaced apart bayonet locking ears 956c of connector cap 956 are first inserted into circumferentially spaced slots 966c formed in end 966b of body 966. Relative rotation of the adapter subassembly and the immobilized drug vial assembly will then effect a sterile interconnection between the components. As the adapter subassembly 1036 is thus aseptically mated with the immobilized drug vial assembly, cannula 960 of connector cap 956 will pierce pierceable, slit septum 1000 of vial assembly 1038. This done, an inward pressure exerted on the closed closure member 1024 will cause sleeve 1022 to move forwardly of an annular space 1039 that is formed between member 1032 and the inner wall of housing 1040 of adapter subassembly 1036. As sleeve 1022 and container subassembly 1020 are urged forwardly, the fluid contained within reservoir 1028 will flow into cannula 1042 which is carried by pusher member 1032 and then into a central passageway 1032a formed in pusher member 1032. The fluid flowing through passageway 1032a will be urged into a central aperture 1045 formed in the end wall of housing 1040 where it will flow past an umbrella check valve 1044, into a passageway 1046 formed in connector cap 956 and then into cannula 960. The fluid flowing through cannula 960 will impinge on collector plate 980 where it will be dispersed for uniform flow through support structure 938a in the manner previously described herein.

Referring particularly to FIG. 118, the fluid dispenser of the apparatus of this form of the invention, which is generally designated as 1050, is similar in most respects to that shown in FIGS. 108 and 111, including a housing assembly comprising a base 991, a capture ring 992, a stored energy source, or distendable membrane 993, and a cover 994 for enclosing the stored energy source, the capture ring and the base. As before, base 991 includes an ullage defining protuberance 991a and a hub-like member 1004 having a receiving chamber 1004a. However, in this latest embodiment, septum 1008 has been replaced by a hollow cannula 1052 mounted within receiving chamber 1004a of hub-like member 1004. With this construction, when end portion 966a is interlocked with hub-like member 1004, cannula 1052 will pierce septum 1054 thereby permitting fluid flow from the immobilized drug vial assembly toward reservoir 931 via umbrella check valve 998.

With the components interconnected, an inward force exerted on container assembly 1020 will permit the controlled filling of reservoir 931 in the manner previously described. In this latest form of the invention, it is to be noted that body 1022 is provided with a plurality of longitudinally spaced locking teeth 1055. As the container assembly moves inwardly of adapter subassembly 1036, teeth 1055 will ride under a resiliently deformable locking finger 1057 provided on housing 1040 (FIGS. 118 and 124). However, while finger 1057 permits inward movement of the container assembly, it will engage teeth 1055 in a manner to prevent movement of the container assembly in an opposite direction. Accordingly, once the container assembly is inserted into the adapter assembly it cannot be removed for reuse.

Prior to use, the cooperating components of the reservoir fill assembly are maintained in a protected and substantially sterile configuration by tear-away end caps of the character shown in FIG. 115. As indicated in FIG. 115, previously bonded, peelable barrier caps 1056 and 1056a are receivable over and close the forward and rearward ends of adapter assembly 1036, while previously bonded, peelable barrier cap 1057 is received over and closes the open end portion of container 1020. Similarly, a barrier cap 1059 is received over and close the open end of immobilized drug vial assembly 1038.

Turning next to FIGS. 126 through 131, still another form of the immobilized drug vial assembly of the invention is there shown. This form of drug vial is similar in most respects to that shown in FIGS. 107 through 114 and like numerals are used to identify like components. The principal difference between this latest form of vial assembly and that earlier described resides in the novel construction of the safety end cap 1060.

As best seen in FIG. 131, safety end cap 1060 here comprises a generally cylindrical body portion 1062, and a dome shaped top portion 1064 having a closure flange 1064a (FIG. 127). Provided on body portion 1062 are circumferentially spaced bayonet-type locking ears 1066 which are lockably received within slots 966c formed in end 966b of body 966. With this novel construction, when body 1062 of cap 1060 is inserted into open end 966b of body 966 and rotated, cap 1060 will be securely locked in position until time of use thereby maintaining septum 1000 in an aseptic condition. An O-ring 1063 prevents leakage between the mating components. In a similar vein, a tear-away cap 1067 with affixed septum 1002, covers the other end of body 966 to maintain cannula 967a in an aseptic condition until time of use.

Referring next to FIGS. 111, 111A, 116, 116A, 127 and 127A it is to be noted that body 935a of vial assembly 934 as well as body 966 of drug vial assembly 938 may be constructed of a plastic material such as, for example, a polycarbonate, an acrylic polystyrene, polyvinylchloride, polyethylene, polyester, PMMA, polysulfone, polytirethane, polyamide, polyvinylalcohol, polypropylene. With this construction, the interior surface of these bodies as well as fluid flow passageways which carry fluid to the dispensing device can be surface modified or coated with various materials to form thin conformable, protective, interfacial barriers "B" for biological compatibility or to promote wetlubricity or wettability.

These barriers or surface treatments "B" can include hydrophilic agents that offer a wide range of wettability characteristics which can be taylored to meet the required surface wetting, priming, reduction of gas bubble adhesions, and other flow performance characteristics. Other forms of these coatings can also reduce the absorption and denaturation of other biomaterials, including proteins. Alternatively, modified proteins, peptides, carbohydrates and synthetic polymers can also be covalently bonded to surfaces to generate ultrathin coatings or crosslinked to generate other three dimensional intermediate polymer matrices to either inhibit other biochemical responses or for immobilization of related biomaterials. These coatings and surface modification treatments are readily available from multiple sources and well known to those skilled in the art.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for use in infusing medicinal fluid into a patient at a controlled rate comprising:
    (a) a fluid dispenser including:
        (i) a base having a receiving chamber;
        (ii) a stored energy means for forming, in conjunction with said base a fluid reservoir having an inlet in communication with said chamber and an outlet, said stored energy means comprising at least one distendable member superimposed over said base, said member being distendable as a result of pressure imparted by the fluids to be infused to establish internal stresses, said stresses tending to move said member toward a less distended configuration;
        (iii) an outlet port in communication with said outlet of said fluid reservoir for dispensing fluids from the device; and
    (b) a reservoir fill assembly interconnectable with said base of said fluid dispenser for filling said fluid reservoir thereof, said reservoir fill assembly comprising:
        (i) a container assembly including a container having a fluid chamber and displacement means movable within said fluid chamber;
        (ii) an adapter assembly comprising a hollow housing having an outlet in communication with said inlet of said fluid reservoir and also having a barrel portion receivable within said receiving chamber of said base of said fluid dispenser to connect said adapter assembly to said base, said container being telescopically receivable in said housing; and
        (iii) pusher means for engagement with said displacement means of said container assembly to move said displacement means within said fluid chamber to urge fluid flow toward said outlet of said adapter assembly.

2. The device as defined in claim 1 in which said pusher means comprises a pusher member disposed within said hollow housing of said adapter subassembly.

3. The device defined in claim 1 in which said displacement means comprises a plunger member and a connector member, said connector member being interconnectable with said pusher means.

4. The device as defined in claim 1 in which said recieving chamber includes a pierceable septum and in which said adapter assembly includes a cannula for piercing said pierceable septum.

5. The device as defined in claim 1 in which said displacement means comprises a plunger member and a connector member, said connector member having a pierceable wall, and in which said pusher means includes a fluid passageway and a cannula for piercing said pierceable wall.

6. The device as defined in claim 1 in which said adapter assembly of said reservoir fill assembly accommodates a plurality of container assemblies.

7. A device as defined in claim 1 in which said fluid dispenser further includes fluid actuated indicator means for visually indicating fluid flow from said fluid reservoir, said indicator means comprising at least one thin film movable in response to fluid flowing from said fluid reservoir.

8. A device as defined in claim 7 in which said indicator means includes actuator means movable by fluid flowing from said reservoir between a first position wherein said actuator means is spaced from said thin film to a second position wherein said actuator means engages said thin film.

9. A device for use in infusing medicinal fluid into a patient at a controlled rate comprising:
    (a) a fluid dispenser including:
        (i) a base having, a receiving chamber;
        (ii) a stored energy means for forming, in conjunction with said base a fluid reservoir having an inlet in communication with said chamber and an outlet, said stored energy means comprising at least one distendable member superimposed over said base, said member being distendable as a result of pressure imparted by the fluids to be infused to establish internal stresses, said stresses tending to move said member toward a less distended configuration; and
        (iii) an outlet port in communication with said outlet of said fluid reservoir for dispensing fluids from the device;
        (iv) fluid actuated indicator means for visually indicating fluid flow from said reservoir; and
    (b) a reservoir fill assembly interconnectable with said base of said fluid dispenser for filling said fluid reservoir thereof, said reservoir fill assembly comprising:

(i) a container subassembly including a container having a fluid chamber and displacement means movable within said fluid chamber;

(ii) an adapter assembly comprising a hollow housing having an outlet in communication with said inlet of said fluid reservoir and also having a barrel portion receivable within said receiving chamber of said base of said fluid dispenser to connect said adapter assembly to said base, said container being telescopically receivable in said housing; and (iii) pusher means for engagement with said displacement means of said container assembly to move said displacement means within said fluid chamber to urge fluid flow toward said outlet of said adapter assembly.

10. The device as defined in claim 9 in which said fluid dispenser includes fluid recovery means for recovering fluid from said fluid reservoir.

11. The device as defined in claim 9 in which said fluid dispenser further includes vent means for venting to atmosphere gases contained within said adapter assembly.

12. The device as defined in claim 11 in which said chamber includes a pierceable septum and in which said outlet of said adapter assembly comprises a cannula for piercing said pierceable septum.

13. The apparatus as defined in claim 12 in which said vent means comprises means for venting to atmosphere gases trapped within said cannula.

14. The device as defined in claim 12 in which said displacement means comprises a plunger member and a connector member, said connector member having a pierceable wall, and in which said pusher means includes a fluid passageway and a cannula for piercing said pierceable wall.

15. The device as defined in claim 14 in which fluid actuated indicator means comprises at least one thin film, said film being movable in response to fluid flowing from said fluid reservoir.

16. A device for use in infusing medicinal fluid into a patient at a controlled rate comprising:

(a) a fluid dispenser including:

(i) a base having an upper surface and a lower surface, said lower surface having a dispenser connector comprising circumferentially spaced slots;

(ii) a stored energy means for forming, in conjunction with said base, a fluid reservoir having an inlet in communication with said dispenser connector and an outlet, said stored energy means comprising at least one prestressed, distendable elastomeric membrane superimposed over said base, said membrane being further distendable as a result of pressure imparted by the fluids to be infused to establish internal stresses, said stresses tending to move said member toward a less distended configuration; and (iii) an outlet port in communication with said outlet of said fluid reservoir for dispensing fluids from the device; and (b) a reservoir fill assembly interconnectable with said fluid dispenser for filling said fluid reservoir thereof, said reservoir fill assembly comprising:

(i) a container subassembly including a container having a body portion, a fluid chamber, and first and second ends and displacement means telescopically movable within said container from a first location proximate said second end to a second, spaced-apart location, said displacement means comprising a plunger and a connector;

(ii) an adapter subassembly having an outlet in communication with said inlet of said reservoir, said adapter subassembly comprising a hollow housing for telescopically receiving a part of said body portion of said container of said container subassembly and a second end, said hollow housing further including an adapter connector comprising circumferentially spaced tabs mateably interconnectable with said dispenser connector of said fluid dispenser for removably interconnecting said adapter subassembly with said fluid dispenser; and (iii) pusher means disposed within said hollow housing for engagement with said displacement means of said container assembly to move said plunger within said container between said first and second locations to urge fluid to flow toward said outlet of said adapter subassembly, said pusher means being connected to said connector of said displacement means.

17. The device as defined in claim 16 in which said displacement means includes a pierceable wall and in which said pusher means includes a fluid passageway and a cannula for piercing said pierceable wall upon interconnection of said pusher means with said connector of said displacement means.

18. The device as defined in claim 16 further including infusion means connected to said outlet port of said fluid reservoir for infusing the medicinal fluid into the patient.

19. The device as defined in claim 18 in which said fluid dispenser further includes rate control means for controlling the rate of fluid flow toward said infusion means.

20. The device as defined in claim 18 in which said fluid dispenser further includes fluid actuated indicator means disposed intermediate said fluid outlet of said reservoir, said fluid actuated indicator means comprising at least one thin film, said thin film being movable in response to fluid flow from said fluid reservoir.

21. The device as defined in claim 18 in which said adapter assembly includes fill flow control means for controlling flow from said container assembly toward said fluid reservoir of said fluid dispenser.

22. The device as defined in claim 21 in which said flow control means comprises a hollow cannula connected to said hollow housing of said adapter assembly.

23. The device as defined in claim 21 in which said flow control means comprises a valve disposed between said pusher means and said hollow cannula.

24. A device for use in infusing medicinal fluid into a patient at a controlled rate comprising:

(a) a fluid dispenser including:

(i) a base having, a receiving chamber provided with a plurality of circumferentially spaced tab receiving openings;

(ii) a stored energy means for forming, in conjunction with said base a fluid reservoir having an inlet in communication with said connector and an outlet, said stored energy means comprising at least one distendable member superimposed over said base, said member being distendable as a result of pressure imparted by the fluids to be infused to establish internal stresses, said stresses tending to move said member toward a less distended configuration;

(iii) an outlet port in communication with said outlet of said fluid reservoir for dispensing fluids from the device; and (b) a reservoir fill assembly interconnectable with said base of said fluid dispenser for filling said fluid reservoir thereof, said reservoir fill assembly comprising:

(i) a container subassembly including a container having a fluid chamber and displacement means movable within said fluid chamber;

(ii) an adapter assembly comprising a hollow housing having a barrel portion receivable within said receiving chamber of said base of said fluid dispenser to connect said adapter assembly to said base, said barrel portion having a plurality of circumferentially spaced tabs receivable within said tab receiving openings of said receiving chamber, said container being telescopically receivable in said housing; and (iii) pusher means for engagement with said displacement means of said container assembly to move said displacement means within said fluid chamber.

25. The apparatus as defined in claim 24 in which said pusher means comprises a pusher member disposed within said hollow housing of said adapter subassembly.

26. The apparatus as defined in claim 24 in which said displacement means comprises a plunger member and a connector member, said connector member being interconnectable with said pusher means.

27. The apparatus as defined in claim 24 in which said displacement means includes flow control means for controlling fluid flow through said displacement means.

28. The apparatus as defined in claim 24 further including valving means disposed within said receiving chamber of said fluid dispenser for controlling fluid flow from said reservoir fill assembly toward said fluid dispenser.

29. The device as defined in claim 24 in which said adapter assembly of said filling means further includes flow control means for controlling fluid flow from said container assembly toward said fluid dispenser reservoir.

30. The device as defined in claim 24 in which said receiving chamber of said base of said fluid dispenser includes a pair of circumferentially spaced tab receiving slots having a pair of circumferentially spaced tabs receivable within said tab receiving slots.

31. The device as defined in claim 24 in which said adapter assembly has three circumferentially spaced tabs.

32. The device as defined in claim 24 in which said adapter assembly has four circumferentially spaced tabs.

33. The device as defined in claim 24 in which said adapter assembly has five circumferentially spaced tabs.

34. The device as defined in claim 24 in which said adapter assembly has six circumferentially spaced tabs.

35. A device for use in infusing medicinal fluid into a patient at a controlled rate comprising:

(a) a fluid dispenser including:
  (i) a base having connector means;
  (ii) a stored energy means for forming, in conjunction with said base a fluid reservoir having an inlet in communication with said chamber and an outlet, said stored energy assembly comprising at least one distendable member superimposed over said base, said member being distendable as a result of pressure imparted by the fluids to be infused to establish internal stresses, said stresses tending to move said member toward a less distended configuration;
  (iii) an outlet port in communication with said outlet of said fluid reservoir for dispensing fluids from the device; and (b) a reservoir fill assembly interconnectable with said base of said fluid dispenser for filling said fluid reservoir thereof, said reservoir fill assembly comprising:
  (i) a container assembly including a container having a fluid chamber and displacement means movable within said fluid chamber;
  (ii) an adapter assembly comprising:
    a. a hollow housing having an outlet, said container being telescopically receivable in said housing; and
    b. pusher means for engagement with said displacement means of said container assembly to move said displacement means within said fluid chamber to urge fluid flow toward said outlet of said adapter assembly; and
  (iii) an immobilized drug vial assembly connected to said adapter assembly, said immobilized drug vial assembly including:
    a. a hollow housing having an inlet in communication with said outlet of said adapter means and an outlet
    b. an additive disposed between said inlet and said outlet of said hollow housing; and
    c. an additive presentation means carried by said housing for presenting said additive to fluid flowing toward said outlet of said housing.

36. The apparatus as defined in claim 35 in which said additive presentation means comprises a functional support disposed within said hollow housing of said immobilized drug vial assembly and in which said additive comprises a beneficial agent carried by said functional support.

37. The apparatus defined in claim 35 in which said immobilized drug vial assembly further comprises a rate control element for controlling the rate of fluid flow toward said additive presentation means.

38. The apparatus as defined in claim 35 in which said immobilized drug vial assembly further comprises a rate control element for controlling the rate of fluid flow from said additive presentation means toward said fluid dispenser.

39. The apparatus as defined in claim 35 in which said immobilized drug vial assembly further includes a fluid collector disposed between said inlet of said hollow housing and said additive presentation means to disperse the fluid flowing from said inlet toward said additive presentation means.

40. The apparatus as defined in claim 35 in which said immobilized drug vial assembly further includes a fluid collector disposed between said additive presentation means and said base of said dispensing means for collecting fluid flowing through said additive presentation means.

41. The apparatus as defined in claim 35 in which said pusher means comprises a pusher member disposed within said hollow housing of said adapter subassembly.

42. The apparatus defined in claim 35 in which said displacement means comprises a plunger member and a connector member, said connector member being interconnectable with said pusher means.

43. The apparatus as defined in claim 35 in which said connector means of said base includes a pierceable septum and in which said immobilized drug vial assembly includes a cannula for piercing said pierceable septum.

44. The apparatus as defined in claim 35 in which said connector means of said base includes a cannula and in which said immobilized drug vial assembly includes a septum pierceable by said cannula of said connector means of said base.

45. A device for use in infusing medicinal fluid into a patient at a controlled rate comprising:

(a) a fluid dispenser including:
  (i) a base having connector means;
  (ii) a stored energy means for forming, in conjunction with said base a fluid reservoir having an inlet in communication with said chamber and an outlet, said stored energy means comprising at least one distendable member superimposed over said base, said member being distendable as a result of pressure imparted by the fluids to be infused to establish internal stresses, said stresses tending to move said member toward a less distended configuration;

(iii) an outlet port in communication with said outlet of said fluid reservoir for dispensing fluids from the device; and (b) a reservoir fill assembly interconnectable with said base of said fluid dispenser for filling said fluid reservoir thereof, said reservoir fill assembly comprising:

(i) a container assembly including a container having a fluid chamber and displacement means movable within said fluid chamber;

(ii) an adapter assembly comprising:

a. a hollow housing having an outlet, said container being telescopically receivable in said housing; and b. pusher means for engagement with said displacement means of said container assembly to move said displacement means within said fluid chamber to urge fluid flow toward said outlet of said adapter assembly; and (iii) an immobilized drug vial assembly connected to said adapter assembly, said immobilized drug vial assembly including:

a. a hollow housing having interior surfaces and an inlet in communication with said outlet of said adapter assembly and an outlet;

b. an additive disposed between said inlet and said outlet of said hollow housing; and c. an additive presentation means carried by said housing for presenting said additive to fluid flowing toward said outlet of said housing said additive presentation means comprising a functional support disposed within said hollow housing.

46. The apparatus defined in claim 45 in which said additive comprises a beneficial agent.

47. The apparatus as defined in claim 45 in which said additive comprises a drug.

48. The apparatus as defined in claim 45 in which the interior surfaces of said housing are modified to provide a protective barrier.

49. The apparatus as defined in claim 45 in which the interior surfaces of said housing are modified to provide wetlubricity.

50. The apparatus as defined in claim 45 in which the interior surfaces of said housing are modified to provide wettability.

51. The apparatus as defined in claim 45 in which the interior surfaces of said housing are modified to provide biological compatibility.

52. The apparatus as define din claim 45 in which an intermediate polymer matrix for immobilization of biomaterials.

* * * * *